US007313357B2

(12) United States Patent
Stuyver et al.

(10) Patent No.: US 7,313,357 B2
(45) Date of Patent: Dec. 25, 2007

(54) METHOD FOR TYPING AND DETECTING HBV

(75) Inventors: Lieven Stuyver, Herzele (BE); Rudi Rossau, Ekeren (BE); Geert Maertens, Brugge (BE)

(73) Assignee: Innogenetics N.V., Ghent (BE)

( * ) Notice: Subject to any disclaimer, the term of this patent is extended or adjusted under 35 U.S.C. 154(b) by 280 days.

(21) Appl. No.: 10/453,792

(22) Filed: Jun. 4, 2003

(65) Prior Publication Data

US 2004/0029110 A1    Feb. 12, 2004

Related U.S. Application Data

(62) Division of application No. 09/155,885, filed as application No. PCT/EP97/02002 on Apr. 21, 1997, now Pat. No. 6,709,812.

(30) Foreign Application Priority Data

Apr. 19, 1996  (EP) .................................. 96870053

(51) Int. Cl.
*C12Q 1/10* (2006.01)
*C12N 7/00* (2006.01)
(52) U.S. Cl. ...................... 434/5; 435/235.1; 435/193; 424/189.1; 424/227.1
(58) Field of Classification Search ................. 435/239
See application file for complete search history.

(56) References Cited

U.S. PATENT DOCUMENTS

| 6,228,575 B1 | 5/2001 | Gingeras |
| 6,555,311 B1 | 4/2003 | Locarnini |
| 2005/0175990 A1 | 8/2005 | Stuyver |

FOREIGN PATENT DOCUMENTS

| EP | 0 229 701 A | 7/1987 |
| EP | 0 569 237 A | 11/1993 |
| WO | WO91 10746 A | 7/1991 |
| WO | WO93 13120 A | 7/1993 |
| WO | 94/12670 | 6/1994 |
| WO | 94/26904 | 11/1994 |
| WO | WO95 02690 A | 1/1995 |
| WO | 95/11995 | 5/1995 |
| WO | 97/40193 | 10/1997 |

OTHER PUBLICATIONS

Ling R. et al. "Selection of mutations in the hepatitis B virus polymerase during therapy of transplan recipients with lamivudine" Hepatology, vol. 24(1996), pp. 711-713.*
Tipples Ga et al. "Mutation in HBV RNA-dependent DNA polymerase confers resistant to lamivudine in vivo". Hepatology, vol. 24 (1996), pp. 714-717.*
G.A. Tipples et al.: "Mutation in HBV RNA-dependent DNA polymerase confers resistance to lamivudine in vitro" Hepatology, vol. 24, No. 3, Sep. 1996, Philadelphia US, pp. 714-717, XP002044246 cited in the application see the whole document.
R. Ling et al.: "Selection of mutations in the hepatitis B virus polymerase during therapy of transplant recipients with lamivudine" Hepatology, vol. 24, No. 3, Sep. 1996, Philadelphia US, pp. 711-713, XP002044247 cited in teh application see the whole document.
A. Bartholomeusz et al.: "Mutations in the hepatitis B virus polymerase gene that are associated with resistance to famciclovir and lamivudine" International Antiviral News, vol. 5, No. 8, 1997, London GB, pp. 123-124, XP002044248 see the whole document.
Grandjacques et al.: "Rapid detection of genotypes and mutations in the pre-core promoter and the pre-core region of hepatitis B virus genome: correlation with viral; persistence and disease severity", Journal of Hepatology 2000; 33:430-439.
Lau et al.:"Features of response and resistance to lamivudine in patients with chronic hepatitis B with and without HbeAg", AASLD Abstract, Hepatology Oct. 1998, p. 318A.
Stuyver et al.: A new genotype of hepatitis B virus: complete genome and phylogenetic relatedness:, Journal of General Virlogy (2000) 81, 67-74.
Blum, H.E., Digestion 56:85-95 (1995).
Harrison, T.J., European Journal of Gastroenterology & Hepatology 8(4): 306-311 (1996).
Carman et al., Hepatitis and Chronic Liver Disease. 16(2): 407-428 (Jun. 1996).
Ling et al., Hepatology 24(3): 711-713 (Sep. 1996).

(Continued)

*Primary Examiner*—Bruce R. Campell
*Assistant Examiner*—Bo Peng
(74) *Attorney, Agent, or Firm*—Nixon & Vanderhye P.C.

(57) ABSTRACT

The present invention relates to a method for detection and/or genetic analysis of HBV in a biological sample, comprising hybridizing the polynucleic acids of the sample with a combination of at least two nucleotide probes, with said combination hybridizing specifically to a mutant target sequence chosen from the HBV RT pol gene region and/or to a mutant target sequence chosen from the HBV preCore region and/or to a mutant target sequence chosen from the HBsAg region of HBV and/or to a HBV genotype-specific target sequence, with said target sequences being chosen from FIG. 1, and with said probes being applied to known locations on a solid support and with said probes being capable of hybridizing to the polynucleic acids of the sample under the same hybridization and wash conditions, or with said probes hybridizing specifically with a sequence complementary to any of said target sequences, or a sequence wherein T of said target sequence is replaced by U; and detecting the hybrids formed; and inferring the HBV genotype and/or mutants present in said sample from the differential hybridization signal(s) obtained. The invention further relates to sets of nucleotide probes and possibly primers useful in said methods as well as to their use in a method for typing and/or detecting HBV and to assay kits using the same.

4 Claims, 28 Drawing Sheets

OTHER PUBLICATIONS

Figure 1B:
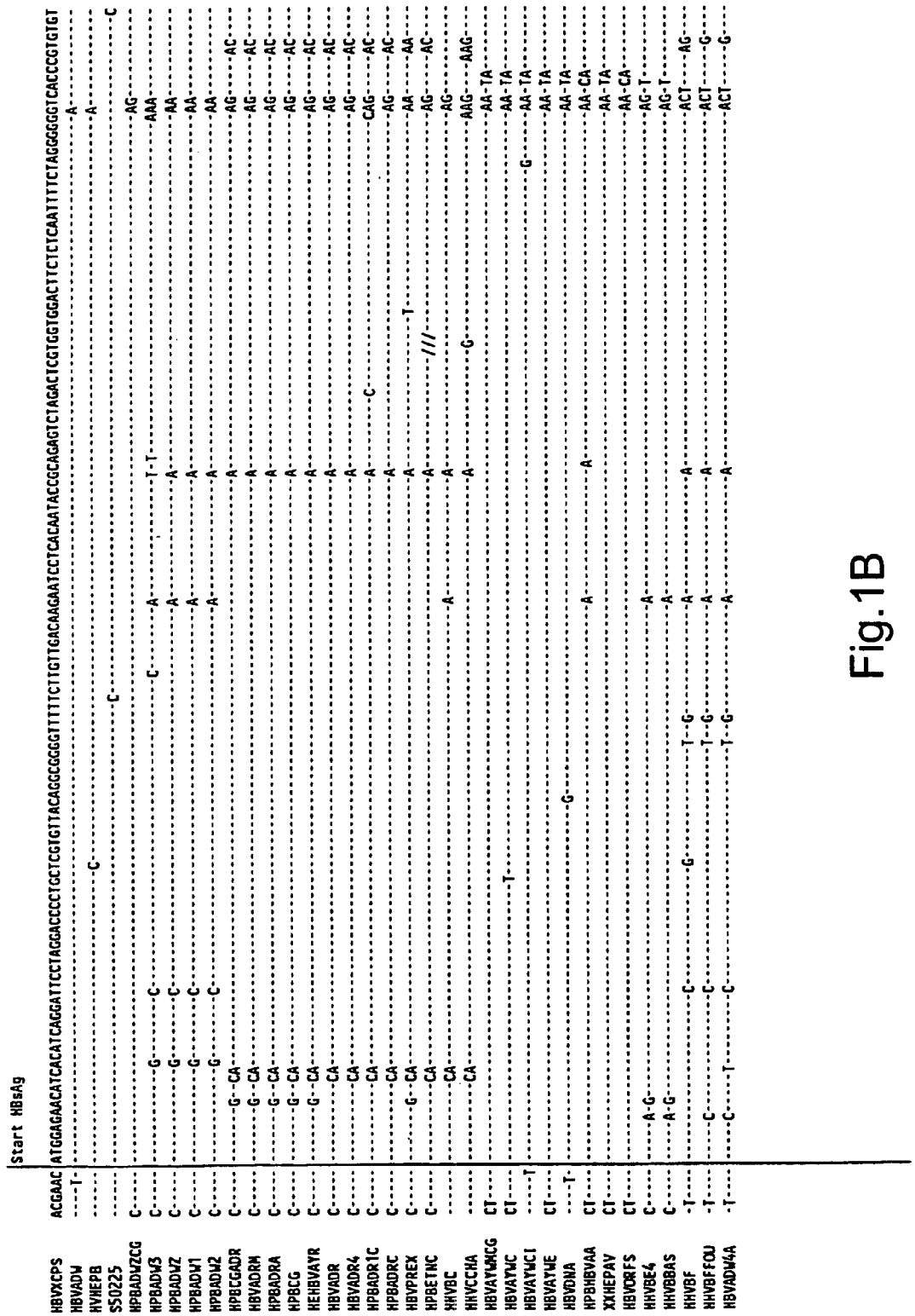
Figure 1D:
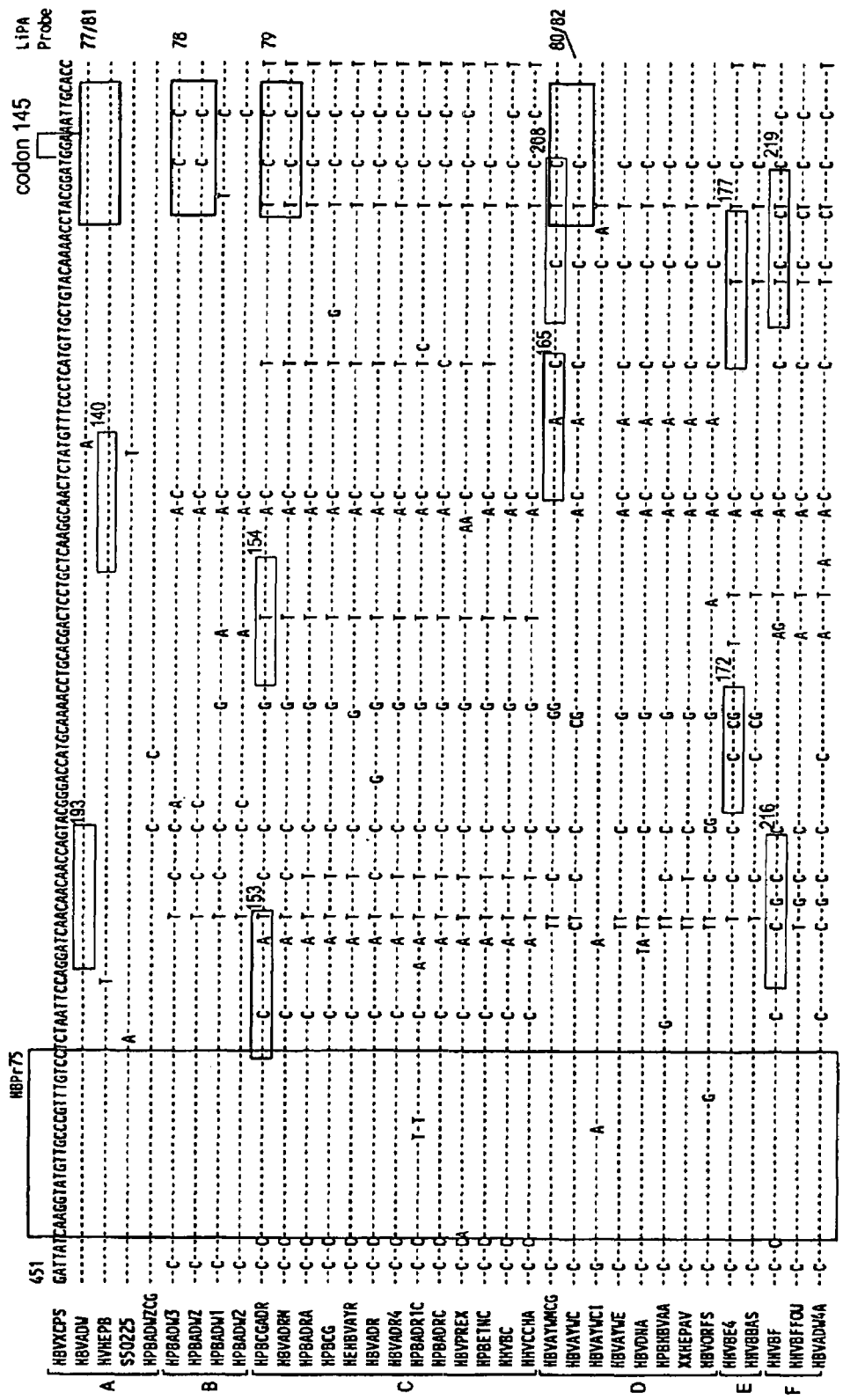
Figure 1E:
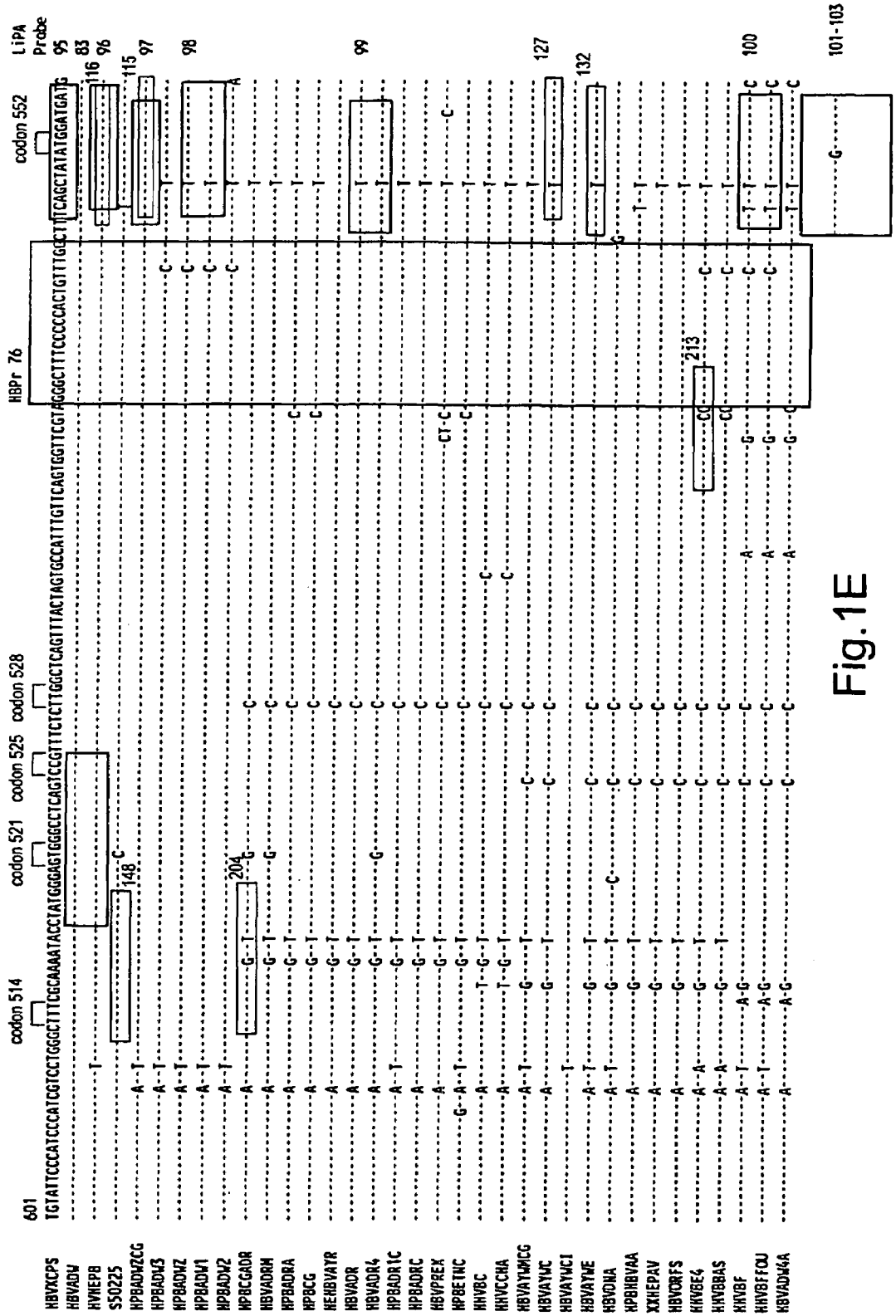
Figure 1L:
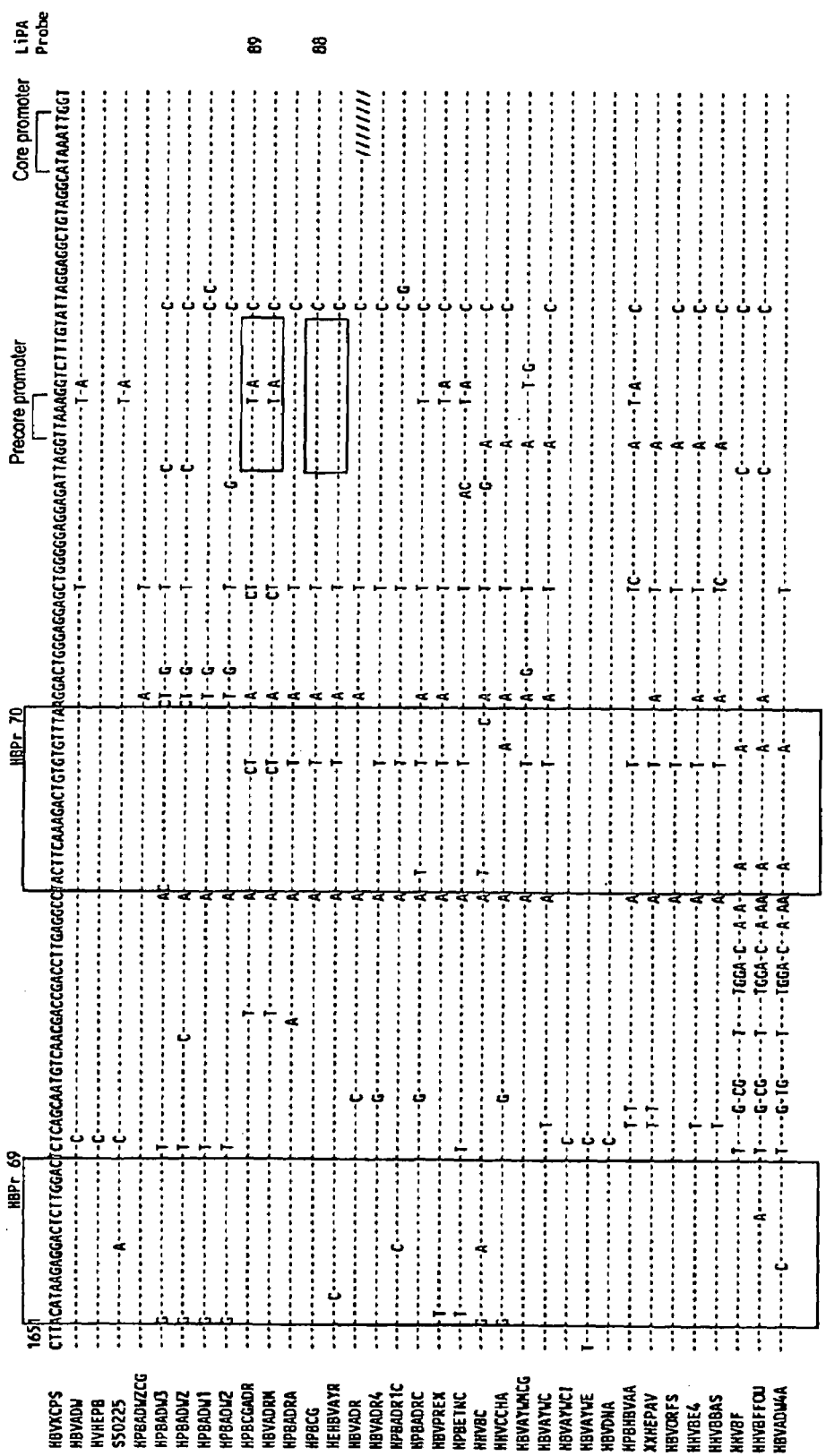
Figure 1M:
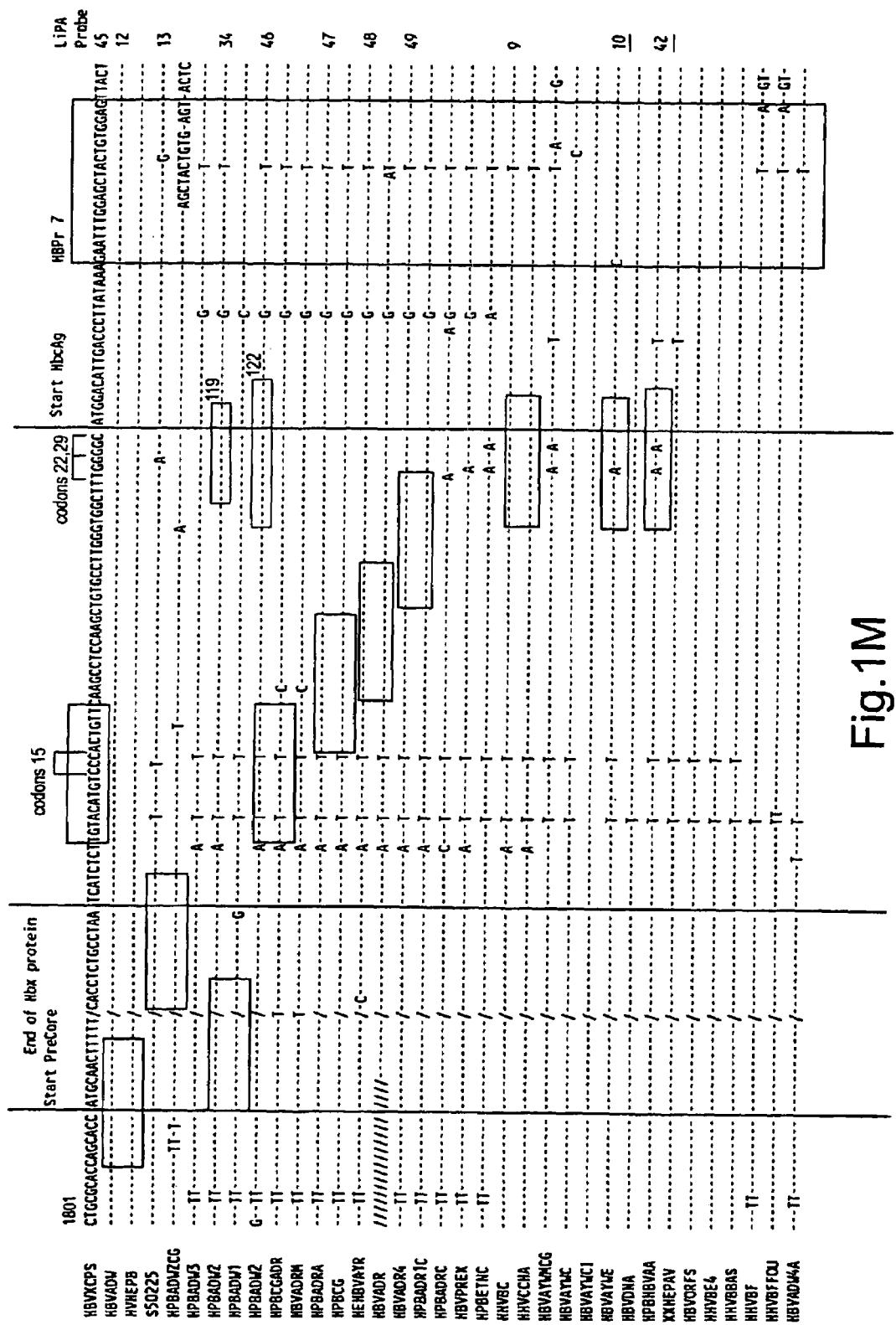
Figure 1T:
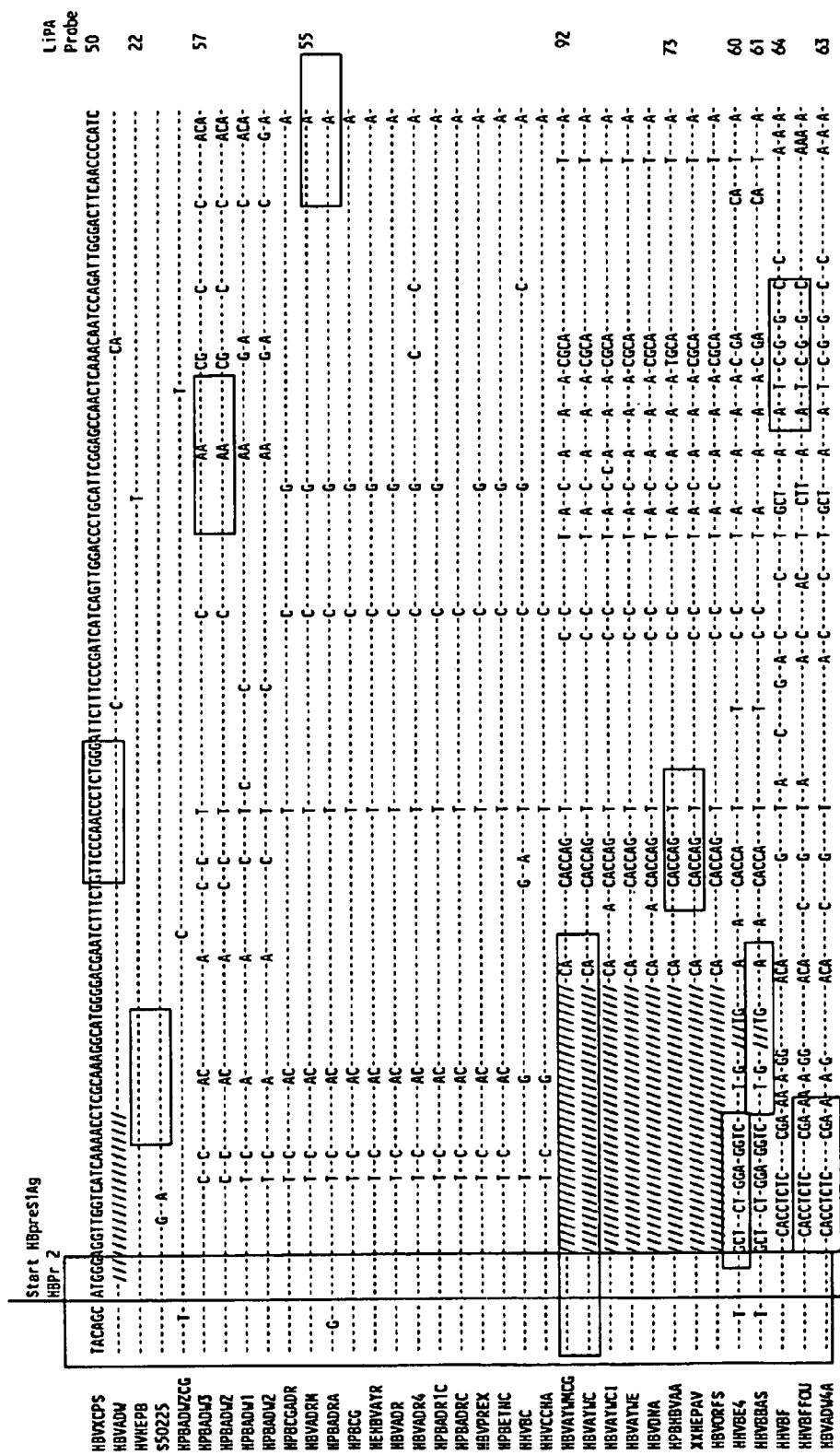
Figure 1V:
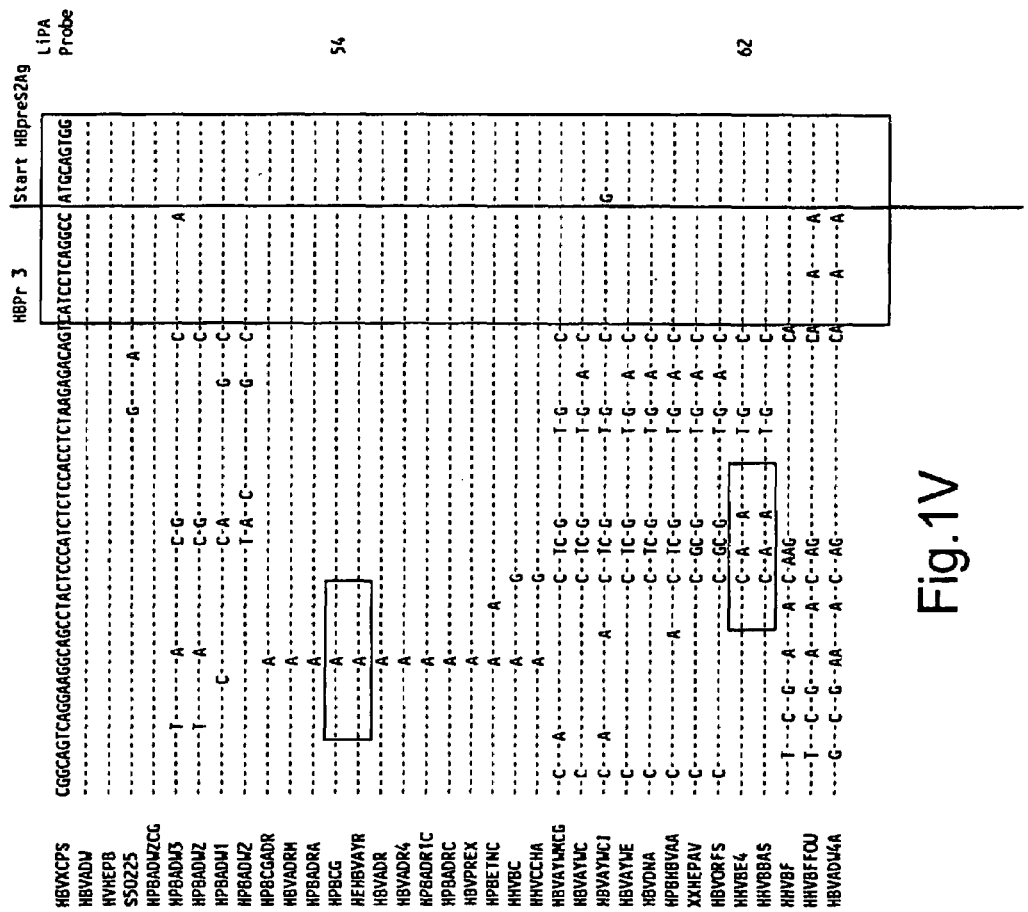

Ni et al., (Res. Virol. 146:397-407, 1995).
Zhang et al., (Journal of Medical Virology 48:8-16, 1996).
Rodriquez-Frias et al., (Hepatology 22(6): 1641-1647, 1995).
Norder (Journal of General Virology 73:1201-1208, 1992).
Blum, Journal of Virology, Apr. 1991, pp. 1836-1842, vol. 65, No. 4.
Nature(1979), vol. 282, Pasek M et al, pp. 575-579, "Hepatitis B virus genes and their expression in E. coli" Figure 2.
Nucleic Acids Research(1983), vol. 11(6), Ono Y et al, pp. 1747-1757, "The complete nucleotide of the cloned hepatitis B virus DNA; subtype adr and adw" Figure 2 and 3.
J. General Virology (1988), vol. 69, Vaudin M et al, pp. 1383-1389, "The complete nucleotide sequence of the genome of a hepatitis B virus isolated from a naturally infected chimpanzee" Figure 1.
J. General Virology (1988), vol. 69, Okamoto F et al, pp. 2575-2583, "Typing hepatitis B virsu by homology in nucleotide sequence: comparison of surface antigen subtypes" Figure 1.
Gene (1988), vol. 64, Rivkina M et al, pp. 285-296, "Nucleotide sequence of integrated hepatitis B virus DNA and human flanking regions in the genome of the PLC/PRF/5 cell line" Figure 5.
J General Virology (1993), vol. 74, Norder H et al, pp. 1341-1348, "Genetic relatedness of hepatitis B viral strains of diverse geographical origin and natural variations in the primary structure of the surface antigen" Figure 2.
J Medical Virology (1994), vol. 44(1), Horikita M et al, pp. 96-103, "Differences in the entire nucleotide sequence between hepatitis B virus genomes from carriers positive for antibody to hepatitis B e antigen with and without active disease" Table IV.
GenBank Accession No. D50489, "Hepatitis B virus DNA, complete genome", no date available.
J General Virology (1995), vol. 45, Uchida T et al, pp. 247-252, Complete nucleotide sequences and the characteristics of two hepatitis B virus mutants causing serologically negtive acute or chronic hepatitis B: p. 249.
J General Virology (1996), vol. 3, Alexopoulou A et al, pp. 173-181, "Whole genome analysis of hepatitis B virus from four cases of fulminant hepatitis: genetic variability and its potential role in disease pathogenicity" Table 3.
J General Virology (1997), vol. 78, Bowyer S et al, pp. 1719-1729, "A unique segment of the hepatitis B virus group A genotype identified in isolates from South Africa" Figure 5.
Carman et al, "Vaccine-induced escape mutant . . . ", The Lancet, vol. 336, 1990 (8711) pp. 325-329.
Fujii et al, "Gly$^{145}$ to Arg Substitution in HBs Antigen of . . . ", Biochemical and Biophysical Research Communications, vol. 184, No. 3, May 15, 1992, pp. 1152-1157.
Yamamoto et al, "Naturally Ocurring Escape Mutants of Hepatitis B Virus with . . . ", Journal of Virology, vol. 68, No. 4, Apr. 1994, pp. 2671-2676.
Carman, "The clinical significance of surface antigen variants . . . ", Journal of Viral Hepatitis, 1997. 4 (Suppl. 1) 11-20.
Wang GT et al, Chung Hua I Hseuh Tsa Chih, "Sequencing of hepatitis B Virus DNA fragment coding major HBsAg of escape mutant", Jun. 1994 74(6) pp. 355-357, 391 (PubMed English Abstract PMID 7994645).
Ren H et al, Chung Hua I Hseuh Tsa Chih, "Expression of 12 antibody escape mutants of hepatitis B virus surfce antigen gene in mammalian cell by using an Epstein-Barr based vector", 1995 75(7) pp. 396-398 (PubMed English Abstract PMID 7553156).
Chenault, "Patterns of nucleotide sequence variation among cauliflower mosaic virus isolates", (Biochimie 76:3-8, 1994).
Fischer, "Generation of Duck Hepatitis B Virus Polymerase Mutants through Site-Directed Mutagenesis . . . " , (Antimicrobial Agents and Chemotherapy 40(8): 1957-1960, Aug. 7, 1996.
Norder, "Complete Genomes, Phylogenetic Relatedness, and Structural Proteins of Six Strains of the Hepatitis B Virus, Four of Which Represent Two New Genotypes", (Virology 198: 489-503, 1994).
Bartholomew, "Hepatitis-B-Virus resistance to lamivudine given for recurrent infection after orthotopic liver transplantation", (Lancet 349: Jan. 20-22, 1997).
Aye et al, "Hepatitis B virus polymerase mutations Famciclovir therapy in patients following liver transplantation", Hepatology vol. 24, No. 4, Pt.2, Sep. 1996.
Delaney et al, "Resistance of hepatitis B virus to antiviral drugs: current aspects and directions for future investigation", Antiviral Chemistry & Chemotherapy 12:1-35 (2001).
Ashton-Rickardt "Mutants of the Hepatitis B Virus surface antigen that define some antigenically essential residues in the immunodominant region" J. Med. Virol. Nov. 1989, 29(3):196-203.
Aye et al, "Hepatitis B virus polymerase mutations during antiviral therapy in a patient following liver transplantation", Journal of Hepatology, 1997; 26: 1148-1153.
de Man et al, "The sequential occurrence of viral mutations in a liver transplant recipient re-infected with hepatitis B: hepatitis B immune globulin escape, famciclovir non-response, followed by lamivudine resistance resulting in graft loss", Journal of Hepatology, 1998; 29: 669-675.
Norder et al, "Molecular basis of hepatitis B virus serotype variations within the four major subtypes", Journal of General Virology 1992, vol. 73, pp. 3141-3145.
Ho et al, "A Family Cluster of an Immune Escape Variant of Hepatitis B Virus Infecting a Mother and Her Two Fully Immunized Children", Clinical and Diagnostic Laboratory Immunology, 1995, vol. 2, No. 6, pp. 760-762.
Weiss et al, "The HBV-Producing Cell Line HepG2-4A5: A New in vitro System for Studying the Regulation of HBV Replication and for Screening Anti-Hepatitis B Virus Drugs", Virology 216:214-218, 1996.
Poch et al, "Identification of four conserved motifs among the RNA-dependent polymerase encoding elements", EMBO Journal 8:3867-3874, 1989.

* cited by examiner

| LiPA HBV design | | | | |
|---|---|---|---|---|
| | | | HBPr | |
| LiPA line | Region | Purpose | Probe number/SEQ ID NO | sequence |
| 0 | | Pencil line | | |
| 1 | | biotinylated DNA | | |
| 2 | PreS1 | ampl. contr. | 33 | CTGAGGGCTCCACCCCA |
| 3 | PreS1 | Genotype A | 22 | AACCTCGCAAAGGCAT |
| 4 | PreS1 | Genotype A | 50 | CCCAGAGGGTTGGGAAC |
| | PreS1 | Genotype A | 15 | GCCAGCAGCCAACCAG |
| 5 | PreS1 | Genotype B | 57 | CTGCATTCAAAGCCAACT |
| | PreS1 | Genotype B | 58 | CCCCATGGGGGACTGTTG |
| 6 | PreS1 | Genotype B | 59 | CATACTCACAACTGTGCCA |
| 7 | PreS1 | Genotype C | 55 | TTCAACCCCAACAAGGATC |
| 8 | PreS1 | Genotype C | 54 | TCAGGAAGACAGCCTAC |
| 9 | PreS1 | Genotype D | 92 | TTCTGCCCCATGCTGTA |
| 10 | PreS1 | Genotype D | 56 | AATGCTCCAGCTCCTAC |
| 11 | PreS1 | Genotype D | 73 | TTCCACCAGCAATCCTC |
| 12 | PreS1 | Genotype E | 60 | GGGCTTTCTTGGACGGTCC |
| | PreS1 | Genotype E | 61 | CTCTCGAATGGGGGAAGA |
| | PreS1 | Genotype E | 62 | CCTACCCCAATCACTCCA |
| 13 | PreS1 | Genotype F | 63 | AGCACCTCTCTCAACGACA |
| 14 | PreS1 | Genotype F | 64 | GCAAATTCCAGCAGTCCCG |
| | PreS1 | Genotype F | 65 | GCCAATGGCAAACAAGGTA |
| 15 | preCore | promotor | 88 | TAGGTTAAAGGTCTTTGT |
| 16 | preCore | promotor | 89 | TAGGTTAATGATCTTTGT |
| 17 | preCore | scan codon -2 to +3 | 12 | AAGTTGCATGGTGCTG |
| 18 | preCore | scan codon 1 to 5 | 34 | ATGCAACTTTTTTCACC |
| 19 | preCore | scan codon 5 to 9 | 13 | CACCTCTGCCTAATCAT |
| 20 | preCore | scan codon 12 to 17 | 45 | TGTACATGTCCCACTGTT |
| 21 | preCore | scan codon 12 to 17 | 46 | TGTTCATGTCCTACTGTT |
| 22 | preCore | scan codon 16 to 20 | 47 | ACTGTTCAAGCCTCCAAG |
| 23 | preCore | scan codon 19 to 23 | 48 | GGCACAGCTTGGAGGCTT |
| 24 | preCore | scan codon 23 to 27 | 49 | AAAGCCACCCAAGGCACA |
| 25 | preCore | codon 28 wt | 9 | TGGCTTTGGGGCATGG |
| 26 | preCore | codon 28 mt | 10 | TGGCTTTAGGGCATGG |
| 27 | preCore | codon 28+29 mt | 42 | TGGCTTTAGGACATGGA |

Fig. 2

Genotyping in HBsAg

| Genotype | Oligo | Sequence |
|---|---|---|
| A | HBPr 193 | GGA TCA ACA ACA ACC AGT |
|  | HBPr 140 | CT CAA GGC AAC TCT ATG GG |
|  | HBPr 77 | CTA CGG ATG GAA ATT GC |
| B | HBPr 78 | TAC GGA CGG AAA CTG C |
| C | HBPr 153 | CT CTA CTT CCA GGA ACA G |
|  | HBPr 154 | C TGC ACG ATT CCT GCT |
|  | HBPr 204 | CT TTC GCA AGA TTC CTA TGG G |
| D | HBPr 165 | AC TCT ATG TAT CCC TCC T |
|  | HBPr 208 | GC TGT ACC AAA CCT TCG GAT |
| E | HBPr 172 | G GGA CCC TGC CGA AC |
|  | HBPr 213 | AG TGG TTC GCC GGG CTG G |
| F | HBPr 216 | CA GGA TCC ACG ACC ACC AGG |
|  | HBPr 219 | GC TGT TCC AAA CCC TCG GAG |
|  | HBPr 186 | G CCA AAT CTG TGC AGC |
| A/B | HBPr 148 | CT TTC GCA AAA TAC CTA TG |
| C/D/E | HBPr 80 | CTT CGG ACG GAA ATT GC |
| E/F | HBPr 177 | ATG TTG CTG TTC AAA ACC TG |

Drug resistance in RT pol gene

| Genotype | Oligo | Sequence | |
|---|---|---|---|
| A | HBPr 115 | TCA GCT ATA TGG ATG ATG | wild type |
|  | HBPr 116 | TTC AGC TAT GTG GAT GAT | mutant |
| D | HBPr 127 | TC AGT TAT ATG GAT GAT G | wild type |
|  | HBPr 132 | T TTC AGT TAT GTG GAT GAT | mutant |

PreCore region

| Genotype | Oligo | Sequence | |
|---|---|---|---|
|  | HBPr 88 | TAG GTT AAA GGT CTT TGT | promoter wild type |
|  | HBPr 89 | TAG GTT AAT GAT CTT TGT | promoter mutant |
|  | HBPr 119 | TGG CTT TGG GGC ATG | wild type codon 28 |
|  | HBPr 10 | TGG CTT TAG GGC ATG G | mutant M2 codon 28 |
|  | HBPr 122 | TGG CTT TGG GAC ATG G | mutant M4 codon 29 |
|  | HBPr 42 | TGG CTT TAG GAC ATG GA | mutant M2/M4 codo |

Fig. 4

SEQUENCE LISTING (1) GENERAL INFORMATION:

(iii) NUMBER OF SEQUENCES: 313

(2) INFORMATION FOR SEQ ID NO: 1:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

GGGTCACCAT ATTCTTGGG                                                      19

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

GAACAAGAGC TACAGCATGG G                                                   21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

CCACTGCATG GCCTGAGGAT G                                                   21

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

GTTCCKGAAC TGGAGCCACC AG                                                  22

(2) INFORMATION FOR SEQ ID NO: 5:

(i) SEQUENCE CHARACTERISTICS:
        (A) LENGTH: 22 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

TCTTTGTATT AGGAGGCTGT AG                                           22

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

GCTGTAGGCA TAAATTGGTC TG                                           22

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

CTCCACAGWA GCTCCAAATT C                                            21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

GAAGGAAAGA AGTCAGAAGG C                                            21

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 9:

TGGCTTTGGG GCATGG                                                16

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

TGGCTTTAGG GCATGG                                                16

(2) INFORMATION FOR SEQ ID NO: 11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

TGGCTTTAGG ACATGG                                                16

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

AAGTTGCATG GTGCTG                                                16

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:

CACCTCTGCC TAATCAT                                                              17

(2) INFORMATION FOR SEQ ID NO: 14:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

TGGGGTGGAG CCCTCAG                                                              17

(2) INFORMATION FOR SEQ ID NO: 15:

(i) SEQUENCE CHARACTERISTICS:
                (A) LENGTH: 16 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

GCCAGCAGCC AACCAG                                                               16

(2) INFORMATION FOR SEQ ID NO: 16:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 16:

CCCATGGGGG ACTGT                                                                15

(2) INFORMATION FOR SEQ ID NO: 17:

(i) SEQUENCE CHARACTERISTICS:
                (A) LENGTH: 16 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

AACCCCAACA AGGATG                                                16

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 18:

TCCACCAGCA ATCCT                                                 15

(2) INFORMATION FOR SEQ ID NO: 19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

TGGGGGAAGA ATATTT                                                16

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

AAATTCCAGC AGTCCC                                                16

(2) INFORMATION FOR SEQ ID NO: 21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

GTTCCCAACC CTCTGG                                                16

(2) INFORMATION FOR SEQ ID NO: 22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

AACCTCGCAA AGGCAT                                                16

(2) INFORMATION FOR SEQ ID NO: 23:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

TGCATTCAAA GCCAAC                                                16

(2) INFORMATION FOR SEQ ID NO: 24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

TACTCACAAC TGTGCC                                                16

(2) INFORMATION FOR SEQ ID NO: 25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

ACCCTGCGTT CGGAGC                                                16

(2) INFORMATION FOR SEQ ID NO: 26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

CAGGAAGACA GCCTAC                                            16

(2) INFORMATION FOR SEQ ID NO: 27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

GATCCAGCCT TCAGAG                                            16

(2) INFORMATION FOR SEQ ID NO: 28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

ATGCTCCAGC TCCTAC                                            16

(2) INFORMATION FOR SEQ ID NO: 29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

GCTTTCTTGG ACGGTC                                            16

(2) INFORMATION FOR SEQ ID NO: 30:

(i) SEQUENCE CHARACTERISTICS:

(A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

CTACCCCAAT CACTCC                                                    16

(2) INFORMATION FOR SEQ ID NO: 31:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

AGCACCTCTC TCAACG                                                    16

(2) INFORMATION FOR SEQ ID NO: 32:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

CCAATGGCAA ACAAGG                                                    16

(2) INFORMATION FOR SEQ ID NO: 33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

CTGAGGGCTC CACCCCA                                                   17

(2) INFORMATION FOR SEQ ID NO: 34:

(i) SEQUENCE CHARACTERISTICS:
            (A) LENGTH: 16 base pairs
            (B) TYPE: nucleic acid
            (C) STRANDEDNESS: single

```
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

ATCTCTTGTA CATGTC                                                          16

(2) INFORMATION FOR SEQ ID NO: 35:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

ATCTCTTGTA CATGTC                                                          16

(2) INFORMATION FOR SEQ ID NO: 36:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

ATCTCATGTT CATGTC                                                          16

(2) INFORMATION FOR SEQ ID NO: 37:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

CAGTGGGACA TGTACA                                                          16

(2) INFORMATION FOR SEQ ID NO: 38:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)
```

(iii) HYPOTHETICAL: NO (iv) ANTI-SENSE: NO (xi) SEQUENCE DESCRIPTION: SEQ ID NO: 38:

CAGTAGGACA TGAACA                                                               16

(2) INFORMATION FOR SEQ ID NO: 39:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

CTGTTCAAGC CTCCAA                                                               16

(2) INFORMATION FOR SEQ ID NO: 40:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

AGCCTCCAAG CTGTGC                                                               16

(2) INFORMATION FOR SEQ ID NO: 41:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

AAAGCCACCC AAGGCA                                                               16

(2) INFORMATION FOR SEQ ID NO: 42:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

TGGCTTTAGG ACATGGA                                                  17

(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

GACATGTACA AGAGATGA                                                 18

(2) INFORMATION FOR SEQ ID NO: 44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

GACATGAACA TGAGATGA                                                 18

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

TGTACATGTC CCACTGTT                                                 18

(2) INFORMATION FOR SEQ ID NO: 46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

```
TGTTCATGTC CTACTGTT                                                      18

(2) INFORMATION FOR SEQ ID NO: 47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

ACTGTTCAAG CCTCCAAG                                                      18

(2) INFORMATION FOR SEQ ID NO: 48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

GGCACAGGCT TGGAGGCTT                                                     19

(2) INFORMATION FOR SEQ ID NO: 49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

AAAGCCACCC AAGGCACA                                                      18

(2) INFORMATION FOR SEQ ID NO: 50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

CCCAGAGGGT TGGGAAC                                                       17
```

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

CAGCATGGGG CAGAATCT                                                  18

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

TCCACCAGCA ATCCTCTG                                                  18

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

GGATCCAGCC TTCAGAGC                                                  18

(2) INFORMATION FOR SEQ ID NO: 54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

TCAGGAAGAC AGCCTAC                                                   17

(2) INFORMATION FOR SEQ ID NO: 55:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

TTCAACCCCA ACAAGGATC                                                    19

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AATGCTCCAG CTCCTAC                                                      17

(2) INFORMATION FOR SEQ ID NO: 57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

CTGCATTCAA AGCCAACT                                                     18

(2) INFORMATION FOR SEQ ID NO: 58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

CCCCATGGGG GACTGTTG                                                     18

(2) INFORMATION FOR SEQ ID NO: 59:

(i) SEQUENCE CHARACTERISTICS:
        (A) LENGTH: 19 base pairs
        (B) TYPE: nucleic acid
```

(C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

CATACTCACA ACTGTGCCA                19

(2) INFORMATION FOR SEQ ID NO: 60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

GGGCTTTCTT GGACGGTCC                19

(2) INFORMATION FOR SEQ ID NO: 61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

CTCTCGAATG GGGGAAGA                                                 18

(2) INFORMATION FOR SEQ ID NO: 62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

CCTACCCCAA TCACTCCA                                                 18

(2) INFORMATION FOR SEQ ID NO: 63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear -continued (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

AGCACCTCTC TCAACGACA                                               19

(2) INFORMATION FOR SEQ ID NO: 64:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

GCAAATTCCA GCAGTCCCG                                               19

(2) INFORMATION FOR SEQ ID NO: 65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

GCCAATGGCA AACAAGGTA                                               19

(2) INFORMATION FOR SEQ ID NO: 66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

GACATGAACA TGAGATG                                                 17

(2) INFORMATION FOR SEQ ID NO: 67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GGACATGAAC AAGAGAT                17

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

GACATGTACA AGAGATG                17

(2) INFORMATION FOR SEQ ID NO: 69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

ACATAAGAGG ACTCTTGGAC             20

(2) INFORMATION FOR SEQ ID NO: 70:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

TACTTCAAAG ACTGTGTGTT TA          22

(2) INFORMATION FOR SEQ ID NO: 71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

ACAAAGACCT TTAAYCT                                                      17

(2) INFORMATION FOR SEQ ID NO: 72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

ACAAAGATCA TTAAYCT                                                      17

(2) INFORMATION FOR SEQ ID NO: 73:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

TTCCACCAGC AATCCTC                                                      17

(2) INFORMATION FOR SEQ ID NO: 74:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

GATCCAGCCT TCAGAGC                                                      17

(2) INFORMATION FOR SEQ ID NO: 75:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

CAAGGTATGT TGCCCGTTTG TCC                                               23

(2) INFORMATION FOR SEQ ID NO: 76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

CCAAACAGTG GGGGAAAGCC C                                            21

(2) INFORMATION FOR SEQ ID NO: 77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

CTACGGATGG AAATTGC                                                17

(2) INFORMATION FOR SEQ ID NO: 78:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

TACGGACGGA AACTGC                                                 16

(2) INFORMATION FOR SEQ ID NO: 79:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

TTCGGACGGA AACTGC                                                 16

(2) INFORMATION FOR SEQ ID NO: 80:

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

CTTCGGACGG AAATTGC                                                    17

(2) INFORMATION FOR SEQ ID NO: 81:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

CTACGGATAG AAATTGC                                                    17

(2) INFORMATION FOR SEQ ID NO: 82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

CTTCGGACAG AAATTGC                                                    17

(2) INFORMATION FOR SEQ ID NO: 83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

CTATGGGAGT GGGCCTCAGY C                                               21

(2) INFORMATION FOR SEQ ID NO: 84:

(i) SEQUENCE CHARACTERISTICS:
        (A) LENGTH: 22 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

GCTGTAGGCA TAAATTGGTC TG                                            22

(2) INFORMATION FOR SEQ ID NO: 85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

CTCCACAGWA GCTCCAAATT C                                             21

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

ACATAAGAGG ACTCTTGGAC                                               20

(2) INFORMATION FOR SEQ ID NO: 87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

TACTTCAAAG ACTGTGTGTT TA                                            22

(2) INFORMATION FOR SEQ ID NO: 88:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

TAGGTTAAAG GTCTTTGT                                                           18

(2) INFORMATION FOR SEQ ID NO: 89:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

TAGGTTAATG ATCTTTGT                                                           18

(2) INFORMATION FOR SEQ ID NO: 90:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

CATGTCCCAC TGTTCAA                                                            17

(2) INFORMATION FOR SEQ ID NO: 91:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

CATGTCCTAC TGTTCAA                                                            17

(2) INFORMATION FOR SEQ ID NO: 92:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

TTCTGCCCCA TGCTGTA                                                  17

(2) INFORMATION FOR SEQ ID NO: 93:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

TTCTGCCCCA TGCTGTAG                                                 18

(2) INFORMATION FOR SEQ ID NO: 94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 94:

GGTAWAAAGG GACTCAMGAT G                                             21

(2) INFORMATION FOR SEQ ID NO: 95:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

TCAGCTATAT GGATGAT                                                  17

(2) INFORMATION FOR SEQ ID NO: 96:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

CAGCTATATG GATGAT                                                                16

(2) INFORMATION FOR SEQ ID NO: 97:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

TTCAGCTATA TGGATG                                                                16

(2) INFORMATION FOR SEQ ID NO: 98:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

TCAGTTATAT GGATGAT                                                               17

(2) INFORMATION FOR SEQ ID NO: 99:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

TTTCAGTTAT ATGGATG                                                               17

(2) INFORMATION FOR SEQ ID NO: 100:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 100:

-continued

TTTAGTTATA TGGATGA                                                     17

(2) INFORMATION FOR SEQ ID NO: 101:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 101:

TCAGCTATGT GGATGAT                                                     17

(2) INFORMATION FOR SEQ ID NO: 102:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 102:

TCAGTTATGT GGATGAT                                                     17

(2) INFORMATION FOR SEQ ID NO: 103:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 103:

TTTCAGCTAT GTGGATG                                                     17

(2) INFORMATION FOR SEQ ID NO: 104:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 104:

CAAGGTATGT TGCCCGTTTG TCC                                              23

(2) INFORMATION FOR SEQ ID NO: 105:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 105:

GGYAWAAAGG GACTCAMGAT G                                              21

(2) INFORMATION FOR SEQ ID NO: 106:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 106:

GGGTCACCAT ATTCTTGGG                                                 19

(2) INFORMATION FOR SEQ ID NO: 107:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 107:

GTTCCKGAAC TGGAGCCACC AG                                             22

(2) INFORMATION FOR SEQ ID NO: 108:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 108:

CCGGAAAGCT TGAGCTCTTC TTTTTCACCT CTGCCTAATC                          40

(2) INFORMATION FOR SEQ ID NO: 109:

(i) SEQUENCE CHARACTERISTICS:

```
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 109:
```

CCGGAAAGCT TGAGCTCTTC AAAAAGTTGC ATGGTGCTGG                                 40

```
(2) INFORMATION FOR SEQ ID NO: 110:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 110:
```

GTGGTTCGCC GGGCTTG                                                         17

```
(2) INFORMATION FOR SEQ ID NO: 111:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 111:
```

CTGCGAGGCG AGGGAGTTCT TCTTC                                                25

```
(2) INFORMATION FOR SEQ ID NO: 112:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 112:
```

TGCCATTTGT TCAGTGGTTC GTAGGGC                                              27

```
(2) INFORMATION FOR SEQ ID NO: 113:

(i) SEQUENCE CHARACTERISTICS:
         (A) LENGTH: 25 base pairs
         (B) TYPE: nucleic acid
         (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 113:

CCGGCAGATG AGAAGGCACA GACGG                                                  25

(2) INFORMATION FOR SEQ ID NO: 114:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 114:

TTCAGCTATA TGGATGAT                                                          18

(2) INFORMATION FOR SEQ ID NO: 115:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 115:

TCAGCTATAT GGATGATG                                                          18

(2) INFORMATION FOR SEQ ID NO: 116:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 116:

TTCAGCTATG TGGATGAT                                                          18

(2) INFORMATION FOR SEQ ID NO: 117:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 117:

TCAGCTATGT GGATGATG                                                                     18

(2) INFORMATION FOR SEQ ID NO: 118:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 118:

GGCTTTGGGG CATGG                                                                        15

(2) INFORMATION FOR SEQ ID NO: 119:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 119:

TGGCTTTGGG GCATG                                                                        15

(2) INFORMATION FOR SEQ ID NO: 120:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 120:

GTGGCTTTGG GGCATG                                                                       16

(2) INFORMATION FOR SEQ ID NO: 121:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO

-continued (iv) ANTI-SENSE: NO (xi) SEQUENCE DESCRIPTION: SEQ ID NO: 121:

GGCTTTGGGG CATGGA                                                16

(2) INFORMATION FOR SEQ ID NO: 122:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 122:

TGGCTTTGGG ACATGG                                                16

(2) INFORMATION FOR SEQ ID NO: 123:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 123:

GGCTTTGGGA CATGG                                                 15

(2) INFORMATION FOR SEQ ID NO: 124:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 124:

TGGCTTTGGG ACATG                                                 15

(2) INFORMATION FOR SEQ ID NO: 125:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 125:

```
GTGGCTTTGG GACATG                                                         16

(2) INFORMATION FOR SEQ ID NO: 126:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 126:

GGCTTTGGGA CATGGA                                                         16

(2) INFORMATION FOR SEQ ID NO: 127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 127:

TCAGTTATAT GGATGATG                                                       18

(2) INFORMATION FOR SEQ ID NO: 128:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 128:

TTCAGTTATA TGGATGAT                                                       18

(2) INFORMATION FOR SEQ ID NO: 129:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 129:

TTTCAGTTAT ATGGATGAT                                                      19
```

(2) INFORMATION FOR SEQ ID NO: 130:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 130:

TCAGTTATGT GGATGATG                                           18

(2) INFORMATION FOR SEQ ID NO: 131:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 131:

TTCAGTTATG TGGATGAT                                           18

(2) INFORMATION FOR SEQ ID NO: 132:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 132:

TTTCAGTTAT GTGGATGAT                                          19

(2) INFORMATION FOR SEQ ID NO: 133:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 133:

TTTCAGTTAT GTGGATGA                                           18

(2) INFORMATION FOR SEQ ID NO: 134:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 134:

TGCTGCTATG CCTCATCTTC                                                   20

(2) INFORMATION FOR SEQ ID NO: 135:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 135:

CARAGACAAA AGAAAATTGG                                                   20

(2) INFORMATION FOR SEQ ID NO: 136:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 136:

CTATGGATGG AAATTGC                                                      17

(2) INFORMATION FOR SEQ ID NO: 137:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 137:

CCTATGGATG GAAATTG                                                      17

(2) INFORMATION FOR SEQ ID NO: 138:

(i) SEQUENCE CHARACTERISTICS:
        (A) LENGTH: 17 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 138:

ACCTATGGAT GGAAATT                                                      17

(2) INFORMATION FOR SEQ ID NO: 139:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 139:

CTCAAGGCAA CTCTATGTGG                                                   20

(2) INFORMATION FOR SEQ ID NO: 140:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 140:

CTCAAGGCAA CTCTATGGG                                                    19

(2) INFORMATION FOR SEQ ID NO: 141:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 141:

TCAAGGCAAC TCTATGTTG                                                    19

(2) INFORMATION FOR SEQ ID NO: 142:

(i) SEQUENCE CHARACTERISTICS:
            (A) LENGTH: 16 base pairs
            (B) TYPE: nucleic acid
            (C) STRANDEDNESS: single
            (D) TOPOLOGY: linear

```
        (ii) MOLECULE TYPE: DNA (genomic)

(iii) HYPOTHETICAL: NO (iv) ANTI-SENSE: NO (xi) SEQUENCE DESCRIPTION: SEQ ID NO: 142:

ATCCCATCAT CTTGGG                                                 16

(2) INFORMATION FOR SEQ ID NO: 143:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 143:

ATCCCATCAT CTTGGGCGG                                              19

(2) INFORMATION FOR SEQ ID NO: 144:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 144:

TCCCATCATC TTGGGCGG                                               18

(2) INFORMATION FOR SEQ ID NO: 145:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 145:

CCCATCATCT TGGGCTGG                                               18

(2) INFORMATION FOR SEQ ID NO: 146:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO: 146:

TTCGCAAAAT ACCTATGG                                                         18

(2) INFORMATION FOR SEQ ID NO: 147:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 147:

TTTCGCAAAA TACCTATG                                                         18

(2) INFORMATION FOR SEQ ID NO: 148:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 148:

CTTTCGCAAA ATACCTATG                                                        19

(2) INFORMATION FOR SEQ ID NO: 149:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 149:

TCGCAAAATA CCTATGGG                                                         18

(2) INFORMATION FOR SEQ ID NO: 150:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 150:

TCTACTTCCA GGAACAT                                          17

(2) INFORMATION FOR SEQ ID NO: 151:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 151:

TCTACTTCCA GGAACATC                                         18

(2) INFORMATION FOR SEQ ID NO: 152:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 152:

CTCTACTTCC AGGAACAT                                         18

(2) INFORMATION FOR SEQ ID NO: 153:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 153:

CTCTACTTCC AGGAACAG                                         18

(2) INFORMATION FOR SEQ ID NO: 154:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 154:

CTGCACGATT CCTGCT                                           16

-continued (2) INFORMATION FOR SEQ ID NO: 155:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 155:

TGCACGATTC CTGCTCA                                                  17

(2) INFORMATION FOR SEQ ID NO: 156:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 156:

CTGCACGATT CCTGCTC                                                  17

(2) INFORMATION FOR SEQ ID NO: 157:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 157:

TGCACGATTC CTGCTCAA                                               18

(2) INFORMATION FOR SEQ ID NO: 158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 158:

TTCGCAAGAT TCCTATG                                                  17

(2) INFORMATION FOR SEQ ID NO: 159:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 159:

CTTTCGCAAG ATTCCTAT                                              18

(2) INFORMATION FOR SEQ ID NO: 160:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 160:

CTTTCGCAAG ATTCCTA                                               17

(2) INFORMATION FOR SEQ ID NO: 161:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 161:

CTTTCGCAAG ATTCCTATG                                             19

(2) INFORMATION FOR SEQ ID NO: 162:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 162:

CTCTATGTAT CCCTCCT                                               17

(2) INFORMATION FOR SEQ ID NO: 163:

(i) SEQUENCE CHARACTERISTICS:
        (A) LENGTH: 17 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 163:

TCTATGTATC CCTCCTG                                                  17

(2) INFORMATION FOR SEQ ID NO: 164:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 164:

CTCTATGTAT CCCTCCTGG                                                19

(2) INFORMATION FOR SEQ ID NO: 165:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 165:

CCTCTATGTA TCCCTCCT                                                 18

(2) INFORMATION FOR SEQ ID NO: 166:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 166:

CTGTACCAAA CCTTCGG                                                  17

(2) INFORMATION FOR SEQ ID NO: 167:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 167:

CTGTACCAAA CCTTCG                                                                16

(2) INFORMATION FOR SEQ ID NO: 168:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 168:

GCTGTACCAA ACCTTCGG                                                              18

(2) INFORMATION FOR SEQ ID NO: 169:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 169:

TGTACCAAAC CTTCGGAG                                                              18

(2) INFORMATION FOR SEQ ID NO: 170:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 170:

GGACCCTGCC GAACCT                                                                16

(2) INFORMATION FOR SEQ ID NO: 171:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 171:

GGACCCTGCC GAACCG                                                              16

(2) INFORMATION FOR SEQ ID NO: 172:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 172:

GGGACCCTGC CGAAC                                                               15

(2) INFORMATION FOR SEQ ID NO: 173:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 173:

GGACCCTGCC GAAC                                                                14

(2) INFORMATION FOR SEQ ID NO: 174:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 174:

GTTGCTGTTC AAAACCTT                                                            18

(2) INFORMATION FOR SEQ ID NO: 175:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 175:

GTTGCTGTTC AAAACCTG                                          18

(2) INFORMATION FOR SEQ ID NO: 176:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 176:

TGTTGCTGTT CAAAACCTG                                         19

(2) INFORMATION FOR SEQ ID NO: 177:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 177:

ATGTTGCTGT TCAAAACCTG                                        20

(2) INFORMATION FOR SEQ ID NO: 178:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 178:

GATCCACGAC CACCA                                             15

(2) INFORMATION FOR SEQ ID NO: 179:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 179:

-continued

GGATCCACGA CCACCA                                                  16

(2) INFORMATION FOR SEQ ID NO: 180:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 180:

GGATCCACGA CCACC                                                   15

(2) INFORMATION FOR SEQ ID NO: 181:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 181:

GATCCACGAC CACCAGG                                                 17

(2) INFORMATION FOR SEQ ID NO: 182:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 182:

TGTTCCAAAC CCTCGG                                                  16

(2) INFORMATION FOR SEQ ID NO: 183:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 183:

CTGTTCCAAA CCCTCG                                                  16

(2) INFORMATION FOR SEQ ID NO: 184:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 184:

CTGTTCCAAA CCCTCGG                                                 17

(2) INFORMATION FOR SEQ ID NO: 185:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 185:

GTTCCAAACC CTCGGAT                                                 17

(2) INFORMATION FOR SEQ ID NO: 186:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 186:

GCCAAATCTG TGCAGC                                                  16

(2) INFORMATION FOR SEQ ID NO: 187:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 187:

CCAAATCTGT GCAGCAT                                                 17

(2) INFORMATION FOR SEQ ID NO: 188:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 188:

GCCAAATCTG TGCAGCAG                                                      18

(2) INFORMATION FOR SEQ ID NO: 189:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 189:

GGCCAAATCT GTGCAGC                                                       17

(2) INFORMATION FOR SEQ ID NO: 190:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 190:

ATCAACAACA ACCAGTA                                                       17

(2) INFORMATION FOR SEQ ID NO: 191:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 191:

GATCAACAAC AACCAGT                                                       17

(2) INFORMATION FOR SEQ ID NO: 192:

(i) SEQUENCE CHARACTERISTICS:
        (A) LENGTH: 18 base pairs
        (B) TYPE: nucleic acid
        (C) STRANDEDNESS: single -continued (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 192:

GATCAACAAC AACCAGTA                                                 18

(2) INFORMATION FOR SEQ ID NO: 193:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 193:

GGATCAACAA CAACCAGT                                                 18

(2) INFORMATION FOR SEQ ID NO: 194:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 194:

TCAAGGCAAC TCTATGTGG                                                19

(2) INFORMATION FOR SEQ ID NO: 195:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 195:

AGGTTAAAGG TCTTTGT                                                  17

(2) INFORMATION FOR SEQ ID NO: 196:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 196:

TAGGTTAAAG GTCTTTGG                                                                 18

(2) INFORMATION FOR SEQ ID NO: 197:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 197:

TTAGGTTAAA GGTCTTT                                                                  17

(2) INFORMATION FOR SEQ ID NO: 198:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 198:

GGTTAAAGGT CTTTGTAGG                                                                19

(2) INFORMATION FOR SEQ ID NO: 199:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 199:

AGGTTAATGA TCTTTGT                                                                  17

(2) INFORMATION FOR SEQ ID NO: 200:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO

-continued (iv) ANTI-SENSE: NO (xi) SEQUENCE DESCRIPTION: SEQ ID NO: 200:

TAGGTTAATG ATCTTTGG                                                         18

(2) INFORMATION FOR SEQ ID NO: 201:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 201:

CTTTCGCAAG ATTCCTATGG                                                 20

(2) INFORMATION FOR SEQ ID NO: 202:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 202:

GCTTTCGCAA GATTCCTATG                                                 20

(2) INFORMATION FOR SEQ ID NO: 203:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 203:

GCTTTCGCAA GATTCCTATG G                                              21

(2) INFORMATION FOR SEQ ID NO: 204:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 204:

CTTTCGCAAG ATTCCTATGG G                    21

(2) INFORMATION FOR SEQ ID NO: 205:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 205:

GCTGTACCAA ACCTTCGGAG                      20

(2) INFORMATION FOR SEQ ID NO: 206:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 206:

TGCTGTACCA AACCTTCGG                       19

(2) INFORMATION FOR SEQ ID NO: 207:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 207:

TGCTGTACCA AACCTTCGGA G                    21

(2) INFORMATION FOR SEQ ID NO: 208:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 208:

GCTGTACCAA ACCTTCGGAT                      20

(2) INFORMATION FOR SEQ ID NO: 209:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 209:

TGGTTCGCCG GGCTTT                                                16

(2) INFORMATION FOR SEQ ID NO: 210:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 210:

GTGGTTCGCC GGGCTTG                17

(2) INFORMATION FOR SEQ ID NO: 211:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 211:

GGTTCGCCGG GCTTTC                                                16

(2) INFORMATION FOR SEQ ID NO: 212:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 212:

TGGTTCGCCG GGCTTTC                                               17

(2) INFORMATION FOR SEQ ID NO: 213:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 213:

AGTGGTTCGC CGGGCTGG                                                       18

(2) INFORMATION FOR SEQ ID NO: 214:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 214:

AGGATCCACG ACCACCAGG                                                      19

(2) INFORMATION FOR SEQ ID NO: 215:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 215:

AGGATCCACG ACCACCAGT                                                      19

(2) INFORMATION FOR SEQ ID NO: 216:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 216:

CAGGATCCAC GACCACCAGG                                                     20

(2) INFORMATION FOR SEQ ID NO: 217:

(i) SEQUENCE CHARACTERISTICS:
        (A) LENGTH: 19 base pairs
        (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 217:

CTGTTCCAAA CCCTCGGAG                                             19

(2) INFORMATION FOR SEQ ID NO: 218:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 218:

CTGTTCCAAA CCCTCGGAT                                             19

(2) INFORMATION FOR SEQ ID NO: 219:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 219:

GCTGTTCCAA ACCCTCGGAG                                            20

(2) INFORMATION FOR SEQ ID NO: 220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 220:

CTGAACCTTT ACCCCGTTGC                                            20

(2) INFORMATION FOR SEQ ID NO: 221:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

```
        (ii) MOLECULE TYPE: DNA (genomic)

(iii) HYPOTHETICAL: NO (iv) ANTI-SENSE: NO (xi) SEQUENCE DESCRIPTION: SEQ ID NO: 221:

CTCGCCAACT TACAAGGCCT TTC                                              23

(2) INFORMATION FOR SEQ ID NO: 222:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 222:

AGAATGGCTT GCCTGAGTGC                                                  20

(2) INFORMATION FOR SEQ ID NO: 223:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 223:

GCTTTCGCAA GATTCCTATG GG                                               22

(2) INFORMATION FOR SEQ ID NO: 224:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 224:

GGCTTTCGCA AGATTCCTAT GG                                               22

(2) INFORMATION FOR SEQ ID NO: 225:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO: 225:

GGCTTTCGCA AGATTCCTAT GGG                                                    23

(2) INFORMATION FOR SEQ ID NO: 226:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 226:

GGCTTTCGCA AGATTCCTAT GGGA                                                   24

(2) INFORMATION FOR SEQ ID NO: 227:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 227:

CAGCTATATG GATGATGTG                                                         19

(2) INFORMATION FOR SEQ ID NO: 228:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 228:

AGCTATATGG ATGATGTGGG                                                        20

(2) INFORMATION FOR SEQ ID NO: 229:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO

```
        (xi) SEQUENCE DESCRIPTION: SEQ ID NO: 229:

GCTATATGGA TGATGTGGT                                                    19

(2) INFORMATION FOR SEQ ID NO: 230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 230:

AGCTATATGG ATGATGTGGT                                                   20

(2) INFORMATION FOR SEQ ID NO: 231:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 231:

CAGCTATATG GATGATATA                                                    19

(2) INFORMATION FOR SEQ ID NO: 232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 232:

AGCTATATGG ATGATATAGG                                                   20

(2) INFORMATION FOR SEQ ID NO: 233:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 233:

GCTATATGGA TGATATAGT                                                    19
```

-continued (2) INFORMATION FOR SEQ ID NO: 234:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 234:

AGCTATATGG ATGATATAGT    20

(2) INFORMATION FOR SEQ ID NO: 235:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 235:

CCATCATCTT GGGCTTG    17

(2) INFORMATION FOR SEQ ID NO: 236:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 236:

CATCATCTTG GGCTTT    16

(2) INFORMATION FOR SEQ ID NO: 237:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 237:

CCATCATCTT GGGCTTT    17

(2) INFORMATION FOR SEQ ID NO: 238:

```
        (i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 238:

CCATCATCTT GGGCTTTC                                                    18

(2) INFORMATION FOR SEQ ID NO: 239:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 239:

CCCACTGTCT GGCTTTC                                                     17

(2) INFORMATION FOR SEQ ID NO: 240:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 240:

CCACTGTCTG GCTTTC                                                      16

(2) INFORMATION FOR SEQ ID NO: 241:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 241:

CCACTGTCTG GCTTT                                                       15

(2) INFORMATION FOR SEQ ID NO: 242:

(i) SEQUENCE CHARACTERISTICS:
            (A) LENGTH: 16 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 242:

CCCACTGTCT GGCTTG                                                    16

(2) INFORMATION FOR SEQ ID NO: 243:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 243:

TATATGGATG ATGTGGTA                                                  18

(2) INFORMATION FOR SEQ ID NO: 244:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 244:

TATGTGGATG ATGTGGTA                                                  18

(2) INFORMATION FOR SEQ ID NO: 245:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 245:

TATATAGATG ATGTGGTA                                                  18

(2) INFORMATION FOR SEQ ID NO: 246:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
    (ii) MOLECULE TYPE: DNA (genomic)

(iii) HYPOTHETICAL: NO (iv) ANTI-SENSE: NO (xi) SEQUENCE DESCRIPTION: SEQ ID NO: 246:

TATATTGATG ATGTGGTA                                                    18

(2) INFORMATION FOR SEQ ID NO: 247:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 247:

TATGTAGATG ATGTGGTA                                                    18

(2) INFORMATION FOR SEQ ID NO: 248:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 248:

TATGTTGATG ATGTGGTA                                                    18

(2) INFORMATION FOR SEQ ID NO: 249:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 249:

TATATGGATG ATATAGTA                                                    18

(2) INFORMATION FOR SEQ ID NO: 250:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (xi) SEQUENCE DESCRIPTION: SEQ ID NO: 250:

TATATGGATG ATATCGTA                                                   18

(2) INFORMATION FOR SEQ ID NO: 251:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 251:

TATGTGGATG ATATAGTA                                                   18

(2) INFORMATION FOR SEQ ID NO: 252:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 252:

TATGTGGATG ATATCGTA                                                   18

(2) INFORMATION FOR SEQ ID NO: 253:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 253:

TATATAGATG ATATAGTA                                                   18

(2) INFORMATION FOR SEQ ID NO: 254:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 254:

TATATAGATG ATATCGTA                                              18

(2) INFORMATION FOR SEQ ID NO: 255:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 255:

TATATTGATG ATATAGTA                                              18

(2) INFORMATION FOR SEQ ID NO: 256:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 256:

TATATTGATG ATATCGTA                                              18

(2) INFORMATION FOR SEQ ID NO: 257:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 257:

TATGTAGATG ATATAGTA                                              18

(2) INFORMATION FOR SEQ ID NO: 258:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 258:

TATGTAGATG ATATCGTA                                                           18

(2) INFORMATION FOR SEQ ID NO: 259:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 259:

TATGTTGATG ATATAGTA                                                           18

(2) INFORMATION FOR SEQ ID NO: 260:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 260:

TATGTTGATG ATATCGTA                                                           18

(2) INFORMATION FOR SEQ ID NO: 261:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 261:

TATATGGATG ATCTGGTA                                                           18

(2) INFORMATION FOR SEQ ID NO: 262:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 262:

TATGTGGATG ATCTGGTA                                                           18

(2) INFORMATION FOR SEQ ID NO: 263:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 263:

TATATAGATG ATCTGGTA                                                  18

(2) INFORMATION FOR SEQ ID NO: 264:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 264:

TATATTGATG ATCTGGTA                                                  18

(2) INFORMATION FOR SEQ ID NO: 265:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 265:

TATGTAGATG ATCTGGTA                                                  18

(2) INFORMATION FOR SEQ ID NO: 266:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 266:

TATGTTGATG ATCTGGTA                                                  18

(2) INFORMATION FOR SEQ ID NO: 267:

(i) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 267:

TATGGGAGTG GGCCTCAG                                                           18

(2) INFORMATION FOR SEQ ID NO: 268:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 268:

TATGGGATTG GGCCTCAG                                                           18

(2) INFORMATION FOR SEQ ID NO: 269:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 269:

CAGTCCGTTT CTCTTGGC                                                           18

(2) INFORMATION FOR SEQ ID NO: 270:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 270:

CAGTCTGTTT CTCTTGGC                                                           18

(2) INFORMATION FOR SEQ ID NO: 271:

(i) SEQUENCE CHARACTERISTICS:
            (A) LENGTH: 18 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 271:

CAGTCCGTTT CTCATGGC                                                 18

(2) INFORMATION FOR SEQ ID NO: 272:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 272:

CAGTCTGTTT CTCATGGC                                                 18

(2) INFORMATION FOR SEQ ID NO: 273:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 273:

CAGTCCGTTT CTCCTGGC                                                 18

(2) INFORMATION FOR SEQ ID NO: 274:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 274:

CAGTCTGTTT CTCCTGGC                                                 18

(2) INFORMATION FOR SEQ ID NO: 275:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 275:

CAGCCCGTTT CTCCTGGC                                          18

(2) INFORMATION FOR SEQ ID NO: 276:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 276:

CAGCCTGTTT CTCCTGGC                                          18

(2) INFORMATION FOR SEQ ID NO: 277:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 277:

CAGCCCGTTT CTCATGGC                                          18

(2) INFORMATION FOR SEQ ID NO: 278:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 278:

CAGCCTGTTT CTCATGGC                                          18

(2) INFORMATION FOR SEQ ID NO: 279:

(i) SEQUENCE CHARACTERISTICS:
       (A) LENGTH: 3221 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 279:

```
AATTCCACTG CCTTCCACCA AGCTCTGCAG GATCCCAAAG TCAGGGGTCT GTATCTTCCT       60
GCTGGTGGCT CCAGTTCAGG AACAGTAAAC CCTGCTCCGA ATATTGCCTC TCACATCTCG      120
TCAATCTCCG CGAGGACTGG GGACCCTGTG ACGAACATGG AGAACATCAC ATCAGGATTT      180
CTAGGACCCC TGCTCGTGTT ACAGGCGGGG TTTTTCTTGT TGACAAGAAT CCTCACAATA      240
CCGCAGAGTC TAGACTCGTG GTGGACTTCT CTCAATTTTC TAGGGGGGTC ACCCGTGTGT      300
CTTGGCCAAA ATTCGCAGTC CCCAACCTCC AATCACTCAC CAACCTCCTG TCCTCCAATT      360
TGTCCTGGTT ATCGCTGGAT GTGTCTGCGG CGTTTTATCA TATTCCTCTT CATCCTGCTG      420
CTATGCCTCA TCTTCTTGTT GGTTCTTCTG GATTATCAAG GTATGTTGCC CGTTTGTCCT      480
CTAATTCCAG GATCAACAAC AACCAGTACG GGACCATGCA AAACCTGCAC GACTCCTGCT      540
CAAGGCAACT CTATGTTTCC CTCATGTTGC TGTACAAAAC CTACGGATGG AAATTGCACC      600
TGTATTCCCA TCCCATCGTC CTGGGCTTTC GCAAAATACC TATGGGAGTG GCCTCAGTC       660
CGTTTCTCTT GGCTCAGTTT ACTAGTGCCA TTTGTTCAGT GGTTCGTAGG CTTTCCCCC       720
ACTGTTTGGC TTTCAGCTAT ATGGATGATG TGGTATTGGG GGCCAAGACT GTACAGCATC      780
GTGAGTCCCT TTATACCGCT GTTACCAATT TTCTTTTGTC TCTGGGTATA CATTTAAACC      840
CTAACAAAAC AAAAAGATGG GGTTATTCCC TAAACTTCAT GGTCTACATA ATTGGAAGTT      900
GGGGAACATT GCCACAGGAT CATATTGTAC AAAAGATCAA ACACTGTTTT AGAAAACTTC      960
CTGTTAACAG GCCTATTGAT TGGAAAGTAT GTCAAAGAAT TGTGGGTCTT TTGGGCTTTG     1020
CTGCTCCATT TACTCAATGT GGATATCCTG CCTTAATGCC TTTGTATGCA TGTATACAAG     1080
CTAAACAGGC TTTCACTTTC TCGCCAACTT ACAAGGCCTT TCTAAGTAAA CAGTACATGA     1140
ACCTTTACCC CGTTGCTCGG CAACGGCCTG GTCTGTGCCA AGTGTTTGCT GACGCAACCC     1200
CCACTGGCTG GGGCTTGGCC ATAGGCCATC AGCGCATGCG TGGAACCTTT GTGGCTCCTC     1260
TGCCGATCCA TACTGCGGAA CTCCTAGCCG CTTGTTTTGC TCGCAGCCGG TCTGGAGCAA     1320
AGCTCATCGG AACTGACAAT TCTGTCGTCC TCTCGCGGAA ATATACATCG TTTCCATGGC     1380
TGCTAGGCTG TACTGCCAAC TGGATCCTTC GCGGGACGTC CTTTGTTTAC GTCCCGTCGG     1440
CGCTGAATCC CGCGGACGAC CCCTCTCGGG GCCGCTTGGG AGTCTCTCGT CCCCTTCTCC     1500
GTCTGCCGTT CCAGCCGACC ACGGGGCGCA CCTCTCTTTA CGCGGTCTCC CCGTCTGTGC     1560
CTTCTCATCT GCCGGTCCGT GTGCACTTCG CTTCACCTCT GCACGTTGCA TGGAGACCAC     1620
CGTGAACGCC CATCAGATCC TGCCCAAGGT CTTACATAAG AGGACTCTTG GACTCTCAGC     1680
AATGTCAACG ACCGACCTTG AGGCCTACTT CAAAGACTGT GTGTTTAAGG ACTGGGAGGA     1740
GCTGGGGGAG GAGATTAGGT TAAAGGTCTT TGTATTAGGA GGCTGTAGGC ATAAATTGGT     1800
CTGCGCACCA GCACCATGCA ACTTTTTCAC CTCTGCCTAA TCATCTCTTG TACATGTCCC     1860
ACTGTTCAAG CCTCCAAGCT GTGCCTTGGG TGGCTTTGGG GCATGGACAT TGACCCTTAT     1920
AAAGAATTTG GAGCTACTGT GGAGTTACTC TCGTTTTTGC CTTCTGACTT CTTTCCTTCC     1980
GTCAGAGATC TCCTAGACAC CGCCTCAGCT CTGTATCGAG AAGCCTTAGA GTCTCCTGAG     2040
CATTGCTCAC CTCACCATAC TGCACTCAGG CAAGCCATTC TCTGCTGGGT GGAATTGATG     2100
ACTCTAGCTA CCTGGGTGGG TAATAATTTG GAAGATCCAG CATCCAGGGA TCTAGTAGTC     2160
AATTATGTTA ATACTAACAT GGGTTTAAAG ATCAGGCAAC TATTGTGGTT TCATATATCT     2220
TGCCTTACTT TTGGAAGAGA GACTGTGCTT GAATATTTGG TCTCTTTCGG AGTGTGGATT     2280
```

```
CGCACTCCTC CAGCCTATAG ACCACCAAAT GCCCCTATCT TATCAACACT TCCGGAAACT      2340

ACTGTTGTTA GACGACGGGA CCGAGGCAGG TCCCCTAGAA GAAGAACTCC CTCGCCTCGC      2400

AGACGCAGAT CTCAATCGCC GCGTCGCAGA AGATCTCAAT CTCGGGAATC TCAATGTTAG      2460

TATTCCTTGG ACTCATAAGG TGGGAAACTT TACTGGGCTT TATTCCTCTA CAGTACCTAT      2520

CTTTAATCCT GAATGGCAAA CTCCTTCCTT TCCTAAGATT CATTTACAAG AGGACATTAT      2580

TAATAGGTGT CAACAATTTG TGGGCCCTCT CACTGTAAAT GAAAAGAGAA GATTGAAATT      2640

AATTATGCCT GCCAGATTCT ATCCTACCCA CACTAAATAT TTGCCCTTAG ACAAAGGAAT      2700

TAAACCTTAT TATCCAGATC AGGTAGTTAA TCATTACTTC CAAACCAGAC ATTATTTACA      2760

TACTCTTTGG AAGGCTGGTA TTCTATATAA GAGGGAAACC ACACGTAGCG CATCATTTTG      2820

CGGGTCACCA TATTCTTGGG AACAAGAGCT ACAGCATGGG AGGTTGGTCA TCAAAACCTC      2880

GCAAAGGCAT GGGGACGAAT CTTTCTGTTC CCAACCCTCT GGGATTCTTT CCCGATCATC      2940

AGTTGGACCC TGCATTCGGA GCCAACTCAA ACAATCCAGA TTGGGACTTC AACCCCATCA      3000

AGGACCACTG GCCAGCAGCC AACCAGGTAG GAGTGGGAGC ATTCGGGCCA AGGCTCACCC      3060

CTCCACACGG CGGTATTTTG GGGTGGAGCC CTCAGGCTCA GGGCATATTG ACCACAGTGT      3120

CAACAATTCC TCCTCCTGCC TCCACCAATC GGCAGTCAGG AAGGCAGCCT ACTCCCATTT      3180

CTCCACCTCT AAGAGACAGT CATCCTCAGG CCATGCAGTG G                         3221

(2) INFORMATION FOR SEQ ID NO: 280:

(i) SEQUENCE CHARACTERISTICS:
        (A) LENGTH: 3200 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 280:

AATTCCACTG CCTTGCACCA AGCTCTGCAG GATCCCAGAG TCAGGGGTCT GTATCTTCCT       60

GCTGGTGGCT CCAGTTCAGG AACAGTAAAC CCTGCTCCGA ATATTGCCTC TCACATCTCG      120

TCAATCTCCG CGAGGACTGG GGACCCTGTG ACGATCATGG AGAACATCAC ATCAGGATTC      180

CTAGGACCCC TGCTCGTGTT ACAGGCGGGG TTTTTCTTGT TGACAAGAAT CCTCACAATA      240

CCGCAGAGTC TAGACTCGTG GTGGACTTCT CTCAATTTTC TAGGGGGATC ACCCGTGTGT      300

CTTGGCCAAA ATTCGCAGTC CCCAACCTCC AATCACTCAC CAACCTCCTG TCCTCCAATT      360

TGTCCTGGTT ATCGCTGGAT GTGTCTGCGG CGTTTTATCA TATTCCTCTT CATCCTGCTG      420

CTATGCCTCA TCTTCTTATT GGTTCTTCTG GATTATCAAG GTATGTTGCC CGTTTGTCCT      480

CTAATTCCAG GATCAACAAC AACCAGTACG GGACCATGCA AAACCTGCAC GACTCCTGCT      540

CAAGGCAACT CTAAGTTTCC CTCATGTTGC TGTACAAAAC CTACGGATGG AAATTGCACC      600

TGTATTCCCA TCCCATCGTC CTGGGCTTTC GCAAAATACC TATGGGAGTG GCCTCAGTC       660

CGTTTCTCTT GGCTCAGTTT ACTAGTGCCA TTTGTTCAGT GGTTCGTAGG GCTTTCCCCC      720

ACTGTTTGGC TTTCAGCTAT ATGGATGATG TGGTATTGGG GGCCAAGTCT GTACAGCATC      780

GTGAGTCCCT TTATACCGCT GTTACCAATT TTCTTTTGTC TCTGGGTATA CATTTAAACC      840

CTAACAAAAC AAAAAGATGG GGTTATTCCC TAAACTTCAT GGGCTACATA ATTGGAAGTT      900
```

```
GGGGAACTTT GCCACAGGAT CATATTGTAC AAAAGATCAA ACACTGTTTT AGAAAACTTC         960

CTGTTAACAG GCCTATTGAT TGGAAAGTAT GTCAAAGAAT TGTGGGTCTT TTGGGCTTTG        1020

CTGCTCCATT TACACAATGT GGATATCCTG CCTTAATGCC TTTGTATGCA TGTATACAAG        1080

CTAAACAGGC TTTCACTTTC TCGCCAACTT ACAAGGCCTT TCTAAGTAAA CAGTACATGA        1140

ACCTTTACCC CGTTGCTCGG CAACGGCCTG GTCTGTGCCA AGTGTTTGCT GACGCAACCC        1200

CCACTGGCTG GGGCTTAGCC ATAGGCCATC AGCGCATGCG TGGAACCTTT GTGGCTCCTC        1260

TGCCGATCCA TACTGCGGAA CTCCTAGCCG CTTGTTTTGC TCGCAGCCGG TCTGGAGCAA        1320

AGCTCATCGG AACTGACAAT TCTGTCGTCC TCTCGCGGAA ATATACATCA TTTCCATGGC        1380

TGCTAGGCTG TACTGCCAAC TGGATCCTTC GCGGGACGTC CTTTGTTTAC GTCCCGTCGG        1440

CGCTGAATCC CGCGGACGAC CCCTCTCGGG GCCGCTTGGG ACTCTCTCGT CCCCTTCTCC        1500

GTCTGCCGTT CCAGCCGACC ACGGGGCGCA CCTCTCTTTA CGCGGTCTCC CCGTCTGTGC        1560

CTTCTCATCT GCCGGTCCGT GTGCACTTCG CTTCACCTCT GCACGTTGCA TGGCGACCAC        1620

CGTGAACGCC CATCAGATCC TGCCCAAGGT CTTACATAAG AGGACTCTTG GACTCCCAGC        1680

AATGTCAACG ACCGACCTTG AGGCCTACTT CAAAGACTGT GTGTTTAAGG ACTGGGAGGA        1740

GTTGGGGGAG GAGATTAGGT TAATGATCTT TGTATTAGGA GGCTGTAGGC ATAAATTGGT        1800

CTGCGCACCA GCACCATGCA ACTTTTTCAC CTCTGCCTAA TCATCTCTTG TACATGTCCC        1860

ACTGTTCAAG CCTCCAAGCT GTGCCTTGGG TGGCTTTGGG GCATGGACAT TGACCCTTAT        1920

AAAGAATTTG GAGCTACTGT GGAGTTACTC TCGTTTTTGC CTTCTGACTT CTTTCCTTCC        1980

GTACGAGATC TCCTAGACAC CGCCTCAGCT CTGTATCGAG AAGCCTTAGA GTCTCCTGAG        2040

CATTGCTCAC CTCACCATAC TGCACTCAGG CAAGCCATTC TCTGCTGGGG GGAATTGATG        2100

ACTCTAGCTA CCTGGGTGGG TAATAATTTG CAAGATCCAG CATCCAGAGA TCTAGTAGTC        2160

AATTATGTTA ATACTAACAT GGGTTTAAAG ATCAGGCAAC TATTGTGGTT TCATATATCT        2220

TGCCTTACTT TTGGAAGAGA GACTGTACTT GAATATTTGG TCTCTTTCGG AGTGTGGACT        2280

CGCACTCCTC CAGCCTATAG ACCACCAAAT GCCCCTATCT TATCAACACT TCCGAAAACT        2340

ACTGTTGTTA GACGACGGGA CCGAGGCAGG TCCCCTAGAA GAAGAACTCC CTCGCCTCGC        2400

AGACGCAGAT CTCAATCGCC GCGTCGCAGA AGATCTCAAT CTCGGGAATC TCAATGTTAG        2460

TATTCCTTGG ACTCATAAGG TCGGAAACTT TACGGGCTTT TATTCCTCTA CAGTACCTAT        2520

CTTTAATCCT GAATGGCAAA CTCCTTCCTT TCCTAAGATT CATTTACAAG AGGACATTAT        2580

TAATAGGTGT CAACAATTTG TGGGCCCTCT CACTGTAAAT GAAAAGAGAA GATTGAAATT        2640

AATTATGCCT GCTAGATTCT ATCCTACCCA CACTAAATAT TTGCCCTTAG ACAAAGGAAT        2700

TAAACCTTAT TATCCAGATC AGGTAGTTAA TCATTACTTC CAAACCAGAC ATTATTTACA        2760

TACTCTTTGG AAGGCTGGTA TTCTATATAA GAGGGAAACC ACACGTAGCG CATCATTTTG        2820

CGGGTCACCA TATTCTTGGG AACAAGAGCT ACAGCATTCG CAAAGGCATG GGACGAATC        2880

TTTCTGTTCC CAACCCTCTG GGATTCCTTC CCGATCATCA GTTGGACCCT GCATTCGGAG        2940

CCAACTCAAC AAATCCAGAT TGGGACTTCA ACCCCATCAA GGACCACTGG CCAGCAGCCA        3000

ACCAGGTAGG AGTGGGAGCA TTCGGGCCAG GGCTCACCCC TCCACACGGC GGTATTTTGG        3060

GGTGGAGCCC TCAGGCTCAG GCATATTGA CCACAGTGTC AACAATTCCT CCTCCTGCCT        3120

CCACCAATCG GCAGTCAGGA AGGCAGCCTA CTCCCATCTC TCCACCTCTA AGAGACAGTC        3180

ATCCTCAGGC CATGCAGTGG                                                    3200
```

(2) INFORMATION FOR SEQ ID NO: 281:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 281:

```
AATTCCACTG CCTTCCACCA AGCTCTGCAA GACCCCAGAG TCAGGGGTCT GTATTTTCCT      60
GCTGGTGGCT CCAGTTCAGG AACAGTAAAC CCTGCTCCGA ATATTGCCTC TCACATCTCG     120
TCAATCTCCG CGAGGACCGG GGACCCTGTG ACGAACATGG AGAACATCAC ATCAGGATTC     180
CTAGGACCCC TGCCCGTGTT ACAGGCGGGG TTTTTCTTGT TGACAAGAAT CCTCACAATA     240
CCGCAGAGTC TAGACTCGTG GTGGACTTCT CTCAATTTTC TAGGGGGATC ACCCGTGTGT     300
CTTGGCCAAA ATTCGCGATC CCCAACCTCC AATCACTCAC CAACCTCCTG TCCTCCAATT     360
TGTCCTGGTT ATCGCTGGAT GTGTCTGCGG CGTTTTATCA TATTCCTCTT CATCCTGCTC     420
CTATGCCTCA TCTTCTTATT GGTTCTTCTG GATTATCAAG GTATGTTGCC CGTTTGTCCT     480
CTAATTCTAG GATCAACAAC AACCAGTACG GGACCATGCA AAACCTGCAC GACTCCTGCT     540
CAAGGCAACT CTATGTTTCC CTCATGTTGC TGTACAAAAC CTACGGATGG AAATTGCACC     600
TGTATTCCCA TCCCATCGTC TTGGGCTTTC GCAAAATACC TATGGGAGTG GGCCTCAGTC     660
CGTTTCTCTT GGCTCAGTTT ACTAGTGCCA TTTGTTCAGT GGTTCGTAGG GCTTTCCCCC     720
ACTGTTTGGC TTTCAGCTAT ATGGATGATG TGGTATTGGG GGCCAAGTCT GTACAGCATC     780
GTGAGTTCCT TTATACCGCT GTTACCAATT TTCTTTTGTC TCTGGGTATA CATTTAAACC     840
CTAACAAAAC AAAAAGATGG GGTTATTCCC TAAACTTCAT GGGTTATGTA ATTGGAAGTT     900
GGGGAACATT GCCACAGGAT CATATTGTAC AAAAAATCAA ACACTGTTTT AGAAAACTTC     960
CTGTTAACAG GCCTATTGAT TGGAAAGTAT GTCAAAGAAT TGTGGGTCTT TTGGGCTTTC    1020
CTGCTCCTTT TACACAATGT GGATATCCTG CCTTAATGCC CTTGTATGCA TGTATACAAG    1080
CTAAACAGGC TTTCACTTTC TCGCCAACTT ACAAGGCCTT TCTAAGTAAA CAGTACATGA    1140
ACCTTTACCC CGTTGCTCGG CAACGGCCTG GTCTGTGCCA AGTATTTGCT GATGCAACCC    1200
CCACTGGCTG GGGCTTGGCC ATAGGCCATC AGCGCATGCG CGGAACCTTT GTGGCTCCTC    1260
TGCCGATCCA TACTGCGGAA CTCCTAGCCG CTTGTTTTGC TCGCAGCCGG TCTGGAGCGA    1320
AACTCATCGG AACTGACAAT TCTGTCGTCC TCTCGCGGAA ATATACCTCG TTTCCATGGC    1380
TACTAGGCTG TGCTGCCAAC TGGATCCTTC GCGGGACGTC CTTTGTTTAC GTCCCGTCGG    1440
CGCTGAATCC CGCGGACGAC CCCTCTCGGG GCCGCTTGGG ACTCTCTCGT CCCCTTCTCC    1500
GTCTGCCGTT CCAGCCGACC ACGGGGCGCA CCTCTCTTTA CGCGGTCTCC CCGTCTGTGC    1560
CTTCTCATCT GCCGGTCCGT GTGCACTTCG CTTCACCTCT GCACGTTGCA TGGAGACCAC    1620
CGTGAACGCC CATCAGATCC TGCCCAAGGT CTTACATAAG AGGACTCTTG GACTCCCAGC    1680
AATGTCAACG ACCGACCTTG AGGCCTACTT CAAAGACTGT GTGTTTAAGG ACTGGGAGGA    1740
GCTGGGGGAG GAGATTAGGT TAAAGGTCTT TGTATTAGGA GGCTGTAGGC ATAAATTGGT    1800
CTGCGCACCA GCACCATGCA ACTTTTTCAC CTCTGCCTAA TCATCTCTTG TACATGTCCC    1860
```

```
ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCC    1980

GTCAGAGATC TCCTAGACAC CGCCTCGGCT CTGTATCGGG AAGCCTTAGA GTCTCCTGAG    2040

CATTGCTCAC CTCACCATAC CGCACTCAGG CAAGCCATTC TCTGCTGGGG GGAATTGATG    2100

ACTCTAGCTA CCTGGGTGGG TAATAATTTG GAAGATCCAG CATCCAGGGA TCTAGTAGTC    2160

AATTATGTTA ATACTAACAT GGGATTAAAG ATCAGGCAAC TCTTGTGGTT TCATATCTCT    2220

TGCCTTACTT TTGGAAGAGA AACTGTACTT GAATATTTGG TCTCTTTCGG AGTGTGGATT    2280

CGCACTCCTC CAGCCTATAG ACCACCAAAT GCCCCTATCT TATCAACACT TCCGGAAACT    2340

ACTGTTGTTA GACGACGGGA CCGAGGCAGG TCCCCTAGAA GAAGAACTCC CTCGCCTCGC    2400

AGACGCAGAT CTCAATCGCC GCGTCGCAGA AGATCTCAAT CTCGGGAATC TCAATGTTAG    2460

TATTCCTTGG ACTCATAAGG TGGGAAACTT CACTGGGCTT TATTCCTCTA CAGCACCTAT    2520

CTTTAATCCT GAATGGCAAA CTCCTTCCTT TCCTAAAATT CATTTACAAG AGGACATTAT    2580

TAATAGGTGT CAACAATTTG TGGGCCCTCT CACTGTAAAT GAAAAGAGAA GATTGAAATT    2640

AATTATGCCT GCTAGATTCT ATCCTACCCA CACTAAATAT TTGCCCTTAG ACAAAGGAAT    2700

TAAACCTTAT TATCCAGATC AGGTAGTTAA TCATTACTTC CAAACCAGAC ATTATTTACA    2760

TACTCTTTGG AAGGCGGGTA TTCTATATAA GAGAGAAACC ACACGTAGCG CATCATTTTG    2820

CGGGTCACCA TATTCTTGGG AACAAGAGCT ACAGCATGGG AGGTTGGTCA TCAAAACCTC    2880

GCAAAGGCAT GGGGACGAAT CTTTCTGTTC CCAACCCTCT GGGATTCTTT CCCGATCATC    2940

AGTTGGACCC TGTATTCGGA GCCAACTCAA ACAATCCAGA TTGGGACTTC AACCCCATCA    3000

AGGACCACTG GCCAGCAGCC AACCAGGTAG GAGTGGGAGC ATTCGGGCCA GGGTTCACCC    3060

CTCCACACGG CGGTGTTTTG GGGTGGAGCC CTCAGGCTCA GGGCATGTTG ACCCCAGTGT    3120

CAACAATTCC TCCTCCTGCC TCCGCCAATC GGCAGTCAGG AAGGCAGCCT ACTCCCATCT    3180

CTCCACCTCT AAGAGACAGT CATCCTCAGG CCATGCAGTG G                        3221

(2) INFORMATION FOR SEQ ID NO: 282:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 282:

AATTCCACTG CCTTCCACCA AGCTCTGCAG GATCCCAGAG TCAGGGGTCT GTATCTTCCT      60

GCTGGTGGCT CCAGTTCAGG AACAGTAAAC CCTGCTCCGA ATATTGCCTC TCACATCTCG     120

TCAATCTCCG CGAGGACTGG GGACCCTGTG ACGAACATGG AGAACATCAC ATCAGGATTC     180

CTAGGACCCC TGCTCGTGTT ACAGGCGGGG TTTTCCTTGT TGACAAGAAT CCTCACAATA     240

CCGCAGAGTC TAGACTCGTG GTGGACTTCT CTCAATTTTC TAGGGGGGTC ACCCGTGTGC     300

CTTGGCCAAA ATTCGCAGTC CCCAACCTCC AATCACTCAC CAACCTCCTG TCCTCCAATT     360

TGTCCTGGTT ATCGCTGGAT GTGTCTGCGG CGTTTTATCA TATTCCTCTT CATCCTGCTG     420

CTATGCCTCA TCTTCTTATT GGTTCTTCTG GATTATCAAG GTATGTTGCC CGTTTGTCCT     480
```

```
ATAATTCCAG GATCAACAAC AACCAGTACG GGACCATGCA AAACCTGCAC GACTCCTGCT       540

CAAGGCAACT CTTTGTTTCC CTCATGTTGC TGTACAAAAC CTACGGATGG AAATTGCACC       600

TGTATTCCCA TCCCATCGTC CTGGGCTTTC GCAAAATACC TATGGGAGCG GGCCTCAGTC       660

CGTTTCTCTT GGCTCAGTTT ACTAGTGCCA TTTGTTCAGT GGTTCGTAGG GCTTTCCCCC       720

ACTGTTTGGC TTTTAGCTAT ATGGATGATG TGGTATTGGG GGCCAAGTCT GTACAGCATC       780

GTGAGGCCCT TTATACCGCT GTTACCAATT TTCTTTTGTC TCTGGGTATA CATTTAAACC       840

CTAACAAAAC AAAAAGATGG GGTTATTCCC TAAACTTCAT GGGTTACAGA ATTGGAAGTT       900

GGGGAACATT GCCACAGGAT CACATTGTAC AAAAGATCAA ACACTGTTTT AGAAAACTTC       960

CTGTTAACAG GCCTATTGAT TGGAAGGTAT GTCAAAGAAT TGTGGGTCTT TTGGGCTTTG      1020

CTGCTCCTTT TACACAATGT GGATATCCTG CCTTAATGCC TTTGTATGCA TGTATACAAG      1080

CTAAACAGGC TTTCTCTTTC TCGCCAACTT ACAAGGCCTT TCTAAGTAAA CAGTACCTGA      1140

ACCTTTACCC CGTTGCTCGG CAACGGCCTG GTCTGTGCCA AGTGTTTGCT GACGCAACCC      1200

CCACTGGCTG GGCTTAGCC ATAGGCCATC AGCGCATGCG TGGAACCTTT GTGGCTCCTC       1260

TGCCGATCCA TACTGCGGAA CTCCTAGCCG CTTGTTTTGC TCGCAGCCGG TCTGGAGCAA      1320

AGCTCATCGG AACTGACAAT TCTGTCGTCC TCTCGCGGAA ATATACATCG TTTCCATGGC      1380

TGCTAGGCTG TGCTGCCAAC TGGATCCTTC GCGGGACGTC CTTTGTTTAC GTCCCGTCGG      1440

CGCTGAATCC CGCGGACGAC CCCTCTCGGG GCCGCTTGGG ACTCTATCGT CCCCTTCTCC      1500

GTCTGCCGTT CCAGCCGACC ACGGGGCGCA CCTCTCTTTA CGCGGTCTCC CCGTCTGTGC      1560

CTTCTCATCT GCCGGTCCGT GTGCACTTCG CTTCACCTCT GCACGTTGCA TGGAGACCAC      1620

CGTGAACGCC CATCAGAGCC TGCCCAAGGT CTTACATAAG AGAACTCTTG GACTCCCAGC      1680

AATGTCAACG ACCGACCTTG AGGCCTACTT CAAAGACTGT GTGTTTAAGG ACTGGGAGGA      1740

GCTGGGGGAG GAGATTAGGT TAATGATCTT TGTATTAGGA GGCTGTAGGC ATAAATTGGT      1800

CTGCGCACCA GCACCATGCA ACTTTTTCAC CTCTGCCTAA TCATCTCTTG TTCATGTCTC      1860

ACTGTTCAAG CCTCCAAGCT GTGCCTTGGG TGGCTTTGAG GCATGGACAT TGACCCTTAT      1920

AAAGAATTTG GAGCTAGTGT GGAGTTACTC TCGTTTTTGC CTCATGACTT CTTTCCTTCC      1980

GTCAGAGATC TCCTAGACAC CGCCTCAGCT CTGTATCGAG AAGCCTTAGA GTCTCCTGAG      2040

CATTGCTCAC CTCACCATAC TGCACTCAGG CAAGCCGTTC TCTGCTGGGG GGAATTAATG      2100

ACTCTAGCTA CCTGGGTGGG TAATAATTTG CAAGATCCAG CATCCAGGGA TCAAGTAGTC      2160

AATTATGTTA ATACTAACAT GGGTTTAAAG ATCAGGCAAC TATTGTGGTT TCATATATCT      2220

TGTCTTATGT TTGGAAGAGA CACTGTACTT GAATATTTGG TCTCTTTCGG AGTGTGGATT      2280

CGCACTCCTC CAGCCTATAG ACCACCAAAT GCCCCTATCT TATCAACACT TCCGGAAACT      2340

ACTGTTGTTA GATGTCGGGA CCGACGCAGG TCCCCTAGAA GAAGAACTCC CTCGCCTCGC      2400

AGACGCAGAT CTCAATCGCC GCGTCGCAGA AGATCTCAAT CTCGGGAATC TCAATGTTAG      2460

TATTCCTTGG ACTCATAAGG TGGGAAACTT TACTGGGCTT TATTCCTCTA CAGTACCTAT      2520

CTTTAATCCT GAATGGCAAA CTCCTTCCTT TCCTAAGATT CATTTACAAG AGGACATTAT      2580

TAATAGGTGT CAACAATTTG TGGGCCCTCT TACTGTAAAT GAAAAGAGAA GATTGAAATT      2640

AATTATGCCT GCTAGATTCT ATCCTACCCA CACAAAATAT TTGCCCTTAG ACAAAGGAAT      2700

TAAACCTTAT TATCCAGATC AGGTAGTTAA TCATTACTTC CAAACCAGAC ACTATTTACA      2760

TACTCTTTTG AAGGCTGGTA TTCTATATAA GAGGGAACCC ACACGTAGCG CATCATTTTC      2820

CCGGTCACCA TATTCTTGGG AACAAGAGCT ACAGCATGGG AGGTGGGACA TCAAAACCTC      2880
```

-continued

```
GCAAAGGCAT GGGGACGAAT CTTTCTGTTC CCAACCCTCT GGGATTCTTT CCCGATCATC    2940

AGTTGGACCC TGCATTCGGA GCCAACTCAA ACAATCCAGA TTGGGACTTC AACCCCATCA    3000

AGGACCACTG GCCAGCAGCC AACCAGGTGG GAGTGGGAGC ATTCGGGCCA GGGCTCACCC    3060

CTCCACACGG CGGTATTTTG GGGTGGAGCC CTCAGGCTCA AGGCATATTG ACCACAGTGT    3120

CAACAATTCC TCCTCCTGCC TCCACCAATC GGCAGTCAGG AAGGCAGCCT ACTCCCATGT    3180

CTCCACCTCT GAGAGAAAGT CATCCTCAGG CCATGCAGTG G                       3221
```

(2) INFORMATION FOR SEQ ID NO: 283:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 283:

```
AATTCCACAG CTTTCCACCA AGCTCTGCAA GATCCCAGAG TCAGGGGCCT GTATTTTCCT      60

GCTGGTGGCT CCAGTTCAGG AACACTCAAC CCTGTTCCAA CTATTGCCTC TCACATCTCG     120

TCAATCTCCT CGAGGATTGG GGACCCTGCA CCGAACATGG AGAACATCAC ATCAGGATTC     180

CTAGGACCCC TGCTCGTGTT ACAGGCGGGG TTTTTCTTGT TGACAAGAAT CCTCACAATA     240

CCGCAGAGTC TAGACTCGTG GTGGACTTCT CTCAATTTTC TAGGGGGAGC ACCCGTGTGT     300

CTTGGCCAAA ATTCGCAGTC CCCAACCTCC AATCACTCAC CAACCTCCTG TCCTCCAATT     360

TGTCCTGGTT ATCGCTGGAT GTGTCTGCGG CGTTTTATCA TATTCCTCTT CATCCTGCTG     420

CTATGCCTCA TCTTCTTATT GGTTCTTCTG GATTATCAAG GTATGTTGCC CGTTTGTCCT     480

CTAATTCCAG GATCAACAAC AACCAGCACG GGACCCTGCA AAACCTGCAC GACTCCTGCT     540

CAAGGCAACT CTATGTTTCC CTCATGTTGC TGTACAAAAC CTACGGATGG AAATTGCACC     600

TGTATTCCCA TCCCATCATC TTGGGCTTTC GCAAAATACC TATGGGAGTG GCCTCAGTC      660

CGTTTCTCTT GGCTCAGTTT ACTAGTGCCA TTTGTTCAGT GGTTCGTAGG GCTTTCCCCC     720

ACTGTTTGGC TTTCAGCTAT ATGGATGATG TGGTACTGGG GGCCAAGTCT GTACAACATC     780

TTGAGTCCCT TTATACCGCT GTTACCAATT TTCTTTTGTC TTTGGGTATA CATTTAAACC     840

CTAACAAAAC AAAGAGATGG GGTTATTCCC TGAATTTCAT GGGTTATGTA ATTGGAAGTT     900

GGGGTACATT GCCACAGGAT CATATTGTAC AAAAAATCAA ACACTGTTTT AGAAAACTTC     960

CTGTTAATCG ACCTATTGAT TGGAAAGTAT GTCAGAGACT TGTAGGTCTT TTAGGCTTTG    1020

CCGCTCCATT TACACAATGT GGTTACCCTG CATTAATGCC TTTGTATGCA TGTATACAAG    1080

CGAAACAGGC TTTTACTTTC TCGCCAACTT ACAAGGCCTT TCTAAGTAAA CAGTATATGA    1140

ACCTTTACCC CGTTGCCCGG CAACGGCCTG GTCTGTGCCA AGTGTTTGCT GACGCAACCC    1200

CCACTGGCTG GGGCTTGGCC ATCGGCCATC AGCGCATGCG TGAAACCTTT GTGGCTCCTC    1260

TGCCGATCCA TACTGCAGAA CTCCTAGCCG CTTGTTTTGC TCGCAGCCGG TCTGGAGCAA    1320

AACTCATCGG GACTGACAAT TCTGTCGTCC TTTCTCAGAA ATATACATCC TTTCCATAGC    1380

TGCTAGGTTG TACTGCCAAC TAGATTCTTC GCGGGACGTC CTTTGTCTAC GTCCCGTCGG    1440

CGCTGAATCC CGCGGACGAC CCCTCGCGAG GCCGCTTGGG ACTGTATCGT CCCCTTCTCC    1500
```

```
GTCTGCCGTA CCGTCCGACC ACGGGGCGCA CCTCTCTTTA CGCGGTCTCC CCGTCTGTGC      1560

CTTCTCATCT GCCGGTCCGT GTGCACTTCG CTTCACCTCT GCACGTTGCA TGGAGACCAC      1620

CGTGAACGCC CATCAGGTCC TGCCCAAGGT CTTACATAAG AGGACTCTTG GACTCTCAGC      1680

AATGTCAACG ACCGACCTTG AGGCCTACTT CAAAGACTGT GTGTTTAAAG ACTGGGAGGA      1740

GTTGGGGGAG GAGATTAGGT TAAAGGTCTT TGTATTAGGA GGCTGTAGGC ATAAATTGGT      1800

CTGCGCACCA TTATCATGCA ACTTTTTCAC CTCTGCCTAA TCATCTCTTG TACATGTCCC      1860

ACTTTTCAAG CCTCCAAGCT GTGCCTTGGA TGGCTTTGGG GCATGGACAT TGACCCTTAT      1920

AAAGAATTTG AGCTACTGTG GAGTTACTCT CATTTTTGCC TTCTGACTTC TTTCCTTCCG      1980

TCCGGGATCT ACTAGAATAC AGCCTCAGCT CTATATCGGG AAGCCTTAGA GTCTCCTGAG      2040

CATTGCTCAC CTCACCATAC AGCACTCAGG CAAGCCATTC TCTGCTGGGG GAAATTAATG      2100

ACTCTAGCTA CCTGGGTGGG TAATAATTTG GAAGATCCAG CATCCAGGGA TCTAGTAGTC      2160

AATTATGTTA ATACTAACAT GGGCCTAAAG ATCAGGCAAT TATTGTGGTT TCATATTTCT      2220

TGCCTTACTT TTGGAAGAGA AACTGTCCTT GAGTATTTGG TCTCTTTCGG AGTGTGGATT      2280

CGCACTCCTC CAGCCTATAG ACCACCAAAT GCCCCTATCT TATCAACACT TCCGGAAACT      2340

ACTGTTGTTA GACGACGAGA CCGAGGCAGG TCCCCTAGAA GAAGAACTCC CTCGCCTCGC      2400

AGACGCAGAT CTCAATCGCC GCGTCGCAGA AGATCTCAAT CTCGGGAATC TCAATGTTAG      2460

TATTCCTTGG ACTCATAAGG TGGGAAATTT TACTGGGCTT TATTCTTCTA CTGTCCCTAT      2520

CTTTAATCCT GAATGGCAAA CACCTTCTTT TCCTAAAATT CATTTACATG AAGACATTGC      2580

TAATAGGTGT CAGCAATTTG TAGGCCCTCT CACTGTAAAT GAAAAAAGAA GACTGAAATT      2640

AATTATGCCT GCTAGGTTTT ATCCTAACAG CACAAAATAT TTGCCCTTAG ACAAAGGGAT      2700

TAAAACTTAT TATCCTGATC ATGTAGTTAA TCATTACTTT CAAACCCGAC ATTATTTACA      2760

TACTCTTTGG AAGGCTGGGA TTCTATATAA GAGGGAAACT ACACGTAGCG CCTCATTTTG      2820

CGGGTCACCA TATTCTTGGG AACAAGAGCT ACATCATGGG AGGTTGGTCA TCAAAACCTC      2880

GCAAAGGCAT GGGGACGAAC CTTTCTGTTC CAACCCTCT GGGATTCTTT CCCGATCATC      2940

AGTTGGACCC TGCATTCGGA GCCAATTCAA ACAATCCAGA TTGGGACTTC AACCCCATCA      3000

AGGACCACTG GCCACAAGCC AACCAGGTAG GAGTGGGAGC ATTTGGGCCA GGGTTCACTC      3060

CCCCACACGG AGGTGTTTTG GGGTGGAGCC CTCAGGCTCA GGGCATATTG GCCACCGTGC      3120

CAGCGATGCC TCCTCCTGCC TCCACCAATC GGCAGTCAGG AAGGCAGCCT ACTCCCATCT      3180

CTCCACCTCT AAGAGACAGT CATCCTCAGG CCATGCAGTG G                        3221
```

(2) INFORMATION FOR SEQ ID NO: 284:

(i) SEQUENCE CHARACTERISTICS:
  (A) LENGTH: 3215 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 284:

```
AACTCCACCA CGTTCCACCA AACTCTTCAA GATCCCAGAG TCAGGGCTCT GTACTTTCCT       60

GCTGGTGGCT CCAGTTCAGG AACAGTAAAC CCTGTTCAGA ACACTGCCTC TTCCATATCG      120
```

```
TCAATCTTAT CGACGACTGG GGACCCTGTG CCGAACATGG AGAACATCGC ATCAGGACTC      180

CTAGGACCCC TGCTCGTGTT ACAGGCGGGG TTTTTCTCGT TGACAAAAAT CCTCACAATA      240

CCTCTGAGTC TAGACTCGTG GTGGACTTCT CTCAATTTTC TAGGGAAAC ACCCGTGTGT       300

CTTGGCCAAA ATTCGCAGTC CCAAATCTCC AGTCACTCAC CAACTTGTTG TCCTCCGATT      360

TGTCCTGGTT ATCGCTGGAT GTGTCTGCGG CGTTTTATCA TCTTCCTCTG CATCCTGCTG      420

CTATGCCTCA TCTTCTTGTT GGTTCTTCTG GACTATCAAG GTATGTTGCC CGTTTGTCCT      480

CTAATTCCAG GATCATCAAC CACCAGCACA GGACCATGCA AAACCTGCAC GACTCCTGCT      540

CAAGGAACCT CTATGTTTCC CTCATGTTGC TGTACAAAAC CTACGGACGG AAACTGCACC      600

TGTATTCCCA TCCCATCATC TTGGGCTTTC GCAAAATACC TATGGGAGTG GGCCTCAGTC      660

CGTTTCTCTT GGCTCAGTTT ACTAGTGCCA TTTGTTCAGT GGTTCGTAGG GCTTTCCCCC      720

ACTGTCTGGC TTTCAGTTAT ATGGATGATG TGGTTTTGGG GGCCAAGTCT GTACAACATC      780

TTGAGTCCCT TTATGCCGCT GTTACCAATT TTCTTTTGTC TTTGGGTATA CATTTAAACC      840

CTCAGAAAAC AAAAAGATGG GGCTACTCCC TTAACTTCAT GGGGTATGTA ATTGGAAGTT      900

GGGGGACCTT ACCCCAAGAA CATATTGTGT TGAAAATCAA ACAATGTTTT AGGAAACTTC      960

CTGTAAACAG GCCTATTGAT TGGAAAGTAT GTCAACGAAT TGTGGGTCTT TTGGGATTTG     1020

CTGCTCCTTT CACACAATGT GGATATCCTG CTTTAATGCC TTTATATGCA TGTATACAAG     1080

CTAAACAGGC TTTTACTTTT TCGCCAACGT ATAAGGCCTT TCTAAACAAA CAATATCTGA     1140

ACCTTTACCC CGTTGCTCGG CAACGGCCAG GTCTGTGCCA AGTGTTTGCT GACGCAACCC     1200

CCACTGGCTG GGGCTTGGCC ATAGGCCATC AGCGCATGCG TGGGACCTTT GTGTCTCCTC     1260

TGCCGATCCA TACTGTGGAA CTCCTAGCAG CTTGTTTTGC TCGCAGCAGG TCTGGAGCAA     1320

AACTTATCGG GACTGACAAT TCTGTCGTCC TTTCCCGCAA ATATACATCG TTTCCATGGC     1380

TGCTAGGCTG TGCTGCCAAC TGGATCCTGC GCGGGACGTC CTTTGTCTAC GTCCCGTCGG     1440

CGCTGAATCC CGCGGACGAC CCCTCCCGGG GCCGCTTGGG GCTCTACCGC CCGCTTCTCC     1500

GCCTGCCGTA CCGTCCGACC ACGGGGCGCA CCTCTCTTTA CGCGGACTCC CCGTCTGTGC     1560

CTTCTCATCT GCCGGACCGT GTGCACTTCG CTTCACCTCT GCACGTCGCA TGGAGACCAC     1620

CGTGAACGCC CATCGGAACC TGCCCAAGGT CTTGCATAAG AGGACTCTTG GACTTTCAGC     1680

AATGTCAACG ACCGACCTTG AGGCACACTT CAAAGACTGT GTGTTTACTG AGTGGGAGGA     1740

GTTGGGGGAG GAGATCAGGT TAAAGGTCTT TGTACTAGGA GGCTGTAGGC ATAAATTGGT     1800

CTGTTCACCA GCACCATGCA ACTTTTTCAC CTCTGCCTAA TCATCTCATG TTCATGTCCT     1860

ACTGTTCAAG CCTCCAAGCT GTGCCTTGGG TGGCTTTGGG GCATGGACAT TGACCCGTAT     1920

AAAGAATTTG GAGCTTCTGT GGAGTTACTC TCTTTTTTGC CTTCTGACTT CTTTCCTTCT     1980

ATTCGAGATC TTCTCGACAC CGCCTCTGCT CTGTATCGGG AGGCCTTAGA GTCTCCGGAA     2040

CATTGTTCAC CTCACCATAC GGCACTCAGG CAAGCTATTC TGTGTTGGGG TGAGTTGATG     2100

AATCTAGCCA CCTGGGTGGG AAGTAATTTG GAAGACCCAG CCTCCCGGGA ATTAGTAGTC     2160

AGTTATGTCA ATGTTAATAT GGGCCTAAAA ATCAGACAAC TATTGTGGTT TCACATTTCC     2220

TGTCTTACGT TTGGAAGAGA AACTGTTCTT GAATATTTGG TGTCTTTTGG AGTGTGGATT     2280

CGCACACCTC CAGCATATAG ACCACCAAAT GCCCCTATCT TATCAACACT TCCGGAAACT     2340

ACTGTTGTTA GACGACGAGG CAGGTCCCCT AGAAGAAGAA CTCCCTCGCC TCGCAGACGA     2400

AGGTCTCAAT CGCCGCGTCG CAGAAGATCT CAATCTCGGG AATCTCAATG TTAGTATTCC     2460
```

```
TTGGACTCAT AAGGTGGGAA ACTTTACGGG GCTTTATTCT TCTACGGTAC CTAGCTTTAA    2520

TCCTCAATGG CAAACTCCTT CATTTCCTGA CATTCATTTG CAGGAGGACA TCATTAATAA    2580

GTGTAAACAA TTTGTGGGAC CCCTTACAGT GAATGAAAAA AGGAGACTAA AATTGATTAT    2640

GCCTGCTAGG TTCTATCCCA ATGTTACTAA ATATTTGCCC TTAGATAAAG GAATTAAACC    2700

TTATTATCCA GAGCATGTAG TTAATCATTA CTTCCAGACG AGACATTATT TACATACTCT    2760

TTGGAAGGCG GGTATCTTAT ATAAAAGAGA GACAACACGT AGCGCCTCAT TTTGCGGGTC    2820

ACCATATTCT TGGGAACAAG AGCTACAGCA TGGGAGGTTG GTCCTCCAAA CCTCGACAAG    2880

GCATGGGGAC AAATCTTTCC GTCCCCAATC CTCTGGGATT CTTTCCCGAT CACCAGTTGG    2940

ACCCTGCATT CAAAGCCAAC TCCGACAATC CCGATTGGGA CCTCAACCCA CACAAGGACA    3000

ACTGGCCGGA CTCCAACAAG GTGGGAGTGG GAGCATTCGG GCCGGATTC ACTCCACCCC     3060

ATGGGGGACT GTTGGGGTGG AGCCCTCAAG CTCAGGGCAT ACTCACAACT GTGCCAACAG    3120

CTCCTCCTCC TGCCTCCACC AATCGGCAGT TAGGAAGGAA GCCTACTCCC CTGTCTCCAC    3180

CTCTAAGAGA CACTCATCCT CAGGCAATGC AGTGG                               3215
```

(2) INFORMATION FOR SEQ ID NO: 285:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 285:

```
AACTCCACCA CGTTCCACCA AACTCTTCAA GATCCCAGAG TCAGGGCTCT GTACTTTCCT      60

GCTGGTGGCT CCAGTTCAGG AACAGTAAAC CCTGTTCAGA ACACTGTCTC TTCCATATCG     120

TCAATCTTAT CGAAGACTGG GGACCCTGTG CCGAACATGG AGAACATCGC ATCAGGACTC     180

CTAGGACCCC TGCTCGTGTT ACAGGCGGGG TTTTTCTTGT TGACAAAAAT CCTCACAATA     240

CCACAGAGTC TAGACTCGTG GTGGACTTCT CTCAATTTTC TAGGGGGAAC ACCCGTGTGT     300

CTTGGCCAAA ATTCGCAGTC CCAAATCTCC AGTCACTCAC CAACTTGTTG TCCTCCGATT     360

TGTCCTGGTT ATCGCTGGAT GTGTCTGCGG CGTTTTATCA TCTTCCTCTG CATCCTGCTG     420

CTATGCCTCA TCTTCTTGTT GGTTCTTCTG GACTATCAAG GTATGTTGCC CGTTTGTCCT     480

CTAATTCCAG GATCATCAAC CACCAGCACC GGACCATGCA AAACCTGCAC GACTCCTGCT     540

CAAGGAACCT CTATGTTTCC CTCATGTTGC TGTACAAAAC CTACGGACGG AAACTGCACC     600

TGTATTCCCA TCCCATCATC TTGGGCTTTC GCAAAATACC TATGGGAGTG GGCCTCAGTC     660

CGTTTCTCTT GGCTCAGTTT ACTAGTGCCA TTTGTTCAGT GGTTCGTAGG GCTTTCCCCC     720

ACTGTCTGGC TTTCAGTTAT ATGGATGATG TGGTTTTGGG GGCCAAGTCT GTACAACATC     780

TTGAGTCCCT TTATGCCGCT GTTACCAATT TTCTTTTGTC TTTGGGTATA CATTTAAACC     840

CTCAGAAAAC AAAAAGATGG GGCTACTCCC TCAACTTCAT GGGGTATGTA ATTGGAAGTT     900

GGGGCACCTT ACCCCAAGAA CATATTGTGT TGAAACTCAA ACAATGCTTT AGAAAACTTC     960

CTGTAAACAG ACCTATTGAT TGGAAGGTGT GTCAACGAAT TGTGGGTCTT TTGGGATTTG    1020

CTGCTCCTTT CACACAATGT GGTTATCCTG CTTTAATGCC TTTATATGCA TGTATACAAG    1080
```

```
-continued

CTAAACAGGC TTTTACTTTT TCGCCAACGT ATAAGGCCTT TCTAACCAAA CAATATCTGA    1140

ACCTTTACCC CGTTGCTCGG CAACGGCCAG GTCTGTGCCA AGTGTTTGCT GACGCAACCC    1200

CCACTGGCTG GGGCTTGGCC ATAGGCCATC AGCGCATGCG TGGAACCTTT GTGTCTCCTC    1260

TGCCGATCCA TACTGCGGAA CTCCTAGCCG CTTGTTTTGC TCGCAGCAGG TCTGGAGCAA    1320

AACTTATCGG GACTGACAAT TCTGTTGTCC TTTCCCGCAA ATATACATCG TTTCCATGGC    1380

TGCTAGGCTG TGCTGCCAAC TGGATCCTGC GCGGGACGTC CTTTGTCTAC GTTCCGTCGG    1440

CGCTGAATCC CGCGGACGAC CCCTCCCGGG GCCGCTTGGG GCTCTACCGC CCGCTTCTCC    1500

GTCTGCCGTA CCGACCGACC ACGGGGCGCA CCTCTCTTTA CGCGGACTCC CCGTCTGTGC    1560

CTTCTCGTCT GCCGGACCGT GTGCACTTCG CTTCACCTCT GCACGTCGCA TGGAGACCAC    1620

CGTGAACGCC CATCGGAACC TGCCCAAGGT CTTGCATAAG AGGACTCTTG GACTTTCAGC    1680

AATGTCACCG ACCGACCTTG AGGCATACTT CAAAGACTGT GTGTTTACTG AGTGGGAGGA    1740

GTTGGGGGAG GAGATCAGGT TAAAGGTCTT TGTACTAGGA GGCTGTAGGC ATAAATTGGT    1800

CTGTTCACCA GCACCATGCA ACTTTTTCAC CTCTGCCTAA TCATCTCATG TTCATGTCCT    1860

ACTGTTCAAG CCTCCAAGCT GTGCCTTGGG TGGCTTTGGG GCATGGACAT TGACCCGTAT    1920

AAAGAATTTG GAGCTTCTGT GGAGTTACTC TCTTTTTTGC CTTCTGACTT CTTTCCTTCT    1980

ATTCGAGATC TTCTCGACAC CGCCTCTGCT CTGTATCGGG AGGCCTTAGA GTCTCCGGAA    2040

CATTGTTCAC CTCACCATAC GGCACTCAGG CAAGCTATTT TGTGTTGGGG TGAGTTGATG    2100

AATCTAGCCA CCTGGGTGGG AAGTAATTTG GAAGACCCAG CATCCCGGGA ATTAGTAGTC    2160

AGTTATGTCA ATGTTAATAT GGGCCTAAAA ATCAGACAAC TATTGTGGTT TCACATTTCC    2220

TGTCTTACTT TTGGAAGAGA AACTGTTCTT GAATATTTGG TGTCTTTTGG AGTGTGGATT    2280

CGCACACCTC CTGCATATAG ACCACCAAAT GCCCCTATCT TATCAACACT TCCGGAAACT    2340

ACTGTTGTTA GACGACGAGG CAGGTCCCCT AGAAGAAGAA CTCCCTCACC TCGCAGACGA    2400

AGGTCTCAAT CGCCCGGTCG CAGAAGATCT CAATCTCGGG AATCTCAATG TTAGTATCCC    2460

TTGGACTCAT AAGGTGGGAA ACTTTACGGG GCTTTATTCT TCTACGGTAC CTAGCTTTAA    2520

TCCTAAATGG CAAACTCCTT CCTTTCCTGA CATTCATTTG CAGGAGGATA TCATTAATAG    2580

GTGTGAACAA TTTGTGGGAC CCCTCACAGT GAATGAAAAC AGGAGACTAA AATTGATTAT    2640

GCCTGCTAGG TTCTATCCCA ATGTTACTAA ATATTTGCCC TTAGATAAAG GAATCAAACC    2700

TTATTATCCA GAGCATGTAG TTAATCATTA CTTCCAGACG AGACATTATT TACATACTCT    2760

TTGGAAGGCG GGTATCTTAT ATAAAAGAGA GACAACACGT AGCGCCTCAT TTTGCGGGTC    2820

ACCATATTCT TGGGAACAAG ATCTACAGCA TGGGAGGTTG GTCCTCCAAA CCTCGACAAG    2880

GCATGGGGAC AAATCTTTCC GTCCCCAATC CTCTGGGATT CTTTCCCGAT CACCAGTTGG    2940

ACCCTGCATT CAAAGCCAAC TCCGACAATC CCGATTGGGA CCTCAACCCA CACAAGGACA    3000

ACTGGCCGGA CTCCAACAAG GTGGGAGTGG GAGCATTCGG GCCGGATTC ACTCCACCCC     3060

ATGGGGGACT GTTGGGGTGG AGCCCTCAAG CTCAGGGCAT ACTCACAACT GTGCCAACAG    3120

CTCCTCCTCC TGCCTCCACC AATCGGCAGT TAGGAAGGAA GCCTACTCCC CTGTCTCCAC    3180

CTCTAAGAGA CACTCATCCT CAGGCCATGC AGTGG                               3215

(2) INFORMATION FOR SEQ ID NO: 286:

(i) SEQUENCE CHARACTERISTICS:
        (A) LENGTH: 3215 base pairs
        (B) TYPE: nucleic acid
        (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 286:

```
AACTCCACCA CTTTCCACCA AACTCTTCAA GATCCCAGAG TCAGGGCTCT GTACTTTCCT      60

GCTGGTGGCT CCAGTTCAGG AACAGTAAGC CCTGCTCAGA ATACTGTCTC AGCCATATCG     120

TCAATCTTAT CGAAGACTGG GGACCCTGTG CCGAACATGG AGAACATCGC ATCAGGACTC     180

CTAGGACCCC TGCTCGTGTT ACAGGCGGGG TTTTTCTTGT TGACAAAAAT CCTCACAATA     240

CCACAGAGTC TAGACTCGTG GTGGACTTCT CTCAATTTTC TAGGGGGAAC ACCCGTGTGT     300

CTTGGCCAAA ATTCGCAGTC CCAAATCTCC AGTCACTCAC CAACCTGTTG TCCTCCAATT     360

TGTCCTGGTT ATCGCTGGAT GTGTCTGCGG CGTTTTATCA TCTTCCTCTG CATCCTGCTG     420

CTATGCCTCA TCTTCTTGTT GGTTCTTCTG GACTATCAAG GTATGTTGCC CGTTTGTCCT     480

CTAATTCCAG GATCATCAAC CACCAGCACG GGACCATGCA AGACCTGCAC AACTCCTGCT     540

CAAGGAACCT CTATGTTTCC CTCATGTTGC TGTACAAAAC CTATGGATGG AAACTGCACC     600

TGTATTCCCA TCCCATCATC TTGGGCTTTC GCAAAATACC TATGGGAGTG GCCTCAGTC      660

CGTTTCTCTT GGCTCAGTTT ACTAGTGCCA TTTGTTCAGT GGTTCGTAGG GCTTTCCCCC     720

ACTGTCTGGC TTTCAGTTAT ATGGATGATG TGGTATTGGG GGCCAAGTCT GTACAACATC     780

TTGAGTCCCT TTATGCCGCT GTTACCAATT TTCTTTTGTC TTTGGGTATA CATTTAAACC     840

CTAACAAAAC AAAAAGATGG GGATATTCCC TTAACTTCAT GGGATATGTA ATTGGGAGTT     900

GGGGCACATG GCCACAGGAT CATATTGTAC AAAACTTCAA ACTATGTTTT AGAAAACTTC     960

CTGTAAACAG GCCTATTGAT TGGAAAGTTT GTCAACGAAT GTGGGTCTT TTGGGGTTTG     1020

CTGCCCCTTT TACGCAATGT GGATATCCTG CTTTAATGCC TTTATATGCA TGTATACAAG    1080

CAAAACAGGC TTTTACTTTC TCGCCAACTT ACAAGGCCTT TCTCAGTAAA CAGTATATGA    1140

CCCTTTACCC CGTTGCTCGG CAACGGCCTG GTCTGTGCCA AGTGTTTGCT GACGCAACCC    1200

CCACTGGTTG GGGCTTGGCC ATAGGCCATC AGCGCATGCG TGGAACCTTT GTGTCTCCTC    1260

TGCCGATCCA TACTGCGGAA CTCCTAGCCG CTTGTTTTGC TCGCAGCAGG TCTGGAGCAA    1320

ACCTCATCGG GACCGACAAT TCTGTCGTAC TCTCCCGCAA GTATACATCG TTTCCATGGC    1380

TGCTAGGCTG TGCTGCCAAC TGGATCCTGC GCGGGACGTC CTTTGTTTAC GTCCCGTCGG    1440

CGCTGAATCC CGCGGACGAC CCCTCCCGGG GCCGCTTGGG GCTCTACCGC CCGCTTCTCC    1500

GTCTGCCGTA CCGTCCGACC ACGGGGCGCA CCTCTCTTTA CGCGGACTCC CCGTCTGTGC    1560

CTTCTCATCT GCCGGACCGT GTGCACTTCG CTTCACCTCT GCACGTCGCA TGGAGACCAC    1620

CGTGAACGCC CACCGGAACC TGCCCAAGGT CTTGCATAAG AGGACTCTTG GACTTTCAGC    1680

AATGTCAACG ACCGACCTTG AGGCATACTT CAAAGACTGT GTGTTTAATG AGTGGGAGGA    1740

GCTGGGGGAG GAGATTAGGT TAAAGGTCTT TGTACTCGGA GGCTGTAGGC ATAAATTGGT    1800

CTGTTCACCA GCACCATGCA ACTTTTTCAC CTCTGCCTAG TCATCTCTTG TTCATGTCCT    1860

ACTGTTCAAG CCTCCAAGCT GTGCCTTGGG TGGCTTTGGG GCATGGACAT TGACCCCTAT    1920

AAAGAATTTG GAGCTACTGT GGAGTTACTC TCTTTTTTGC CTTCTGACTT CTTTCCGTCG    1980

GTGCGGGACC TCCTAGATAC CGTCTCTGCT CTGTATCGGG AAGCCTTAAA ATCTCCTGAG    2040

CATTGCTCAC CTCACCACAC AGCACTCAGG CAAGCTATTC TGTGCTGGGG GGAATTAATG    2100
```

```
ACTCTAGCTA CCTGGGTGGG TAATAATTTG GAAGATCCAG CATCCCGGGA TCTAGTAGTC   2160

AATTATGTTA ACACTAACAT GGGCCTAAAG ATCAGGCAAC TATGGTGGTT TCACATTTCC   2220

TGTCTTACTT TTGGAAGAGA AACTGTTCTG GAATATTTGG TATCTTTTGG AGTGTGGATT   2280

CGCACTCCTC CTGCCTACAG ACCACCAAAT GCCCCTATCT TATCAACACT TCCGGAAACT   2340

ACTGTTGTTA GACGACGAGG CAGGTCCCCT AGAAGAAGAA CTCCCTCGCC TCGCAGACGA   2400

AGGTCTCAAT CACCGCGTCG CAGAAGATCT CAATCTCGGG AATCCCAATG TTAGTATCCC   2460

TTGGACTCAT AAGGTGGGAA ACTTTACGGG GCTTTATTCT TCTACAGTAC CTGTCTTTAA   2520

TCCTGAATGG CAAACTCCTT CTTTTCCAGA CATTCATTTA CAGGAGGACA TTGTTGATAG   2580

ATGTAAGCAA TTTGTGGGAC CCCTTACAGT AAATGAAAAC AGGAGACTAA AATTAATAAT   2640

GCCTGCTAGA TTTTATCCCA ATGTTACCAA ATATTTGCCC TTAGATAAAG GTATCAAACC   2700

TTATTATCCA GAGCATGTAG TTAATCATTA CTTCCAGACT AGACATTATT TGCATACTCT   2760

TTGGAAGGCG GGTATCTTAT ATAAAAGAGA GTCAACACAT AGCGCCTCAT TTTGCGGGTC   2820

ACCTTATTCT TGGGAACAAG ATCTACAGCA TGGGAGGTTG GTCTTCCAAA CCTCGAAAAG   2880

GCATGGGGAC AAATCTTTCT GTCCCCAATC CCCTGGGATT CTTCCCCGAT CATCAGTTGG   2940

ACCCTGCATT CAAAGCCAAC TCAGAAAATC CAGATTGGGA CCTCAACCCA CACAAGGACA   3000

ACTGGCCGGA CGCCCACAAG GTGGGAGTGG GAGCATTCGG GCCAGGATTC ACCCCTCCCC   3060

ATGGGGACT GTTGGGGTGG AGCCCTCAGG CTCAGGGCAT ACTCACATCT GTGCCAGCAG   3120

CTCCTCCTCC TGCCTCCACC AATCGGCAGT CAGGACGGCA GCCTACTCCC CTATCTCCAC   3180

CTCTAAGGGA CACTCATCCT CAGGCCATGC AGTGG                              3215

(2) INFORMATION FOR SEQ ID NO: 287:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 287:

AACTCCACCA CTTTCCACCA AACTCTTCAA GATCCCGGAG TCAGGGCCCT GTACTTTCCT    60

GCTGGTGGCT CCAGTTCAGG AACAGTGAGC CCTGCTCAGA ATACTGTCTC TGCCATATCG   120

TCAATCTTAT CGAAGACTGG GGACCCTGTA CCGAACATGG AGAACATCGC ATCAGGACTC   180

CTAGGACCCC TGCTCGTGTT ACAGGCGGGG TTTTTCTTGT TGACAAAAAT CCTCACAATA   240

CCACAGAGTC TAGACTCGTG GTGGACTTCT CTCAATTTTC TAGGGGAAC ACCCGTGTGT    300

CTTGGCCAAA ATTCGCAGTC CCAAATCTCC AGTCACTCAC CAACCTGTTG TCCTCCAATT   360

TGTCCTGGTT ATCGCTGGAT GTGTCTGCGG CGTTTTATCA TCTTCCTCTG CATCCTGCTG   420

CTATGCCTCA TCTTCTTGTT GGTTCTTCTG GACTATCAAG GTATGTTGCC CGTTTGTCCT   480

CTAATTCCAG GATCATCAAC AACCAGCACC GGACCATGCA AAACCTGCAC AACTCCTGCT   540

CAAGGAACCT CTATGTTTCC CTCATGTTGC TGTACAAAAC CTACGGATGG AAACTGCACC   600

TGTATTCCCA TCCCATCATC TTGGGCTTTC GCAAAATACC TATGGGAGTG GCCTCAGTC   660

CGTTTCTCTT GGCTCAGTTT ACTAGTGCCA TTTGTTCAGT GGTTCGTAGG GCTTTCCCCC   720
```

-continued

| | |
|---|---|
| ACTGTCTGGC TTTCAGTTAT ATGGATGATA TGGTTTTGGG GGCCAAGTCT GTACAACATC | 780 |
| TTGAGTCCCT TTATGCCGCT GTTACCAATT TTCTTTTGTC TTTGGGTATA CATTTAAACC | 840 |
| CTCACAAAAC AAAAAGATGG GGATATTCCC TTAACTTCAT GGGATATGTA ATTGGGAGCT | 900 |
| GGGGCACATT GCCACAGGAA CATATTGTAC AAAAAATCAA AATGTGGTTT AGGAAACTTC | 960 |
| CTGTAAACAG GCCTATTGAT TGGAAAGTAT GTCAACGAAT TGTGGGTCTT TTGGGGTTTG | 1020 |
| CCGCCCCTTT CACGCAATGT GGATATCCTG CTTTAATGCC TTTATATGCA TGTATACAAG | 1080 |
| CAAAACAGGC TTTTACTTTC TCGCCAACTT ACAAGGCCTT TCTAACTAAA CAGTATCTGA | 1140 |
| ACCTTTACCC CGTTGCTCGG CAACGGCCAG GTCTGTGCCA AGTGTTTGCT GACGCAACCC | 1200 |
| CCACTGGTTG GGGCTTGGCC ATAGGCCATC AGCGCATGCG TGGAACCTTT GTGTCTCCTC | 1260 |
| TGCCGATCCA TACTGCGGAA CTCCTAGCCG CTTGTTTTGC TCGCAGCCGG TCTGGGCAA | 1320 |
| AACTCATCGG GACTGACAAT TCTGTCGTGC TCTCCCGCAA GTATACATCA TTTCCATGGC | 1380 |
| TGCTAGGCTG TGCTGCCAAC TGGATCCTGC GCGGGACGTC CTTTGTTTAC GTCCCGTCGG | 1440 |
| CGCTGAATCC CGCGGACGAC CCTTCCCGGG GCCGCTTGGG GCTCTACCGC CCGCTTCTCC | 1500 |
| GCCTGTTGTA CCGACCGACC ACGGGGCGCA CCTCTCTTTA CGCGGACTCC CCGTCTGTGC | 1560 |
| CTTCTCATCT GCCGGACCGT GTGCACTTCG CTTCACCTCT GCACGTCGCA TGGAGACCAC | 1620 |
| CGTGAACGCC CACGGGAACC TGCCCAAGGT CTTGCATAAG AGGACTCTTG GACTTTCAGC | 1680 |
| AATGTCAACG ACCGACCTTG AGGCATACTT CAAAGACTGT GTGTTTAATG AGTGGGAGGA | 1740 |
| GTTGGGGGAG GAGGTTAGGT TAAAGGTCTT TGTACTAGGA GGCTGTAGGC ATAAATTGGT | 1800 |
| GTGTTCACCA GCACCATGCA ACTTTTTCAC CTCTGCCTAA TCATCTCATG TTCATGTCGT | 1860 |
| ACTGTTCAAG CCTCCAAGCT GTGCCTTGGG TGGCTTTGGG GCATGGACAT TGACCCGTAT | 1920 |
| AAAGAATTTG GAGCTTCTGT GGAGTTACTC TCTTTTTTGC CTTCTGACTT CTTTCCGTCG | 1980 |
| GTGCGAGATC TCCTCGACAC CGCCTCTGCT TTGTATCGGG AGGCCTTAGA GTCTCCGGAA | 2040 |
| CATTGTTCAC CTCACCATAC GGCACTCAGG CAAGCTATTC TGTGTTGGGG TGAGTTAATG | 2100 |
| AATCTAGCCA CCTGGGTGGG AAGTAATTTG GAAGATCCGG CATCCAGGGA ATTAGTAGTC | 2160 |
| AGCTATGTCA ACGTTAATAT GGGCCTAAAA ATCAGACAAC TATTGTGGTT TCACATTTCC | 2220 |
| TGTCTTACTT TTGGGAGAGA AACTGTTCTT GAATATTTGG TGTCTTTTGG AGTGTGGATT | 2280 |
| CGCACTCCTC CTGCATATAG ACCACCAAAT GCCCCTATCT TATCAACACT TCCGGAAACT | 2340 |
| ACTGTTGTTA GACGAAGAGG CAGGTCCCCT AGAAGAAGAA CTCCCTCGCC TCGCAGACGA | 2400 |
| AGGTCTCAAT CGCCGCGTCG CAGAAGATCT CAATCTCGGG AATCTCAATG TTAGTATTCC | 2460 |
| TTGGACACAT AAGGTGGGAA ACTTTACGGG GCTTTATTCT TCTACGGTAC CTTGCTTTAA | 2520 |
| TCCTAAATGG CAAACTCCTT CTTTTCCTGA CATTCATTTG CAGGAGGACA TTGTTGATAG | 2580 |
| ATGTAAGCAA TTTGTGGGGC CCCTTACAGT AAATGAAAAC AGGAGACTAA AATTAATTAT | 2640 |
| GCCCGCTAGG TTTTATCCCA ATGTTACTAA ATATTTGCCC TTAGATAAAG GGATCAAACC | 2700 |
| GTATTATCCA GAGTATGTAG TTAATCATTA CTTCCAGACG CGACATTATT TACACACTCT | 2760 |
| TTGGAAGGCG GGGATCTTAT ATAAAAGAGA GTCCACACGT AGCGCCTCAT TTTGCGGGTC | 2820 |
| ACCATATTCT TGGGAACAAG ATCTACAGCA TGGGAGGTTG GTCTTCCAAA CCTCGAAAAG | 2880 |
| GCATGGGGAC AAATCTTTCT GTCCCCAATC CTCTGGGATT CTTCCCCGAT CATCAGTTGG | 2940 |
| ACCCTGCATT CAAAGCCAAC TCAGAAAATC CAGATTGGGA CCTCAACCCG AACAAGGACA | 3000 |
| ACTGGCCGGA CGCCAACAAG GTGGGAGTGG GAGCATTCGG GCCAGGGTTC ACCCCTCCCC | 3060 |

```
ATGGGGGACT GTTGGGGTGG AGCCCTCAGG CTCAGGGCCT ACTCACAACT GTGCCAGCAG      3120

CTCCTCCTCC TGCCTCCACC AATCGGCAGT CAGGAAGGCA GCCTACTCCC TTATCCCCAC      3180

CTCTAAGGGA CACTCATCCT CAGGCCATGC AGTGG                                 3215
```

(2) INFORMATION FOR SEQ ID NO: 288:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 288:

```
AACTCCACCA CATTTCACCA AGTCCTGCTA GATCCCAGAG TGAGGGGCCT ATATTTTCCT        60

CCTGGTGGCT CCAGTTCCGG AACAGTAAAC CCTGTTGCGA CTACTGCCTC ACCCATATCG       120

TCAATCTCCT CGAGGACTGG GGACCCTGCA CCGAACATGG AGAGCACAAC ATCAGGATTC       180

CTAGGACCCC TGCTCGTGTT ACAGGCGGGG TTTTTCTTGT TGACAAGAAT CCTCACAATA       240

CCACAGAGTC TAGACTCGTG GTGGACTTCT CTCAATTTTC TAGGGGAGC ACCCACGTGT        300

CCTGGCCAAA ATTCGCAGTC CCCAACCTCC AATCACTCAC CAACCTCTTG TCCTCCAATT       360

TGTCCTGGCT ATCGCTGGAT GTGTCTGCGG CGTTTTATCA TATTCCTCTT CATCCTGCTG       420

CTATGCCTCA TCTTCTTGTT GGTTCTTCTG GACTACCAAG GTATGTTGCC CGTTTGTCCT       480

CTACTTCCAG GAACATCAAC CACCAGCACG GGACCATGCA AGACCTGCAC GATTCCTGCT       540

CAAGGAACCT CTATGTTTCC CTCTTGTTGC TGTACAAAAC CTTCGGACGG AAACTGCACT       600

TGTATTCCCA TCCCATCATC CTGGGCTTTC GCAAGATTCC TATGGGAGGG GGCCTCAGTC       660

CGTTTCTCCT GGCTCAGTTT ACTAGTGCCA TTTGTTCAGT GGTTCGTAGG GCTTTCCCCC       720

ACTGTTTGGC TTTCAGTTAT ATGGATGATG TGGTATTGGG GGCCAAGTCT GTACAACATC       780

TTGAGTCCCT TTTTACCTCT ATTACCAATT TTCTTTTGTC TTTGGGTATA CATTTGAACC       840

CTAATAAAAC CAAACGTTGG GGCTACTCCC TTAACTTCAT GGGATATGTA ATTGGCAGTT       900

GGGGTACTTT ACCGCAAGAA CATATTGTAC TAAAAATCAA GCAATGTTTT CGGAAACTGC       960

CTGTAAATAG ACCTATTGAC TGGAAAGTAT GTCAAAGAAT TGTGGGTCTT TTGGGCTTTG      1020

CTGCCCCTTT TACACAATGT GGCTATCCTG CCTTAATGCC TTTATATGCA TGTATACAAT      1080

CTAAGCAGGC TTTCACTTTC TCGCCAACTT ACAAGGCCTT TCTGTGTAAA CAATATCTGC      1140

ACCTTTACCC CGTTGCCCGG CGAACGGCTC TCTGCCAAGT ATTTGCTGAC GCAACCCCCA      1200

CTGGATGGGG CTTGGCCATA GGCCATCGGC GCATGCGTGG AACCTTTGTG GCTCCTCTGC      1260

CGATCCATAC TGCGGAACTC CTAGCAGCTT GTTTTGCTCG CAGCCGGTCT GGAGCGAAAC      1320

TCATCGGGAC TGACAACTCG GTTGTTCTCT CTCGGAAATA CACCTCATTC CCATGGCTGC      1380

TCGGGTGTGC TGCCAACTGG ATCCTGCGCG GGACGTACTT TGTTTACGTC CCGTCGGCGC      1440

TGAATCCCGC GGACGACCCG TCTCGCGGCC GTTTGGGCCT CATCCGTCCC CTTCTTCATC      1500

TGCGGTTCCG GCCGACCACG GGGCGCACCT CTCTTTACGC GGTCTCCCCG TCTGTGCCTT      1560

CTCATCTGCC GGACCGTGTG CACTTCGCTT CACCTCTGCA CGTCGCATGG AGACCACCGT      1620

GAACGCCGAT CAGGTCTTGC CCAAGGTCTT ACATAAGAGG ACTCTTGGAC TCTCAGCAAT      1680
```

-continued

```
GTCAACGTCC GACCTTGAGG CATACTTCAA AGACTGCTTG TTTAAAGACT GGGAGGACTT    1740

GGGGGAGGAG ATTAGGTTAA TGATCTTTGT ACTAGGAGGC TGTAGGCATA AATTGGTCTG    1800

TTCACCAGCA CCATGCAACT TTTTTCACCT CTGCCTAATC ATCTCATGTT CATGTCCTAC    1860

TGTTCACGCC TCCAAGCTGT GCCTTGGGTG GCTTTGGGGC ATGGACATTG ACCCGTATAA    1920

AGAATTTGGA GCTTCTGTGG AGTTACTCTC TTTTTTGCCT TCTGATTTCT TTCCTTCCAT    1980

TCGAGATCTC CTCGACACCG CCTCTGCTCT GTATAGGGAG GCCTTAGAGT CTCCGGAACA    2040

TTGTTCACCT CATCATACAG CACTCAGGCA AGCTATTCTG TGTTGGGGTG AGTTGATGAA    2100

TCTGGCCACC TGGGTGGGAA GTAATTTGGA AGACCCAGCA TCCAGGGAAC TAGTAGTCAG    2160

CTATGTCAAT GTTAATATGG GCCTAAAAAT CAGACAACTA TTGTGGTTTC ACATTTCCTG    2220

CCTTACTTTT GGAAGAGAAA CTGTTTTGGA GTATTTGGTA TCTTTTGGAG TGTGGATTCG    2280

CACTCCTCCC GCTTACAGAC CACCAAATGC CCCTATCTTA TCAACACTTC CGGAAACTAC    2340

TGTTGTTAGA CGACGAGGCA GGTCCCCTAG AAGAAGAACT CCCTCGCCTC GCAGACGAAG    2400

ATCTGAATCG CCGCGTCGCA GAAGATCTCA ATCTCGGGAA TCTCAATGTT AGTATCCCTT    2460

GGACTCATAA GGTGGGAAAC TTTACTGGGC TTTATTCTTC TACTGTACCT GTCTTTAATC    2520

CTGAGTGGCA AACTCCCTCC TTTCCTCACA TTCATTTACA GGAGGACATT ATTAATAGAT    2580

GTCAACAATA TGTGGGCCCT CTTACAGTTA ATGAAAAAAG GAGATTAAAA TTAATTATGC    2640

CTGCTAGGTT TTATCCTAAA CTTACCAAAT ATTTGCCCTT GGATAAAGGC ATTAAACCTT    2700

ATTATCCTGA ACATGCAGTT AATCATTACT TCAAAACTAG GCATTATTTA CATACTCTGT    2760

GGAAGGCGGG CATTCTATAT AAGAGAGAAA CTACACGCAG CGCCTCATTT TGTGGGTCAC    2820

CATATTCTTG GGAACAAGAG CTACAGCATG GGAGGTTGGT CTTCCAAACC TCGACAAGGC    2880

ATGGGGACGA ATCTTTCTGT TCCCAATCCT CTGGGATTCT TTCCCGATCA CCAGTTGGAC    2940

CCTGCGTTCG GAGCCAACTC AAACAATCCA GATTGGGACT TCAACCCCAA CAAGGATCGT    3000

TGGCCAGAGG CAAATCAGGT AGGAGCGGGA GCATTCGGGC CAGGGTACCC CCCACCACAC    3060

GGCGGTCTTT TGGGGTGGAG CCCTCAGGCT CAGGGCATAT TGACAACCGT GCCAGCAGCA    3120

CCTCCTCCTG CCTCCACCAA TCGGCAGTCA GGAAGACAGC CTACTCCCAT CTCTCCACCT    3180

CTAAGAGACA GTCATCCTCA GGCCATGCAG TGG                                 3213
```

(2) INFORMATION FOR SEQ ID NO: 289:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 289:

```
AACTCCACCA CATTTCACCA AGTCCTGCTA GATCCCAGAG TGAGGGGCCT ATATTTTCCT      60

CCTGGTGGCT CCAGTTCCGG AACAGTAAAC CCTGTTCCGA CTACTGCCTC ACCCATATCG     120

TCAATCTCCT CGAGGACTGG GGACCCTGCA CCGAACATGG AGAGCACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGGAGC ACCCACGTGT     300
```

-continued

```
CCTGGCCAAA ATTCGCAGTC CCCAACCTCC AATCACTCAC CAACCTCTTG TCCTCCAATT      360

TGTCCTGGCT ATCGCTGGAT GTGTCTGCGG CGTTTTATCA TATTCCTCTT CATCCTGCTG      420

CTATGCCTCA TCTTCTTGTT GGTTCTTCTG GACTACCAAG GTATGTTGCC CGTTTGTCCT      480

CTACTTCCAG GAACATCAAC CACCAGCACG GGACCATGCA AGACCTGCAC GATTCCTGCT      540

CAAGGAACCT CTATGTTTCC CTCTTGTTGC TGTACAAAAC CTTCGGACGG AAACTGCACT      600

TGTATTCCCA TCCCATCATC CTGGGCTTTC GCAAGATTCC TATGGGAGGG GGCCTCAGTC      660

CGTTTCTCCT GGCTCAGTTT ACTAGTGCCA TTTGTTCAGT GGTTCGTAGG GCTTTCCCCC      720

ACTGTTTGGC TTTCAGTTAT ATGGATGATG TGGTATTGGG GGCCAAGTCT GTACAACATC      780

TTGAGTCCCT TTTTACCTCT ATTACCAATT TTCTTTTGTC TTTGGGTATA CATTTGAACC      840

CTAATAAAAC CAAACGTTGG GGCTACTCCC TTAACTTCAT GGGATATGTA ATTGGCAGTT      900

GGGGTACTTT ACCGCAAGAA CATATTGTAC TAAAAATCAA GCAATGTTTT CGGAAACTGC      960

CTGTAAATAG ACCTATTGAC TGGAAAGTAT GTCAAAGAAT TGTGGGTCTT TTGGGCTTTG     1020

CTGCCCCTTT TACACAATGT GGCTATCCTG CCTTAATGCC TTTATATGCA TGTATACAAT     1080

CTAAGCAGGC TTTCACTTTC TCGCCAACTT ACAAGGCCTT TCTGTGTAAA CAATATCTGC     1140

ACCTTTACCC CGTTGCCCGG CGAACGGCTC TCTGCCAAGT ATTTGCTGAC GCAACCCCCA     1200

CTGGATGGGG CTTGGCCATA GGCCATCGGC GCATGCGTGG AACCTTTGTG GCTCCTCTGC     1260

CGATCCATAC TGCGGAACTC CTAGCAGCTT GTTTTGCTCG CAGCCGGTCT GGAGCGAAAC     1320

TCATCGGGAC TGACAACTCG GTTGTTCTCT CTCGGAAATA CACCTCATTC CCATGGCTGC     1380

TCGGGTGTGC TGCCAACTGG ATCCTGCGCG GGACGTACTT TGTTTACGTC CCGTCGGCGC     1440

TGAATCCCGC GGACGACCCG TCTCGCGGCC GTTTGGGCCT CATCCGTCCC CTTCTTCATC     1500

TGCGGTTCCG GCCGACCACG GGGCGCACCT CTCTTTACGC GGTCTCCCCG TCTGTGCCTT     1560

CTCATCTGCC GGACCGTGTG CACTTCGCTT CACCTCTGCA CGTCGCATGG AGACCACCGT     1620

GAACGCCGAT CAGGTCTTGC CCAAGGTCTT ACATAAGAGG ACTCTTGGAC TCTCAGCAAT     1680

GTCAACGTCC GACCTTGAGG CATACTTCAA AGACTGCTTG TTTAAAGACT GGGAGGACTT     1740

GGGGGAGGAG ATTAGGTTAA TGATCTTTGT ACTAGGAGGC TGTAGGCATA AATTGGTCTG     1800

TTCACCAGCA CCATGCAACT TTTTTCACCT CTGCCTAATC ATCTCATGTT CATGTCCTAC     1860

TGTTCACGCC TCCAAGCTGT GCCTTGGGTG GCTTTGGGGC ATGGACATTG ACCCGTATAA     1920

AGAATTTGGA GCTTCTGTGG AGTTACTCTC TTTTTTGCCT TCTGATTTCT TTCCTTCCAT     1980

TCGAGATCTC CTCGACACCG CCTCTGCTCT GTATAGGGAG GCCTTAGAGT CTCCGGAACA     2040

TTGTTCACCT CATCATACAG CACTCAGGCA AGCTATTCTG TGTTGGGGTG AGTTGATGAA     2100

TCTGGCCACC TGGGTGGGAA GTAATTTGGA AGACCCAGCA TCCAGGGAAC TAGTAGTCAG     2160

CTATGTCAAT GTTAATATGG GCCTAAAAAT CAGACAACTA TTGTGGTTTC ACATTTCCTG     2220

CCTTACTTTT GGAAGAGAAA CTGTTTTGGA GTATTTGGTA TCTTTTGGAG TGTGGATTCG     2280

CACTCCTCCC GCTTACAGAC CACCAAATGC CCCTATCTTA TCAACACTTC CGGAAACTAC     2340

TGTTGTTAGA CGACGAGGCA GGTCCCCTAG AAGAAGAACT CCCTCGCCTC GCAGACGAAG     2400

ATCTGAATCG CCGCGTCGCA GAAGATCTCA ATCTCGGGAA TCTCAATGTT AGTATCCCTT     2460

GGACTCATAA GGTGGGAAAC TTTACTGGGC TTTATTCTTC TACTGTACCT GTCTTTAATC     2520

CTGAGTGGCA AACTCCCTCC TTTCCTCACA TTCATTTACA GGAGGACATT ATTAATAGAT     2580

GTCAACAATA TGTGGGCCCT CTTACAGTTA ATGAAAAAAG GAGATTAAAA TTAATTATGC     2640

CTGCTAGGTT TTATCCTAAA CTTACCAAAT ATTTGCCCTT GGATAAAGGC ATTAAACCTT     2700
```

```
ATTATCCTGA ACATGCAGTT AATCATTACT TCAAAACTAG GCATTATTTA CATACTCTGT     2760

GGAAGGCGGG CATTCTATAT AAGAGAGAAA CTACACGCAG CGCCTCATTT TGTGGGTCAC     2820

CATATTCTTG GGAACAAGAG CTACAGCATG GGAGGTTGGT CTTCCAAACC TCGACAAGGC     2880

ATGGGGACGA ATCTTTCTGT TCCCAATCCT CTGGGATTCT TTCCCGATCA CCAGTTGGAC     2940

CCTGCGTTCG GAGCCAACTC AAACAATCCA GATTGGGACT TCAACCCCAA CAAGGATCGT     3000

TGGCCAGAGG CAAATCAGGT AGGAGCGGGA GCATTCGGGC CAGGGTACCC CCCACCACAC     3060

GGCGGTCTTT TGGGGTGGAG CCCTCAGGCT CAGGGCATAT TGACAACCGT GCCAGCAGCA     3120

CCTCCTCCTG CCTCCACCAA TCGGCAGTCA GGAAGACAGC CTACTCCCAT CTCTCCACCT     3180

CTAAGAGACA GTCATCCTCA GGCCATGCAG TGG                                 3213

(2) INFORMATION FOR SEQ ID NO: 290:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 290:

AACTCCACAA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGTCTC ACCCATATCG     120

TCAATCTTCT CGAGGACTGG GGACCCTGCA CCGAACATGG AGAGCACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGGAGC ACCCACGTGT     300

CCTGGCCAAA ATTCGCAGTC CCCAACCTCC AATCACTCAC CAACCTCTTG TCCTCCAATT     360

TGTCCTGGTT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGTG GCCCTCAGTC     660

CGTTTCTCCT GGCTCAGTTT ACTAGTGCCA TTTGTTCAGT GGTTCGCAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CTAATAAAAC CAAACGTTGG GGCTACTCCC TTAACTTCAT GGGATATGTA ATTGGAAGTT     900

GGGGTACTTT ACCACAGGAA CATATTGTAT TAAAACTCAA GCAATGTTTT CGAAAACTGC     960

CTGTAAATAG ACCTATTGAT TGGAAAGTAT GTCAAAGAAT TGTGGGTCTT TTGGGCTTTG    1020

CTGCCCCTTT TACACAATGT GGCTATCCTG CCTTGATGCC TTTGTATGCA TGTATACAAT    1080

CTAAGCAGGC TTTCACTTTC TCGCCAACTT ATAAGGCCTT TCTGTGTCAA CAATACCTGC    1140

ACCTTTACCC CGTTGCCCGG CAACGGTCAG GTCTCTGCCA AGTGTTTGCT GACGCAACCC    1200

CCACTGGATG GGGCTTGGCC ATAGGCCATC GGCGCATGCG TGGAACCTTT GTGGTTCCTC    1260

TGCCGATCCA TACTGCGGAA CTCCTAGCAG CTTGTTTTGC TCGCGACCGG TCTGGAGCAA    1320
```

```
AACTTATCGG GACTGACAAC TCGGTTGTCC TCTCTCGGAA ATACACCTCC TTCCCATGGC    1380

TGCTCGGGTG TGCTGCCAAC TGGATCCTGC GCGGGACGTC CTTTGTCTAC GTCCCGTCGG    1440

CGCTGAATCC CGCGGACGAC CCGTCTCGGG GCCGTTTGGG CCTCTACCGT CCCTTGCTTT    1500

CTCTGCCGTT CCAGCCGACC ACGGGGCGCA CCTCTCTTTA CGCGGTCTCC CCGTCTGTGC    1560

CTTCTCATCT GCCGGACCGT GTGCACTTCG CTTCACCTCT GCACGTCGCA TGGAGACCAC    1620

CGTGAACGGC CACCAGGTCT TGCCCAAGCT CTTACATAAG AGGACTCTTG GACTCTCAGC    1680

AATGTCAACA ACCGACCTTG AGGCATACTT CAAAGACTGT TTGTTTAAAG ACTGGGAGGA    1740

GTTGGGGGAG GAGATTAGGT TAAAGGTCTT TGTACTAGGA GGCTGTAGGC ATAAATTGGT    1800

CTGTTCACCA GCACCATGCA ACTTTTTCAC CTCTGCCTAA TCATCTCATG TTCATGTCCT    1860

ACTGTTCAAG CCTCCAAGCT GTGCCTTGGG TGGCTTTGGG GCATGGACAT TGACCCGTAT    1920

AAAGAATTTG GAGCTTCTGT GGAGTTACTC TCTTTTTTGC CTTCTGACTT CTTTCCTTCT    1980

ATTCGAGATC TCCTCGACAC CGCCTCTGCT CTGTATCGGG AGGCCTTAGA GTCTCCGGAA    2040

CATTGTTCAC CTCACCATAC AGCACTCAGG CAAGCTATTC TGTGTTGGGG TGAGTTGATG    2100

AATTTGGCCA CCTGGGTGGG AAGTAATTTG GAAGACCCAG CATCCAGGGA ATTAGTAGTC    2160

AGCTATGTCA ATGTTAATAT GGGCCTAAAA ATCAGACAAC TATTGTGGTT TCATATTTCC    2220

TGTCTTACTT TTGGAAGAGA AACTGTTCTT GAGTATTTGG TGTCTTTTGG AGTGTGGATT    2280

CGCACTCCTC CCGCTTACAG ACCACCAAAT GCCCCTATCT TATCAACACT TCCGAAAACT    2340

ACTGTTGTTA GACGACGAGG CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATCCC    2460

TTGGACTCAT AAGGTGGGAA ACTTTACTGG GCTTTATTCT TCTACTGTAC CTGTCCTTAA    2520

TCCTGAGTCC CAAACTCCCT CCTTTCCTAA CATTCATTTA CAGGAGGACA TTATTAATAG    2580

ATGTCAACAA TATGTGGGCC CTCTTACAGT TAATGAAAAA AGGAGATTAA AATTAATTAT    2640

GCCTGCTAGG TTCTATCCTA ACCTTACCAA ATATTTGCCC TTGGATAAAG GCATTAAACC    2700

TTATTATCCT GAACATGCAG TTAATCATTA CTTCAAAACT AGGCATTATT TACATACTCT    2760

GTGGAAGGCT GGCATTCTAT ATAAAAGAGA AACTACACGC AGCGCTTCAT TTTGTGGGTC    2820

ACCATATTCT TGGGAACAAG AGCTACGGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCGTT CGGAGCCAAC TCAAACAATC CAGATTGGGA CTTCAACCCC AACAAGGATC    3000

ACTGGCCAGA GGCAATCAAG GTAGGAGCGG GAGACTTCGG GCCAGGGTTC ACCCCACCAC    3060

ACGGCGGTCT TTTGGGGTGG AGCCCTCAGG CTCAGGGCAT ATTGACAACA GTGCCAGCAG    3120

CGCCTCCTCC TGTTTCCACC AATCGGCAGT CAGGAAGACA GCCTACTCCC ATCTCTCCAC    3180

CTCTAAGAGA CAGTCATCCT CAGGCCATGC AGTGG                              3215
```

(2) INFORMATION FOR SEQ ID NO: 291:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 291:

```
AACTCCACAA CATTCCACCA AGCTCTGCTA GATCCCAGAG TGAGGGGCCT ATATTTTCCT      60
GCTGGTGGCT CCAGTTCCGG AACAGTAAAC CCTGTTCCGA CTACTGCCTC ACCCATATCG     120
TCAATCTTCT CGAGGACTGG GGACCCTGCA CCGAACATGG AGAGCACAAC ATCAGGATTC     180
CTAGGACCCC TGCTCGTGTT ACAGGCGGGG TTTTTCTTGT TGACAAGAAT CCTCACAATA     240
CCACAGAGTC TAGACTCGTG GTGGACTTCT CTCAATTTTC TAGGGGAGC ACCCACGTGT      300
CCTGGCCAAA ATTCGCAGTC CCCAACCTCC AATCACTCAC CAACCTCTTG TCCTCCAATT     360
TGTCCTGGCT ATCGCTGGAT GTGTCTGCGG CGTTTTATCA TATTCCTCTT CATCCTGCTG     420
CTATGCCTCA TCTTCTTGTT GGTTCTTCTG GACTACCAAG GTATGTTGCC CGTTTGTCCT     480
CTACTTCCAG GAACATCAAC TACCAGCACG GGACCATGCA AGACCTGCAC GATTCCTGCT     540
CAAGGAACCT CTATGTTTCC CTCTTGTTGG TGTACAAAAC CTTCGGACGG AAACTGCACT     600
TGTATTCCCA TCCCATCATC CTGGGCTTTC GCAAGATTCC TATGGGAGTG GCCTCAGTC     660
CGTTTCTCCT GGCTCAGTTT ACTAGTGCCA TTTGTTCAGT GGTTCGCAGG GCTTTCCCCC     720
ACTGTTTGGC TTTCAGTTAT ATGGATGATG TGGTATTGGG GGCCAAGTCT GTACAACATC     780
TTGAGTCCCT TTTTACCTCT ATTACCAATT TTCTTTTGTC TTTGGGTATA CATTTGAACC     840
CTAATAAAAC CAAACGTTGG GGCTACTCCC TTAACTTCAT GGGATATGTA ATTGGAAGTT     900
GGGGTACTTT ACCACAGGAA CATATTGTAT TAAAACTCAA GCAATGTTTT CGGAAACTGC     960
CTGTAAATAG ACCTATTGAT TGGAAAGTAT GTCAAAGAAT TGTGGGTCTT TTGGGCTTTG    1020
CTGCCCCTTT TACACAATGT GGCTATCCTG CCTTGATGCC TTTATATGCA TGTATACAAT    1080
CTAAGCAGGC TTTCACTTTC TCGCCAACTT ATAAGGCCTT TCTGTGTCAA CAATACCTGC    1140
ACCTTTACCC CGTTGCCCGG CAACGGTCAG GTCTCTGCCA AGTGTTTGGT GACGCAACCC    1200
CCACTGGATG GGGCTTGGCC ATAGGCCATC GGCGCATGCG TGGAACCTTT GTGGCTCCTC    1260
TGCCGATCCA TACTGCGGAA CTCCTAGCAG CTTGTTTTGC TCGCAGCCGG TCTGGAGCAA    1320
AACTTATCGG GACTGACAAC TCTGTTGTCC TCTCTCGGAA ATACACCTCC TTCCCATGGC    1380
TGCTCGGGTG TGCTGCCAAC TGGATCCTGC GCGGGACGTC CTTTGTCTAC GTCCCGTCGG    1440
CGCTGAATCC CGCGGACGAC CCGTCTCGGG GCCGTTTGGG CCTCTACCGT CCCCTTCTTC    1500
ATCTGCCGTT CCAGCCGACC ACGGGGCGCA CCTCTCTTTA CGCGGTCTCC CCGTCTGTGC    1560
CTTCTCATCT GCCGGTCCGT GTGCACTTCG CTTCACCTCT GCACGTCGCA TGGAGACCAC    1620
CGTGAACGCC CACCAGGTCT TGCCTAAGCT CTTACATAAG AGGACTCTTG GACTCTCAGC    1680
AATGTCAACG ACCGACCTTG AGGCATACTT CAAAGACTGT TTGTTTAAAG ACTGGGAGGA    1740
GTTGGGGGAG GAGATTAGGT TAAAGGTCTT TGTACTAGGA GGCTGTAGGC ATAAATTGGT    1800
CTGTTCACCA GCACCATGCA ACTTTTTCAC CTCTGCCTAA TCATCTCATG TTCATGTCCT    1860
ACTGTTCAAG CCTCCAAGCT GTGCCTTGGG TGGCTTTGGG GCATGGACAT TGACCCGTAT    1920
AAAGAATTTG GAGCTTCTGT GGAGTTACTC TCTTTTTTGC CTTCTGACTT CTTTCCTTCT    1980
ATTCGAGATC TCCTCGACAC CGCCTCTGCT CTGTATCGGG AGGCCTTAGA GTCTCCGGAA    2040
CATTGTTCAC CTCACCATAC AGCACTCAGG CAAGCTATCC TGTGTTGGGG TGAGTTGATG    2100
AATTTGGCCA CCTGGGTGGG AAGTAATTTG GAAGACCCAG CATCCAGGGA ATTAGTAGTC    2160
AGCTATGTCA ATGTTAATAT GGGCCTAAAA ATCAGACAAC TATTTGTGGTT TCACATTTCC    2220
TGTCTTACTT TTGGAAGAGA AACTGTTCTT GAGTATTTGG TGTCTTTTGG AGTGTGGATT    2280
```

```
CGCACTCCTC CCGCTTACAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATCCC    2460

TTGGACTCAT AAGGTGGGAA ACTTTACTGG GCTTTATTCT TCTACTGTAC CTGTCTTTAA    2520

TCCTGAGTGC CAAACTCCCT CCTTTCCTAA CATTCATTTA CAAGAGGATA TTATTAATAG    2580

ATGTCAACAA TATGTGGGCC CTCTTACAGT TAATGAAAAA AGGAGATTAA AATTAATTAT    2640

GCCTGCTAGG TTCTATCCTA ACCTTACCAA ATATTTGCCC TTGGATAAAG GCATTAAACC    2700

TTATTATCCT GAACATGCAG TTAATCATTA CTTCAAAACT AGGCATTATT TACATACGCT    2760

GTGGAAGGCT GGCATTCTAT ATAAAAGAGA AACTACACGC AGCGCTTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCGTT CGGAGCCAAC TCAAACAATC CAGATTGGGA CTTCAACCCC AACAAGGATC    3000

ACTGGCCAGA CGGAATCAAG GTAGGAGCGG GAGACTTCGG GCCAGGGTTC ACCCCACCAC    3060

ACGGCGGTCT TTTGGGGTGG AGCCCTCAGG CTCAGGGCAT CTTGACAACA GTGCCAGCAG    3120

CTCCTCCTCC TGCCTCCACC AATCGGCAGT CAGGAAGACA GCCTACTCCC ATCTCTCCAC    3180

CTCTAAGAGA CAGTCATCCT CAGGCCATGC AGTGG                              3215

(2) INFORMATION FOR SEQ ID NO: 292:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 292:

AACTCCACAA CATTCCACCA AGCTCTGCTA GATCCCAGAG TGAGGGGCCT ATATTTTCCT     60

GCTGGTGGCT CCAGTTCCGG AACAGTAAAC CCTGTTCCGA CTACTGCCTC ACCCATATCG    120

TCAATCTTCT CGAGGACTGG GGACCCTGCA CCGAACATGG AGAGCACAAC ATCAGGATTC    180

CTAGGACCCC TGCTCGTGTT ACAGGCGGGG TTTTTCTTGT TGACAAGAAT CCTCACAATA    240

CCACAGAGTC TAGACTCGTG GTGGACTTCT CTCAATTTTC TAGGGGGAGC ACCCACGTGT    300

CCTGGCCAAA ATTCGCAGTC CCCAACCTCC AATCACTCAC CAACCTCTTG TCCTCCAACT    360

TGTCCTGGCT ATCGCTGGAT GTGTCTGCGG CGTTTTATCA TATTCCTCTT CATCCTGCTG    420

CTATGCCTCA TCTTCTTGTT GGTTCTTCTG GACTACCAAG GTATGTTGCC CGTTTGTCCT    480

CTACTTCCAG GAACATCAAC TACCAGCACG GGACCATGCA GAACCTGCAC GATTCCTGCT    540

CAAGGAACCT CTATGTTTCC CTCTTGTTGC TGTACAAAAC CTTCGGACGG AAACTGCACT    600

TGTATTCCCA TCCCATCATC CTGGGCTTTC GCAAGATTCC TATGGGAGTG GCCTCAGTC     660

CGTTTCTCCT GGCTCAGTTT ACTAGTGCCA TTTGTTCAGT GGTTCGTAGG CTTTCCCCC     720

ACTGTTTGGC TTTCAGCTAT ATGGATGATG TGGTATTGGG GGCCAAGTCT GTACAACATC    780

TTGAGTCCCT TTTTACCTCT ATTACCAATT TTCTTTTGTC TTTGGGTATA CATTTGAACC    840

CTAATAAAAC CAAACGTTGG GGCTACTCCC TTAACTTCAT GGGATATGTA ATTGGAAGTT    900
```

```
GGGGTACTTT ACCGCAGGAA CATATTGTAC AAAAACTCAA GCAATGTTTT CGAAAATTGC      960

CTGTAAATAG ACCTATTGAT TGGAAAGTAT GTCAAAGAAT TGTGGGTCTT TTGGGCTTTG     1020

CTGCCCCTTT TACACAATGT GGCTATCCTG CCTTGATGCC TTTATATGCA TGTATACAAT     1080

CTAAGCAGGC TTTCACTTTC TCGCCAACTT ACAAGGCCTT TCTGTGTAAA CAATATCTAA     1140

ACCTTTACCC CGTTGCCCGG CAACGGTCAG GTCTCTGCCA AGTGTTTGCT GACGCAACCC     1200

CCACGGGTTG GGGCTTGGCC ATAGGCCATC GGCGCATGCG TGGAACCTTT GTGGCTCCTC     1260

TGCCGATCCA TACTCGGAA CTCCTAGCAG CTTGTTTTGC TCGCAGCCGG TCTGGAGCGA      1320

AACTTATCGG AACCGACAAC TCAGTTGTCC TCTCTCGGAA ATACACCTCC TTTCCATGGC     1380

TGCTAGGCTG TGCTGCCAAC TGGATCCTGC GCGGGACGTC CTTTGTCTAC GTCCCGTCGG     1440

CGCTGAATCC CGCGGACGAC CCGTCTCGGG GCCGTTTGGG CCTCTACCGT CCCCTTCTTC     1500

ATCTGCCGTT CCGGCCGACC ACGGGGCGCA CCTCTCTTTA CGCGGTCTCC CCGTCTGTGC     1560

CTTCTCATCT GCCGGACCGT GTGCACTTCG CTTCACCTCT GCACGTAGCA TGGAGACCAC     1620

CGTGAACGCC CACCAGGTCT TGCCCAAGGT CTTACACAAG AGGACTCTTG GACTCTCACC     1680

AATGTCAACG ACCGACCTTG AGGCATACTT CAAAGACTGT TTGTTTAAAG ACTGGGAGCA     1740

GTTGGGGGAG GAGATTAGGT TAAAGGTCTT TGTACTAGGA GGCTGTAGGC ATAAATTGGT     1800

CTGTTCACCA GCACCATGCA ACTTTTTCCC CTCTGCCTAA TCATCTCATG TTCATGTCCT     1860

ACTGTTCAAG CCTCCAAGCT GTGCCTTGGG TGGCTTTGGG GCATGGACAT TGACCCGTAT     1920

AAAGAATTTG GAGCTTCTGT GGAGTTACTC TCTTTTTTGC CTTCTGACTT CTTTCCTTCT     1980

ATTCGAGATC TCCTCGACAC CGCCTCTGCT CTGTATCGGG AGGCCTTAGA GTCTCCGGAA     2040

CATTGTTCAC CTCACCATAC AGCACTCAGG CAAGCTATTC TGTGTTGGGG TGAGTTGATG     2100

AATCTGGCCA CCTGGGTGGG AAGTAATTTG GAAGACCCAG CATCCAGGGA ATTAGTAGTC     2160

AGCTATGTCA ATGTTAATAT GGGCCTAAAA ATTAGACAAC TATTGTGGTT TCACATTTCC     2220

TGCCTTACTT TTGGAAGAGA AACTGTCCTT GAGTATTTGG TGTCTTTTGG AGTGTGGATT     2280

CGCACTCCTC CCGCTTACAG ACCACCAAAT GCCCCTATCT TATCAACACT TCCGAAACT      2340

ACTGTTGTTA GACGACGAGG CAGGTCCCCT AGAAGAAGAA CTCCCTCGCC TCGCAGACGA     2400

AGGTCTCAAT CGCCGCGTCG CAGAAGATCT CAATCTCGGG AATCTCAATG TTAGTATCCC     2460

TTGGACTCAT AAGGTGGGAA ACTTTACTGG GCTTTATTCT TCTACTGTAC CTGTCTTTAA     2520

TCCTGATTGG AAAACTCCCT CCTTTCCTCA CATTCATTTA CAGGAGGACA TTATTAATAG     2580

ATGTCAACAA TATGTGGGCC CTCTGACAGT TAATGAAAAA AGGAGATTAA AATTAATTCC     2640

GCCTGCTAGG TTCTATCCTA ACCTTACCAA ATATTTGCCC TTGGACAAAG GCATTAAACC     2700

GTATTATCCT GAATATGCAG TTAATCATTA CTTCAAAACT AGGCATTATT TACATACTCT     2760

GTGGAAGGCT GGCATTCTAT ATAAGAGAGA AACTACACGC AGCGCCTCAT TTTGTGGGTC     2820

ACCATATTCT TGGGAACAAG AGCTACAGCA TGGGAGGTTG GTCTTCCAAA CCTCGACAAG     2880

GCATGGGGAC GAATCTTTCT GTTCCCAATC CTCTGGGATT CTTTCCCGAT CACCAGTTGG     2940

ACCCTGCGTT CGGAGCCAAC TCAAACAATC CAGATTGGGA CTTCAACCCC AACAAGGATC     3000

ACTGGCCAGA GGCAAATCAG GTAGGAGCGG GAGCATTTGG TCCAGGGTTC ACCCCACCAC     3060

ACGGAGGCCT TTTGGGGTGG AGCCCTCAGG CTCAGGGCAT ATTGACAACA CTGCCAGCAG     3120

CACCTCCTCC TGCCTCCACC AATCGGCAGT CAGGAAGACA GCCTACTCCC ATCTCTCCAC     3180

CTCTAAGAGA CAGTCATCCT CAGGCCATGC AGTGG                                3215
```

(2) INFORMATION FOR SEQ ID NO: 293:

(i) SEQUENCE CHARACTERISTICS:
        (A) LENGTH: 3188 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 293:

```
AATTCCACAA CATTCCACCA AGCTCTGCTA GATCCCAGAG TGAGGGGCCT ATATTTTCCT     60
GCTGGTGGCT CCAGTTCCGG AACAGTAAAC CCTGTTCCGA CTACTGCCTC ACCCATATCG    120
TCAATCTTCT CGAGGACTGG GGACCCTGCA CCGAACATGG AGAACACAAC ATCAGGATTC    180
CTAGGACCCC TGCTCGTGTT ACAGGCGGGG TTTTTCTTGT TGACAAGAAT CCTCACAATA    240
CCACAGAGTC TAGACTCGTG GTGGACTTCT CTCAATTTTC TAGGGGAGC ACCCACGTGT     300
CCTGGCCAAA ATTCGCAGTC CCCAACCTCC AATCACTCAC CAACCTCTTG TCCTCCAATT    360
TGTCCTGGCT ATCGCTGGAT GTGTCTGCGG CGTTTTATCA TATTCCTCTT CATCCTGCTG    420
CTATGCCTCA TCTTCTTGTT GGTTCTTCTG GACTACCAAG GTATGTTGCC CGTTTGTCCT    480
CTACTTCCAG GAACATCAAC CACCAGCACG GGGCCATGCA AGACCTGCAC GATTCCTGCT    540
CAAGGAACCT CTATGTTTCC CTCTTGTTGC TGTACAAAAC CTTCGGACGG AAACTGCACT    600
TGTATTCCCA TCCCATCATC CTGGGCTTTC GCAAGATTCC TATGGGAGTG GCCTCAGTC     660
CGTTTCTCCT GGCTCAGTTT ACTAGTGCCA TTTGTTCAGT GGTTCGTAGG GCTTTCCCCC    720
ACTGTTTGGC TTTCAGTTAT ATGGATGATG TGGTATTGGG GGCCAAGTCT GTACAACATC    780
TTGAGTCCCT TTTTACCTCT ATTACCAATT TTCTTTTGTC TTTGGGTATA CATTTAAACC    840
CTAATAAAAC CAAACGTTGG GGCTACTCCC TTAACTTCAT GGGATATGTA ATTGGAAGTT    900
GGGGTACTTT ACCGCAGGAA CATATTGTAC TAAAACTCAA GCAATGTTTT CGAAAATTGC    960
CTGTAAATAG CCCTATTGAT TGGAAAGTAT GTCAAAGAAT TGTGGGTCTT TTGGGCTTTG   1020
CTGCCCCTTT TACACAATGC GGCTATCCTG CCTTGATGCC TTTATATGCA TGTATACAAT   1080
CTAAGCAGGC TTTCACTTTC TCGCCAACTT ATAAGGCCTT TCTGTGTAAA CAATATCTGA   1140
ACCTTTACCC CGTTGCCCGG CAACGGTCAG GTCTCTGCCA AGTGTTTGCT GACGCAACCC   1200
CCACTGGATG GGGCTTGGCC ATAGGCCATC GGCGCATGCG TGGAACCTTT GTGGCTCCTC   1260
TGCCGATCCA TACTGCGGAA CTCCTAGCAG CTTGTTTTGC TCGCAGCCGG TCTGGAGCGA   1320
AACTTATCGG AACCGACAAC TCTGTTGTCC TCTCTCGGAA ATACACCTCC TTTCCATGGC   1380
TGCTAGGGTG TGCTGCCAAC TGGATCCTGC GCGGGACGTC CTTTGTCTAC GTCCCGTCGG   1440
CGCTGAATCC CGCGGACGAC CCGTCTCGGG GCCGTTTGGG GCTCTACCGT CCCCTTCTTC   1500
TTCTGCCGTT CCGGCCGACC ACGGGGCGCA CCTCTCTTTA CGCGGTCTCC CCGTCTGTGC   1560
CTTCTCATCT GCCGGACCGT GTGCACTTCG CTTCACCTCT GCACGTCGCA TGGAGACCAC   1620
CGTGAACGCC CACCAGGTCT TGCCCAAGGT CTTACATAAG AGGACTCTTG GACTCTCAGC   1680
CATGTCAACG ACCGACCTTG AGGCATACTT CAAAGACTGT GTGTTTAAAG ACTGGGAGGA   1740
GTTGGGGGAG GAGATTAGGT TAAAGGTCTT TGTACTAGGA GGCTGTAGGC ATAACTTTTT   1800
CACCTCTGCC TAATCATCTC ATGTTCATGT CCTACTGTTC AAGCCTCCAA GCTGTGCCTT   1860
GGGTGGCTTT GGGGCATGGA CATTGACCCG TATAAAGAAT TTGGAGCATC TGTGGAGTTA   1920
```

```
CTCTCTTTTT TGCCTTCTGA CTTCTTTCCG TCTATTCGAG ATCTCCTTGA CACCGCCTCT    1980

GCTCTGTATC GGGAGGCCTT AGAGTCTCCG GAACATTGTT CACCTCACCA TACAGCACTC    2040

AGGCAAGCTA TTCTGTGTTG GGGTGAGTTA ATGAATCTGG CCACCTGGGT GGGAAGTAAT    2100

TTGGAAGACC CAGCATCCAG GGAATTAGTA GTCAGCTATG TCAATGTTAA TATGGGCCTA    2160

AAAATCAGAC AACTATTGTG GTTTCACATT TCCTGCCTTA CTTTTGGAAG AGAAACTGTT    2220

TTGGAGTATT TGGTATCTTT TGGAGTGTGG ATTCGCACTC CTCCCGCTTA CAGACCACCA    2280

AATGCCCCTA TCTTATCAAC ACTTCCGGAA ACTACTGTTG TTAGACGACG AGGCAGGTCC    2340

CCTAGAAGAA GAACTCCCTC GCCTCGCAGA CGAAGGTCTC AATCGCCGCG TCGCAGAAGA    2400

TCTCAATCTC GGGAATCTCA ATGTTAGTAT CCCTTGGACT CATAAGGTGG GAAACTTTAC    2460

TGGGCTTTAT TCTTCTACTG TACCTGTCTT TAATCCCGAG TGGCAAACTC CCTCCTTTCC    2520

TCACATTCAT TTACAGGAGG ACATTATTAA TAGATGTCAA CAATATGTGG GCCCTCTTAC    2580

GGTTAATGAA AAAAGGAGAT TAAAATTAAT TATGCCTGCT AGGTTCTATC CTAACCTTAC    2640

TAAATATTTG CCCTTAGACA AAGGCATTAA ACCGTATTAT CCTGAACATG CAGTTAATCA    2700

TTACTTCAAA ACTAGGCATT ATTTACATAC TCTGTGGAAG GCTGGCATTC TATATAAGAG    2760

AGAAACTACA CGCAGCGCCT CATTTTGTGG GTCACCATAT TCTTGGGAAC AAGAGCTACA    2820

GCATGGGAGG TTGGTCTTCC AAACCTCGAC AAGGCATGGG GACGAATCTT TCTGTTCCCA    2880

ATCCTCTGGG ATTCTTTCCC GATCACCAGT TGGACCCTGC GTTCGGAGCC AACTCAAACA    2940

ATCCAGATTG GGACTTCAAC CCCAACAAGG ATCAATGGCC AGAGGCAAAT CAGGTAGGAG    3000

CGGGAGCATT CGGGCCAGGG TTCACCCCAC CACACGGCGG TCTTTTGGGG TGGAGCCCTC    3060

AGGCTCAGGG CATATTGACA ACAGTGCCAG CAGCACCTCC TCCTGCCTCC ACCAATCGGC    3120

AGTCAGGAAG ACAGCCTACT CCCATCTCTC CACCTCTAAG AGACAGTCAT CCTCAGGCCA    3180

TGCAGTGG                                                              3188

(2) INFORMATION FOR SEQ ID NO: 294:

(i) SEQUENCE CHARACTERISTICS:
        (A) LENGTH: 3214 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 294:

AACTCCACAA CATTCCACCA AGCTCTGCTA GACCCCAGAG TGAGGGGCCT ATACTTTCCT      60

GCTGGTGGCT CCAGTTCCGG AACAGTAAAC CCTGTTCCGA CTACTGCCTC ACCCATATCG    120

TCAATCTCCT CGAGGACTGG GGACCCTGCA CCGAACATGG AGAACACAAC ATCAGGATTC    180

CTAGGACCCC TGCTCGTGTT ACAGGCGGGG TTTTTCTTGT TGACAAGAAT CCTCACAATA    240

CCACAGAGTC TAGACTCGTG GTGGACTTCT CTCAATTTTC TAGGGGAGC ACCCACGTGT    300

CCTGGCCAAA ATTCGCAGTC CCCAACCTCC AATCACTCAC CAACCTCTTG TCCTCCAATT    360

TGTCCTGGCT ATCGCTGGAT GTGTCTGCGG CGTTTTATCA TATTCCTCTT CATCCTGCTG    420

CTATGCCTCA TCTTCTTGTT GGTTCTTCTG GACTACCAAG GTATGTTGCC CGTTTGTCCT    480

CTACTTCCAG GAACATCAAC TACCAGCACG GGACCATGCA AGACCTGCAC GATTCCTGCT    540
```

| | |
|---|---|
| CAAGGAACCT CTATGTTTCC CTCTTGTTGC TGTACAAAAC CTTCGGACGG AAACTGCACT | 600 |
| TGTATTCCCA TCCCATCATC CTGGGCTTTC GCAAGATTCC TATGGGAGGG GGCCTCAGTC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAACATC | 780 |
| TTGAGTCCCT TTTTACCTCT ATTACCAATT TTCTTTTGTC TTTGGGTATA CATTTAAACC | 840 |
| CTAATAAAAC CAAACGTTGG GGCTACTCCC TTAACTTCAT GGGATATGTA ATTGGATGTT | 900 |
| GGGGTACTTT ACCGCAAGAA CATATTGTAC TAAAAATCAA GCAATGTTTT CGAAAACTGC | 960 |
| CTGTAAATAG ACCTATTGAT TGGAAAGTAT GTCAGAGACT TGTGGGTCTT TTGGGCTTTG | 1020 |
| CTGCCCCTTT TACACAATGT GGCTATCCTG CCTTAATGCC TTTATATGCA TGTATACAAT | 1080 |
| CTAAGCAGGC TTTCACTTTC TCGCCAACTT ACAAGGCCTT TCTGTGTAAA CAATATCTGA | 1140 |
| ACCTTTACCC CGTTGCCCGG CAACGGTCAG GTCTCTGCCA AGTGTTTGCT GACGCAACCC | 1200 |
| CCACTGGATG GGCTTGGCT ATCGGCCATA GCCGCATGCG CGGACCTTTG TGGCTCCTCT | 1260 |
| GCCGATCCAT ACTGCGGAAC TCCTAGCAGC TTGTTTTGCT CGCAGGCGGT CTGGAGCGAA | 1320 |
| ACTTATCGGC ACCGACAACT CTGTTGTCCT CTCTCGGAAA TACACCTCCT TTCCATGGCT | 1380 |
| GCTAGGGTGT GCTGCCAACT GGATCCTGCG CGGGACGTCC TTTGTCTACG TCCCGTCGGC | 1440 |
| GCTGAATCCC GCGGACGACC CGTCTCGGGG CCGTTTGGGA CTCTACCGTC CCCTTCTTCA | 1500 |
| TCTGCCGTTC CGGCCGACCA CGGGGCGCAC CTCTCTTTAC GCGGTCTTTT TGTCTGTGCC | 1560 |
| TTCTCATCTG CCGGTCCGTG TGCACTTCGC TTCACCTCTG CACGTCGCAT GGAGACCACC | 1620 |
| GTGAACGCCC ACCAGGTCTT GCCCAAGGTC TTACATAAGA GGACTCTTGG ACTCTCAGCG | 1680 |
| ATGTCAACGA CCGACCTTGA GGCATACTTC AAAGACTGTT TGTTTAAGGA CTGGGAGGAG | 1740 |
| TTGGGGAGG AGATTAGGTT AAAGGTCTTT GTACTAGGAG GCTGTAGGCA TAAATTGGTC | 1800 |
| TGTTCACCAG CACCATGCAA CTTTTTCACC TCTGCCTAAT CATCTCATGT TCATGTCCTA | 1860 |
| CTGTTCAAGC CTCCAAGCTG TGCCTTGGGT GGCTTTGGGG CATGGACATT GACCCGTATA | 1920 |
| AAGAATTTGG AGCTTCTGTG GAGTTACTCT CTTTTTTGCC TTCTGACTTC TTTCCTTCTA | 1980 |
| TTCGAGATCT CCTCGACACC GCCTCAGCTC TATATCGGGA GGCCTTAGAG TCTCCGGAAC | 2040 |
| ATTGTTCTCC TCATCATACA GCACTCAGGC AAGCTATTCT GTGTTGGGGT GAGTTGATGA | 2100 |
| ATCTGGCCAC CTGGGTGGGA AGTAATTTGG AAGACCCAGC ATCCAGGGAA TTAGTAGTCA | 2160 |
| GCTATGTCAA TGTTAATATG GGCCTAAAAA TCAGACAACT ACTGTGGTTT CACATTTCCT | 2220 |
| GTCTTACTTT TGGAAGAGAA ACTGTTCTTG AGTATTTGGT GTCTTTTGGA GTGTGGATTC | 2280 |
| GCACTCCTCC TGCTTACAGA CCACCAAATG CCCCTATCTT ATCAACACTT CCGGAAACTA | 2340 |
| CTGTTGTTAG ACGACGAGGC AGGTCCCCTA GAAGAAGAAC TCCCTCGCCT CGCAGACGAA | 2400 |
| GGTCTCAATC GCCGCGTCGC AGAAGATCTC AATCTCGGGA ATCTCAATGT TAGTATCCCT | 2460 |
| TGGACTCATA AGGTGGGAAA CTTTACTGGG CTTTATTCTT CTACTGTACC TGTCTTTAAT | 2520 |
| CCTGAGTGGC AAACTCCCTC CTTTCCTCAC ATTCATTTAC AGGAGGACAT TATTAATAGA | 2580 |
| TGTCAACAAT ATGTGGGCCC TCTTACAGTT AATGAAAAAA GGAGATTAAA ATTAATTATG | 2640 |
| CCTGCTAGGT TCTATCCTAA CCTTACCAAA TATTTGCCAT GGACAAAGG CATTAAACCA | 2700 |
| TATTATCCTG AACATGCAGT TAATCATTAC TTCAAAACTA GGCATTATTT ACATACTCTG | 2760 |
| TGGAAGGCGG GCATTCTATA TAAGAGAGAA ACTACACGCA GTGCCTCATT CTGTGGGTCA | 2820 |
| CCATATTCTT GGGAACAAGA GCTACAGCAT GGGAGGTTGG TCTTCCAAAC CTCGACAAGG | 2880 |

```
CATGGGACG AATCTTTCTG TTCCCAATCC TCTGGGATTC TTTCCCGATC ACCAGTTGGA    2940

CCCTGCGTTC GGAGCCAACT CACACAATCC CGATTGGGAC TTCAACCCCA ACAAGGATCA    3000

TTGGCCAGAG GCAAATCAGG TAGGAGCGGG AGCATTCGGG CCAGGGTTCA CCCCACCACA    3060

CGGCGGTCTT TTGGGGTGGA GCCCGCAGGC TCAGGGCGTA TTGACAACCG TGCCAGTAGC    3120

ACCTCCTCCT GCCTCCACCA ATCGGCAGTC AGGAAGACAG CCTACTCCCA TCTCTCCACC    3180

TCTAAGAGAC AGTCATCCTC AGGCCATGCA GTGG                               3214
```

(2) INFORMATION FOR SEQ ID NO: 295:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 295:

```
AACTCCACAA CATTCCACCA AGCTCTGCTA GACCCCAGAG TGAGGGGCCT ATACTTTCCT      60

GCTGGTGGCT CCAGTTCCGG AACAGTAAAC CCTGTTCCGA CTACTGCCTC ACCCATATCG     120

TCAATCTTCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TACACTCGTG GTGGACTTCT CTCAATTTTC TAGGGGCAGC ACCCACGTGT     300

CTTGGCCAAA ATTCGCAGTC CCCAACCTCC AATCACTCAC CAACCTCTTG TCCTCCAATT     360

TGTCCTGGTT ATCGTTGGAT GTGTCTGCGG CGTTTTATCA TATTCCTCTT CATCCTGCTG     420

CTATGCCTCA TCTTCTTGTT GGTTCTTCTG GACTACCAAG GTATGTTGTC TGTTTGTCCT     480

CTACTTCCAA GAACATCAAC TACCAGCACG GGACCATGCA AGACCTGCAC GATTCCTGCT     540

CAAGGAACCT CTATGTTTCC CTCTTCTTGC TGTACAAAAC CTTCGGACGG AAACTGCACT     600

TGTATTCCCA TCCCATCATC TTGGGCTTTC GCAAGATTCC TATGGGAGTG GCCTCAGTC      660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CCAATAAAAC CAAACGTTGG GGCTATTCCC TTAATTTCAT GGGATATGTA ATTGGATGTT     900

GGGGTACTTT ACCGCAAGAA CATATTGTAC TAAAAATCAA GCAATGTTTT CGAAAACTGC     960

CTGTAAATAG ACCTATTGAT TGGAAAGTAT GTCAGAGAAT TGTGGGTCTT TTGGGCTTTG    1020

CTGCCCCTTT TACACAATGT GGCTATCCTG CCTTGATGCC TTTATATGCA TGTATACAAT    1080

CTAAGCAAGC TTTCACTTTC TCGCCAACTT ACAAGGCCTT TCTGTGTAAA CAATATCTGA    1140

ACCTTTACCC CGTTGCCCGG CAACGGTCAG GTCTCTGCCA AGTGTTTGCT GACGCAACCC    1200

CCACTGGATG GGGCTTGGCT ATTGGCCATC GCCGCATGCG TGGAACCTTT GTGGCTCCTC    1260

TGCCGATCCA TACTGCGGAA CTCCTGGCAG CCTGTTTTGC TCGCAGCCGG TCTGGAGCAA    1320

AACTTATCGG AACCGACAAC TCTGTTGTCC TCTCTCGGAA ATACACCTCC TTTCCATGGC    1380

TGCTCGGGTG TGCTGCCAAC TGGATCCTGC GCGGGACGTC CTTTGTCTAC GTCCCGTCGG    1440

CGCTGAATCC CGCGGACGAC CCGTCTCGGG GCCGTTTGGG CCTCTATCGT CCCCTTCTTC    1500
```

-continued

```
ATCTACCGTT CCGGCCGACC ACGGGGCGCA CCTCTCTTTA CGCGGTCTCC CCGTCTGTGC      1560

CTTCTCATCT GCCGGACCGT GTGCACTTCC CTTCACCTCT GCACGTCGCA TGGAGACCAC      1620

CGTGAACGCC CACCAGGTCT TGCCCAAGGT CTTACATAAG AGCACTCTTG GACTCTCAGC      1680

AATGTCAACG ACCGACCTTG AGGCATACTT CAAAGACTGT TTGTTTAAGG ACTGGGAGGA      1740

GTTGGGGGAG GAGATTAGGT TAAAGGTCTT TGTACTGGGA GGCTGTAGGC ATAAATTGGT      1800

CTGTTCACCA GCACCATGCA ACTTTTTCAC CTCTGCCTAA TCATCTCATG TTCATGTCCT      1860

ACTGTTCAAG CCTCCAAGCT GTGCCTTGGG TGGCTTTGGG GCATGGACAT TGACCCGTAT      1920

AAAGAATTTG GAGCTTCTGT GGAGTTACTC TCTTTTTTGC CTTCTGACTT CTTTCCTTCT      1980

ATTCGAGATC TCCTCGACAC CGCCTCAGCT CTGTATCGGG AGGCCTTAGA GTCTCCGGAA      2040

CATTGCTCAC CTCACCATAC CGCACTCAGG CAAGCTATTC TGTGTTGGCG TGAGTTGATG      2100

AATCTGGCCA CCTGGGTGGG AAGTAATTTG GAAGACCCAG CATCCAGGGA ATTAGTAGTC      2160

AGCTATGTCA ATGTTAATAT CGGCCTAAAA ATCAGACAAC TACTGTGGTT TCACATTTCC      2220

TGTCTTACTT TTGGAAGAGA AACTGTTCTT GAGTATTTGG TGTCTTTTGG AGTGTGGATT      2280

CGCACTCCTC CTGCTTACAG ACCACCAAAT GCCCCTATCT TATCAACACT TCCGAAAACT      2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATCCC      2460

TTGGACTCAT AAGGTGGGAA ACTTTACTGG GCTTTATTCT TCTACTGTAC CTATCTTTAA      2520

TCCTGAGTGG CAAACTCCCT CCTTTCCTCA CATTCATTTA CAGGAGGACA TTATTAATAG      2580

ATGTCAACAA TATGTGGGCC CTCTTACAGT TAATGAAAAA AGGAGATTAA AGTTAATTAT      2640

GCCTGCTAGG TTCTATCCTA ACCTTACCAA ATATCTGCCC TTGGACAAAG GCATTAAACC      2700

ATATTATCCT GAACATGCAG TTAATCATTA CTTCAAAACT AGGCATTATT TACATACTCT      2760

GTGGAAGGCG GGCATTCTAT ATAAGAGAGA AACTACGCGC AGCGCCTCAT TTTGTGGGTC      2820

ACCATATTCT TGGGAACAAG AGCTACAGCA TGGGAGGTTG GTCTTCCAAA CCTCGACAAG      2880

GCATGGGGAC GAATCTTTCT GTTCCCAATC CTCTGGGATT CTTTCCCGAT CACCAGTTGG      2940

ACCCTGCGTT CGGAGCCAAC TCAAACAATC CAGATTGGGA CTTCAACCCC AACAAGGATC      3000

ACTGGCCAGA GGCAAATCAG GTAGGAGCGG GAGCATTCGG GCCAGGGTTC ACCCCACCAC      3060

ACGGCGGTCT TTTGGGGTGG AGCCCTCAGG CTCAGGGCAT ATTGACAACA GTGCCAGTAG      3120

CACCTCCTCC TGCCTCCACC AATCGGCAGT CAGGAAGACA GCCTACTCCC ATCTCTCCAC      3180

CTCTAAGAGA CAGTCATCCT CAGGCCATGC AGTGG                                3215
```

(2) INFORMATION FOR SEQ ID NO: 296:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 296:

```
AACTCCACAA CATTCCACCA AGCTGTGCTA GATCCCAGAG TGAGGGGCCT ATATCTTCCT        60

GCTGGTGGCT CCAGTTCCGG AACAGTGAAC CCTGTTCCGA CTACTGCCTC ACCCATATCG       120
```

-continued

```
TCAATCTTCT CGAGGACTGG GGACCCTGCA CCGAACATGG AGAACACAAC ATCAGGATTC    180
CTAGGACCCC TGCTCGTGTT ACAGGCGGGG TTTTTCTTGT TGACAAGAAT CCTCACAATA    240
CCACAGAGTC TAGACTCGTG GTGGACTTCT CTCAATTTTC TAGGGGGAGC ACCCACGTGT    300
CCTGGCCCAA ATTCGCAGTC CCCAACCTCC AATCACTCAC CAACCTCTTG TCCTCCAATT    360
TGTCCTGGCT ATCGCTGGAT GTGTCTGCGG CGTTTTATCA TATTCCTCTT CATCCTGCTG    420
CTATGCCTCA TCTTCTTGTT GGTTCTTCTG GACTACCAAG GTATGTTGCC CGTTTGTCCT    480
CTACTTCCAG GAACATCAAC TACCAGCACG GGACCATGCA AGACCTGCAC GATTCCTGCT    540
CAAGGAACCT CTATGTTTCC CTCCTGTTGC TGTACAAAAC CTTCGGACGG AAACTGCACT    600
TGTATTCCCA TCCCATCATC CTGGGCTTTC GCAAGATTCC TATGGGAGTG GGCCTCAGTC    660
CGTTTCTCCT GGCTCAGTTT ACTAGTGCCA TTTGTTCAGT GGTTCGTAGG CTTTCCCCC     720
ACTGTTTGGC TTTCAGTTAT ATGGATGATG TGGTATTGGG GGCCAAGTCT GTACAACATC    780
TTGAGTCCCT TTTTACCTCT ATTACCAATT TTCTTTTGTC TTTGGGTATA CATTTGAACC    840
CTCATAAAAC CAAACGTTGG GGCTACTCCC TTAACTTCAT GGGATATGTA ATTGGAAGTT    900
GGGGTACTTT ACCACAGGAA CATATTGTAC TAAAAATCAA GCAATGTTTT CGGAAGCTGC    960
CTGTAAATAG ACCTATTGAT TGGAAAGTAT GTCAAAGGAT TGTGGGTCTT TTGGGCTTTG    1020
CTGCCCCTTT TACACAATGT GGCTATCCTG CCTTGATGCC TTTATATGCA TGTATACAAT    1080
CTAAGCAGGC TTTCACTTTC TCGCCAACTT ACAAGGCCTT TCTGTGTAAA CAATATCTGC    1140
ACCTTTACCC CGTTGCCCGG CAACGGTCAG GTCTCTGCCA AGTGTTTGCT GACGCAACCC    1200
CCACTGGATG GGGCTTGGCC ATTGGCCAAT CGGGCATGCG TGGAACCTTT GTGGCTCCTC    1260
TGCCGATCCA TACTGCGGAA CTCCTAGCAG CTTGTTTTGC TCGCAGCCGG TCTGGAGCGA    1320
AACTTATCGG GACTGACAAC TCTGTTGTCC TCTCTCGGAA ATACACCTCC TTCCCATGGC    1380
TGCTCGGGTG TGCTGCCAAC TGGATCCTGC GCGGGACGTC CTTTGTCTAC GTCCCGTCGG    1440
CGCTGAATCC CGCGGACGAC CCGTCTCGGG GCCGTTTGGG CCTCTACCGT CCCCTTCTTC    1500
ATCTGCCGTT CCGGCCGACC ACGGGGCGCG CCTCTCTTTA CGCGGTCTCC CCGTCTGTGC    1560
CTTCTCATCT GCCGGTCCGT GTGCACTTCG CTTCACCTCT GCACGTCGCA TGGAGACCAC    1620
CGTGAACGCC CACCAGGTCT TGCCCAAGGT CTTACATAAG AGGACTCTTG GACTCTCAGC    1680
GATGTCAACG ACCGACCTTG AGGCATATTT CAAAGACTGT TTGTTTAAAG ACTGGGAGGA    1740
GTTGGGGGAG GAGATTAGGT TAATGGTCTT TGTACTAGGA GGCTGTAGGC ATAAATTGGT    1800
CTGTTCACCA GCACCATGCA ACTTTTTCAC CTCTGCCTAA TCATCTCCTG TTCATGTCCT    1860
ACTGTTCAAG CCTCCAAGCT GTGCCTTGGG TGGCTTAGGG GCATGGACAT TGACACGTAT    1920
AAAGAATTTG GAGCTTCTGT GGAGTTACTC TCTTTTTTGC CTTCTGACTT CTTTCCTTCT    1980
ATTCGAGATC TCCTCGACAC CGCCTTTGCT CTGCATCGGG AGGCCTTAGA GTCTCCGGAA    2040
CATTGTTCAC CTCACCATAC AGCACTCAGG CAAGCTATTG TGTGTTGGGG TGAGTTGATG    2100
AATCTGGCCA CCTGGGTGGG AAGTAATTTG GAAGACCCAG CATCCAGGGA ATTGGTAGTC    2160
AGCTATGTCA ATGTTAATAT GGGCCTAAAA ATCAGACAAC TATTGTGGTT TCACATTTCC    2220
TGTCTTACTT TTGGAAGAGA AACGGTTCTT GAGTATTTGG TATCTGTTGG AGTGTGGATT    2280
CGCACTCCTC AAGCCTACAG ACCACCAAAT GCCCCTATCT TATCAACACT TCCGGAAACT    2340
ACTGTTGTTA GACGACGAGG CAGGTCCCCT AGAAGAAGAA CTCCCTCGCC TCGCAGACGA    2400
AGGTCTAAAT CGCCGCGTCG CAGAAGATCT CAATCTCGGG AATCTCAATG TTAGTATCCC    2460
TTGGACTCAT AAGGTGGGAA ACTTTACTGG TCTCTATTCT TCTACTGTAC CTGTCTTTAA    2520
```

```
TCCTGAGTGG CAAACTCCCT CCTTTCCTAA TATTCATTTA CAGGAGGATA TTATTAATAG    2580

ATGTCAACAA TATGTAGGCC CTCTTACAGT TAATGAAAAA AGGAGATTAA AATTAATTAT    2640

GCCTGCTAGG TTCTATCCTA ACCTTACCAA ATATTTGCCC TTGGATAAAG GTATTAAACC    2700

TTATTATCCT GAACATGCAG TTAATCATTA TTTCAAAACT AGGCATTATT TACATACTCT    2760

GTGGAAGGCT GGCATTCTAT ATAAGAGAGA AACTACACGT AGTGCCTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCATT CGGAGCCAAC TCAAACAATC CAGATTGGGA CTTCAACCCC AACAAGGATC    3000

ATTGGCCAGA GGCAAATCAG GTAGGAGCGG GAGCATTTGG GCCAGGGTTC ACTCCACCAC    3060

ACGGCGGTCT TTTGGGGTGG AGCCCTCAGG CTCAGGGCAT ATTGACAACA GTGCCAGCAG    3120

CGCCTCCTCC TGCCTCTACC AATCGGCAGT CAGGAAGACA GCCTACTCCC ATCTCTCCAC    3180

CTCTAAGAGA CAGTCATCCT CAGGCCATGC AGTGG                               3215
```

(2) INFORMATION FOR SEQ ID NO: 297:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 297:

```
AACTCCACAA CATTCCACCA AGCTGTGCTA GATCCCAGAG TGAGGGGCCT ATATCTTCCT      60

GCTGGTGGCT CCAGTTCCGG AACAGTGAAC CCTGTTCCGA CTACTGCCTC ACCCATATCG     120

TCAATCTTCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCCAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCCTGTTGC TGTACAAAAC CTTCGGACGG AAACTGCACT     600

TGTATTCCCA TCCCATCATC CTGGGCTTTC GCAAGATTCC TATGGGAGTG GCCTCAGTC      660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CTCATAAAAC CAAACGTTGG GGCTACTCCC TTAACTTCAT GGGATATGTA ATTGGAAGTT     900

GGGGTACTTT ACCACAGGAA CATATTGTAC TAAAAATCAA GCAATGTTTT CGGAAGCTGC     960

CTGTAAATAG ACCTATTGAT TGGAAAGTAT GTCAAAGGAT TGTGGGTCTT TTGGGCTTTG    1020

CTGCCCCTTT TACACAATGT GGCTATCCTG CCTTGATGCC TTTATATGCA TGTATACAAT    1080

CTAAGCAGGC TTTCACTTTC TCGCCAACTT ACAAGGCCTT TCTGTGTAAA CAATATCTGC    1140
```

```
ACCTTTACCC CGTTGCCCGG CAACGGTCAG GTCTCTGCCA AGTGTTTGCT GACGCAACCC    1200

CCACTGGATG GGGCTTGGCC ATTGGCCAAT CGGGCATGCG TGGAACCTTT GTGGCTCCTC    1260

TGCCGATCCA TACTGCGGAA CTCCTAGCAG CTTGTTTTGC TCGCAGCCGG TCTGGAGCGA    1320

AACTTATCGG GACTGACAAC TCTGTTGTCC TCTCTCGGAA ATACACCTCC TTCCCATGGC    1380

TGCTCGGGTG TGCTGCCAAC TGGATCCTGC GCGGGACGTC CTTTGTCTAC GTCCCGTCGG    1440

CGCTGAATCC CGCGGACGAC CCGTCTCGGG GCCGTTTGGG CCTCTACCGT CCCCTTCTTC    1500

ATCTGCCGTT CCGGCCGACC ACGGGGCGCG CCTCTCTTTA CGCGGTCTCC CCGTCTGTGC    1560

CTTCTCATCT GCCGGTCCGT GTGCACTTCG CTTCACCTCT GCACGTCGCA TGGAGACCAC    1620

CGTGAACGCC CACCAGGTCT TGCCCAAGGT CTTACATAAG AGGACTCTTG GACTCTCAGC    1680

GATGTCAACG ACCGACCTTG AGGCATATTT CAAAGACTGT TTGTTTAAAG ACTGGGAGGA    1740

GTTGGGGGAG GAGATTAGGT TAATGGTCTT TGTACTAGGA GGCTGTAGGC ATAAATTGGT    1800

CTGTTCACCA GCACCATGCA ACTTTTTCAC CTCTGCCTAA TCATCTCCTG TTCATGTCCT    1860

ACTGTTCAAG CCTCCAAGCT GTGCCTTGGG TGGCTTAGGG GCATGGACAT TGACACGTAT    1920

AAAGAATTTG GAGCTTCTGT GGAGTTACTC TCTTTTTTGC CTTCTGACTT CTTTCCTTCT    1980

ATTCGAGATC TCCTCGACAC CGCCTTTGCT CTGCATCGGG AGGCCTTAGA GTCTCCGGAA    2040

CATTGTTCAC CTCACCATAC AGCACTCAGG CAAGCTATTG TGTGTTGGGG TGAGTTGATG    2100

AATCTGGCCA CCTGGGTGGG AAGTAATTTG GAAGACCCAG CATCCAGGGA ATTGGTAGTC    2160

AGCTATGTCA ATGTTAATAT GGGCCTAAAA ATCAGACAAC TATTGTGGTT TCACATTTCC    2220

TGTCTTACTT TTGGAAGAGA AACGGTTCTT GAGTATTTGG TATCTGTTGG AGTGTGGATT    2280

CGCACTCCTC AAGCCTACAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGGTCTAAAT CGCCGCGTCG CAGAAGATCT CAATCTCGGG AATCTCAATG TTAGTATCCC    2460

TTGGACTCAT AAGGTGGGAA ACTTTACTGG TCTCTATTCT TCTACTGTAC CTGTCTTTAA    2520

TCCTGAGTGG CAAACTCCCT CCTTTCCTAA TATTCATTTA CAGGAGGATA TTATTAATAG    2580

ATGTCAACAA TATGTAGGCC CTCTTACAGT TAATGAAAAA AGGAGATTAA AATTAATTAT    2640

GCCTGCTAGG TTCTATCCTA ACCTTACCAA ATATTTGCCC TTGGATAAAG GTATTAAACC    2700

TTATTATCCT GAACATGCAG TTAATCATTA TTTCAAAACT AGGCATTATT TACATACTCT    2760

GTGGAAGGCT GGCATTCTAT ATAAGAGAGA AACTACACGT AGTGCCTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCATT CGGAGCCAAC TCAAACAATC CAGATTGGGA CTTCAACCCC AACAAGGATC    3000

ATTGGCCAGA GGCAAATCAG GTAGGAGCGG GAGCATTTGG GCCAGGGTTC ACTCCACCAC    3060

ACGGCGGTCT TTTGGGGTGG AGCCCTCAGG CTCAGGGCAT ATTGACAACA GTGCCAGCAG    3120

CGCCTCCTCC TGCCTCTACC AATCGGCAGT CAGGAAGACA GCCTACTCCC ATCTCTCCAC    3180

CTCTAAGAGA CAGTCATCCT CAGGCCATGC AGTGG                              3215
```

(2) INFORMATION FOR SEQ ID NO: 298:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 298:

| | | | | | |
|---|---|---|---|---|---|
| AACTCCACCA | CATTCCACCA | AGCTCTGCTA | GATCCCAGAG | TGAGGGGCCT | ATATTTTCCT | 60 |
| GCTGGTGGCT | CCAGTTCCGG | AACAGTAAAC | CCTGTTCCGA | CTACTGCCTC | ACCCATATCG | 120 |
| TCAATCTTCT | CGAGGACTGG | GGACCCTGCG | CCGAACATGG | AGAACACAAC | ATCAGGATTC | 180 |
| CTAGGACCCC | TGCTCGTGTT | ACAGGCGGGG | TTTTTCTTGT | TGACAAGAAT | CCTCACAATA | 240 |
| CCACAGAGTC | TAGACTCGTG | GACTTCTCTC | AATTTTCTAG | GGGGAGCACC | CACGTGTCCT | 300 |
| GGCCAAAATT | CGCAGTCCCC | AACCTCCAAT | CACTCACCAA | CCTCTTGTCC | TCCAATTTGT | 360 |
| CCTGGCTATC | GCTGGATGTG | TCTGCGGCGT | TTTATCATAT | TCCTCTTCAT | CCTGCTGCTA | 420 |
| TGCCTCATCT | TCTTGTTGGC | TCTTCTGGAC | TACCAAGGTA | TGTTGCCCGT | TTGTCCTCTA | 480 |
| CTTCCAGGAA | CATCAACTAC | CAGCACGGGA | CCATGCAAGA | CCTGCACGAT | TCCTGCTCAA | 540 |
| GGAACCTCTA | TGTTTCCCTC | TTGTTGCTGT | ACAAAACCTT | CGGACGGAAA | TTGCACTTGT | 600 |
| ATTCCCATCC | CGTCATCTTG | GGCTTTCGCA | AGATTCCTAT | GGGAGTGGGC | CTCAGTCCGT | 660 |
| TTCTCCTGGC | TCAGTTTACT | AGTGCCATTT | GTTCAGTGGT | TCGCAGGGCT | TTCCCCCACT | 720 |
| GTTTGGCTTT | CAGTTATATG | GATGATGTGG | TATTGGGGGC | CAAGTCTGTA | CAACATCTTG | 780 |
| AGTCCCTTTA | TACCTCTATT | ACCAATTTTC | TTGTGTCTTT | GGGTATACAT | TTGAACCCTA | 840 |
| ATAAAACCAA | ACGTTGGGGC | TACTCCCTTA | ACTTCATGGG | ATATGTAATT | GGAAGTTGGG | 900 |
| GTACGTTACC | ACAGGAACAT | ATTGTACAAA | AAATCAAGCA | ATGTTTTCGG | AAACTGCCTG | 960 |
| TAAATAGACC | TATTGATTGG | AAAGTATGTC | AAAGAATTGT | GGGTCTTTTG | GGCTTTGCTG | 1020 |
| CCCCTTTTAC | ACAATGTGGT | TATCCTGCCT | TGATGCCTTT | ATATGCATGT | ATACAAGCTA | 1080 |
| AGCAGGCTTT | TACTTTCTCG | TCAACTTACA | AGGCCTTTCT | GTGTAAACAA | TATCTGCACC | 1140 |
| TTTACCCCGT | TGCCCGGCAA | CGGTCAGGTC | TCTGCCAAGT | GTTTGCTGAC | GCAACCCCCA | 1200 |
| CTGGATGGGG | CTTGGCCATA | GGCCATCGGC | GCATGCGTGG | AACCTTTGTG | GCTCCTCTGC | 1260 |
| CGATCCATAC | TGCGGAACTC | CTAGCAGCTT | GTTTTGCTCG | CAGCCGGTCT | GGAGCGAAAC | 1320 |
| TTATCGGGAC | TGACAACTCT | GTTGTCCTCT | CTCGGAAATA | CACCTCCTTC | CCATGGCTGC | 1380 |
| TCGGATGTGC | TGCCAACTGG | ATCCTGCGCG | GGACGTCCTT | TGTCTACGTC | CCGTCGGCGC | 1440 |
| TGAATCCCGC | GGACGACCCG | TCTCGGGGTC | GTTTGGGCCT | CTACCGTCCC | CTTCTTCATC | 1500 |
| TGCCGTTCCG | GCCGACCACG | GGGCGCACCT | CTCTTTACGC | GGTCTCCCCG | TCTGTGCCTT | 1560 |
| CTCATCTGCC | GGACCGTGTG | CACTTCGCTT | CACCTCTGCA | CGTCGCATGG | AGACCACCGT | 1620 |
| GAACGCCCAT | CAGGTGTTGC | CCAAGGTCTT | ATATAAGAGG | ACTCTTGGAC | TTTCAGCAAT | 1680 |
| GTCAACGACC | GACCTTGAGG | CATACTTCAA | AGACTGTTTG | TTTAAGGACT | GGGAGGAGTT | 1740 |
| GGGGGAGGAA | CTTAGGTTAA | TGATCTTTGT | ACTAGGAGGC | TGTAGGCATA | AATTGGTCTG | 1800 |
| TTCACCAGCA | CCATGCAACT | TTTTCACCTC | TGCCTAATCA | TCTCTTGTTC | ATGTCCTACT | 1860 |
| GTTCAAGCCT | CCAAGCTGTG | CCTTGGGTGG | CTTTAGGACA | TGGACATTGA | CCCATATAAA | 1920 |
| GAATTTGGAG | CTTCTGTGGA | GTTACTCTCT | TTTTTGCCTT | CTGACTTCTT | TCCTTCTATT | 1980 |
| CGAGATCTCC | TCGACACCGC | CTCTGCTCTG | TATCGGAGG | CCCTAGAGTC | TCCGAGCAT | 2040 |
| TGTACACCTC | ACCATACAGC | ACTCAGGCAA | GCTATTCTGT | GTTGGGGTGA | GTTGATGAAC | 2100 |

```
CTGGCCACCT GGGTGGGAAG TAATTTGGAA GATCCAACAT CCAGGGAAGC AGTAGTCAGC      2160

TATGTCAATG TTAATATGGG CCTAAAACTC AGACAACTAT TGTGGTTTCA CATTTCCTGT      2220

CTTACTTTTG GAAGAGATAC TGTTCTTGAG TATTTGGTGT CTTTTGGAGT GTGGATTCGC      2280

ACTCCTACCG CTTACAGACC ACCAAATGCC CCTATCTTAT CAACACTTCC GGAAACTACT      2340

GTTGTTAGAC GACGAGGCAG GTCCCCTAGA AGAAGAACTC CCTCGCCTCG CAGACGAAGG      2400

TCTCAATCGC CGCGTCGCAG AAGATCTCAA TCTCGGGAAC CTCAATGTTA ATGTCCCTTG      2460

GACTCATAAG GTGGGAAACT TTACAGGACT TTACTCTTCT ACTGTACCTG TCTTTAATCC      2520

TGAGTGGCAA ACTCCCTCCT TTCCTAACAT TCATTTACAG GAGGACATTA TTGATAGATG      2580

TCAACAATAT GTGGGCCCTC TTACAGTTAA TGAAAAAAGG AGATTAAAAT TAATTATGCC      2640

TGCTAGGTTT TATCCAAACC TTACCAAATA TTTGCCCTTG GATAAAGGCA TTAAACCTTA      2700

TTATCCTGAA CATGCAGTTA ATCATTACTT TCAAACTAGG CATTATTTAC ATACTCTGTG      2760

GAAGGCTGGC ATTCTATATA AGAGAGAAAC TACCCGCAGC GCTTCATTTT GTGGGTCACC      2820

ATATTCTTGG GAACAAGAGC TACAGCATGG GAGGTTGGTC TTCCAAACCT CGACAAGGCA      2880

TGGGGACGAA TCTTTCTGTT CCCAATCCTC TGGGATTCTT TCCCGATCAC CAGTTGGACC      2940

CTGCGTTCGG AGCCAACTCA AACAATCCAG ATTGGGACTT CAACCCCAAC AAGGATCATT      3000

GGCCAGAGGC CAATCAGGTA GGAGTGGGAG CATTCGGGCC AGGGTTCACC CCACCACACG      3060

GCGGTCTTTT GGGGTGGAGC CCTCAGGCTC AGGGCATATT GACAACAGTG CCAGCAGCGC      3120

CTCCTCCTGC CTCTACCAAT CGGCAGTCAG GAAGACAGCC AACTCCCATC TCTCCACCTC      3180

TAAGAGACAG TCATCCTCAG GCCATGCAGT GG                                   3212

(2) INFORMATION FOR SEQ ID NO: 299:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 299:

AACTCCACAA CATTCCAACA AGCTCTGCAG GATCCCAGAG TCAGGGTCCT TTATTTTCCT        60

GCTGGTGGCT CCAGTTCCGG AACAGTAAAC CCTGTTCCGA CTACTGCCTC TCTCATTTCG       120

TCAATCTTCT CGAGGATTGG GGACCCTGTA ACGAACATGG AGAACACAAC ATCAGGATTC       180

CTAGGACCCC TGCTCGTGTT ACAGGCGGGG TTTTTCTTGT TGACAAAAAT CCTCACAATA       240

CCACAGAGTC TAGACTCGTG GTGGACTTCT CTCAATTTTC TAGGGGAGC ACCCGTGTGT       300

CCTGGCCAAA ATTCGCAGTC CCCAACCTCC AATCACTCAC CAACCTCTTG TCCTCCAATT       360

TGTCCTGGCT ATCGCTGGAT GTGTCTGCGG CGTTTTATCA TCTTCCTCTT CATCCTGCTG       420

CTATGCCTCA TCTTCTTGTT GGTTCTTCTG GACTACCAAG GTATGTTGCC CGTTTGTCCT       480

CTACTTCCAG GAACATCAAC TACCAGCACG GGACCATGCA AGACCTGCAC GATTCCTGCT       540

CAAGGAACCT CTATGTTTCC CTCATGTTGC TGTACAAAAC CTTCGGACGG AAACTGCACT       600

TGTATTCCCA TCCCATCATC CTGGGCTTTC GTAAGATTCC TATGGGAGTG GCCTCAGTC       660

CGTTTCTCCT GGCTCAGTTT ACTAGCGCCA TTTGTTCAGT GGTTCGTAGG GCTTTCCCCC       720
```

```
ACTGTTTGGC TTTCAGTTAT ATGGATGATG TGGTATTGGG GGCCAAGTCT GTACAACATC    780

TTGAGTCCCT TTATACCTCT ATTACCAATT TTCTTTTGTC TTTGGGTATA CATTTAAACC    840

CTAATAAAAC CAAAAGATGG GGCTATTCCC TTAACTTCAT GGGCTATGTA ATTGGAAGTT    900

GGGGTACCTT ACCACAAGAA CATATTGTAC TAAAAATCAC ACAATGTTTT CGAAAACTTC    960

CTGTTAATAG GCCTATTGAT TGGAAAGTGT GTCAAAGAAT TGTGGGTCTT TTGGGCTTTG   1020

CTGCCCCTTT TACACAATGT GGGTATCCTG CCTTAATGCC CTTGTATGCC TGTATTCAAG   1080

CTAAGCAGGC TTTCACTTTC TCGCCAACTT ATAAGGCCTT TCTGTGTAAA CAATATCTGA   1140

ACCTTTACCC CGTTGCCCGG CAACGGTCTG GTCTTTGCCA AGTGTTTGCT GACGCAACCC   1200

CCACTGGCTG GGGCTTGGCC ATGGGCCATC AGCGCATGCG TGGAACCTTT GTGGCTCCTC   1260

TGCCGATCCA TACTGCGGAA CTCCTAGCGG CTTGTTTTGC TCGCAGCCGG TCTGGAGCAA   1320

ACATTATCGG AACCGACAAC TCTGTCGTCC TCTCTCGGAA ATACACATCC TTTCCATGGC   1380

TGCTCGGGTG TGCTGCCAAC TGGATCCTAC GCGGGACGTC CTTTGTTTAC GTCCCGTCGG   1440

CGCTGAATCC CGCGGACGAC CCGTCTCGCG GCCGTTTGGG GCTCTACCGT CCCCTTCTTT   1500

GTCTGCGGTT CCGGCCAACC ACGGGGCGCA CCTCTCTTTA CGCGGTCTCC CCGTCTGTGC   1560

CTTCTCATCT GCCGGACCGT GTGCACTTCG CTTCACCTCT GCACGTCGCA TGGAAACCAC   1620

CGTGAACGCC CACATGGTCT TGCCCAAGGT CTTGCATAAG AGAACTCTTG GACTCTCAGC   1680

AATGTCAACG ACCGACCTTG AGGCATATTT CAAAGACTGT GTGTTCAAAG ACTGGGAGGA   1740

GTTGGGGGAG GAGGTTAGAT TAAAGGTCTT TGTACTAGGA GGCTGTAGGC ATAAATTGGT   1800

CTGCGCACCA GCACCATGCA ACTTTTTCAC CTCTGCCTAA TCATCTCATG TTCATGTCCT   1860

ACTGTTCAAG CCTCCAAGCT GTGCCTTGGG TGGCTTTGGG GCATGGACAT TGACCCTTAT   1920

AAAGAATTTG GAGCTTCTGT GGAGTTACTC TCTTTTTTGC CTTCTGATTT CTTTCCATCT   1980

ATTCGAGACC TCCTCGACAC CGCCTCAGCT CTGTATCGGG AGGCCTTAGA GTCTCCGGAG   2040

CATTGTTCAC CTCACCATAC AGCACTCAGG CAAGCTGTTC TGTGTTGGGG TGAGTTAATG   2100

AATCTGGCTA CCTGGGTGGG AAGTAATTTG GAAGACCCAG CATCAAGAGA ATTGGTAGTC   2160

AGTTATGTCA ATGTTAATAT GGGCCTAAAA ATCAGGCAAC TGTTGTGGTT TCATATTTCC   2220

TGTCTTACTT TTGGAAGAGA AACTGTTCTT GAGTACTTGG TGTCCTTTGG AGTGTGGATT   2280

CGCACTCCTC CCGCTTACAG ACCACCAAAT GCCCCTATCT TATCAACACT TCCGGAAACT   2340

ACTGTTGTTA GACGAAGAGG CAGGTCCCCT AGAAGAAGAA CTCCCTCGCC TCGCAGACGA   2400

AGGTCTCAAT CGCCGCGTCG CAGAAGATCT CAATCTCGGG AATCCCAATG TTAGTATCCC   2460

TTGGACTCAT AAGGTGGGAA ACTTTACTGG GCTTTATTCT TCTACTGTAC CTGTCTTTAA   2520

TCCTGAATGG CAAACTCCCT CTTTTCCTGA CATTCATTTG CAGGAGGACA TTATTAATAG   2580

ATGTCAACAA TATGTGGGCC CTCTTACAGT TAATGAAAAA AGAAGATTAA AATTAATTAT   2640

GCCTGCTAGG TTTTATCCTA ACCTTACTAA ATATTTGCCC TTAGACAAAG GCATTAAACC   2700

TTATTATCCA GAACAGACAG TTAATCATTA CTTCAAAACT AGGCATTATT GCATACTCT    2760

GTGGAAGGCT GGTAGTCTAT ATAAGAGAGA AACTACACGC AGCGCCTCAT TTTGTGGGTC   2820

ACCATATTCT TGGGAACAAG AGCTACAGCA TGGGAGGTTG GTCTTCAAAA CCTCGGAAAG   2880

GCATGGGGAC GAATCTTTCG GTACCCAATC CTCTGGGATT CTTTCCCGAT CACCAGTTCC   2940

ACCCTGCGTT CGGAGCCAAC TCAAACAATC CCGATTGGGA CTTCAACCCC AACAAGGATC   3000

ACTGGCCAGA GGCAAATCAG GTAGGAGCGG GAGCATTCGG GCCAGGGTTC ACCCCACCAC   3060

ACGGAGGTCT TTTGGGGTGG AGCCCTCAGG CCCAGGGCAT ATTGACAACA GTGCCAGCAG   3120
```

```
CTCCTCCTTC TGCCTCCACC AATCGGCAGT CAGGAAGACA GCCTACGCCC ATCTCTCCAC    3180

CTCTAAGAGA CAGTCATCCT CAGGCCATGC AGTGG                              3215
```

(2) INFORMATION FOR SEQ ID NO: 300:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 300:

```
AACTCCACAA CATTCCAACA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC TCTCATTTCG     120

TCAATCTTCT CGAGGACTGG GGACCCTGTA ACGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGGG GTGGACTTCT CTCAATTTTC TAGGGAAGC ACCAAGGTGT      300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TCTTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCATGTTGC TGTACAAAAC CTTCGGACGG AAACTGCACT     600

TGTATTCCCA TCCCATCATC CTGGGCTTTC GTAAGATTCC TATGGGAGTG GGCCTCAGTC     660

CGTTTCTCCT GGCTCAGTTT ACTAGCGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTATACCTCT ATTACCAATT TTCTTTTGTC TTTGGGTATA CATTTGAACC     840

CTAATAAGAC CAAAAGATGG GGCTATTCCC TTAACTTCAT GGGCTATGTA ATTGGAAGTT     900

GGGGTACCTT ACCACAAGAA CATATTGTAC TAAAAATCAA ACAATGTTTT CGAAAACTTC     960

CTGTAAATAG GCCTATTGAT TGGAAGGTCT GCCAAAGAAT TGTGGGTCTT TTGGGATTTG    1020

CTGCCCCTTT TACACAATGT GGATATCCTG CCTTAATGCC TTTGTATGCA TGTATTCAAG    1080

CTAAGCAAGC TTTCACTTTT TCGTCAACTT ACAAAGCCTT TCTGTGTAAA CAATATCTGA    1140

ACCTTTACCC CGTTGCCCGG CAACGGTCTG GTCTCTGCCA AGTGTTTGCT GACGCAACCC    1200

CCACTGGCTG GGGCTTGGCC ATTGGCAATC AGCGCATGCG TGGAACCTTT GTGGCTCCTC    1260

TGCCGATCCA TACTGCGGAA CTCCTAGCAG CTTGTTTTGC TCGCAGCCGG TCTGGAGCAA    1320

AACTTATCGG AACTGACAAC TCTGTCGTCC TCTCTCGCAA ATACACATCC TTTCCATGGC    1380

TGCTCGGCTG TGCTGCCAAC TGGATCCTAC GAGGGACGTC CTTTGTTTAC GTCCCGTCGG    1440

CGCTGAATCC CGCGGACGAC CCGTCTCGGG GCCGTTTGGG GATCTACCGT CCCCTTCTTC    1500

GTCTGCGGTT CCGGCCAACC ACGGGGCGCA CCTCTCTTTA CGCGGTCTCC CCGTCTGTGC    1560

CTTCTCATCT GCCGGACCGT GTGCACTTCG CTTCACCTCT GCACGTCGCA TGGAGACCAC    1620

CGTGAACGCC CACATGGTAT TGCCCAAGGT CTTGCATAAG AGGACTCTTG GACTCTCAGC    1680

GATGTCAACG ACCGACCTTG AGGCATACTT CAAAGACTGT GTATTTAAAG ACTGGGAGGA    1740
```

```
GTTGGGGGAG GAGATTAGAT TAAAGGTCTT TGTACTAGGA GGCTGTAGGC ATAAATTGGT      1800

CTGCGCACCA GCACCATGCA ACTTTTTCAC CTCTGCCTAA TCATCTCATG TTCATGTCCT      1860

ACTGTTCAAG CCTCCAAGCT GTGCCTTGGG TGGCTTTGGG GCATGGACAT TGACCCTTAT      1920

AAAGAATTTG GAGCTTCTGT GGAGTTACTC TCTTTTTTGC CTTCTGATTT CTTTCCATCT      1980

ATTCGAGACC TCCTCGACAC CGCCTCAGCT CTGTATCGGG AGGCCTTAGA GTCTCCGGAA      2040

CATTGTTCAC CTCACCATAC AGCACTCAGG CAAGCTGTTC TGTGTTGGGG TGAGTTAATG      2100

AATCTGGCTA CCTGGGTGGG AAGTAATTTG GAAGACCCAG CATCCAGGGA ATTAGTGGTC      2160

AGTTATGTCA ACATTAATAT GGGCCTAAAA ATCAGACAAC TATTGTGGTT TCACATTTCC      2220

TGTCTTACTT TTGGAAGAGA AACTGTTCTT GAGTATTTGG TGTCTTTTGG AGTGTGGATT      2280

CGCACTCCTC CCGCTTACAG ACCACCAAAT GCCCCTATCT TATCAACACT TCCGGAAACT      2340

ACTGTTGTTA GACGTCGAGG CAGGTCCCCT AGAAGAAGAA CTCCCTCGCC TCGCAGACGA      2400

AGGTCTCAAT CACCGCGTCG CAGAAGATCT CAATCTCGGG AATCCCAATG TTAGTATCCC      2460

TTGGACTCAT AAGGTGGGAA ACTTTACTGG GCTTTATTCT TCTACTGTAC CTGTCTTTAA      2520

TCCTGAATGG CAAACTCCCT CTTTTCCTGA CATTCATTTG CAGGAGGACA TTATTAATAG      2580

ATGTCAACAA TATGTGGGCC CTCTTACAGT AATGAAAAA AGAAGATTAA AATTAATTAT      2640

GCCTGCTAGG TTTTATCCTA ACCTTACCAA ATATTTGCCC TTAGATAAAG GCATTAAACC      2700

TTATTATCCT GAACATGCAG TTAATCATTA CTTCAAAACA AGGCATTATT TACATACTCT      2760

GTGGAAGGCT GGCATCTTAT ATAAAAGAGA AACTACACGC AGTGCCTCAT TTTGTGGGTC      2820

ACCATATTCT TGGGAACAAG AGCTACAGCA TGGGAGGTTG GTCTTCCAAA CCTCGGAAAG      2880

GCATGGGGAC GAATCTTTCT GTTCCCAATC CTCTGGGATT CTTTCCCGAT CACCAGTTGG      2940

ACCCTGCATT CGGAGCCAAC TCAAACAATC CAGATTGGGA CTTCAACCCC AACAAGGATC      3000

AATGGCCAGA GGCAAATCAG GTAGGAGCGG GAGCATTCGG GCCAGGGTTC ACCCCACCAC      3060

ACGGAGGTCT TTTGGGGTGG AGCCCTCAGG CACAAGGCAT ATTGACAACA CTGCCAGCAG      3120

CTCCTCCTCC TGCCTCCACC AATCGGCAGT CAGGAAGACA GCCTACGCCC ATCTCTCCAC      3180

CTCTAAGAGA CAGTCATCCT CAGGCCATGC AGTGG                                3215

(2) INFORMATION FOR SEQ ID NO: 301:

(i) SEQUENCE CHARACTERISTICS:
        (A) LENGTH: 3161 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 301:

AATTCCACAA CCTTCCACCA AACTCTACAA GATCCCCCTG CTGGTGGCTC CAGTTCAGGA        60

ACAGTAAACC CTGTTCCGAC TACTGTCTCT CACATATCGT CAATCTTCAC GAGGATTGGG       120

GACCCTGCAC TGAACATGGA GAACATCACA TCAGGATTCC TAGGACCCCT GCTCGTGTTA       180

CAGGCGGGGT TTTTCTTGTT GACAAGAATC CTCACAATAC CGCAGAGTCT AGACTCGTGG       240

TGGACTTCTC TCAATTTTCT AGGGGGAACT ACCGTGTGTC TTGGCCAAAA TTCGCAGTCC       300

CCAACCTCCA ATCACTCACC AACCTCCTGT CCTCCAACTT GTCCTGGTTA TCGCTGGATG       360
```

```
TGTCTGCGGC GTTTTATCAT CTTCCTCTTC ATCCTGCTGC TATGCCTCAT CTTCTTGTTG    420

GTTCTTCTGG ACTATCAAGG TATGTTGCCC GTTTGTCCTC TAATTCCAGG ATCTTCAACC    480

ACCAGCACGG GACCATGCAG GACCTGCACG ACTCCTGCTC AAGGCAACTC TATGTATCCC    540

TCCTGTTGCT GTACCAAACC TTCGGACGGA AATTGCACCT GTATTCCCAT CCCATCATCT    600

TGGGCTTTCG GAAAATTCCT ATGGGAGTGG GCCTCAGCCC GTTTCTCCTG GCTCAGTTTA    660

CTAGTGCCAT TTGTTCAGTG GTTCGTAGGG CTTTCCCCCA CTGTTTGGCT TTCAGTTATA    720

TGGATGATGT GGTATTGGGG GCCAAGTCTG TACAGCATCT TGAGTCCCTT TTTACCGCTG    780

TTACCAATTT TCTTTTGTCT TTGGGCATAC ATTTAAACCC TAACAAAACA AAAAGATGGG    840

GTTACTCTTT ACACTTCATG GGCTATGTCA TTGGATGTTA TGGGTCATTG CCACAAGATC    900

ACATCAGACA GAAAATCAAA GAATGTTTTA GAAAACTTCC TGTTAACAGG CCTATTGATT    960

GGAAAGGCTG TCAACGAATT GTGGGTTTAT TGGGTTTTGC TGCCCCTTTT ACACAATGTG   1020

GTTATCCTGC GTTGATGCCT TTGTATGCAT GTATTCAATC TAAGCAGGCT TTCACTTTCT   1080

CGCCAACTTA CAAGGCCTTT CTGTGTAAAC AATACCTGAA CCTTTACCCC GTTGCCCGGC   1140

AACGGCCAGG TCTGTGCCAA GTGTTTGCTG ACGCAACCCC CACTGGCTGG GGCTTGGTCA   1200

TGGGCCATCA GCGCATGCGT GGAACCTTTC GGGCTCCTCT GCCGATCCAT ACTGCGGAAC   1260

TCCTAGCCGC TTGTTTTGCT CGCAGCAGGT CTGGAGCAAA CATTCTCGGG ACGGATAACT   1320

TTGTTGTCCT ATCCCGCAAA TATACATCGT TTCCATGGCT GCTAGGCTGT GCTGCCAACT   1380

GGATCCTGAG CGGGACGTCC TTCGTTTACG TCCCGTCGGC GCTGAATCCA GCGGACGACC   1440

CTTCTCGGGG CCGCTTGGGA CTCTCTCGTC CCCTTCTCCG TCTGCCGTTT CGTCCGACCA   1500

CGGGGCGCAC CTCTCTTTAC GCGGACTCCC CGTCTGTGCC TTCTCATCTG CCGGACCGTG   1560

TGCACTTCGC TTCACCTCTG CACGTCGCAT GGAGACCACC GTGAACGCCC ACCAATTCTT   1620

GCCCAAGGTC TTACATAAGA GGACTCTTGG ACTCTCAGCA ATGTCAACGA CCGACCTTGA   1680

GGCATACTTC AAAGACTGTT TGTTTAAAGA GTGGGAGGAG TTGGGGGAGG AGATTAGATT   1740

AAAGTTGTTT GTATTAGGAG GCTGTAGGCA TAAATTGGTC TGCGCACCAG CACCATGCAA   1800

CTTTTTCACC TCTGCCTAAT CATCTCTTGT TCATGTCCTA CTGTTCAAGC CTCCAAGCTG   1860

TGCCTTGGGT GGCTTAGGA CATGGACATT GATCCTTATA AAGAATTTGG AGCTTCTATG   1920

GAGTTGCTCT CGTTTTTGCC TTCTGACTTC TATCCTTCAG TACGAGATCT TCTAGATACC   1980

GCCTCAGCTC TATATCGGGA AGCCTTAGAG TCTCCTGAGC ATTGTACACC TCATCATACT   2040

GCACTCAGGC AAGCAATTCT TTGCTGGGGG GAATTAATGA CTCTAGCCAC CTGGGTGGGT   2100

GGTAATTTGC AAGATCCAAC ATCCAGGAC CTAGTAGTCA GTTATGTTAA CACTAATATG   2160

GGCCTAAAGT TCAGGCAACT ATTGTGGTTT CACGTTTCTT GTCTCACTTT TGGAAGAGAA   2220

ACAGTCGTAG AGTATTTGGT GTCTTTTGGA GTGTGGATTC GCACTCCTCA AGCTTATAGA   2280

CCACCAAATG CCCCTATCTT ATCAACACTT CCGGAGACTT GTGTTGTTAG ACGACGAGGC   2340

AGGTCCCCTA GAAGAAGAAC TCCCTCGCCT CGCAGACGAA GGTCTCAATC GCCGCGTCGC   2400

AGAAGATCTC AATCTCGGGA ATCTCAATGT TAGTATTCCT TGGACTCATA AGGTGGGAAA   2460

CTTTACGGGG CTTTATTCTT CTACTGTTCC TGTCTTTAAC CCTCATTGGA AAACACCCTC   2520

TTTTCCTAAT ATACATTTAC ACCAAGACAT TATCAAAAAA TGTGAACAAT TGTAGGCCC   2580

ACTCACAGTC AATGAGAAAA GAAGACTGCA ATTGATTATG CCTGTCAGGT TTTATCCAAT   2640

GGTTACCAAA TATTTGCCAT TGGATAAGGG TATTAAACCG TATTATCCAG AACATCTAGT   2700
```

| | |
|---|---:|
| TAATCATTAC TTCCAAACCA GACATTATTT ACACACTCTA TGGAAGGCGG GTGTATTATA | 2760 |
| TAAGAGAGAA ACAACACATA GCGCCTCATT TTGTGGATCA CCATATTCTT GGGAACAAGA | 2820 |
| GATACAGCAT GGGGCAGAAT CTTTCCACCA GCAATCCTCT GGGATTCTTT CCCGACCACC | 2880 |
| AGTTGGATCC AGCCTTCAGA GCAAACACCG CAAATCCAGA TTGGGACTTC AATCCCAACA | 2940 |
| AGGACACCTG GCCAGACGCC AACAAGGTAG GAGCTGGAGC ATTCGGGCTG GGACTCACCC | 3000 |
| CACCGCACGG AGGCCTTTTG GGGTGGAGCC CTCAGGCTCA GGGCATACTA CAGACCGTGC | 3060 |
| CAGCAAATCC GCCTCCTGCC TCTACCAATC GCCAGACAGG AAGGCAGCCT ACCCCTCTGT | 3120 |
| CTCCACCTTT GAGAGACACT CATCCTCAGG CCATGCAGTG G | 3161 |

(2) INFORMATION FOR SEQ ID NO: 302:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 302:

| | |
|---|---:|
| AACTCCACAA CCTTCCACCA AACTCTGCAA GATCCCAGAG TGAGAGGCCT GTATTTCCCT | 60 |
| GCTGGTGGCT CCAGTTCAGG AACAGTAAAC CCTGTTCCGA CTACTGCCTC TCACTTATCG | 120 |
| TCAATCTTCT CGAGGATTGG GGACCCTGCG CTGAACATGG AGAACATCAC ATCAGGATTC | 180 |
| CTAGGACCCC TTCTCGTGTT ACAGGCGGGG TTTTTCTTGT TGACAAGAAT CCTCACAATA | 240 |
| CCGCAGAGTC TAGACTCGTG GTGGACTTCT CTCAATTTTC TAGGGGGAAC TACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG CGTTTTATCA TCTTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCCTCAAC CACCAGCACG GGACCATGCC GAACCTGCAC GACTCCTGCT | 540 |
| CAAGGAACCT CTATGTATCC CTCCTGTTGC TGTACCAAAC CTTCGGACGG AAATTGCACC | 600 |
| TGTATTCCCA TCCCATCATC CTGGGCTTTC GGAAAATTCC TATGGGAGTG GCCTCAGCC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAGCATC | 780 |
| TTGAGTCCCT TTTTACCGCT GTTACCAATT TTCTTTTGTC TTTGGGTATA CATTTAAACC | 840 |
| CTAACAAAAC AAAGAGATGG GGTTACTCTC TAAATTTTAT GGGCTATGTC ATTGGATGTT | 900 |
| ATGGGTCCTT GCCACAAGAA CACATCATAC AAAAAATCAA AGAATGTTTT AGAAAACTTC | 960 |
| CTGTTAACAG GCCTATTGAT TGGAAAGTAT GTCAACGAAT TGTGGGTCTT TTGGGTTTTG | 1020 |
| CTGCCCCTTT TACTCAATGT GGTTATCCTG CTTTAATGCC CTTGTATGCA TGTATTCAAT | 1080 |
| CTAAGCAGGC TTTCACTTTC TCGCCAACTT ACAAGGCCTT TCTGTGTAAA CAATACCTGA | 1140 |
| ACCTTTACCC CGTTGCCGGG CAACGGCCAG GTCTATGCCA AGTGTTTGCT GACGCAACCC | 1200 |
| CCACTGGCTG GGGCTTGGCT ATGGGCCATC AGCGCATGCG TGGAACCTTT TCGGCTCCTC | 1260 |
| TGCCGATCCA TACTGCGGAA CTCCTAGCCG CTTGTTTTGC TCGCAGCAGG TCTGGAGCAA | 1320 |
| ACATTATCGG GACTGATAAC TCTGTTGTCC TCTCCCGCAA ATATACATCG TTTCCATGGC | 1380 |

```
TGCTAGGCTG TGCTGCCAAC TGGATCCTGC GCGGGACGTC CTTTGTTTAC GTCCCGTCGG    1440

CGCTGAATCC CGCGGACGAC CCGTCTCGGG GTCGCTTGGG ACTCTCTCGT CCCCTTCTCC    1500

GTCTGCCGTT CCGACCGACC ACGGGGCGCA CCTCTCTTTA CGCGGACTCC CCGTCTGTGC    1560

CTTCTCATCT GCCTGACCTT GTGCACTTCG CTTCACCTCT GCACGTCGCA TGGAGACCAC    1620

CGTGAACGCC CACCAAATAT TGCCCAAGGT CTTACATAAG AGGACTCTTG GACTCTCTGC    1680

AATGTCAACG ACCGACCTTG AGGCATACTT CAAAGACTGT TTGTTTAAAG ACTGGGAGGA    1740

GTTGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACCGT GGAGTTACTC TCGTTTTTGC CTTCTGACTT CTTTCCTTCA    1980

GTACGAGATC TTCTAGATAC CGCCTCAGCT CTGTATCGGG ATGCCTTAGA GTCTCCTGAG    2040

CATTGTTCAC CTCACCATAC TGCACTCAGG CAAGCAATTC TTTGCTGGGG GGAACTAATG    2100

ACTCTAGCTA CCTGGGTGGG TGTTAATTTG GAAGATCCAG CATCTAGGGA CCTAGTAGTC    2160

AGTTATGTCA ACACTAATAT GGGCCTAAAG TTCAGACAAC TCTTGTGGTT TCACATTTCT    2220

TGTCTCATTT TTGGAAGAGA AACAGTTATA GAGTATTTGG TGTCTTTCGG AGTGTGGATT    2280

CGCACTCCTC CAGCTTATAG ACCACCAAAT GCCCCTATCC TATCAACACT TCCGGAGACT    2340

ACTGTTGTTA GACGACGAGG CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATTCC    2460

TTGGACTCAT AAGGTGGGGA ATTTTACTGG GCTTTATTCT TCTACTGTAC CTGTCTTTAA    2520

TCCTCATTGG AAAACACCAT CTTTTCCTAA TATACATTTA CACCAAGACA TTATCAAAAA    2580

ATGTGAACAG TTTGTAGGCC CACTCACAGT TAATGAGAAA AGAAGATTGC AATTGATCAT    2640

GCCTGCTAGG TTTTATCCAA AGGTTACCAA ATATTTACCA TTGGATAAGG GTATTAAACC    2700

TTATTATCCA GAACATCTAG TTAATCATTA CTTCCAAACT AGACACTATT TACACACTCT    2760

ATGGAAGGCG GGTATATTAT ATAAGAGAGA AACAACACAT AGCGCCTCAT TTTGTGGGTC    2820

ACCATATTCT TGGGAACAAG ATCTACAGCA TGGGCAGAA TCTTTCCACC AGCAATCCTC     2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGTTTCACC CCACCGCACG GAGGCCTTTT GGGGTGGAGC CCTCAGGCTC    3060

AGGGCATACT ACAAACTTTG CCAGCAAATC CGCCTCCTGC CTCCACCAAT CGCCAGTCAG    3120

GAAGGCAGCC TACCCCTCTG TCTCCACCTT TGAGAAACAC TCATCCTCAG GCCATGCAGT    3180

GG                                                                  3182
```

(2) INFORMATION FOR SEQ ID NO: 303:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 303:

```
AACTCCACAA CTTTCCACCA AACTCTGCAA GATCCCAGAG TGAGAGGCCT ATATTTCCCT    60
GCTGGTGGCT CCAGTTCAGG AACAGTAAAC CCTGTTCCGA CTACTGCCTC TCCCTTATCG   120
TCAATCTTCT CGAGGATTGG GGACCCTGTG ACGAATATGG AGAACATCAC ATCAGGATTC   180
CTAGGACCCC TGCTCGTGTT ACAGGCGGGG TTTTTCTTGT TGACAAGAAT CCTCACAATA   240
CCGCAGAGTC TAGACTCGTG GTGGACTTCT CTCAATTTTC GAGGGGGAAC TACCGTGTGT   300
CTTGGCCAAA ATTCGCAGTC CCCAACCTCC AATCACTCAC CAACCTCCTG TCCTCCAACT   360
TGTCCTGGTT ATCGCTGGAT GTGTCTGCGG GGTTTTATCA TCTTCCTCTT CATCCTGCTG   420
CTATGCCTCA TCTTCTTGTT GGTTCTTCTG GAGTATCAAG GTATGTTGCA CGTTTGTCCT   480
CTAATTCCAG GAACAACAAC AACCAGTACG GGACCATGCA AAACCTGCAC GACTCCTGCT   540
CAAGGCAACT CTATGTTTCC CTCATGTTGC TGTACCAAAA CTTCGGATGG AAATTGCACC   600
TGTATTCCCA TCCCATCGTC TTGGGCTTTC GCAAAATACC TATGGGAGTG GCCTCAGTC    660
CGTTTCTCTT GGCTCAGTTT ACTAGTGCCA TTTGTTCAGT GGTTCGTAGG GCTTTCCCCC   720
ACTGTTTGGC TTTCAGCTAT ATGGATGATG TGGTATTGGG GGCCAAGTCT GTACAGCATC   780
TTGAGTCCCT TTTTACCGCT GTTACCAATT TTCTTTTGTC TTTGGGTATA CATTTAAACC   840
CTAACAAAAC AAAGAGATGG GGTTACTCTT TACATTTCAT GGGCTATGTC ATTGGATGTT   900
ATGGGTCCTT GCCACAAGAA CACATCATAC AAAAAATCAA AGAATGTTTT AGAAAAGTTC   960
CTGTTAACAG GCCTATTGAT TGGAAAGTAT GTCAACGAAT TGTGGGTCTT TTAGGTTTTG  1020
CTGCCCCTTT CACACAATGT GGTTATCCTG CTTTAATGCC CTTGTATGCT TGTATTCAAT  1080
TTAAGCAGGC TTTCACTTTC TCGCCAACTT ACAAGGCCTT TCTGTGTAAA CAATACCTGA  1140
ACCTTTACCC CGTTGCCCGG CAACGGCCAG GTCTATGCCA AGTGTTTGCT GACGCAACCC  1200
CCACTGGCTG GGGCTTGGGT ATGGGCCATC AGCGCATGCG TGGAACCTTT TCGGCTCCTC  1260
TGCCGATCCA TACTGCGGAA CTCCTAGCCG CCTGTTTTGC TCGCAGCAGG TCTGGAGCAA  1320
ACATTCTCGG GACGGATAAC TCTGTTGTTC TCTCCCGCAA ATATACATCG TTTCCATGGC  1380
TGCTAGGCTG TGCTGCCAAC TGGATCCTGC GCGGGACGTC CTTTGTTTAC GTCCCGTCGG  1440
CGCTGAATCC CGCGGACGAC CCTTCTCGGG GCCGCTTGGG ACTCTCTCGT CCCCTTCTCT  1500
GTCTGCCGTT TCGACCGACC ACGGGGCGCA CCTCTCTTTA CGCGGACTCC CCGTCTGTGC  1560
CTTCTCATCT GCCGGACCGT GTGCACTTCG CTTCACCTCT GCACGTCGCA TGGAGACCAC  1620
CGTGAACGCC CATCAGATCC TGCCCAAGGT CTTACATAAG AGGACTCTTG GACTCCCAGC  1680
AATGTCAACG ACCGACCTTG AGGCCTACTT CAAAGACTGT GTGTTTAAGG ACTGGGAGGA  1740
GCTGGGGGAG GAGATTAGGT TAAAGGTCTT TGTATTAGGA GGCTGTAGGC ATAAATTGGT  1800
CTGCGCACCA GCACCATGCA ACTTTTTCAC CTCTGCCTAA TCATCTCTTG TACATGTCCC  1860
ACTGTTCAAG CCTCCAAGCT GTGCCTTGGG TGGCTTTGGG GCATGGACAT TGACCCTTAT  1920
AAAGAATTTG GAGCTACTGT GGAGTTACTC TCGTTTTTGC CTTCTGACTT CTTTCCTTCC  1980
GTACGAGATC TCCTAGACAC CGCCTCAGCT CTGTATCGGG AAGCCTTAGA GTCTCCTGAG  2040
CATTGTTCAC CTCACCATAC TGCACTCAGG CAAGCAATTC TTTGCTGGGG GAACTAATG   2100
ACTCTAGCTA CCTGGGTGGG TGTTAATTTG GAAGATCCAG CATCTAGAGA CCTAGTAGTC  2160
AGTTATGTCA ACACTAATAT GGGCTTAAAG TTCAGGCAAC TCTTGTGGTT TCACATTTCT  2220
TGTCTCACTT TTGGAAGAGA AACAGTTATA GAGTATTTGG TGGCTTTCGG AGTGTGGATT  2280
CGCACTCCTC CAGCTTATAG ACCACCAAAT GCCCCTATCC TATCAACACT TCCGGAGACT  2340
ACTGTTGTTA GACGACGAGG CAGGTCCCCT AGAAGAAGAA CTCCCTCGCC TCGCAGACGA  2400
```

```
AGGTCTCAAT CGCCGCGTCG CAGAAGATCT CAATCTCGGG AATCTCAATG TTAGTATTCC      2460

TTGGACTCAT AAGGTGGGAA ACTTTACGGG GTTTTATTCT TCTACTGTTC CTGTCTTTAA      2520

CCCTCATTGG GAAACCCCCT CTTTTCCTAA TATACATTTA CACCAAGACA TTATCAAAAA      2580

ATGTGAACAG TTTGTAGGCC CACTCACAGT TAATGAGAAA AGAAGATTGC AATTGATTAT      2640

GCCTGCTAGG TTTTATCCAA AGGTTACCAA ATATTTACCA TTGGATAAGG GTATTAAACC      2700

TTATTATCCA GAACATCTAG TTAATCATTA CTTCCAAACT AGACACTATT TACACACTCT      2760

ATGGAAGGCG GGTATATTAT ATAAGAGAGA ACAACACAT AGCGCCTCAT TTTGTGGGTC       2820

ACCATATTCT TGGGAACAAG ATCTACAGCA TGGGGCAGAA TCTATCCACC AGCAATCCTC      2880

TGGGATTCTT TCCCGACCAC CAGTTGGATC CAGCCTCCAG AGCAAACACC GCAAATCCAG      2940

ATTGGGACTT CAATCCCAAC AAGGACACCT GGCCAGACGC CAACAAGGAT GGAGCTGGAG      3000

CATTCGGGCT GGGACTCACC CCACCGCACG GAGGCCTTTT GGGGTGGAGC CCTCAGGCTC      3060

AGGGCATACT ACACACCGTG CCAGCAAATC CGCCTCCTGC CTCTACCAAT CGCCAGACAG      3120

GAAGGCAACC TACCCCTCTG TCTCCACCTT TGAGAGACAC TCATCCTCAG GCCGTGCAGT      3180

GG                                                                    3182

(2) INFORMATION FOR SEQ ID NO: 304:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 304:

AACTCCACAA CCTTCCACCA AACTCTGCAA GATCCCAGAG TGAGAGGCCT GTATTTCCCT        60

GCTGGTGGCT CCAGTTCAGG AACAGTAAAC CCTGTTCTGA CTACTGCCTC TCCCTTATCG       120

TCAATCTCCG CGAGGACTGG GGACCCTGCA CTGAACATGG AGAACATCAC ATCAGGATTC       180

CTAGGACCCC TGCTCGTGTT ACAGGCGGGG TTTTTCTTGT TGACAAGAAT CCTCACAATA       240

CCGCAGAGTC TAGACTCGTG GTGGACTTCT CTCAATTTTC TAGGGGGAAC TACCGTGTGT       300

CTTGGCCAAA ATTCGCAGTC CCCAACCTCC AATCACTCAC CAACCTCTTG TCCTCCAACT       360

TGTCCTGGTT ATCGCTGGAT GTGTCTGCGG CGTTTTATCA TCTTCCTCTT CATCCTGCTG       420

CTATGCCTCA TCTTCTTGTT GGTTCTTCTG GACTATCAAG GTATGTTGCC CGTTTGTCCT       480

CTAATTCCAG GATCTTCAAC AACCAGCACG GGACCATGCA GAACCTGCAC GACTCCTGCT       540

CAAGGAACCT CTATGTATCC CTCCTGTTGC TGTACCAAAC CTTCGGACGG AAATTGCACC       600

TGTATTCCCA TCCCATCATC TTGGGCTTTC GGAAAATTCC TATGGGAGTG GCCTCAGCC       660

CGTTTCTCCT GGCTCAGTTT ACTAGTGCCA TTTGTTCAGT GGTTCGTAGG GCTTTCCCCC       720

ACTGTTTGGC TTTCAGTTAT ATGGATGATG TGGTATTGGG GGCCAAGTCT GTACAGCATC       780

TTGAGTCCCT TTTTACCGCT GTTACCAATT TTCTTTTGTC TCTGGGTATA CATTTAAACC       840

CTAACAAAAC AAAAAGATGG GGTTATTCCC TAAACTTCAT GGGTTACATA ATTGGAAGTT       900

GGGGAACGTT GCCACAAGAT CATATTGTAC AAAAGATCAA AGAATGTTTT AGAAAACTTC       960

CTGTTAACAG GCCTATTGAT TGGAAAGTAT GGCAACGAAT TGTGGGTCTT TTGGGCTTTH      1020
```

-continued

```
CTGCTCCATT TACACAATGT GGATATCCTG CCTTAATGCC TTTGTATGCC TGTATACAAG    1080

CTAAACAGGC TTTCACTTTC TCGCCAACTT ACAAGGCCTT TCTAAGTAAA CAGTACATGA    1140

ACCTTTACCC CGTTGCTCGG CAACGGCCTG GTCTGTGCCA AGTGTTTGCT GACGCAACCC    1200

CCACTGGCTG GGGCTTGGCA ATAGGCAATC AGCGCATGCG TGGAACCATT GTGGCTCCTC    1260

TGCCGATCCA TACTGCGGAA CTCCTAGCCG CTTGTTTTGC TCGCAGCCGG TCTGGGGCAA    1320

AGCTCATCGG AACTGACAAT TCTGTTGTCC TCTCGCGGAA ATATACATCG TTTCCATGGG    1380

TGCTAGGTTG TACTGCCAAC TGGATCCTTC GCGGGACGTC CTTTGTTTAC GTCCCGTCGG    1440

CGCTGAATCC CGCGGACGAC CCTTCTCGGG GCCGCTTGGG ACTCTCTCGT CCCCTTCTCC    1500

GTCTGCCGTT CCAGCCGACC ACGGGGCGCA CCTCTCTTTA CGCGGTCTCC CCGTCTGTGC    1560

CTTCTCATCT GCCGGTCCGT GTGCACTTCG CTTCACCTCT GCACATTGCA TGGAGACCAC    1620

CGTGAACGCC CATCAGATTA TGCCCAAGGT TTTACATAAG AGGACTCTTG GACTCCCAGC    1680

AATGTCAACG ACCGACCTTG AGGCCTACTT CAAAGACTGT GTGTTTAAGG ACTGGGAGGA    1740

GCTGGGGGAG GAGATTAGGT TAAAGGTCTT TGTATTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTAGG GCATGGACAT TGACCCTTAT    1920

AAACAATTTG GAGCTACTGT GGAGTTACTC CCGTATTTGC CTTCTGACTT CTTTCTCTAC    1980

GTACGAGATC TCCTAGATAC CGCCTCAGCT CTGTATCGGG AAGCCTTAGA GTCTCCTGAG    2040

CATTGTTCAC CTCACCATAC TGCACTCAGG CAAGCAATTC TTTGCTGGGG GGAACTAATG    2100

ACTCTAGCTA CCTGGGTGGG TGTTAATTTG GAAGATCCAG CATCTAGAGA CTTAGTAGTC    2160

AGTTATGTCA ACACTAATAT GGGCCTAAAG TTCAGGCAAC TCTTGTGGTT TCACATTTCT    2220

TGTCTCACTT TTGGAAGAGA AACAGTTATA GAGTATTTGG TGTCTTTCGG AGTGTGGATT    2280

CGCACTCCTC CAGCTTATAG ACCACCAAAT GCCCCTATCC TATCAACACT TCCGGAGACT    2340

ACTGTTGTTA CACGACGAGG CAGGTCCCCT AGAAGAAGAA CTCCCTCGCC TGCCAGACCA    2400

AGGTCTCAAT CGCCGCGTCG CAGAAGATCT CAATCTCGGG AATCTCAATG TTAGTATTCC    2460

TTGGACTCAT AAGGTGGGGA ACTTTACGGG GCTTTATTCT TCTACTGTTC CTGTCTTTAA    2520

TCCTCATTGG AAAACACCTT CTTTTCCTAA TATACATTTA CACCAAGACA TTATCAAAAA    2580

ATGTGAACAA TTTGTAGGCC CACTCACAGT CAATGAGAAA AGAAGACTGC AATTGATTAT    2640

GCCTGCTAGG TTTTATCCAA ATGTCACCAA ATATTTGCCA TTGGATAAGG GTATTAAACC    2700

TTATTATCCA GAGCATCTAG TTAATCATTA CTTCCAAACC AGACATTATT TACACACTCT    2760

ATGGAAGGCG GGTATATTAT ATAAGAGAGA ACAACACAT AGCGCCTCAT TTTGTGGGTC    2820

ACCATATTCT TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGTTTCACC CCACCGCACG GAGGTCTTTT GGGGTGGAGC CCTCAGGCTC    3060

AGGGCATACT ACATACCGTG CCAGCAAATC CGCCTCCTGC CTCTACCAAT CGCCAGTCAG    3120

GAAGGCAGCC TACCCCTCTG TCTCCACCTT TGAGAAACAC TCATCCTCAG GCCATGCAGT    3180

GG                                                                  3182
```

(2) INFORMATION FOR SEQ ID NO: 305:

(i) SEQUENCE CHARACTERISTICS:

(A) LENGTH: 3182 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 305:

```
AACTCCACAA CCTTCCACCA AACTCTGCAA GATCCAAGAG TGAGAGGCCT GTATTTCCCT      60
GCTGGTGGCT CCAGTTCAGG AACAGTAAAC CCTGTTCTGA CTACTGCCTC TCCCTTATCG     120
TCAATCTCCG CGAGGACTGG GGACCCTGTG ACGATCATGG AGAACATCAC ATCAGGATTC     180
CTAGGACCCC TGCTCGTGTT AGAGGCGGGG TTTTTCTTGT TGACAAGAAT CCTCACAATA     240
CCGCAGAGTC TAGACTCGTG GTGGACTTCT CTCAATTTTC TAGGGGAAC TACCGTGTGT      300
CTTGGCCAAA ATTCGCAGTC CCCAACCTCC CATCACTCAC CAACCTCCTG TCCTCCAATT     360
TGTCCTGGTT ATCGCTGGAT GTGTCTGCGG CGTTTTATCA TATTCCTCTT CATCCTGCTG     420
CTATGCCTCA TCTTCTTGTT GGTTCTTCTG GACTATCAAG GTATGTTGCC CGTTTGTCCT     480
CTAATTCCAG GTACTTCAAC AACCAGCACG GGACCATGCA GAACCTGCAC GACTCCTGCT     540
CAAGGAACCT CTATGTATCC CTCCTGTTGC TGTACCAAAC CTTCGGACGG AAATTGCACC     600
TGTATTCCCA TCCCATCATC TTGGGCTTTC GGAAAATTCC TATGGCAGTG GGCCTCAGCC     660
CGTTTCTCCT GGCTCAGTTT ACTAGTGCCA TTTGTTCAGT GGTTCGTAGG GCTTTCCCCC     720
ACTGTTTGGG TTTCAGCTAT ATGGATGATG TGGTATTGGG GGCCAAGTCT GTACAGCATC     780
GTGAGTCCCT TTATACCGCT GTTACCAATT TTCTTTTGTC TCTGGGTATA CATTTAAACC     840
CTAACAAAAC AAAAAGATGG GGTTATTCCC TAAACTTCAT GGGTTACATA ATTGGAAGTT     900
GGGGAACGTT GCCACAGGAT CATATTGTAC AAAAGATCAA ACACTGTTTT AGAAAACTTC     960
CTGTTAACAG GCCTATTGAT TGGAAAGTAT GGCAACGAAT TGTGGGTCTT TTGGGTTTTG    1020
CTGCTCCATT TACACAATGT GGTTATCCTG CCTTAATGCC TTTGTATGCC TGTATACAAG    1080
CTAAACAGGC TTTCACTTTC TCGCCAACTT ACAAGGCCTT TCTAAGTAAA CAGTACATGA    1140
ACCTTTACCC CGTTGCTCGG CAACGGCCTG GTCTGTGCCA AGTGTTTGCT GACGCAACCC    1200
CCACTGGCTG GGGCTTGGCA TAGGGCCATC AGCGCATGCG TGGAACCTTT GAGGCTCCTC    1260
TGCCGATCCA TACTGCGGAA CTCCTAGCCG CTTGTTTTGC TCGCAGCAGG TCTGGAGCAA    1320
ACATTATCGG GACTGATAAC TCTGTTGTCC TATCGCGGAA ATATACATCG TTTCCATGGC    1380
TGCTAGGTTG TACTGCCAAC TGGATCCTTC GCGGGACGTC CTTTGTTTAC GTCCCGTCGG    1440
CGCTGAATCC CGCGGACGAC CCCTCTCGGG GCCGCTTGGG ACTCTCTCGT CCCCTTCTCC    1500
GTCTGCCGTT CCAGCCGACC ACGGGGCGCA CCTCTCTTTA CGCGGTCTCA CCGTCTGTGC    1560
CTTCTCATCT GCCGGTCCGT GTGCACTTCG CTTCACCTCT GCACGTCGCA TGGAGACCAC    1620
CGTGAACGCC CATCAAAGTC TGCCCAAGGT CTTACATAAG AGGACTCTTG GACTCCCAGC    1680
AATGTCAACG ACCGACCTTG AGGCCTACTT CAAAGACTGT GTGTTTAAGG ACTGGGAGGA    1740
GCTGGGGGAG GAGATTAGGT TAAAGGTCTT TGTATTAGGA GGCTGTAGGC ATAAATTGGT    1800
CTGCGCACCA GCACCATGCA ACTTTTTCAC CTCTGCCTAA TCATCTCTTG TTCATGTCCC    1860
ACTGTTCAAG CCTCCAAGCT GTGCCTTGGG TGGCTTTGGG GCATGGACAT TGACCCTTAT    1920
AAAGAATTTG GAGCTACTGT GGAGTTACTC TCGTTTTTGC CTTCTGACTT CTTTCCTTCC    1980
```

```
GTAAGAGATC TCCTAGACAC CGCCTCAGCT CTGTATCGAG AAGCCTTAGA GTCTCCTGAG    2040

CATTGCTCAC CTCACCATAC TGCACTCAGG CAAGCCATTC TCTGCTGGGG GGAACTGATG    2100

ACTCTAGCAT CCTGGGTGGG TGATAATTTG GAAGATCCAG CGTCTAGGGA CCTAGTAGTC    2160

AGTTATGTTA ACACTAATAT GGGCCTAAAG ATCAGGCAAC TATTGTGGTT TCATATATCT    2220

TGCCTTACTT TTGGAAGAGA GACTGTACTT GAATATTTGG TCTCTTTCGG AGTGTGGATT    2280

CGCACTCCTC CAGCCTATAG ACCACCAAAT GCCCCTATCT TATCAACACT TCCGGAAACT    2340

ACTGTTGTTA GACGACGGGA CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATTCC    2460

TTGGACTCAT AAGGTGGGGA ACTTTACTGG GCTTTATTCT TCTACTGTAC CTGTCTTTAA    2520

TCCTCATTGG AAAACACCAT CTTTTCCTAA TATACATTTA CACCAAGACA TTATCAAAAA    2580

ATGTGAACAG TTTGTAGGCC CACTCACAGT TAATGAGAAA AGAAGATTGC AATTGATTAT    2640

GCCTGCTAGG TTTTATCCAA AGGTTACCAA ATATTTACCA TTGGATAAGG GTATTAAACC    2700

TTATTATCCA GAACATCTAG TTAATCATTA CTTCCAAACT AGACACTATT TACACACTCT    2760

ATGGAAGGCG GGTATATTAT ATAAGAGAGA ACAACACAT AGCGCCTCAT TTTGTGGGTC    2820

ACCATATTCT TGGGAACAAG ATCTACAGCA TGGGGCAGAA TCTATCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGTTTCACC CCACCGCACG GAGGCCTTTT GGGGTGGAGC CCTCAGGCTC    3060

AGGGCATACT ACAAACTTTG CCAGCAAATC CGCCTCCTGC CTCCACCAAT CGCCAGTCAG    3120

GAAGGCAGCC TACCCCTCTG TCTCCACCTT TGAGAAACAC TCATCCTCAG GCCATGCAGT    3180

GG                                                                   3182

(2) INFORMATION FOR SEQ ID NO: 306:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 306:

AACTCCACAA CCTTCCACCA AACTCTGCAA GATCCCAGAG TGAGAGGCCT GTATCTCCCT      60

GCTGGTGGCT CCAGTTCAGG AACAGTAAAC CCTGTTCCGA CTACTGTCTC TCCCATATCG     120

TCAATCTTCT CGAGGATTGG GGACCCTGCG CTGAACATGG AGAACATCAC ATCAGGATTC     180

CTAGGACCCC TGCTCGTGTT ACAGGCGGGG TTTTTCTTGT TGACAAAAAT CCTCACAATA     240

CCGAAGAGTC TAGACTCGTG GTGGACTTCT CTCAATTTTC TAGGGGGAAC CACCGTGTGT     300

CTTGGCCAAA ATTCGCAGTC CCCAACCTCC AATCACTCAC CAACCTCCTG TCCTCCAACT     360

TGTCCTGGTT ATCGCTGGAT GTGTCTGCGG CGTTTTATCA TCTTCCTCTT CATCCTGCTG     420

CTATGCCTCA TCTTCTTGTT GGTTCTTCTG GACTATCAAG GTATGTTGCC CGTTTGTCCT     480

CTGATTCCAG GATCTTCAAC CACCAGCACG GGACCATGCA GAACCTGCAC GACTCCTGCT     540

CAAGGAACCT CTATGTATCC CTCCTGTTGC TGTACCAAAC CTTCGGACGG AAATTGCACC     600
```

```
TGTATTCCCA TCCCATCATC CTGGGCTTTC GGAAAATTCC TATGGGAGTG GGCCTCAGCC      660

CGTTTCTCCT GGCTCAGTTT ACTAGTGCCA TTTGTTCAGT GGTTCGTAGG GCTTTCCCCC      720

ACTGTTTGGC TTTTAGTTAT ATGGATGATG TGGTATTGGG GGCCAAAACT GTTCACCATC      780

TTGAGTCCCT TTTTACCGCT GTTACCAATT TTCTTTTGTC TTTGGGTATA CATCTAAACC      840

CTAACAAAAC AAAAAGATGG GGTTACTCTT TACATTTTAT GGGCTATGTC ATTGGATGTT      900

ATGGGTCTTT GCCACAAGAT CACATCATAC AGAAAATCAA AGAATGTTTT AGAAAACTTC      960

CTGTTAACAG GCCTATTGAT TGGAAAGTCT GTCAACGTAT TGTGGGTCTT TTGGGATTTG     1020

CTGCTCCTTT TACACAATGT GGTTATCCTG CTTTAATGCC CTTGTATGCA TGTATTCAAT     1080

CTAAGCAGGC TTTCACTTTC TCGCCAACTT ACAAGGCCTT TCTGTGTAAA CAATACCTGA     1140

ACCTTTACCC CGTTGCCCGG CAACGCCCAG GTCTGTGCCA AGTGTTTGCT GACGCAACCC     1200

CCACTGGCTG GGGCTTGGTC ATGGGCCATC AGCGCATGCG TGGAACCTTT CAGGCTCCTC     1260

TGCCGATCCA TACTGCGGAA CTCCTAGCCG CTTGTTTTGC TCGCAGCCGG TCTGGAGCAA     1320

ACATTCTCGG GACGGATAAC TCTGTTGTTC TCTCCCGCAA ATATACGTCG TTTCCATGGC     1380

TGCTAGGCTG TGCTGCCAAC TGGATCCTGC GCGGGACGTC CTTTGTTTAC GTCCCGTCGA     1440

CGCTGAATCC CGCGGACGAC CCTTCTCGGG GCCGCTTGGG ACTCTCTCGT CCCCTTCTCC     1500

GTCTGCCGTT TCGACCGACC ACGGGGCGCA CCTCTCTTTA CGCGGACTCC CCGTCTGTGC     1560

CTTCTCATCT GCCGGACCGT GTGCACTTCG CTTCACCTCT GCACGTCGCA TGGAGACCAC     1620

CGTGAACGCC CACCAATTCT TGCCCAAGGT CTTACATAAG AGGACTCTTG GACTCTCTGT     1680

AATGTCAACG ACCGACCTTG AGGCATACTT CAAAGACTGT TTGTTTAAGG ACTGGGAGGA     1740

GTCGGGGGAG GAGATTAGAT TAATGATCTT TGTACTAGGA GGCTGTAGGC ATAAATTGGT     1800

CTGCGCACCA GCACCATGCA ACTTTTTCAC CTCTGCCTAA TCATCTCTTG TTCATGTCCT     1860

ACTGTTCAAG CCTCCAAGCT GTGCCTTGGG TGGCTTTAGG ACATGGACAT TGATCCTTAT     1920

AAAGAATTTG GAGCTACTGT GGAGTTACTC TCGTTTCTGC CTTCTGACTT CTTTCCTTCA     1980

GTACGAGATC TTCTAGATAC CGCCTCAGCT CTATATCGGG AAGCCTTAGA ATCTCCTGAG     2040

CATTGTTCAC CTCACCATAC TGCACTCAGG CAAGCAATTC TCTGCTGGGG GGATCTAATA     2100

ACTCTATCCA CCTGGGTGGG TGGTAATTTG GAAGATCCAA CATCTAGGGA CCTAGTAGTC     2160

AGTTATGTTA ACACTAATAT GGGCCTAAAG TTCAGGCAAC TATTGTGGTT TCACATTTCT     2220

TGTCTCACTT TTGGAAGAGA AACGGTCATA GAGTATTTGG TGTCTTTTGG AGTGTGGATT     2280

CGCACTCCTC CAGCTTATAG ACCACCAAAT GCCCCTATCT TATCAACACT TCCGGAGACT     2340

ACTGTTGTTA GACGACGAGG CAGGTCCCCT AGAAGAAGAA CTCCCTCGCC TCGCAGACGA     2400

AGGTCTCAAT CGCCACGTCG CAGAAGAACT CAATCTCGGG AATCTCAATG TTAGTATTCC     2460

CTGGACTCAT AAGGTGGGAA ACTTTACGGG GCTTTATTCT TCTACTGTTC CTGTCTTTAA     2520

CCCTCATTGG AAAACACCCT CTTTTCCTAA TATACATTTA CACCAAGACA TTATCAAAAA     2580

ATGTGAACAA TTTGTAGGCC CACTCACAGT CAATGAGAAA AGAAGACTGC AATTGATTAT     2640

GCCTGCTAGG TTTTATCCAA AGGTTACCAA ATATTTGCCA TTGGATAAGG GTATTAAACC     2700

TTATTATCCA GAACATCTAG TTAATCATTA CTTCCAAACC AGACATTATT TACACACTCT     2760

ATGGAAGGCG GGTGTATTAT ATAAGAGAGA AACTACACAT AGCGCCTCAT TTTGTGGGTC     2820

ACCATATTCC TGGGAACAAG AGCTACAGCA TGGGGCAGAA TCTTTCCACC AGCAATCCTC     2880

TGGGATTCTT TCCCGACCAC CAGTTGGATC CAGCCTTCAG AGCAAACACT GCAAATCCAG     2940

ATTGGGACTT CAATCCCAAC AAGGACTCCT GGCCAGACGC CAACAAGGTA GGAGCTGGAG     3000
```

```
CATTCGGGCT GGGATTCACC CCACCGCACG GAGGCCTTTT GGGGTGGAGC CCTCAGGCTC   3060

AGGGCATACT ACAAACCTTG CCAGCAAATC CGCCTCCTGC CTCCACCAAT CGCCAGTCAG   3120

GAAGGCAACC TACCCCTCTG TCTCCACCTT TGAGAAACAC TCATCCTCAG GCCATGCAGT   3180

GG                                                                 3182
```

(2) INFORMATION FOR SEQ ID NO: 307:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 307:

```
AACTCCACAA CCTTCCACCA AACTCTGCAA GATCCCAGAG TGAGAGGCCT GTATTTCCCT     60

GCTGGTGGCT CCAGTTCAGG AACAGTAAAC CCTGTTCCGA CTACTGTCTC TCCCATATCG    120

TCAATCTTCT CGAGGATTGG GGACCCTGCG CTGAACATGG AGAACATCAC ATCAGGATTC    180

CTAGGACCCC TGCTCGTGTT ACAGGCGGGG TTTTTCTTGT TGACAAGAAT CCTCACAATA    240

CCGCAGAGTC TAGACTCGTG GTGGACTTCT CTCAATTTTC TAGGGGGAAC TACCGTGTGT    300

CTTGGCCAAA ATTCGCAGTC CCCAACCTCC AATCACTCAC CAACCTCCTG TCCTCCAACT    360

TGTCCTGGTT ATCGCTGGAT GTGTCTGCGG CGTTTTATCA TCTTCCTCTT CATCCTGCTG    420

CTATGCCTCA TCTTCTTGTT GGTTCTTCTG GACTATCAAG GTATGTTGCC CGTTTGTCCT    480

CTAATTCCAG GATCTTCAAC TACCAGCACG GGACCATGCA GAACCTGCAC GACTCCTGCT    540

CAAGGAACCT CTATGTATCC CTCCTGTTGC TGTACCAAAC CTTCGGACGG AAATTGCACC    600

TGTATTCCCA TCCCATCATC CTGGGCTTTC GGAAAATTCC TATGGGAGTG GGCCTCAGCC    660

CGTTTCTCCT GGCTCAGTTT ACTAGTGCCA TTTGTTCAGT GGTTCGTAGG GCTTTCCCCC    720

ACTGTTTGGC TTTCAGTTAT ATGGATGATG TGGTATTGGG GGCCAAGTCT GTACAGCATC    780

TTGAGTCCCT TTTTACCGCT GTTACCAATT TTCTTCTGTC TTTGGGTATA CATTTAAACC    840

CTAACAAAAC AAAAAGATGG GGTTACTCTT TACATTTCAT GGGCTATGTC ATTGGATGTT    900

ATGGGTCATT GCCACAAGAT CACATCATAC AGAAAATCAA AGAATGCTTT AGAAAACTTC    960

CTGTTAACAG GCCTATTGAT TGGAAAGTCT GTCAACGTAT TGTGGGTCTT TTGGGTTTTG   1020

CTGCCCCTTT TACACAATGT GGTTATCCTG CTTTAATGCC TTTGTATGCA TGTATTCAGT   1080

CGAAGCAGGC TTTTACTTTC TCGCCAACTT ACAAGGCCTT TCTGTGTAAA CAATACCTGA   1140

ACCTTTACCC CGTTGCCCGG CAACGGCCAG GTCTGTGCCA AGTGTTTGCT GACGCAACCC   1200

CCACTGGCTG GGGCTTGGTC ATGGGCCATC AGCGCATGCG TGGAACCTTT CTGGCTCGTC   1260

TGCCGATCCA TACTGCGGAA CTCCTAGCCG CTTGTTTTGC TCGCAGCAGG TCTGGAGCAA   1320

ACATTCTCGG GACGGATAAC TCTGTTGTTC TCTCCCGCAA ATATACATCG TATCCATGGC   1380

TGCTAGGCTG TGCTGCCAAC TGGATCCTGC GCGGGACGTC CTTTGTTTAC GTCCCGTCGG   1440

CGCTGAATCC CGCGGACGAC CCTTCTCGGG GTCGCTTGGG ACTCTCTCGT CCCCTTCTCC   1500

GTCTGCCGTT TCGACCGACC ACGGGGCGCA CCTCTCTTTA CGCGGACTCC CCGTCTGTGC   1560

CTTCTCATCT GCCGGACCGT GTGCACTTCG CTTCACCTCT GCACGTCGCA TGGAGACCAC   1620
```

```
CGTGAAAGCC CAACCATTCT TGCCCAAGGT CTTACATAAG AGGACTCTTG GACTCTCTGT      1680

AATGTCAACG ACCGACCTTG AGGCATACTT CAAAGACTGT TTGTTTAAAG ACTGGGAGGA      1740

GTTGGGGGAG GAGATTAGAT TAAAGGTCTT TGTATTAGGA GGCTGTAGGC ATAAATTGGT      1800

CTGCGCACCA GCACCATGCA ACTTTTTCAC CTCTGCCTAA TCATCTCTTG TTCATGTCCT      1860

ACTGTTCAAG CCTCCAAGCT GTGCCTTGGG TGGCTTTGGG GCATGGACAT TGATCCTTAT      1920

AAAGAATTTG GAGCTACTGT GGAGTTACTC TCGTTTTTGC CTTCTGACTT CTTTCCTTCA      1980

GTACGAGATC TTCTAGATAA CGCCTCAGCT CTGTATCGGG AAGCCTTAGA GTCTCCTGAG      2040

CATTGTTCAC CTCACCATAC TGCACTCAGG CAAGCAATAC TGTGCTGGGG GAACTAATG       2100

ACTCTAGCTA CCTGGGTGGG TGGTAATTTG GAAGATCCAA TATCCAGGGA CCTAGTAGTC      2160

AGTTATGTCA ACACTAATAT GGGCCTAAAA TTCAGGCAAC TATTGTGGTT TCACATTTCT      2220

TGTCTCACTT TTGGAAGAGA AACAGTTATA GAGTATTTGG TGTCTTTTGG AGTGTGGATT      2280

CGCACTCCTC CAGCTTATAG ACCACCAAAT GCCCCTATCT TATCAACACT TCCGGAGACT      2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATTCC      2460

TTGGACTCAT AAGGTGGGAA ACTTTACGGG GCTTTATTCT TCTACTGTAC CTGTCTTTAA      2520

CCCTCATTGG AAAACACCCT CTTTTCCTAA TATACATTTA CACCAAGACA TTATCAAAAA      2580

ATGTGAACAA TTTGTAGGCC CACTCACAGT CAATGAGAAA AGAAGACTGC AATTGATTAT      2640

GCCAGCTAGG TTTTATCCAA ATGTTACCAA ATATTTGCCA TTGGATAAGG GTATTAAACC      2700

TTATTATCCA GAATATTTAG TTAATCATTA CTTCCAAACT AGACATTATT TACACACTCT      2760

ATGGAAGGCG GGTATATTAT ACAAGAGAGA AACTACACAT AGCGCCTCAT TTTGTGGGTC      2820

ACCATATTCT TGGGAACAAG AGCTACAGCA TGGGGCAGAA TCTTTCCACC AGCAATCCTC      2880

TGGGATTCTT TCCCGACCAC CAGTTGGATC CAGCCTTCAG AGCAAACACC GCAAATCCAG      2940

ATTGGGACTT CAATCCCAAC AAGGACACCT GGCCAGACGC CAACAAGGTA GGAGCTGGAG      3000

CATTCGGGCT GGGATTCACC CCACCACACG GAGGCCTTTT GGGGTGGAGC CCTCAGGCTC      3060

AGGGCATACT AGAAACGTTG CCAGCAAATC CGCCTCCTGC CTCTACCAAT CGCCAGTCAG      3120

GAAGGCAGCC TACCCCGCTG TCTCCACCTT TGAGAAACAC TCATCCTCAG GCCATGCAGT      3180

GG                                                                    3182

(2) INFORMATION FOR SEQ ID NO: 308:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 308:

AACTCCACAA CTTTCCACCA AACTCTGCAA GATCCCAGGG TGAGAGGCCT GTATTTCCCT        60

GCTGGTGGCT CCAGTTCAGG AACAGTAAAC CCTGTTCCGA CTACTGCCTC TCCCATATCG       120

TCAATCTTCT CGAGGATTGG GGACCCTGCA CTGAACATGG AGAACATCAC ATCAGGATTC       180

CTAGGACCCC TGCTCGTGTT ACAGGCGGGG TTTTTCTTGT TGACAAGAAT CCTCACAATA       240
```

-continued

```
CCGCAGAGTC TAGACTCGTG GTGGACTTCT CTCAATTTTC TAGGGGGAAC CACCGTGTGT      300
CTTGGCCAAA ATTCGCAGTC CCCAACCTCC AATCACTCAC CAACCTCCTG TCCTCCAACT      360
TGTCCTGGTT ATCGCTGGAT GTGTCTGCGG CGTTTTATCA TCTTCCTCTT CATCCTGCTT      420
CTATGCCTCA TCTTCTTGTT GGTTCTACTG GACTATCAAG GTATGTTGCC CGTGTGTCCT      480
CTAATTCCAG GATCTTCAAC CACCAGCGCG GGACCATGCA GAACCTGCAC GACTACTGCT      540
CAAGGAACCT CTATGTATCC CTCCTGTTGC TGTACCAAAC CTTCGGACGG AAATTGCACC      600
TGTATTCCCA TCCCATCATC CTGGGCTTTC GGAAAATTCC TATGGGAGTG GGCCTCAGCC      660
CGTTTCTCCT GGCTCAGTTT ACTAGTGCCA TTTGTTCAGT GGTTCGTAGG GCTTTCCCCC      720
ACTGTTTGGC TTTCAGTTAT ATGGATGATG TGGTATTGGG GGCCAAGTCT GTACAGCATC      780
TTGAGTCCCT TTTTACCGCT GTTACCAATT TTCTTTTGTC TTTGGGTATA CATTTAAACC      840
CTAACAAAAC TAAGAGATGG GGTTACTCTT TACATTTCAT GGGCTATGTC ATTGGAAGTT      900
ATGGGTCATT GCCACAAGAT CACATCATAC AGAAAATCAA AGAATGTTTT AGAAAACTTC      960
CTATTAACAG GCCTATTGAT TGGAAAGTCT GTCAACGTAT TGTGGGTCTT TTGGGTTTTG     1020
CTGCCCCTTT TACACAATGT GGTTATCCTG CTTTAATGCC CTTGTATGCC TGTATTCAAT     1080
CTAAACAGGC TTTCACTTTC TCGCCAACTT ACAAGGCCTT TCTGTGTAAA CAATACCTGA     1140
ACCTTTACCC CGTTGCTAGG CAACGGCCAG GTCTGTGCCA AGTGTTTGCT GACGCAACCC     1200
CCACTGGCTG GGGCTTGGTC ATGGGCCATC AGCGCATGCG TGGAACCTTT CTGGCTCCTC     1260
TGCCGATCCA TACTGCGGAA CTCCTAGCCG CTTGTTTTGC TCGCAGCAGG TCTGGAGCAA     1320
ACATTCTCGG GACGGATAAC TCTGTTGTTC TCTCCCGCAA ATATACATCG TTTCCATGGC     1380
TGCTAGGCTG TGCTGCCAAC TGGATCCTGC GCGGGACGTC CTTTGTTTAC GTCCCGTCGG     1440
CGCTGAATCC CGCGGACGAC CCTTCTCGGG GCCGCTTGGG GATCTTTCGT CCCCTTCTCC     1500
GTCTGCCGTT CCGTCCGACC ACGGGGCGCA CCTCTCTTTA CGCGGACTCC CCGTCTGTGC     1560
CTTCTCATCT GCCGGTCCGT GTGCACTTCG CTTCACCTCT GCACGTCGCA TGGAGACCAC     1620
CGTGAACGCC CACCACTTCT TGCCCAAGGT CTTACATAAG AGGACTCTTG GACTCTCAGC     1680
AATGTCAACG ACCGACCTTG AGGCATACTT CAAAGACTGT TTGTTTAAGG ACTGGGAGGA     1740
GTTGGGGGAG GAGATTAGAT TAAAGGTCTT TGTACTAGGA GGCTGTAGGC ATAAATTGGT     1800
CTGCGCACCA GCACCATGCA ACTTTTTCAC CTCTGCCTAA TCATCTCTTG TTCATGTCCT     1860
ACTGTTCAAG CCTCCAAGCT GTGCCTTGGG TGGCTTTGGG GCATGGACAT TGACCCTTAT     1920
AAAGAATTTG GAGCTACTGT GGAGTTACTC TCATTTTTGC CTTCTGACTT TTTTCCTTCG     1980
GTACGAGATC TTCTAGATAC CGCCTCAGCT CTGTATCGGG ATGCCTTAGA GTCTCCTGAG     2040
CATTGTTCAC CTCACCATAC TGCACTCAGG CAAGCAATTC TTTGCTGGGG GAACTAATG     2100
ACTCTAGCTA CCTGGGTGGG TGTTAATTTG GAAGATCCAG CATCTAGGGA CCTAGTAGTC     2160
AGTTATGTCA ACACTAATAT GGGCCTAAAG TTCAGGCAAC TATTGTGGTT TCACATTTCT     2220
TGTCTCACTT TTGGAAGAGA AACAGTCATA GAGTATTTGG TGTCTTTCGG AGTGTGGATT     2280
CGCACTCCTC CAGCTTATAG ACCACCAAAT GCCCCTATCT TATCAACACT TCCGGAAACT     2340
ACTGTTGTTA GACGACGAGG CAGGTCCCCT AGAAGAAGAA CTCCCTCGCC TCGCAGACGA     2400
AGATCTCAAT CGCCGCGTCG CAGAAGATCT CAATCTCGGG AATCTCAATG TTAGTATTCC     2460
TTGGACTCAT AAAGTGGGTA ACTTTACGGG GCTTTATTCC TCTACTGTAC CTGTCTTTAA     2520
CCCTCATTGG AAAACACCCT CTTTTCCTAA TATACATCTA CACCAAGACA TTATCAAAAA     2580
```

-continued

| | |
|---|---|
| ATGTGAACAA TTTGTAGGCC CACTCACAGT AAATGAGAAA CGAAGACTGC AATTAATTAT | 2640 |
| GCCTGCTAGG TTTTATCCAA ATGTTACTAA ATATTTGCCA TTAGATAAGG GTATTAAACC | 2700 |
| TTATTATCCG GAACATTTAG TTAATCATTA CTTCCAAACC AGACATTATT TACACACTCT | 2760 |
| ATGGAAGGCG GGTATATTAT ATAAGAGGGA AACAACACGT AGCGCCTCAT TTTGTGGGTC | 2820 |
| ACCATATTCT TGGGAACAAG AGCTACAGCA TGGGGCAGAA TCTTTCCACC AGCAATCCTC | 2880 |
| TGGGATTCTT TCCCGACCAC CAGTTGGATC CAGCCTTCAG AGCAAACACC GCAAATCCAG | 2940 |
| ATTGGGACTT CAATCCCAAC AAGGACACCT GGCCAGACGC CAACAAGGTA GGAGCTGGAG | 3000 |
| CATTCGGGCT GGGATTCACC CCACCGCACG GAGGCCTTTT GGGGTGGAGC CCTCAGGCTC | 3060 |
| AGGGCATAAT ACAAACCTTG CCAGCAAATC CGCCTCCTGC ATCTACCAAT CGCCAGTCAG | 3120 |
| GAAGGCAGCC TACCCCGCTG TCTCCACCTT TGAGAAACAC TCATCCTCAG GCCATGCAGT | 3180 |
| GG | 3182 |

(2) INFORMATION FOR SEQ ID NO: 309:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 309:

| | |
|---|---|
| AACTCCACAA CATTTCATCA AGCTCTGCAG GATCCCAGAG TAAGAGGCCT GTATTTTCCT | 60 |
| GCTGGTGGCT CCAGTTCCGG AACAGTGAAC CCTGTTCCGA CTACTGCCTC ACTCATCTCG | 120 |
| TCAATCTTCT CGAGGATTGG GGACCCTGCA CCGAACATGG AAAGCATCAC ATCAGGATTC | 180 |
| CTAGGACCCC TGCTCGTGTT ACAGGCGGGG TTTTTCTTGT TGACAAAAAT CCTCACAATA | 240 |
| CCGCAGAGTC TAGACTCGTG GTGGACTTCT CTCAATTTTC TAGGGGGAGC TCCCGTGTGT | 300 |
| CTTGGCCAAA ATTCGCAGTC CCCAACCTCC AATCACTCAC CAACCTCTTG TCCTCCAATT | 360 |
| TGTCCTGGCT ATCGCTGGAT GTGTCTGCGG CGTTTTATCA TCTTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCATCAAC CACCAGCACG GGACCCTGCC GAACCTGCAT GACTCTTGCT | 540 |
| CAAGGAACCT CTATGTTTCC CTCATGTTGC TGTTCAAAAC CTTCGGACGG AAATTGCACT | 600 |
| TGTATTCCCA TCCCATCATC ATGGGCTTTC GGAAAATTCC TATGGGAGTG GGCCTCAGCC | 660 |
| CGTTTCTCCT GGCTCAGTTT ACTAGTGCCA TTTGTTCAGT GGTTCGCCGG GCTTTCCCCC | 720 |
| ACTGTCTGGC TTTCAGTTAT ATGGATGATG TGGTATTGGG GGCCAAGTCT GTACGACATC | 780 |
| TTGAGTCCCT TTATACCTCT GTTACCAATT TTCTTTTGTC TTTGGGTATA CATTTAAATC | 840 |
| CCAACAAAAC AAAAAGATGG GGATATTCCC TAAATTTCAT GGGTTATGTA ATTGGAAGTT | 900 |
| GGGGGTCATT ACCACAGGAA CACATCATAC AAAAAATCAA ACACTGTTTT GGAAAACTCC | 960 |
| CTGTTAACCG GCCTATTGAT TGGAAAGTAT GTCAAGGAAT TGTGGGTCTT TTGGGCTTTG | 1020 |
| CTGCCCCTTT TACACAATGT GGGTATCCTG CTTTAATGCC TCTGTATACG TGTATTCAAT | 1080 |
| CTAAGCAGGC TTTCACTTTC TCGCCAACTT ACAAGGCCTT TCTGTGTAAA CAATACCTGA | 1140 |
| ACCTTTACCC CGTTGCCCGG CAACGGCCAG GTCTGTGCCA AGTGTTTGCT GATGCAACCC | 1200 |

```
CCACTGGCTG GGGCTTGGCC ATAGGCATTC AGCGCATGCG CGGAACCTTT GTGGCTCCTC    1260

TGCCGATCCA TACTGCGGAA CTCCTAGCCG CTTGTTTTGC TCGCAGCAGG TCTGGAGCAA    1320

AACTTATCGG GACCGATAAT TCTGTCGTTC TCTCCCGGAA ATATACATCC TTTCCATGGC    1380

TGCTAGGCTG TGCTGCCAAC TGGATCCTGC GAGGGACGTC CTTTGTCTAC GTCCCGTCAG    1440

CGCTGAATCC TGCGGACGAC CCGTCTCGGG GTCGCTTGGG GATCTTTCGT CCCCTTCTCC    1500

GTCTGCGGTT CCGGCCGACC ACGGGGCGCA CCTCTCTTTA CGCGGTCTCC CCGTCTGTGC    1560

CTTCTCATCT GCCGGACCGT GTGCACTTCG CTTCACCTCT GCACGTCGCA TGGAGACCAC    1620

CGTGAACGCC CACCAAATCT TGCCCAAGGT CTTACATAAG AGGACTCTTG GACTCTCTGC    1680

AATGTCAACG ACCGACCTTG AGGCATACTT CAAAGACTGT TTGTTTAAAG ACTGGGAGGA    1740

GTTGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCA    1980

GTAAGAGATC TTCTAGATAC CGCCTCAGCT CTGTATCGGG ATGCCTTAGA ATCTCCTGAA    2040

CATTGTTCAC CGCACCACAC TGCACTCAGG CAAGCCATTC TTTGCTGGGG GGAACTAATG    2100

ACTCTAGCTA CCTGGGTGGG TGTAAATTTG GAAGATCCAG CATCCAGGGA CCTAGTAGTC    2160

AGTTATGTCA ATACTAATAT GGGCCTAAAG TTCAGGCAAT TATTGTGGTT TCACATTTCT    2220

TGTCTCACTT TTGGAAGAGA AACCGTCATA GAGTATTTGG TGTCTTTTGG AGTGTGGATT    2280

CGCACTCCTC CAGCTTATAG ACCACCAAAT GCCCCTATCT TATCAACACT TCCGGAGAAT    2340

ACTGTTGTTA GACGAAGAGG CAGGTCCCCT AGAAGAAGAA CTCCCTCGCC TCGCAGACGA    2400

AGATCTCAAT CGCCGCGTCG CAGAAGATCT CAATCTCCAG CTTCCCAATG TTAGTATTCC    2460

TTGGACTCAT AAGGTGGGAA ATTTTACGGG GCTCTACTCT TCTACTATTC CTGTCTTTAA    2520

TCCTAACTGG AAAACTCCAT CTTTTCCTGA TATTCATTTG CACCAGGACA TTATTAACAA    2580

ATGTGAACAA TTTGTAGGTC CTCTAACAGT AAATGAAAAA CGAAGATTAA ACTTAGTCAT    2640

GCCTGCTAGA TTTTTTCCCA TCTCTACAAA ATATTTGCCC CTAGAGAAAG GTATAAAACC    2700

TTATTATCCA GATAATGTAG TTAATCATTA CTTCCAAACC AGACACTATT TACATACCCT    2760

ATGGAAGGCT GGGCATCTAT ATAAAAGAGA AACTACACGT AGCGCCTCAT TTTGTGGGTC    2820

ACCATATTCT TGGGAACAAG AGCTACATCA TGGGGCTTTC TTGGACGGTC CCTCTCGAAT    2880

GGGGGAAGAA TATTTCCACC ACCAATCCTC TGGGATTTTT TCCCGACCAC CAGTTGGATC    2940

CAGCATTCAG AGCAAACACC AGAAATCCAG ATTGGGACCA CAATCCCAAC AAAGACCACT    3000

GGACGGAAGC CAACAAGGTA GGAGTGGGAG CCTTCGGGCC GGGGTTCACT CCCCCACACG    3060

GAGGCCTTTT GGGGTGGAGC CCTCAGGCTC AAGGCATGCT AAAAACATTG CCAGCAGACC    3120

CGCCTCCTGC CTCCACCAAT CGGCAGTCAG GAAGGCAGCC TACCCAATC ACTCCACCTT    3180

TGAGAGACAC TCATCCTCAG GCCATGCAGT GG                                  3212
```

(2) INFORMATION FOR SEQ ID NO: 310:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 310:

```
AATTCCACAA CATTCCACCA AGCTCTGCAG GATCCCAGAG TAAGAGGCCT GTATTTTCCT     60
GCTGGTGGCT CCAGTTCCGG AACAGTGAAC CCTGTTCCGA CTACTGCCTC ACTCATCTCG    120
TCAATCTTCT CGAGGATTGG GGACCCTGCA CCGAACATGG AAAGCATCAC ATCAGGATTC    180
CTAGGACCCC TGCTCGTGTT ACAGGCGGGG TTTTTCTTGT TGACAAAAAT CCTCACAATA    240
CCGCAGAGTC TAGACTCGTG GTGGACTTCT CTCAATTTTC TAGGGGGAGC TCCCGTGTGT    300
CTTGGCCAAA ATTCGCAGTC CCCAACCTCC AGTCACTCAC CAACCTCTTG TCCTCCAATT    360
TGTCCTGGCT ATCGCTGGAT GTGTCTGCGG CGTTTTATCA TCTTCCTCTT CATCCTGCTG    420
CTATGCCTCA TCTTCTTGTT GGTTCTTCTG GACTATCAAG GTATGTTGCC CGTTTGTCCT    480
CTAATTCCAG GATCATCAAC CACCAGTACG GGACCCTGCC GAACCTGCAC GACTCTTGCT    540
CAAGGAACCT CTATGTTTCC CTCATGTTGC TGTTCAAAAC CTTCGGACGG AAATTGCACT    600
TGTATTCCCA TCCCATCATC ATGGGCTTTC GGAAAATTCC TATGGGAGTG GGCCTCAGCC    660
CGTTTCTCCT GGCTCAGTTT ACTAGTGCCA TTTGTTCAGT GGTTCGCCGG GCTTTCCCCC    720
ACTGTCTGGC TTTCAGTTAT ATGGATGATG TGGTATTGGG GGCCAAGTCT GTACAACATC    780
TTGAGTCCCT TTATACCGCT GTTACCAATT TTCTTTTGTC TTTGGGTATA CATTTAAATC    840
CCAACAAAAC AAAAAGATGG GGCTATTCCC TTAATTTCAT GGGTTATGTA ATTGGAAGTT    900
GGGGCTCATT ACCACAGGAA CACATCATAC AAAAAATCAA AGACTGTTTT AGAAAACTCC    960
CTGTTAACCG GCCTATTGAT TGGAAAGTAT GTCAAAGAAT TGTGGGTCTT TTGGGCTTTG   1020
CTGCCCCCTT TACACAATGT GGATATCCTG CTTTAATGCC TCTGTATGCA TGTACTCAAT   1080
CTAAGCAGGC TTTCACTTTC TCGCCAACTT ACAAGGCCTT TCTGTGTAAA CAATACCTGA   1140
ACCTTTACCC CGTTGCCCGG CAACGGCCAG GTCTGTGCCA AGTGTTTGCT GATGCAACCC   1200
CCACTGGCTG GGGCTTGGCC ATAGGCATTC AGCGCATGCG CGGAACCTTT GTGGCTCCTC   1260
TGCCGATCCA TACTGCGGAA CTCCTAGCCG CTTGTTTTGC TCGCAGCAGG TCTGGAGCAA   1320
AACTTATCGG GACCGATAAT TCTGTCGTTC TCTCCCGGAA GTATACATCC TTTCCATGGC   1380
TGCTAGGCTG TGCTGCCAAC TGGATCCTGC GAGGGACGTC CTTTGTCTAC GTCCCGTCAG   1440
CGCTGAATCC TGCGGACGAC CCGTCTCGGG GTCGCTTGGG GATCTATCGT CCCCTTCTCC   1500
GTCTGCCGTT CCAGCCGACC ACGGGGCGCA CCTCTCTTTA CGCGGTCTCC CCGTCTGTTC   1560
CTTCTCATCT GCCGGACCGT GTGCACTTCG CTTCACCTCT GCACGTCGCA TGGAGACCAC   1620
CGTGAACGCC CACCAAATAT TGCCCAAGGT CTTACATAAG AGGACTCTTG GACTCTCTGC   1680
AATGTCAACG ACCGACCTTG AGGCATACTT CAAAGACTGT TTGTTTAAAG ACTGGGAGGA   1740
GTCGGGGGAG GAGATTAGAT TAAAGGTCTT TGTACTAGGA GGCTGTAGGC ATAAATTGGT   1800
CTGCGCACCA GCACCATGCA ACTTTTTCAC CTCTGCCTAA TCATCTCTTG TTCATGTCCT   1860
ACTGTTCAAG CCTCCAAGCT GTGCCTTGGG TGGCTTTGGG GCATGGACAT TGACCCTTAT   1920
AAAGAATTTG GAGCTACTGT GGAGTTACTC TCGTTTTTGC CTTCTGACTT CTTTCCTTCA   1980
GTAAGAGATC TTCTAGATAC CGCCTCAGCT CTGTATCGGG ATGCCTTAGA GTCTCCTGAG   2040
CATTGTTCAC CTCACCACAC TGCACTCAGG CAAGCCATTC TTTGCTGGGG AGAACTAATG   2100
ACTCTAGCTA CCTGGGTGGG TGTAAATTTG GAAGATCCAG CATCCAGGGA CCTAGTAGTC   2160
AGTTATGTCA ATACTAATAT GGGCCTAAAG TTCAGGCAAT TATTGTGGTT TCACATTTCT   2220
```

```
TGTCTCACTT TTGGAAGAGA AACCGTCATA GAGTATTTGG TGTCTTTTGG AGTGTGGATT      2280

CGCACTCCTC CAGCTTATAG ACCACCAAAT GCCCCTATCT TATCAACACT TCCGGAGAAT      2340

ACTGTTGTTA GACGAAGAGG CAGGTCCCCT AGAAGAAGAA CTCCCTCGCC TCGCAGACGA      2400

AGATCTCAAT CGCCGCGTCG CAGAAGATCT CAATCTCCAG CTTCCCAATG TTAGTATTCC      2460

TTGGACTCAT AAGGTGGGAA ATTTTACGGG GCTTTACTCT TCTACTATAC CTGTCTTTAA      2520

TCCTAACTGG AAAACTCCAT CTTTTCCTGA TATTCATTTG CACCAGGACA TTATTAACAA      2580

ATGTGAACAA TTTGTAGGTC CTCTAACTGT AAATGAAAAA CGAAGATTAA ACTTAGTCAT      2640

GCCTGCTAGA TTTTTTCCCA TCTCTACGAA ATATTTGCCC CTAGAGAAAG GTATAAAACC      2700

TTATTATCCA GATAATGTAG TTAATCATTA CTTCCAAACC AGACACTATT TACATACCCT      2760

ATGGAAGGCG GGCATCTTAT ATAAAAGAGA AACTACACGT AGCGCCTCAT TTTGTGGGTC      2820

ACCTTATTCT TGGGAACAAG AGCTACATCA TGGGGCTTTC TTGGACGGTC CCTCTCGAAT      2880

GGGGGAAGAA TATTTCCACC ACCAATCCTC TGGGATTTTT TCCCGACCAC CAGTTGGATC      2940

CAGCATTCAG AGCAAACACC AGAAATCCAG ATTGGGACCA CAATCCCAAC AAAGACCACT      3000

GGACAGAAGC CAACAAGGTA GGAGTGGGAG CATTCGGGCC TGGGTTCACT CCCCCACACG      3060

GAGGCCTTTT GGGGTGGAGC CCTCAGGCTC AAGGCATGCT AAAAACATTG CCAGCAGATC      3120

CGCCTCCTGC CTCCACCAAT CGGCAGTCAG GAAGGCAGCC TACCCAATC ACTCCACCTT       3180

TGAGAGACAC TCATCCTCAG GCCATGCAGT GG                                   3212

(2) INFORMATION FOR SEQ ID NO: 311:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 311:

AACTCAACTC ACTTCCACCA AGCTCTGTTG GATCCCAGGG TAAGGGCACT GTATTTTCCT        60

GCTGGTGGCT CCAGTTCAGG AACACAGAAC CCTGCTCCGA CTATTGCCTC TCTCACATCA       120

TCAATCTCCT CGAAGACTGG GGGCCCTGCT ATGAACATGG AGAACATCAC ATCAGGACTC       180

CTAGGACCCC TGCGCGTGTT ACAGGCGGTG TGTTTCTTGT TGACAAAAAT CCTCACAATA       240

CCACAGAGTC TAGACTCGTG GTGGACTTCT CTCAATTTTC TAGGGGGACT ACCCAGGTGT       300

CCTGGCCAAA ATTCGCAGTC CCCAACCTCC AATCACTTAC CAACCTCCTG TCCTCCAACT       360

TGTCCTGGCT ATCGTTGGAT GTGTCTGCGG CGTTTTATCA TCTTCCTCTT CATCCTGCTG       420

CTATGCCTCA TCTTCTTGTT GGTTCTTCTG GACTACCAAG GTATGTTGCC CGTTTGTCCT       480

CTACTTCCAG GATCCACGAC CACCAGCACG GGACCATGCA AAACCTGCAC AGCTCTTGCT       540

CAAGGAACCT CTATGTTTCC CTCCTGTTGC TGTTCCAAAC CCTCGGACGG AAACTGCACC       600

TGTATTCCCA TCCCATCATC TTGGGCTTTA GGAAATACC TATGGGAGTG GGCCTCAGCC        660

CGTTTCTCCT GGCTCAGTTT ACTAGTGCAA TTTGTTCAGT GGTGCGTAGG GCTTTCCCCC       720

ACTGTCTGGC TTTTAGTTAT ATGGATGATC TGGTATTGGG GGCCAAATCT GTGCAGCATC       780

TTGAGTCCCT TTATACCGCT GTTACCAATT TTCTGTTATC TGTGGGTATC CATTTAAATA       840
```

-continued

```
CTGCTAAAAC AAAAAGATGG GGTTACAACC TACATTTCAT GGGTTATGTT ATTGGTAGTT      900
GGGGAACGTT ACCCCAAGAT CATATTGTAC ACAAAATCAA AGATTGTTTT CGAAAAGTTC      960
CTGTAAATCG CCCAATTGAT TGGAAAGTTT GTCAAAGTAT TGTGGGTCTT TTGGGCTTTG     1020
CGGCCCCTTT TACCCAATGT GGTTATCCTG CTCTCATGCC TTTGTATGCC TGTATTACTG     1080
CTAAACAGGC TTTTGTCTTC TCGCCAACTT ACAAGGCCTT TCTGTGTAAA CAATACATGA     1140
ACCTTTACCC CGTTGCTCGG CAACGGCCAG GCCTGTGCCA AGTGTTTGCT GACGCAACCC     1200
CCACTGGCTG GGGCTTGGCC ATAGGCCATC AGCGCATGCG TGGAACCTTT GTGGCTCCTC     1260
TGCCGATCCA TACTGCGGAA CTCCTTGCAG CTTGCTTCGC TCGCAGCCGG TCTGGAGCAA     1320
TCCTCATCGG CACAGACAAT TCTGTCGTCC TCTCTCGGAA GTATACATCC TTTCCATGGC     1380
TGCTCGGTTG TGCTGCCAAC TGGATCCTGC GCGGGACGTC CTTTGTTTAC GTCCCGTCGG     1440
CGCTGAATCC AGCGGACGAA CCCTCCCGGG GTCGCTTGGG GCTGTACCGC CCCCTTCTTC     1500
GTCTGCCGTT CCAGCCGACA ACGGGTCGCA CCTCTCTTTA CGCGGACTCC CCGTCTGTTC     1560
CTTCTCATCT GCCGGACCGT GTGCACTTCG CTTCACCTCT GCACGTCGCA TGGAGACCAC     1620
CGTGAACGCC CCCTGGAGTT TGCCAACAGT CTTACATAAG AGGACTCTTG GACTTTCAGG     1680
ACGGTCAATG ACCTGGATCG AAGACTACAT CAAAGACTGT GTATTTAAGG ACTGGGAGGA     1740
GCTGGGGGAG GAGATCAGGT TAAAGGTCTT TGTACTAGGA GGCTGTAGGC ATAAATTGGT     1800
CTGTTCACCA GCACCATGCA ACTTTTTCAC CTCTGCCTAA TCATCTCTTG TTCATGTCCC     1860
ACTGTTCAAG CCTCCAAGCT GTGCCTTGGG TGGCTTTGGG GCATGGACAT TGACCCTTAT     1920
AAAGAATTTG GAGCTTCTGT GGAATTGTTC TCTTTTTTGG CTTCTGACTT CTTTCCGTCT     1980
GTTCGGGACC TCCTCGACAC CGCCTCAGCC CTGTACCGGG ATGCCTTAGA GTCACCGGAA     2040
CATTGCACCC CCAATCATAC CGCTCTCAGG CAAGCTATTT TGTGCTGGGG TGAGTTAATG     2100
ACTTTGGCTT CCTGGGTGGG TAATAATTTG GAAGACCCTG CAGCTAGGGA TTTAGTAGTT     2160
AATTATGTCA ACACTAATAT GGGCTTAAAG ATTAGACAAC TATTGTGGTT TCACATCTCC     2220
TGTCTTACTT TTGAAGAGA AACAGTTCTT GAGTATTTGG TGTCCTTTGG AGTGTGGATT     2280
CGCACTCCAC CTGCTTATAG ACCACCAAAT GCCCCTATCC TATCCACACT TCCGGAAACT     2340
ACTGTTGTTA GACGACGAGG CAGGTCCCCT AGAAGAAGAA CTCCCTCGCC TCGCCGACGA     2400
AGGTCTCAAT CGCCGCGTCG CAGAAGATCT CAATCTCCAG CTTCCCAATG TTAGTATTCC     2460
TTGGACTCAT AAGGTGGGAA ATTTTACGGG GCTCTACTCT TCTACTGTAC CTGCTTTCAA     2520
TCCTAACTGG TTAACTCCTT CTTTTCCTGA TATTCATTTA CATCAGGATA TGATATCTAA     2580
ATGTGAACAA TTTGTAGGCC CGCTCACTAA AAATGAATTG AGAAGATTAA AATTGGTCAT     2640
GCCAGCTAGA TTTTATCCTA AGCATACCAA ATATTTCCTA TTGGAGAAAG GGATTAAACC     2700
CTATTATCCA GATCAGGCAG TTAATCATTA TTTTCAAACC AGACATTATT TGCATACTTT     2760
ATGGAAGGCG GGAATTCTAT ATAAGAGAGA AACCACACGT AGCGCCTCAT TTTGTGGGTC     2820
ACAATATTCC TGGGAACAAG AGCTACAGCA TGGGAGCACC TCTCTCAACG ACAAGAAGGG     2880
GCATGGGACA GAATCTTTCT GTGCCCAATC CACTGGGCTT CTTGCCAGAC CATCAGCTGG     2940
ATCCGCTATT CAGAGCAAAT TCCAGCAGTC CCGACTGGGA CTTCAACACA AACAAGGACA     3000
GTTGGCCAAT GGCAAACAAG GTAGGAGTGG GAGGCTACGG TCCAGGGTTC ACACCCCCAC     3060
ACGGTGGCCT GCTGGGGTGG AGCCCTCAGG CACAGGGTGT TTTAACAACC TTGCCAGCAG     3120
ATCCGCCTCC TGCTTCCACC AATCGGCTGT CCGGGAGGAA GCCAACCCAA GTCTCTCCAC     3180
```

```
CTCTAAGAGA CACACATCCT CAGGCCATGC AGTGG                          3215
```

(2) INFORMATION FOR SEQ ID NO: 312:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 312:

```
AACTCAACTC ACTTCCACCA GGCTCTGTTG GATCCGAGGG TAAGGGCACT GTATTTTCCTT   60
GCTGGTGGCT CCAGTTCAGG CACGCAGAAC CCTGCTCCGA CTATTGCCTC TCTCACATCA  120
TCAATCTCCT CGAAGACTGG GGGCCCTGCT ATGAACATGG ACAACATCAC ATCAGGACTC  180
CTAGGACCCC TGCTCGTGTT ACAGGCGGTG TGTTTCTTGT TGACAAAAAT CCTCACAATA  240
CCACAGAGTC TAGACTCGTG GTGGACTTCT CTCAATTTTC TAGGGGGACT ACCCGGGTGT  300
CCTGGCCAAA ATTCGCAGTC CCCAACCTCC AATCACTTAC CAACCTCCTG TCCTCCAACT  360
TGTCCTGGCT ATCGTTGGAT GTGTCTGCGG CGTTTTATCA TCTTCCTCTT CATCCTGCTG  420
CTATGCCTCA TCTTCTTGTT GGTTCTTCTG GACTATCAAG GTATGTTGCC CGTTTGTCCT  480
CTAATTCCAG GATCTACGAC CACCAGCACG GGACCATGCA AAACCTGCAC AACTCTTGCT  540
CAAGGAACCT CTATGTTTCC CTCCTGTTGC TGTTCCAAAC CCTCGGACGG AAACTGCACC  600
TGTATTCCCA TCCCATCATC TTGGGCTTTA GGAAAATACC TATGGGAGTG GGCCTCAGCC  660
CGTTTCTCCT GGCTCAGTTT ACTAGTGCAA TTTGTTCAGT GGTGCGTAGG GCTTTCCCCC  720
ACTGTCTGGC TTTTAGTTAT ATGGATGATC TGGTATTGGG AGCCAAATCT GTGCAGCATC  780
TTGAGTCCCT TTATACCGCT GTTACCAATT TTCTGTTATC TGTGGGTATC CATTTGAATA  840
CCTCTAAAAC AAAAAGATGG GGTTACAATT TACATTTCAT GGGTTATGTC ATTGGCAGTT  900
GGGGAGCATT ACCCCAAGAT CATATTGTAC ACAAAATCAA AGAATGTTTT CGAAAAGTTC  960
CTGTAAATCG TCCAATTGAC TGGAAAGTTT GTCAACGTAT TGTGGGACTT TTGGGCTTTG 1020
CTGCTCCTTT TACCCAATGT GGTTATCCTG CTCTCATGCC TCTGTATAAC TGTATCACTG 1080
CGAAACAGGC TTTTGTCTTT TCGCCAACTT ACAAGGCCTT TCTCTGTAAA CAGTACATGA 1140
ACCTTTACCC CGTTGCTCGG CAACGGCCAG GCCTGTGCCA AGTGTTTGCT GACGCAACCC 1200
CCACTGGTTG GGGCTTGGCC ATTGGCCATC AGCGCATGCG TGGAACCTTT GTGGCTCCTC 1260
TGCCGATCCA TACTGCGGAA CTCCTTGCAG CTTGCTTCGC TCGCAGCCGG TCTGGAGCAA 1320
TCCTCATCGG CACAGACAAT TCTGTCGTCC TCTCCCGGAA GTATACATCC TTTCCATGGC 1380
TGCTCGGATG TGCTGCCAAC TGGATCCTGC GCGGGACGTC CTTTGTTTAC GTCCCGTCGG 1440
CGCTGAATCC AGCGGACGAA CCCTCCCGGG GCCGCTTGGG GCTCTACCGC CTCTTCTGC  1500
GTCTGCCGTT CCAGCCGACC ACGGGTCGCA CCTCTCTTTA CGCGGACTCC CCGTCTGTTC 1560
CTTCTCATCT GCCGGTCCGT GTGCACTTCG CTTCACCTCT GCACGTCGCA TGGAGACCAC 1620
CGTGAACGCC CCCTGGAGTT TGCCAACAGT CTTACATAAG AGGACTATTG GACTTTCAGG 1680
ACGGTCAATG ACCTGGATCG AAGAATACAT CAAAGACTGT GTATTTAAAG ACTGGGAGGA 1740
GCTGGGGGAG GAGATCAGGT TAAAGGTCTT TGTACTAGGA GGCTGTAGGC ATAAATTGGT 1800
```

```
CTGCGCACCA GCACCATGCA ACTTTTTCAC CTCTGCCTAA TCATCTCTTG TTTATGTCCC    1860

ACTGTTCAAG CCTCCAAGCT GTGCCTTGGG TGGCTTTGGG GCATGGACAT TGACCCTTAT    1920

AAAGAATTTG GAGCTTCTGT GGAATTGTTC TCTTTTTTGC CTTCTGACTT CTTTCCGTCA    1980

ATCCGAGACC TTCTCGACAC CGCCTCAGCT CTGTATCGGG ATGCGTTAGA GTCACCGGAA    2040

CATTGCACCC CCAATCATAC CGCTCTCAGG CAAGCTATTT TGTGTTGGGG TGAATTAATG    2100

ACTTTGGCTT CCTGGGTGGG CAATAATTTG GAGGACCCTG CAGCCAGGGA TTTAGTAGTT    2160

AACTATGTTA ACACTAATAT GGGCTTAAAG ATTAGACAAC TATTGTGGTT TCACATTTCC    2220

TGCCTTACTT TTGGAAGAGA AACAGTTCTT GAGTATTTGG TGTCCTTTGG AGTGTGGATT    2280

CGCACTCCTC CAGCTTATAG ACCACCAAAT GCCCCTATCC TATCCACACT TCCGGAAACT    2340

ACTGTTGTTA GACGACGAGG CAGGTCCCCT AGAAGAAGAA CTCCCTCGCC TCGCAGACGA    2400

AGGTCTCAAT CGCCGCGTCG CAGAAGATCT CAATCTCCAG CTTCCCAATG TTAGTATTCC    2460

TTGGACTCAT AAGGTGGGAA ATTTTACGGG GCTCTACTCT TCTACTGTAC CTGCTTTCAA    2520

TCCTCACTGG TTAACTCCTT CTTTTCCTGA TATTCATTTG CATCAAGACC TGATATCTAA    2580

ATGTGAACAA TTTGTAGGCC CACTTACCAA AAATGAATTG AGAAGGTTGA AATTGATTAT    2640

GCCAGCCAGA TTCTTTCCTA AACTTACTAA ATATTTCCCT CTGGAGAAAG ACATTAAACC    2700

TTATTATCCA GAGCATGCAG TTAATCATTA TTTTCAAACC AGACATTATT TGCATACTTT    2760

ATGGAAGGCG GGAATTTTAT ATAAGAGAGA ATCCACACGT AGCGCCTCAT TTTGTGGGTC    2820

ACCATATTCT TGGAACAAG AGCTACAGCA TGGGAGCACC TCTCTCAACG ACAAGAAGCC    2880

GCATGGGACA GAATCTCTCT GTGCCCAATC CACTGGGATT CTTTCCAGAC CATCAACTGG    2940

ATCCTCTTTT CAGAGCAAAT TCCAGCAGTC CCGATTGGGA CTTCAACAAA ACAAGGACA    3000

CTTGGCCAAT GGCAAACAAG GTAGGAGTGG GAGGTTACGG TCCAGGGTTC ACACCCCAC    3060

ACGGTGGCCT GTTGGGGTGG AGCCCTCAGG CACAAGGTGT TCTAACAACC TTGCCAGCAC    3120

ATCCGCCTCC TGCCTCCACC AATCGGCTGT CCGGGAGGAA GCCAACCCCA GTCTCTCCAC    3180

CTCTAAGAGA CACACATCCA CAGGCAATGC AGTGG                              3215

(2) INFORMATION FOR SEQ ID NO: 313:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 313:

AACTCAACCC AGTTCCACCA AGCTCTGTTG GATCCCAGGG TAAGGGCTCT GTACTTCCCT      60

GCTGGTGGCT CCAGTTCAGG GACACAGAAC CCTGCTCCGA CTATTGCCTC TCTCACATCA    120

TCAATCTTCT CGAAGACTGG GGGCCCTGCT ATGAACATGG ACAACATTAC ATCAGGACTC    180

CTAGGACCCC TGCTCGTGTT ACAGGCGGTG TGTTTCTTGT TGACAAAAAT CCTCACAATA    240

CCACAGAGTC TAGACTCGTG GTGGACTTCT CTCAATTTTC TAGGGGGACT ACCCGGGTGT    300

CCTGGCCAAA ATTCGCAGTC CCCAACCTCC AATCACTTAC CAACCTCCTG TCCTCCAACT    360

TGTCCTGGCT ATCGTTGGAT GTGTCTGCGG CGTTTTATCA TCTTCCTCTT CATCCTGCTG    420
```

-continued

| | |
|---|---|
| CTATGCCTCA TCTTCTTGTT GGTTCTTCTG GACTATCAAG GTATGTTGCC CGTTTGTCCT | 480 |
| CTACTTCCAG GATCCACGAC CACCAGCACG GGACCCTGCA AAACCTGCAC AACTCTTGCA | 540 |
| CAAGGAACCT CTATGTTTCC CTCCTGTTGC TGTTCCAAAC CCTCGGACGG AAACTGCACT | 600 |
| TGTATTCCCA TCCCATCATC CTGGGCTTTA GGAAAATACC TATGGGAGTG GGCCTCAGCC | 660 |
| CGTTTCTCCT GGCTCAGTTT ACTAGTGCAA TTTGTTCAGT GGTGCGTCGG GCTTTCCCCC | 720 |
| ACTGTTTGGC TTTTAGTTAT ATGGATGATC TGGTATTGGG GGCCAAATCT GTGCAGCATC | 780 |
| TTGAGTCCCT TTATACCGCT GTTACCAATT TTCTGTTATC TGTGGGTATC CATTTAAATA | 840 |
| CCTCTAAAAC AAAAAGATGG GGTTACTCCC TACATTTTAT GGGTTATGTC ATTGGTAGTT | 900 |
| GGGGATCATT ACCCCAAGAT CACATTGTAC ACAAAATCAA GGAATGCTTT CGAAAACTGC | 960 |
| CTGTAAATCG TCCAATTGAT GGAAAGTTT GTCAACGCAT AGTGGGTCTT TTGGGCTTTG | 1020 |
| CTGCCCCTTT CACCCAATGC GGTTATCCTG CTCTCATGCC TCTGTATGCC TGTATTACTG | 1080 |
| CTAAACAGGC TTTTGTCTTC TCGCCAACCT ACAAGGCCTT TCTGTGTAAA CAATACATGA | 1140 |
| ACCTTTACCC GGTTGCTCGG CAACGGCCAG GCCTGTGCCA AGTGTTTGCT GACGCAACCC | 1200 |
| CCACTGGTTG GGGCTTGGCC ATTGGCCATC AGCGCATGCG TGGAACCTTT GTGGCTCCTC | 1260 |
| TGCCGATCCA TACTGCGGAA CTCCTAGCAG CTTGTTTCGC TCGCAGCAGG TCTGGAGCGA | 1320 |
| CTCTCATCGG CACGGACAAT TCTGTTGTCC TCTCTAGGAA GTACACCTCC TTTCATGGC | 1380 |
| TGCTCGGATG TGCTGCAAAC TGGATCCTGC GCGGGACGTC CTTTGTTTAC GTCCCATCGG | 1440 |
| CGCTGAATCC CGCGGACGAC CCCTCCCGGG GCCGCTTGGG GCTGTACCGC CCTCTTCTCC | 1500 |
| GTCTGCCGTT CCAGCCGACG ACGGGTCGCA CCTCTCTTTA CGCGGACTCC CCGTCTGTTC | 1560 |
| CTTCTCATCT GCCGGACCGT GTGCACTTCG CTTCACCTCT GCACGTCGCA TGGAGACCAC | 1620 |
| CGTGAACGCC CCCTGGAGTT TGCCAACAGT CTTACATAAG CGGACTCTTG GACTTTCAGG | 1680 |
| ATGGTCAATG ACCTGGATCG AAGAATACAT CAAAGACTGT GTATTTAAGG ACTGGGAGGA | 1740 |
| GTTGGGGGAG GAGATTAGGT TAAAGGTCTT TGTATTAGGA GGCTGTAGGC ATAAATTGGT | 1800 |
| CTGTTCACCA GCACCATGCA ACTTTTTCAC CTCTGCCTAA TCATCTTTTG TTCATGTCCC | 1860 |
| ACTGTTCAAG CCTCCAAGCT GTGCCTTGGG TGGCTTTGGG GCATGGACAT TGACCCTTAT | 1920 |
| AAAGAATTTG GAGCTTCTGT GGAGTTACTC TCGTTTTTGC CTTCTGATTT CTTCCCATCG | 1980 |
| GTTCGGGACC TACTCGACAC CGCTTCAGCT CTTTACCGGG ATGCTTTAGA GTCACCTGAA | 2040 |
| CATTGCACTC CCAACCATAC TGCTCTCAGG CAAGCTATTT TGTGTTGGGG TGAGTTAATG | 2100 |
| ACTTTGGCTT CCTGGGTGGG CAATAATTTG GAGGACCCTG CAGCTAGGGA TTTAGTAGTT | 2160 |
| AACTATGTTA ACACTAACAT GGGCCTAAAA ATTAGACAAC TGTTGTGGTT TCACATTTCC | 2220 |
| TGCCTTACTT TTGGAAGAGA AACAGTTCTA GAGTATTTGG TGTCCTTTGG AGTGTGGATT | 2280 |
| CGCACTCCTC CTGCTTACAG ACCACCAAAT GCCCCTATCC TATCCACACT TCCGGAAACT | 2340 |
| ACTGTTGTTA GACGACGAGG CAGGTCCCCT AGAAGAAGAA CTCCCTCGCC TCGCAGACGA | 2400 |
| AGATCTCAAT CGCCGCGTCG CCGCAGATCT CAATCTCCAG CTTCCCAATG TTAGTATTCC | 2460 |
| TTGGACTCAT AAGGTGGGAA ACTTTACGGG GCTTTACTCT TCTACTGTGC CTGCTTTTAA | 2520 |
| TCCTAACTGG TCCACTCCTT CTTTTCCTGA TATTCATTTG CATCAAGACC TGATTTCTAA | 2580 |
| ATGTGAACAA TTTGTAGGCC CACTTACTAA AAATGAATTA CGAAGATTAA AATTGGTTAT | 2640 |
| GCCAGCTAGA TTTTATCCTA AGGTTACCAA ATATTTTCCC ATGGATAAAG GCATCAAACC | 2700 |
| CTATTATCCT GAGCATGCAG TTAATCATTA CTTTAAAACC AGACATTATT TGCATACTTT | 2760 |
| ATGGAAGGCG GGAATTTTAT ATAAGAGAGA ATCCACACGT AGCGCCTCAT TTTGTGGGTC | 2820 |

-continued

```
ACCATATTCC TGGGAACAAG AGCTACAGCA TGGGAGCACC TCTCTCAACG ACACGAAGAG    2880

GCATGGGACA GAATCTCTCT GTGCCCAATC CTCTGGGATT CTTTCCAGAC CATCAGCTGG    2940

ATCCGCTATT CAGAGCAAAT TCCAGCAGTC CCGACTGGGA CTTCAACACA AACAAGGACA    3000

GTTGGCCAAT GGCAAACAAG GTAGGAGTGG GAGGCTACGG TCCAGGGTTC ACACCCCAC     3060

ACGGTGGCCT GCTGGGGTGG AGCCCTCAAG CACAAGGTGT GTTAACAACC TTGCCAGCAG    3120

ATCCGCCTCC TGCTTCCACC AATCGGCGGT CCGGGAGAAA GCCAACCCCA GTCTCTCCAC    3180

CTCTAAGAGA CACACATCCA CAGGCAATGC AGTGG                               3215
```

METHOD FOR TYPING AND DETECTING HBV

The present application is a divisional of application Ser. No. 09/155,855, filed Oct. 8, 1998, now U.S. Pat. No. 6,709,812 issued Mar. 23, 2004, which is a 371 U.S. National Phase of International Application No. PCT/EP97/02002, filed Apr. 21, 1997.

The present invention relates to the field of Hepatitis B virus (HBV) diagnosis. More particularly, the present invention relates to the field of HBV genotyping and/or determination of the presence of HBV mutants in test samples.

The present invention relates particularly to a method for the rapid and reliable detection of HBV mutants and/or genotypes occuring in a test sample using specific sets of probes optimized to function together in a reverse-hybridisation assay.

Hepatitis B virus is a small enveloped DNA virus of approximately 3200 bp long. Historically it has been characterized on the basis of immunological reaction of the HBsAg with sets of monoclonal antibodies. Isolates were described as a, indicating the common determinant for all different subtypes, followed by subtype-specific combinations: dw, dr, yw, or yr. The latter are mutually exlusive pairs of determinants, covering the HBsAg amino acids 122 (d=lys, y=arg) and 160 (w=lys, r=arg). Several subdeterminants for w exist and can be ascribed to the appearance of certain amino acid variants at codon 127. More recently, a genetic classification has been proposed, based on molecular analysis of the virus. This kind of analysis showed that in total six different genotypes exist, indicated from A to F, with a maximum genetic divergence of 8% when comparing complete genomes (reviewed by Magnius and Norder, 1995).

The genetic variability of HBV might be clinically important. Indeed, the genome variability might include some mechanisms by which HBV avoids immune clearance, and hence induces chronic infection. An important protein marker in inducing immune tolerance, virus elimination, and chronic infection, is HBeAg. The expression of this protein is strictly controlled both at the transcriptional and translational level (Li et al., 1993; Okamoto et al., 1990; Yuan et al., 1995; Sato et al., 1995). Therefore, in the natural course of HBV infection, a well characterized stage of the disease is indicated as HBe-negative chronic hepatitis B (reviewed by Hadziyannis S. J., 1995). This phase is mostly due to the appearance of preCore translational stop codon mutations. The overall genetic variability determines the frequency and physical location on the viral genome where these translational stop-codon mutations appear. The transcriptional regulation was proposed to be the mechanism for genotype A (and possibly also F), whereas the translational control was more likely to be found in the other genotypes (Li et al.; 1993; Sato et al., 1995). Contradictory to the translational regulation, it was shown that the transcriptional regulation was unable to block the HBeAg expression completely and was therefore proposed to categorize the phenotype of this mutant as HBe-suppressed, rather than as HBe-negative (Takahashi et al., 1995). In any case, these preCore mutants would lead to a destruction of the pre-existing balance between HBeAg in circulation and the HBc-derived peptides presented by class I HLA molecules on the surface of infected hepatocytes, thereby diminishing the suppressive effect of HBeAg on T cells, finally resulting in partial liberation of core-specific CTLs and leading to apoptosis of the infected hepatocytes. In general, after the emergence of the HBe-minus variants, the course of the viral infection is characterized by the progression of chronic hepatitis, which may lead to the development of cirrhosis and hepatocellular carcinoma (Hadziyannis, 1995).

Another issue for which the genetic variability or genotyping of the virus might be of relevance is in the development of vaccines where the response may be mediated by the virus type. Protection against HBV infection of all subtypes is conferred by antibodies to the common 'a' determinant of the HB surface antigen (HBsAg). It has been shown that this 'a' determinant presents a number of epitopes, and that its tertiary structure is most important for its antigenicity. The most important region lies between amino acid 124 and 147, but can be extended from amino acid 114 to 150. An adequate anti-HBs response, built up after vaccination, is in principle fully protective infection with a HBV strain harboring mutations in the 'a' determinant region might result in vaccine failure, because the vaccine-induced humoral immune response does not recognize the mutant HBsAg. The most common vaccine-associated escape mutants are the substitutions of a glycine at position 145 to an arginine (G145R), K141E, and T126N. But a 2-aa insertion between aa position 122 and 123, and 8-aa insertion between aa 123 and 124 have also been found (Carman et al., 1990, 1995; Crawford, 1990; Waters et al., 1992).

Lamivudine is a (−) enantiomer of 3' thiacytidine, a 2'3'-dideoxynucleoside analogue, and is known to be a potent inhibitor of HBV replication through inhibition of the reverse transcriptase (RT) activity of the HBV polymerase. Lamivudine treatment can result in histological improvements in chronic hepatitis patients, and when given pre- and post-liver transplantation, it can prevent graft reinfection (Honkoop et al., 1995; Naoumov et al., 1995). However, after treatment, a hepatitis flare-up can be observed in most patients, with ALT elevations and HBV DNA that becomes detectable again. This HBV DNA rebound is associated with a new quasi species equilibrium. In a few cases, virus breakthrough during therapy was observed, due to the selection of lamivudine resistant HBV strains. The exact nature of this breakthrough has been ascribed to the accumulation of mutations in the RT part of the Polymerase. A similar mechanism in the HIV RT polymerase has been found, where upon lamivudine treatment, mutations accumulate in the YMDD motif (Gao et al., 1993). This YMDD motif is also present in the RT part of the HBV polymerase, and lamivudine-selected mutations in HBV have been found in this region (Tipples et al., 1996), as well as in other regions of the RT part of the polymerase (Ling et al., 1996). Penciclovir is another drug that has been shown to inhibit the reverse transcriptase activity of the HBV polymerase (Shaw et al., 1996), and mutations in the HBV polymerase may also be detected upon treatment with this drug.

From all this it can be concluded that the information on the following issues is essential for proper in vitro diagnosis, monitoring and follow-up of HBV infections:
  genotype;
  preCore mutations;
  vaccine escape mutations;
  RT gene mutations selected by treatment with drugs such as lamivudune and penciclovir.

To obtain all this information using existing technologies is complicated, time-consuming, and requires highly-skilled and experienced personnel.

It is thus an aim of the present invention to develop a rapid and reliable detection method for determination of the presence or absence of one or more HBV genotypes possibly present in a biological sample.

More particularly, it is an aim of the present invention to develop a rapid and reliable detection method for determination of the presence or absence of one or more variations in the HBV preS1 region and/or in the HBsAg region representing one or more HBV genotypes possibly present in a biological sample in one single experiment.

More particularly, it is an aim of the present invention to develop a rapid and reliable detection method for determination of the presence or absence of one or more HBV mutants possibly present in a biological sample in one single experiment.

More particularly, it is an aim of the present invention to develop a rapid and reliable detection method for determination of one or more mutations in the preCore region of HBV possibly present in a biological sample in one single experiment.

More particularly, it is an aim of the present invention to develop a rapid and reliable detection method for determination of one or more mutations in the HBsAg region of HBV possibly present in a biological sample in one single experiment.

More particularly, it is an aim of the present invention to develop a rapid and reliable detection method for determination of one or more mutations in the polymerase (pol) gene region of HBV possibly present in a biological sample in one single experiment.

More particularly, it is an aim of the present invention to develop a rapid and reliable detection method for the simultaneous determination of one or several HBV genotypes in combination with one or several HBV mutants possibly present in a biological sample in one single experiment.

It is also an aim of the present invention to provide a genotyping assay or method which allows to infer the nucleotide sequence at codons of interest and/or the HBV mutants of interest, and/or infer the HBV genotype possibly present in a biological sample.

Even more particularly it is also an aim of the present invention to provide a genotyping assay allowing the detection of the different HBV mutants and genotypes in one single experimental setup.

It is another aim of the present invention to select particular probes able to discriminate one or more HBV mutations in one of the above mentioned regions of the HBV genome and/or able to discriminate one or more HBV genotypes.

It is more particularly an aim of the present invention to select particular probes able to discriminate wild-type HBV from mutant HBV sequences.

It is also an aim of the present invention to select particular probes able to discriminate wild-type and polymorphic variants of HBV from mutant HBV sequences.

It is also an aim of the present invention to select particular probes able to discriminate HBV genotype sequences.

It is moreover an aim of the present invention to combine a set of selected probes able to genotype HBV and/or discriminate different HBV mutants possibly present in a biological sample, whereby all probes can be used under the same hybridisation and wash conditions.

It is also an aim of the present invention to select primers enabling the amplification of the gene fragments) determining the HBV genomic mutations or variations of interest as discussed above.

The present invention also aims at diagnostic kits comprising said probes useful for developing such a genotyping assay and/or assays for detecting, monitoring or following-up HBV infection and/or assays for detecting HBV mutations.

All the aims of the present invention have been met by the following specific embodiments.

As a solution to the above-mentioned problem that it is essential for proper diagnosis, monitoring and follow-up of HBV infection to have information on the genotype of HBV present, the present invention provides an elegant way to tackle problems of such complexity which involves residing to a reverse hybridization approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant polymorphisms in the HBV gene regions of interest.

The present invention thus particularly relates to a method for determining the presence or absence of one or more HBV genotypes in a biological sample, comprising:

(i) if need be releasing, isolating or concentrating the polynucleic acids present in the sample;
(ii) if need be amplifying the relevant part of a suitable HBV gene present in said sample with at least one suitable primer pair;
(iii) hybridizing the polynucleic acids of step (i) or (ii) with at least two nucleotide probes hybridizing specifically to a HBV genotype specific target sequence chosen from FIG. 1; with said probes being applied to known locations on a solid support and with said probes being capable of hybridizing to polynucleic acids of step (i) or (ii) under the same hybridization and wash conditions or with said probes hybridizing specifically with a sequence complementary to any of said target sequences, or a sequence wherein T of said target sequence is replaced by U;
(iv) detecting the hybrids formed in step (iii);
(v) inferring the HBV genotype present in said sample from the differential hybridization signal(s) obtained in step (iv).

The genotype specific target sequences can be any nucleotide variation appearing upon alignment of the different HBV genomes that permits classification of a certain HBV isolate as a certain genotype (see FIG. 1).

The expression "relevant part of a suitable HBV gene" refers to the part of the HBV gene encompassing the HBV genotype specific target sequence chosen from FIG. 1 to be detected.

According to a preferred embodiment of the present invention, step (iii) is performed using a set of at least 2, preferably at least 3, more preferably at least 4 and most preferably at least 5 probes all meticulously designed such that they show the desired hybridization results, when used in a reverse hybridisation assay format, more particularly under the same hybridization and wash conditions implying that each of said probes is able to form a complex upon hybridisation with its target sequence present in the polynucleic acids of the sample as obtained after step (i) or (ii).

The numbering of the HBV gene encoded amino acids and nucleotides is as generally accepted in literature.

More particularly, the present invention relates to a set of at least 2 probes allowing the detection of a genotype specific variation, possibly also including one or more probes allowing the detection of a wild-type sequence, a polymorphic or a mutated sequence at any one of the nucleotide positions showing a sequence diversity upon alignment of all known or yet to be discovered HBV sequences as represented in FIG. 1 for all complete HBV genomes found in the EMBL/NCBI/DDBJ/Genbank.

The sets of probes according to the present invention have as a common characteristic that all the probes in said set are designed so that they can be used together in a reverse-hybridization assay, more particularly under similar or identical hybridization and wash conditions as indicated above and below.

Selected sets of probes according to the present invention include probes which allow to differentiate any of the HBV genotype specific nucleotide changes as represented in FIG. 1, preferably in the preS1 or HBsAg region of HBV. Said probes being characterized in that they can function in a method as set out above.

In order to solve the above-mentioned problem of obtaining information on the possible presence of HBV mutants in a given sample, the present invention provides an elegant way to tackle this problem which involves residing to a reverse hybridisation approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant mutations and possibly also wild-type sequences or polymorphisms in the HBV gene regions of interest.

Another particularly preferred embodiment of the present invention thus is a method for determining the presence or absence of one or more HBV mutants in a biological sample, comprising:
(i) if need be releasing, isolating or concentrating the polynucleic acids present in the sample;
(ii) if need be amplifying the relevant part of a suitable HBV gene present in said sample with at least one suitable primer pair;
(iii) hybridizing the polynucleic acids of step (i) or (ii) with at least two nucleotide probes hybridizing specifically to a HBV mutant target sequence chosen from FIG. 1, with said probes being applied to known locations on a solid support and with said probes being capable of hybridizing to the polynucleic acids of step (i) or (ii) under the same hybridization and wash conditions, or with said probes hybridizing specifically with a sequence complementary to any of said target sequences, or a sequence wherein T of said target sequence is replaced by U and with said set or probes possibly also comprising one or more wild-type HBV probes corresponding with the respective mutated HBV target sequence;
(iv) detecting the hybrids formed in step (iii);
(v) inferring the HBV mutant(s) present in said sample from the differential hybridization signal(s) obtained in step (iv).

It is to be understood that the term "mutant target sequence" not only covers the sequence containing a mutation, but also the corresponding wild-type sequence. The HBV mutant target sequence according to the present invention can be any sequence including a HBV mutated codon known in the art or yet to be discovered. Particularly preferred HBV mutant target regions are set out below.

In order to solve the problem as referred to above of obtaining information on the essential issues for proper diagnosis of HBV (namely genotype and different mutations particularly mutations in the preCore region, vaccine escape mutations and RT gene mutations selected by treatment with drugs such as lamivudine and penciclovir), the present invention provides a particularly elegant way to obtain such complex information.

Moreover, careful analysis of the data obtained by the present inventors clearly revealed that combining the information concerning the preCore and escape mutants with data on the genotype is essential to allow adequate interpretation of the results. Hence it is highly advantageous to be able to produce all relevant data simultaneously.

In this method for diagnosing HBV mutants, preferably in combination with HBV genotyping, a set of probes selected as defined above may be used, wherein said set of probes is characterized as being chosen such that for a given HBV mutation, the following probes are included in said set:
at least one probe for detecting the presence of the mutated nucleotide(s) at said position;
at least one probe for detecting the presence of the wild-type nucleotide(s) at said position;
possibly also (an) additional probe(s) for detecting wild-type polymorphisms at positions surrounding the mutation position.

Inclusion of the latter two types of probes greatly contributes to increasing the sensitivity of said assays as demonstrated in the examples section.

Selected sets of probes according to the present invention include at least one probe, preferably at least two probes, characterizing the presence of a HBV mutation at nucleotide positions chosen from the preCore region of HBV, more particularly from the following list of codons susceptible to mutations in the HBV preCore region, such as codon 15 in genotype A, and for all genotypes: codon 28, codon 29, and codon 28 and 29, or in the preCore promoter region (see FIG. 1).

Said probes being characterized in that they can function in a method as set out above.

An additional embodiment of the present invention includes at least one probe, preferably at least two probes, characterizing the presence of a vaccine escape mutation in codon positions chosen from the HBsAg region of HBV, more particularly from the list of codons susceptible to mutations in the HBV HBsAg region, such as at codons 122, 126, 141, 143, 144 or 145 (see FIG. 1).

An additional embodiment of the present invention includes at least one probe, preferably at least two probes, characterizing the presence of a mutation in the RT pol gene region of HBV, that gives rise to resistance to drugs such as lamivudine and penciclovir, for instance mutation of M to V or to I at position 552 (in the YMDD motif), mutation of V to I at position 555, mutation of F to L at position 514, mutation of V to L at position 521, mutation of P to L at position 525 and mutation of L to M at position 528 (see FIG. 1).

In a selected embodiment, a combination of at least two oligonucleotide probes is used and said combination of probes hybridizes specifically to at least two of the following groups of target sequences:
a mutant target sequence chosen from the HBV RT pol gene region,
a mutant target sequence chosen from the HBV preCore region,
a mutant target sequence chosen from the HBsAg region of HBV,
a HBV genotype-specific target sequence.

For instance, an embodiment involves hybridizing with at least one nucleotide probe hybridizing specifically to a genotype specific target sequence chosen from FIG. 1 and at least one nucleotide probe hybridizing specifically to a HBV mutant target sequence chosen from FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV mutant target sequence chosen from the RT pol gene region as represented FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV mutant target sequence chosen from the preCore region as represented in FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV vaccine escape mutant target sequence within the HBsAg region as represented in FIG. 1.

In a selected embodiment, a combination of at least three oligonucleotide probes is used and said combination of probes hybridizes specifically to at least three of the following groups of target sequences:

a mutant target sequence chosen from the HBV RT pol gene region, a mutant target sequence chosen from the HBV preCore region, a mutant target sequence chosen from the HBsAg region of HBV, a HBV genotype-specific target sequence.

For instance, an embodiment involves hybridizing with at least one nucleotide probe hybridizing specifically to a genotype specific target sequence chosen from FIG. 1, and at least one nucleotide probe hybridizing specifically to a HBV mutant target sequence chosen from the preCore region as represented in FIG. 1, and at least one nucleotide probe hybridizing specifically to a HBV vaccine escape mutant target sequence chosen from the HBsAg region as represented in FIG. 1.

For instance, another embodiment involves hybridizing with at least one probe hybridizing specifically to a mutant target sequence from the HBV RT pol gene region of HBV, and at least one probe hybridizing specifically to a mutant target sequence from the HBsAg region of HBV, and at least one probe hybridizing specifically to a genotype-specific target sequence from the HBsAg region of HBV. According to this embodiment, the relevant part of the HBV genome can be amplified by use of one primer pair, for instance HBPr 75 and HBPr 94.

In a selected embodiment, a combination of at least four oligonucleotide probes is used and said combination of probes hybridizes specifically to all of the following groups of target sequences:

a mutant target sequence chosen from the HBV RT pol gene region, a mutant target sequence chosen from the HBV preCore region, a mutant target sequence chosen from the HBsAg region of HBV, a HBV genotype-specific target sequence.

Particularly preferred embodiments of the invention thus include a set of probes as set out above comprising at least one, preferably at least two, at least three, at least four or more probe(s) for targeting one, preferably two, three or more nucleotide changes appearing in the alignment of HBV genomes as represented in FIG. 1.

Even more preferred selected sets of probes according to the present invention include probes derived from two of the same or different regions of HBV bearing HBV mutated nucleotides, or in addition also a third (set of) probe(s) characterizing the presence of a third HBV mutation at any of the positions shown in FIG. 1, or particular combinations thereof.

Particularly preferred is also a set of probes which allows simultaneous detection of HBV mutations at codons 15, 28 and 29 in the preCore region, possibly in combination with mutations in the preCore promoter regions, in combination with mutations at codons 122, 126, 141, 143, 144, 145 in the HBsAg region, possibly also in combination with mutations in the HBV pol gene at codons 514, 521, 525, 528, 552 or 555.

In the instances where the alignment of HBV genomes of FIG. 1 is referred to in this invention, it should be construed as referring to an alignment of all existing and future HBV genomes. The existing HBV genome sequences can be deduced from any database, such as the EMBL/NCBI/DDBJ/GENBANK database.

A preferred set of preCore, preS1, HBsAg and RT pol gene probes of this invention are the probes with SEQ ID NO 1 to 278 of Table 1 (see also FIG. 1).

Particularly preferred sets of probes in this respect are shown in FIG. 2 and in FIG. 4. The probes in FIG. 2 and in FIG. 4 were withheld after a first selection for preCore, preS1, HBsAg and AT pol probes.

The probes of the invention are designed for obtaining optimal performance under the same hybridization conditions so that they can be used in sets of at least 2 probes for simultaneous hybridization. This highly increases the usefulness of these probes and results in a significant gain in time and labour. Evidently, when other hybridization conditions would be preferred, all probes should be adapted accordingly by adding or deleting a number of nucleotides at their extremities. It should be understood that these concomitant adaptations should give rise to essentially the same result, namely that the respective probes still hybridize specifically with the defined target. Such adaptations might also be necessary if the amplified material should be RNA in nature and not DNA as in the case for the NASBA system.

The selection of the preferred probes of the present invention is based on a reverse hybridization assay format using immobilized oligonucleotide probes present at distinct locations on a solid support. More particularly the selection of preferred probes of the present invention is based on the use of the Line Probe Assay (LiPA) principle which is a reverse hybridization assay using oligonucleotide probes immobilized as parallel lines on a solid support strip (Stuyver et al. 1993; international application WO 94/12670). This approach is particularly advantageous since it is fast and simple to perform. The reverse hybridization format and more particularly the LiPA approach has many practical advantages as compared to other DNA techniques or hybridization formats, especially when the use of a combination of probes is preferable or unavoidable to obtain the relevant information sought.

It is to be understood, however, that any other type of hybridization assay or format using any of the selected probes as described further in the invention, is also covered by the present invention.

The reverse hybridization approach implies that the probes are immobilized to certain locations on a solid support and that the target DNA is labelled in order to enable the detection of the hybrids formed.

The following definitions serve to illustrate the terms and expressions used in the present invention.

The term "genetic analysis" refers to the study of the nucleotide sequence of the genome of HBV by any appropriate technique.

The term "HBV mutant" refers to any HBV strain harbouring genomic variations with serological, genetical or clinical consequences.

The term "vaccine escape mutant" is reviewed in the introduction section and in Example 7. The most important region lies between amino acid 124 and 147 of the HBsAg region, but can be extended from amino acid 114 to 150.

The term "mutant resistant to drugs such as lamivudine and penciclovir" is reviewed in the introduction section and in Example 8.

The term "HBV genotype" refers to HBV strains with an intergenotype variation of 8% or more based on a comparison of complete genomes.

The target material in the samples to be analyzed may either be DNA or RNA, e.g. genomic DNA, messenger RNA, viral RNA or amplified versions thereof. These molecules are also termed polynucleic acids.

It is possible to use genomic DNA or RNA molecules from samples susceptible of containing HBV in the methods according to the present invention.

Well-known extraction and purification procedures are available for the isolation of RNA or DNA from a sample (f.i. in Maniatis et al., Molecular Cloning: A Laboratory Manual, 2nd Edition, Cold Spring Harbour Laboratory Press (1989)).

The term "probe" refers to single stranded sequence-specific oligonucleotides which have a sequence which is complementary to the target sequence to be detected.

The term "target sequence" as referred to in the present invention describes the nucleotide sequence of a part of wild-type, polymorphic or mutant HBV gene sequence to be specifically detected by a probe according to the present invention. The polymorphic sequence may encompass one or more polymorphic nucleotides; the mutant sequence may encompass one or more nucleotides that are different from the wild-type sequence. It is to be understood that the term "mutant target sequence" not only covers the sequence containing a mutation, but also the corresponding wild-type sequence. Target sequences may generally refer to single nucleotide positions, codon positions, nucleotides encoding amino acids or to sequences spanning any of the foregoing positions. In the present invention said target sequence often includes one, two or more variable nucleotide positions. In the present invention polynucleic acids detected by the probes of the invention will comprise the target sequence against which the probe is detected.

It is to be understood that the complement of said target sequence is also a suitable target sequence in some cases. The target sequences as defined in the present invention provide sequences which should at least be complementary to the central part of the probe which is designed to hybridize specifically to said target region. In most cases the target sequence is completely complementary to the sequence of the probe.

The term "complementary" as used herein means that the sequence of the single stranded probe is exactly the (inverse) complement of the sequence of the single-stranded target, with the target being further defined as the sequence where the mutation to be detected is located.

Since the current application requires the detection of single basepair mismatches, stringent conditions for hybridization are required, allowing in principle only hybridization of exactly complementary sequences. However, variations are possible in the length of the probes (see below). It should also be noted that, since the central part of the probe is essential for its hybridization characteristics, possible deviations of the probe sequence versus the target sequence may be allowable towards head and tail of the probe when longer probe sequences are used. These variations, which may be conceived from the common knowledge in the art, should however always be evaluated experimentally, in order to check if they result in equivalent hybridization characteristics as the exactly complementary probes.

Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridisation characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phospho-triester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5-50 nucleotides long. Specific length and sequence will depend on the complexity of the required DNA or RNA targets, as well as on the conditions of primer use such as temperature and ionic strength.

The expression "suitable primer pair" in this invention refers to a pair of primers allowing the amplification of part or all of the HBV gene for which probes are immobilized.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc.

The sets of probes of the present invention will include at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more probes. Said probes may be applied in two or more (possibly as many as there are probes) distinct and known positions on a solid substrate. Often it is preferable to apply two or more probes together in one and the same position of said solid support.

For designing probes with desired characteristics, the, following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2-10° C. higher than the temperature at which the final assay will be performed. The base composition of the probe is significant because G–C base pairs exhibit greater thermal stability as compared to A-T base pairs due to additional hydrogen bonding. Thus, hybridization involving complementary nucleic acids of higher G–C content will be stable at higher temperatures.

Conditions such as ionic strength and incubation temperature under which a probe will be used should also be taken into account when designing a probe. It is known that hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid In the present case, single base pair changes need to be detected, which requires conditions of very high stringency.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularly 10-25) bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

Standard hybridization and wash conditions are disclosed in the Materials & Methods section of the Examples. Other conditions are for instance 3× SSC (Sodium Saline Citrate), 20% deionized FA (Formamide) at 50° C.

Other solutions (SSPE (Sodium saline phosphate EDTA), TMACI (Tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances.

In a more preferential embodiment, the above-mentioned polynucleic acids from step (i) or (ii) are hybridized with at least two, three, four, five, six, seven, eight, nine, ten, eleven, twelve, thirteen, fourteen, fifteen, sixteen, seventeen, eighteen, nineteen, twenty, or more of the above-mentioned target region specific probes, preferably with 5 or 6 probes, which, taken together, cover the "mutation region" of the relevant HBV gene.

The term "mutation region" means the region in the relevant HBV gene sequence where a least one mutation encoding a HBV mutant is located In a preferred part of this mutation region is represented in FIG. 1.

Apart from mutation regions as defined above the HBV wild-type or mutant genomes may also show polymorphic nucleotide variations at positions other than those referred to as genotype specific or mutant specific variated positions as shown in FIG. 1.

Since some mutations may be more frequently occurring than others, e.g. in certain geographic areas or in specific circumstances (e.g. rather closed communities) it may be appropriate to screen only for specific mutations, using a selected set of probes as indicated above. This would result in a more simple test, which would cover the needs under certain circumstances.

In order to detect HBV genotypes and/or HBV mutants with the selected set of oligonucleotide probes, any hybridization method known in the art can be used (conventional dot-blot, Southern blot, sandwich, etc.).

However, in order to obtain fast and easy results if a multitude of probes are involved, a reverse hybridization format may be most convenient.

In a preferred embodiment the selected set of probes are immobilized to a solid support in known distinct locations (dots, lines or other figures). In another preferred embodiment the selected set of probes are immobilized to a membrane strip in a line fashion. Said probes may be immobilized individually or as mixtures to delineated locations on the solid support.

A specific and very user-friendly embodiment of the above-mentioned preferential method is the LiPA method, where the above-mentioned set of probes is immobilized in parallel lines on a membrane, as further described in the examples.

The invention also provides for a set of primers allowing amplification of the region of the respective HBV gene to be detected by means of probes. Examples of such primers of the invention are given in Table 1 and FIG. 1.

Primers may be labelled with a label of choice (e.g. biotine). Different primer-based target amplification systems may be used, and preferably PCR-amplification, as set out in the examples. Single-round or nested PCR may be used The invention also provides a kit for detection and/or genetic analysis of HBV genotypes and/or HBV mutants present in a biological sample comprising the following components:

(i) when appropriate, a means for releasing, isolating or concentrating the polynucleic acids present in said sample;
(ii) when appropriate, at least one suitable primer pair;
(iii) at least two of the probes as defined above, possibly fixed to a solid support;
(iv) a hybridization buffer, or components necessary for producing said buffer;
(v) a wash solution, or components necessary for producing said solution;
(vi) when appropriate, a means for detecting the hybrids resulting from the preceding hybridization.
(vii) when appropriate, a means for attaching said probe to a known location on solid support.

The term "hybridization buffer" means a buffer enabling a hybridization reaction to occur between the probes and the polynucleic acids present in the sample, or the amplified products, under the appropriate stringency conditions.

The term "wash solution" means a solution enabling washing of the hybrids formed under the appropriate stringency conditions.

As illustrated in the Examples section, a line probe assay (LiPA) was designed for screening for HBV genotypes and/or HBV mutants. The principle of the assay is based on reverse hybridization of an amplified polynucleic acid fragment such as a biotinylated PCR fragment of the HBV gene onto short oligonucleotides. The latter hybrid can then, via a biotine-streptavidine coupling, be detected with a non-radioactive colour developing system.

The following examples only serve to illustrate the present invention. These examples are in no way intended to limit the scope of the present invention.

FIGURE AND TABLE LEGENDS

FIG. 1: Alignment of 35 complete HBV genomes. Isolates belonging to genotype A are: HBVXCPS, HBVADW, HVHEPB, S50225, HPBADWZCG; genotype B: HPBADW3, HPBADWZ, HPBADW1, HPBADW2; genotype C: HPBCGADR, HBVADRM, HPBADRA, HPBCG, HEHBVAYR, HBVADR, HBVADR4, HPBADR1C, HPBADRC, HBVPREX, HPBETNC, HHVBC, HHVCCHA; genotype D: HBVAYWMCG, HBVAYWC, HBVAYWCI, HBVAYWE, HBVDNA, HPBHBVAA, XXHEPAV, HBVORFS; genotype E: HHVBE4, HHVBBAS; and genotype F: HHBF, HHVBFFOU, HBVADW4A. To preserve alignment, several gaps were created in the alignment and are indicated with /. Positions of start and end of the different HBV encoded genes is indicated: HBsAg: hepatitis B surface antigen (small surface antigen); HBx: hepatitis B X protein; HB Pol: hepatits B polymerase protein, encoding a terminal protein, a spacer, a RT/DNA polymerase region, and an RNAse H activity; HBcAg: hepatitis B Core antigen; HBpreS1Ag: hepatitis B preS1 antigen (large surface antigen); HBpreS2Ag: hepatitis B preS2 antigen (middle surface antigen). The position of the PCR primers is indicated with a large box over all 35 sequences. The polarity of the PCR primer can be deduced from the position of the name above these boxes: left=antisense primer; right=sense primer. LiPA probes are indicated with small boxes, the numbers of the probes are indicated next to the probes or to the right of the alignment, and correspond to the probe numbers in Table 1.

The following lists the correspondence between the sequence of FIG. 1 and the sequence of the Sequence Listing: HBVXCPS, SEQ ID NO:279; HBVADW, SEQ ID NO:280; HVHEPB, SEQ ID NO:281; S50225, SEQ ID NO:282; HPBADWZCG, SEQ ID NO:283; HPBADW3, SEQ ID NO:284; HPBADWZ, SEQ ID NO:285; HPBADW1, SEQ ID NO:286; HPBADW2, SEQ ID NO:287; HPBCGADR, SEQ ID NO:288; HBVADRM, SEQ ID NO:289; HPBADRA, SEQ ID NO:290; HPBCG, SEQ ID NO:291; HEHBVAYR, SEQ ID NO:292; HBVADR, SEQ ID NO:293; HBVADR4, SEQ ID NO:294; HPBADR1C, SEQ ID NO:295; HPBADRC, SEQ ID NO:296; HBVPREX, SEQ ID NO:297; HPBETNC, SEQ ID NO:298; HHVBC, SEQ ID NO:299; HHVCCHA, SEQ ID NO:300; HBVAYWMCG, SEQ ID NO:301; HBVAYWC, SEQ ID NO:302; HBVAYWCI, SEQ ID NO:303; HBVAYWE, SEQ ID NO:304; HBVDNA, SEQ ID NO:305; HPBHBVAA, SEQ ID NO:306; XXHEPAV, SEQ ID NO:307; HBVORFS, SEQ ID NO:308; HHVBE4, SEQ ID NO:309; HHVBBAS, SEQ ID NO:310; HHBF, SEQ ID NO:311; HHVBFFOU, SEQ ID NO:312, ; and HBVADW4A, SEQ ID NO:313.

FIG. 2: LiPA HBV design. The content of a HBV LiPA strip is detailed. For each line number, the region on the viral genome is indicated, together with the genotype that is detected, the probe number that corresponds with the boxes from the alignment in FIG. 1, and the sequence of the probe.

Figure 3:
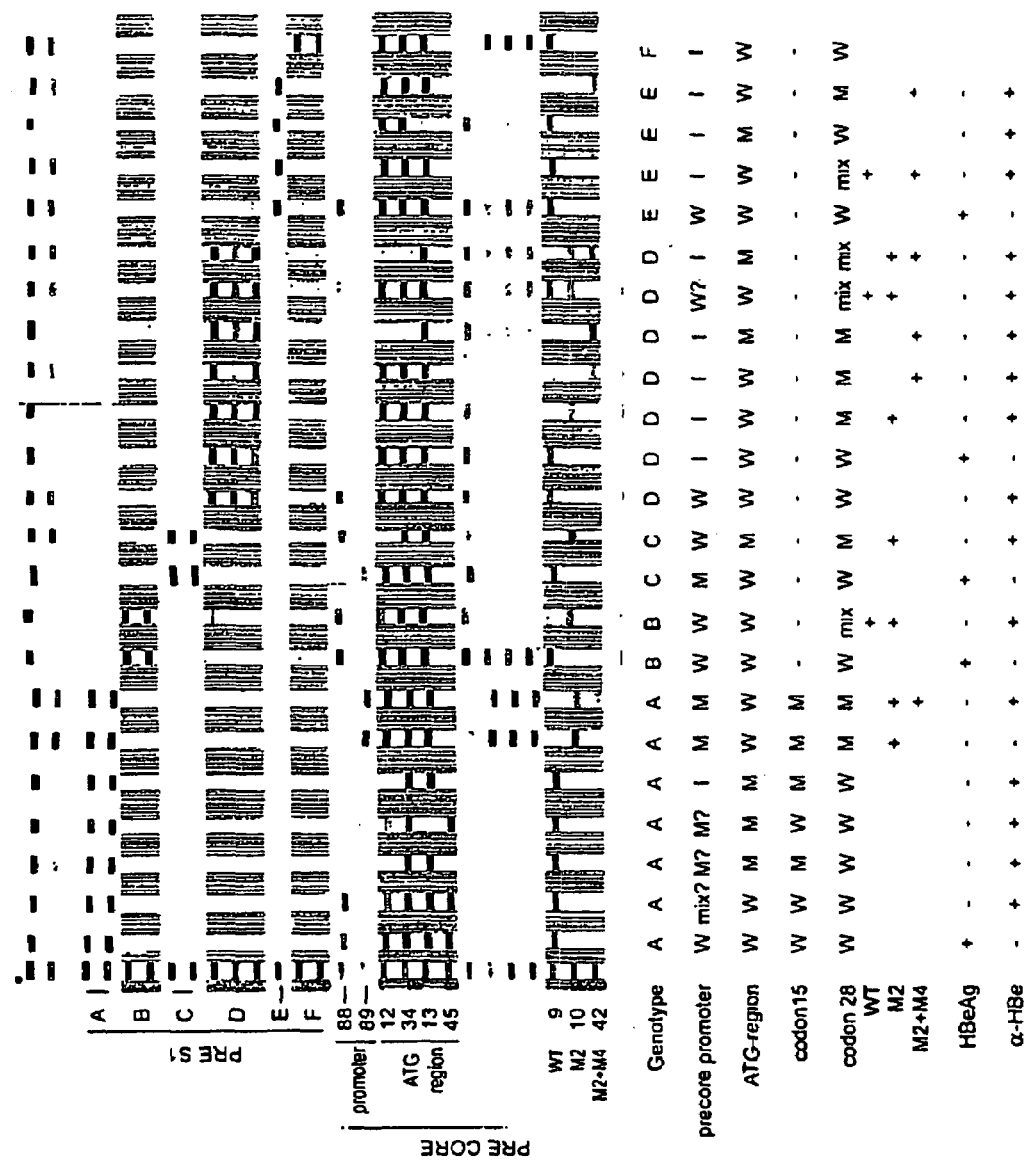

FIG. 3: Combined result of genotype determination in the preS1 region and preCore scanning on 24 samples. The interpretation of each sample is given under each strip. Probe reactivities on lines 3 to 14 are obtained form the preS1 PCR fragment, probe reactivities on lines 15 to 27 are due to the preCore PCR fragment. Genotypes are indicated from A to F. The interpretation for the preCore region is as follows: W=wild type; M=mutant; I=indeterminate, meaning that no reactivity is observed, which is due to mutations that could not yet be detected with the selected probes; mix=mixture of wild type and mutant; interpretation of codon 15 is only relevant for genotype A, the absence of reactivity on HBPr 45 for genotypes B to F is of no use as is indicated with—(not applicable). Since the presence or absence of preCore mutations has effect on the serological HBeAg status, this is also indicated.

FIG. 4: Probes used in HBV LiPA. Probes were designed for genotyping in the HBsAg region and for detection of drug resistance mutations in the YMDD motif (see also FIG. 5), as well as for detection of mutations in the pre Core region (see also FIG. 6).

Figure 5:
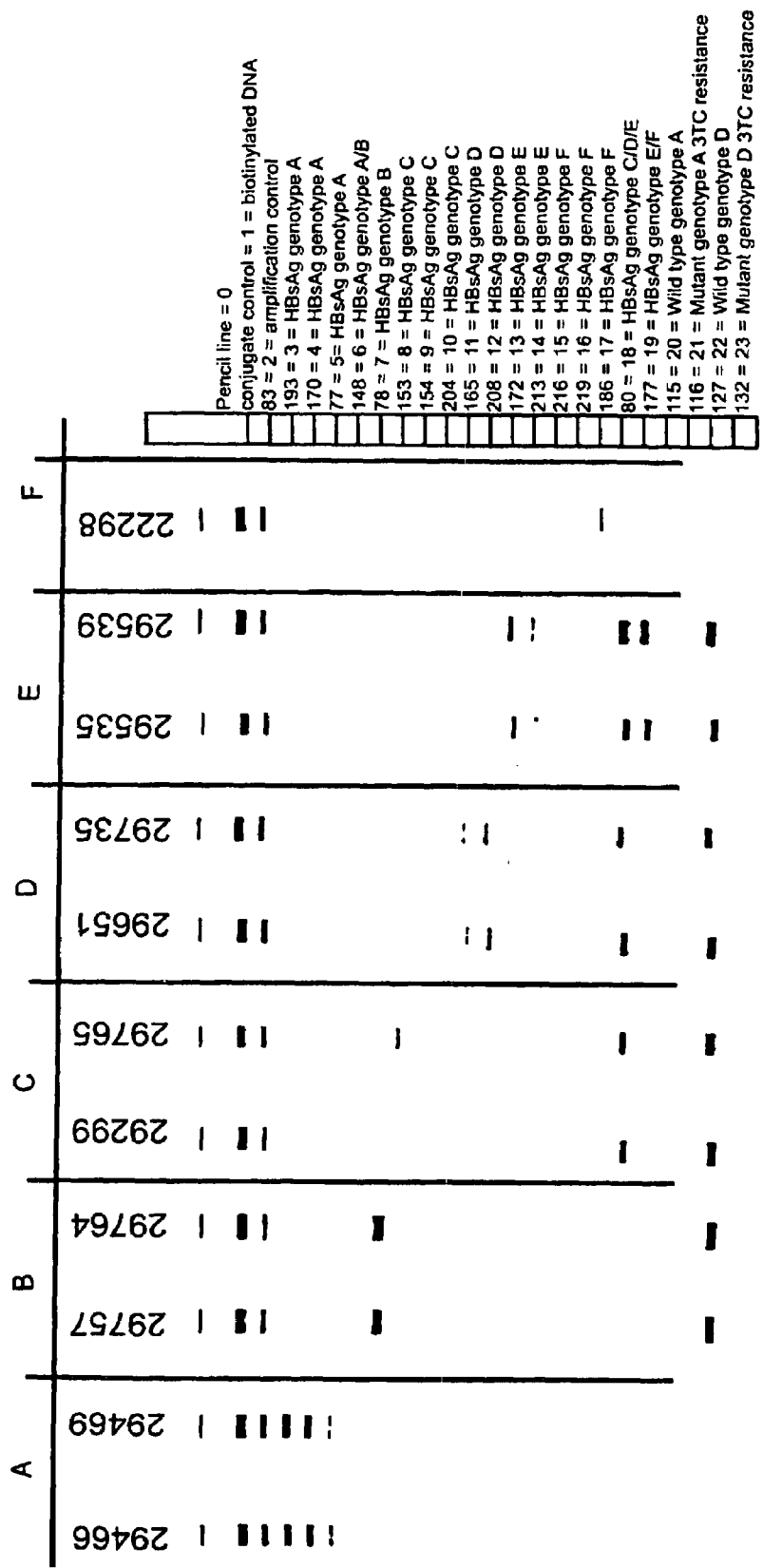

FIG. 5: Example of a LiPA assay combining HBV genotyping in the HBsAg region and detection of drug resistance mutations in the YMDD motif. Genotypes are indicated from A to F. The design of the strip is shown to the right, with the numbers of the probes corresponding to the numbers in Table 1 and in FIG. 4. The genotypes and mutant motifs to which each probe hybridizes are written to the outer right. The combination of reactive probes allows the determination of a unique genotype.

Figure 6:
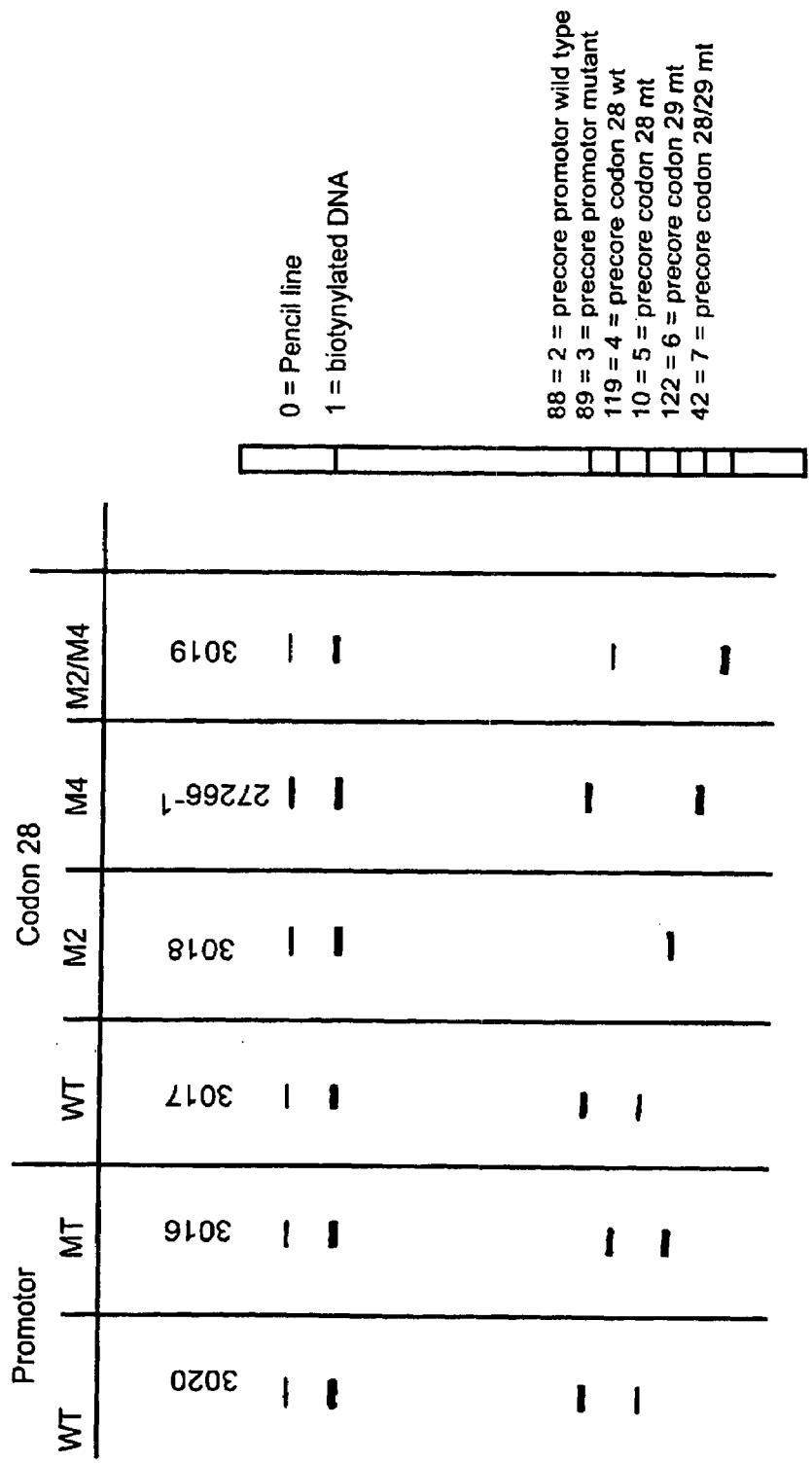

FIG. 6: Example of the determination of preCore mutations by the LiPA technique. The design of the strip is shown to the right, with the numbers of the probes corresponding to the numbers in Table 1. The mutant target sequences to which the probes hybridize are indicated to the outer right. Motif M2 corresponds to a mutation in codon 28, M4 corresponds to a mutation in codon 29. M2/M4 has mutations in both 28 and 29.

Figure 7:
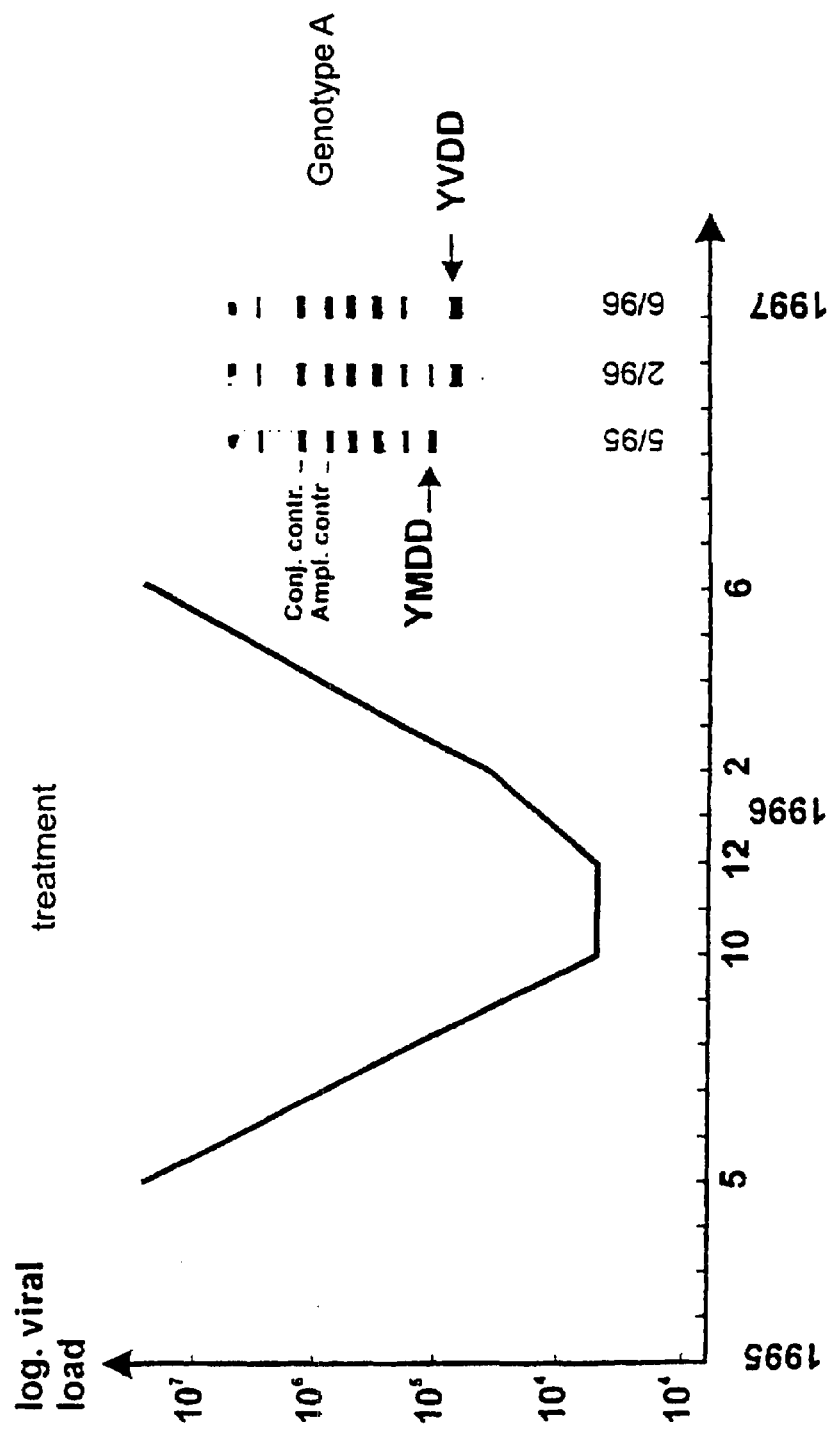

FIG. 7: Detection of a mutation in the YMDD motif of HBV pol upon treatment with lamivudine. The graph shows a time course of the viral load during lamivudine treatment. To the right LiPA strips are shown, corresponding to assays at the beginning of the treatment (5/95), 10 months of treatment (2/96) and 14 months of treatment (6/96). The assay shows that during treatment the YMDD motif mutates to YVDD.

Table 1: Overview of all primers and probes referred to in the Figures with an indication of their respective SEQ ID NO and the region of the HBV genome they are designed for. Primers from the PreS1 region include 1, 106, 2 (sense primers) and 4, 107 and 3 (antisense primers). Primers from the HBsAg region include 75 and 104 (sense primers) and 76, 94 and 103 (antisense primers). Primers from the Pre-Core region include 5, 6, 69, 70, 84, 86, 87 and 108 (sense primers) and 7, 8, 85 and 109 (antisense primers). The remaining oligonucleotides are probes from the PreCore, PreS1, HBsAg and RT pol gene regions of HBV as indicated. The YMDDV motif and its mutants consist of amino acids 551 to 555 of the RT pol protein; the sequence MGVGL and its mutant consist of amino acids 519 to 523 of the RT pol protein; the sequence SPFLL and its mutants and genotypic variants consist of amino acids 524 to 528 of the RT pol protein.

TABLE 1

HBV probe and primer design

| Name | Sequence | SEQ ID NO | Region |
| --- | --- | --- | --- |
| HBPr1 | GGGTCACCATATTCTTGGG | 1 | preS1 primer sense |
| HBPr2 | GAACAAGAGCTACAGCATGGG | 2 | preS1 primer sense |
| HBPr3 | CCACTGCATGGCCTGAGGATG | 3 | preS1 primer anti-sense |
| HBPr4 | GTTCCT/GGAACTGGAGCCACCAG | 4 | preS1 primer anti-sense |
| HBPr5 | TCTTTGTATTAGGAGGCTGTAG | 5 | preCore primer sense |
| HBPr6 | GCTGTAGGCATAAATTGGTCTG | 6 | preCore primer sense |
| HBPr7 | CTCCACAGT/AAGCTCCAAATTC | 7 | preCore primer anti-sense |
| HBPr8 | GAAGGAAAGAAGTCAGAAGGC | 8 | preCore primer anti-sense |
| HBPr9 | TGGCTTTGGGGCATGG | 9 | preCore |
| HBPr10 | TGGCTTTAGGGCATGG | 10 | preCore |
| HBPr11 | TGGCTTAGGACATGG | 11 | preCore |
| HBPr12 | AAGTTGCATGGTGCTG | 12 | preCore |
| HBPr13 | CACCTCTGCCTAATCAT | 13 | preCore |
| HBPr14 | TGGGGTGGAGCCCTCAG | 14 | preS1 |
| HBPr15 | GCCAGCAGCCAACCAG | 15 | preS1 |
| HBPr16 | CCCATGGGGGACTGT | 16 | preS1 |
| HBPr17 | AACCCCAACAAGGATG | 17 | preS1 |
| HBPr18 | TCCACCAGCAATCCT | 18 | preS1 |

TABLE 1-continued

HBV probe and primer design

| Name | Sequence | SEQ ID NO | Region |
| --- | --- | --- | --- |
| HBPr19 | TGGGGGAAGAATATTT | 19 | preS1 |
| HBPr20 | AAATTCCAGCAGTCCC | 20 | preS1 |
| HBPr21 | GTTCCCAACCCTCTGG | 21 | preS1 |
| HBPr22 | AACCTCGCAAAGGCAT | 22 | preS1 |
| HBPr23 | TGCATTCAAAGCCAAC | 23 | preS1 |
| HBPr24 | TACTCACAACTGTGCC | 24 | preS1 |
| HBPr25 | ACCCTGCGTTCGGAGC | 25 | preS1 |
| HBPr26 | CAGGAAGACAGCCTAC | 26 | preS1 |
| HBPr27 | GATCCAGCCTTCAGAG | 27 | preS1 |
| HBPr28 | ATGCTCCAGCTCCTAC | 28 | preS1 |
| HBPr29 | GCTTTCTTGGACGGTC | 29 | preS1 |
| HBPr30 | CTACCCCAATCACTCC | 30 | preS1 |
| HBPr31 | AGCACCTCTCTCAACG | 31 | preS1 |
| HBPr32 | CCAATGGCAAACAAGG | 32 | preS1 |
| HBPr33 | CTGAGGGCTCCACCCCA | 33 | preS1 |
| HBPr34 | ATGCAACTTTTTCACC | 34 | preCore |
| HBPr35 | ATCTCTTGTACATGTC | 35 | preCore |
| HBPr36 | ATCTCATGTTCATGTC | 36 | preCore |
| HBPr37 | CAGTGGGACATGTACA | 37 | preCore |
| HBPr38 | CAGTAGGACATGAACA | 38 | preCore |
| HBPr39 | CTGTTCAAGCCTCCAA | 39 | preCore |
| HBPr40 | AGCCTCCAAGCTGTGC | 40 | preCore |
| HBPr41 | AAAGCCACCCAAGGCA | 41 | preCore |
| HBPr42 | TGGCTTTAGGACATGGA | 42 | preCore |
| HBPr43 | GACATGTACAAGAGATGA | 43 | preCore |
| HBPr44 | GACATGAACATGAGATGA | 44 | preCore |
| HBPr45 | TGTACATGTCCCACTGTT | 45 | preCore |
| HBPr46 | TGTTCATGTCCTACTGTT | 46 | preCore |
| HBPr47 | ACTGTTCAAGCCTCCAAG | 47 | preCore |
| HBPr48 | GGCACAGGCTTGGAGGCTT | 48 | preCore |
| HBPr49 | AAAGCCACCCAAGGCACA | 49 | preCore |
| HBPr50 | CCCAGAGGGTTGGGAAC | 50 | preS1 |
| HBPr51 | CAGCATGGGGCAGAATCT | 51 | preS1 |
| HBPr52 | TCCACCAGCAATCCTCTG | 52 | preS1 |
| HBPr53 | GGATCCAGCCTTCAGAGC | 53 | preS1 |
| HBPr54 | TCAGGAAGACAGCCTAC | 54 | preS1 |
| HBPr55 | TTCAACCCCAACAAGGATC | 55 | preS1 |
| HBPr56 | AATGCTCCAGCTCCTAC | 56 | preS1 |
| HBPr57 | CTGCATTCAAAGCCAACT | 57 | preS1 |
| HBPr58 | CCCCATGGGGGACTGTTG | 58 | preS1 |
| HBPr59 | CATACTCACAACTGTGCCA | 59 | preS1 |
| HBPr60 | GGGCTTTCTTGGACGGTCC | 60 | preS1 |
| HBPr61 | CTCTCGAATGGGGGAAGA | 61 | preS1 |
| HBPr62 | CCTACCCCAATCACTCCA | 62 | preS1 |
| HBPr63 | AGCACCTCTCTCAACGACA | 63 | preS1 |
| HBPr64 | GCAAATTCCAGCAGTCCCG | 64 | preS1 |
| HBPr65 | GCCAATGGCAAACAAGGTA | 65 | preS1 |
| HBPr66 | GACATGAACATGAGATG | 66 | preCore |
| HBPr67 | GGACATGAACAAGAGAT | 67 | preCore |
| HBPr68 | GACATGTACAAGAGATG | 68 | preCore |
| HBPr69 | ACATAAGAGGACTCTTGGAC | 69 | preCore primer sense |
| HBPr70 | TACTTCAAAGACTGTGTGTTTA | 70 | preCore primer sense |
| HBPr71 | ACAAAGACCTTTAAC/TCT | 71 | preCore promoter |
| HBPr72 | ACAAAGATCATTAAC/TCT | 72 | preCore promoter |
| HBPr73 | TTCCACCAGCAATCCTC | 73 | preS1 |
| HBPr74 | GATCCAGCCTTCAGAGC | 74 | preS1 |
| HBPr75 | CAAGGTATGTTGCCCGTTTGTCC | 75 | HBsAg primer sense |
| HBPr76 | CCAAACAGTGGGGGAAAGCCC | 76 | HBsAg primer anti-sense |
| HBPr77 | CTACGGATGGAAATTGC | 77 | HBsAg codon 145 wild type |
| HBPr78 | TACGGACGGAAACTGC | 78 | HBsAg codon 145 wild type |
| HBPr79 | TTCGGACGGAAACTGC | 79 | HBsAg codon 145 wild type |
| HBPr80 | CTTCGGACGGAAATTGC | 80 | HBsAg codon 145 wild type |
| HBPr81 | CTACGGATAGAAATTGC | 81 | HBsAg codon 145 mutant |
| HBPr82 | CTTCGGACAGAAATTGC | 82 | HBsAg codon 145 mutant |
| HBPr83 | CTATGGGAGTGGGCCTCAGT/CC | 83 | HB Pol |
| HBPr84 | GCTGTAGGCATAAATTGGTCTG | 84 | preCore primer sense |
| HBPr85 | CTCCACAGT/AAGCTCCAAATTC | 85 | preCore primer anti-sense |
| HBPr86 | ACATAAGAGGACTCTTGGAC | 86 | preCore primer sense |
| HBPr87 | TACTTCAAAGACTGTGTGTTTA | 87 | preCore primer sense |
| HBPr88 | TAGGTTAAAGGTCTTTGT | 88 | preCore promoter |
| HBPr89 | TAGGTTAATGATCTTTGT | 89 | preCore promoter |
| HBPr90 | CATGTCCCACTGTTCAA | 90 | preCore |
| HBPr91 | CATGTCCTACTGTTCAA | 91 | preCore |
| HBPr92 | TTCTGCCCCATGCTGTA | 92 | preS1 |
| HBPr93 | TTCTGCCCCATGCTGTAG | 93 | preS1 |

TABLE 1-continued

HBV probe and primer design

| Name | Sequence | SEQ ID NO | Region |
|---|---|---|---|
| HBPr94 | GGTAA/TAAAGGGACTCAC/AGATG | 94 | HBsAg primer anti-sense |
| HBPr95 | TCAGCTATATGGATGAT | 95 | HB Pol |
| HBPr96 | CAGCTATATGGATGAT | 96 | HB Pol |
| HBPr97 | TTCAGCTATATGGATG | 97 | HB Pol |
| HBPr98 | TCAGTTATATGGATGAT | 98 | HB Pol |
| HBPr99 | TTTCAGTTATATGGATG | 99 | HB Pol |
| HBPr100 | TTTAGTTATATGGATGA | 100 | HB Pol |
| HBPr101 | TCAGCTATGTGGATGAT | 101 | HB Pol |
| HBPr102 | TCAGTTATGTGGATGAT | 102 | HB Pol |
| HBPr103 | TTTCAGCTATGTGGATG | 103 | HB Pol |
| HBPr104 | CAAGGTATGTTGCCCGTTTGTCC | 104 | HBsAg primer sense |
| HBPr105 | GGT/CAA/TAAAGGGACTCAC/AGATG | 105 | HBsAg primer anti-sense |
| HBPr106 | GGGTCACCATATTCTTGGG | 106 | preS1 primer sense |
| HBPr107 | GTTCCT/GGAACTGGAGCCACCAG | 107 | preS1 primer anti-sense |
| HBPr108 | CCGGAAAGCTTGAGCTCTTCTTTTTCACCTCTGCCTAATC | 108 | preCore primer sense |
| HBPr109 | CCGGAAAGCTTGAGCTCTTCAAAAAGTTGCATGGTGCTGG | 109 | preCore primer anti-sense |
| HBPr110 | CCTCTGCCGATCCATACTGCGGAAC | 110 | preX primer sense |
| HBPr111 | CTGCGAGGCGAGGGAGTTCTTCTTC | 111 | HB Core primer anti-sense |
| HBPr112 | TGCCATTTGTTCAGTGGTTCGTAGGGC | 112 | HBsAg primer sense |
| HBPr113 | CCGGCAGATGAGAAGGCACAGACGG | 113 | HBX primer antisense |
| HBPr114 | TTCAGCTATATGGATGAT | 114 | YMDD motif |
| HBPr115 | TCAGCTATATGGATGATG | 115 | YMDD motif |
| HBPr116 | TTCAGCTATGTGGATGAT | 116 | YMDD motif |
| HBPr117 | TCAGCTATGTGGATGATG | 117 | YMDD motif |
| HBPr118 | GGCTTTGGGGCATGG | 118 | preCore codon 28 wild type |
| HBPr119 | TGGCTTTGGGGCATG | 119 | preCore codon 28 wild type |
| HBPr120 | GTGGCTTTGGGGCATG | 120 | preCore codon 28 wild type |
| HBPr121 | GGCTTTGGGGCATGGA | 121 | preCore codon 28 wild type |
| HBPr122 | TGGCTTTGGGACATGG | 122 | preCore codon 28 wild type, codon 29 mutant |
| HBPr123 | GGCTTTGGGACATGG | 123 | preCore codon 28 wild type, codon 29 mutant |
| HBPr124 | TGGCTTTGGGACATG | 124 | preCore codon 28 wild type, codon 29 mutant |
| HBPr125 | GTGGCTTTGGGACATG | 125 | preCore codon 28 wild type, codon 29 mutant |
| HBPr126 | GGCTTTGGGACATGGA | 126 | preCore codon 28 wild type, codon 29 mutant |
| HBPr127 | TCAGTTATATGGATGATG | 127 | YMDD genotype D, wild tpye |
| HBPr128 | TTCAGTTATATGGATGAT | 128 | YMDD genotype D, wild tpye |
| HBPr129 | TTTCAGTTATATGGATGAT | 129 | YMDD genotype D, wild tpye |
| HBPr130 | TCAGTTATGTGGATGATG | 130 | YMDD genotype D, mutant |
| HBPr131 | TTCAGTTATGTGGATGAT | 131 | YMDD genotype D, mutant |
| HBPr132 | TTTCAGTTATGTGGATGAT | 132 | YMDD genotype D, mutant |
| HBPr133 | TTTCAGTTATGTGGATGA | 133 | YMDD genotype D, mutant |
| HBPr134 | TGCTGCTATGCCTCATCTTC | 134 | outer HBsAg primer sense |
| HBPr135 | CA(G/A)AGACAAAAGAAAATTGG | 135 | outer HBsAg primer anti-sense |
| HBPr136 | CTATGGATGGAAATTGC | 136 | HBsAg mutant codon 143 |
| HBPr137 | CCTATGGATGGAAATTG | 137 | HBsAg mutant codon 143 |
| HBPr138 | ACCTATGGATGGAAATT | 138 | HBsAg mutant codon 143 |
| HBPr139 | CT CAA GGC AAC TCT ATG TGG | 139 | HBsAg, genotype A |
| HBPr140 | CT CAA GGC AAC TCT ATG GG | 140 | HBsAg, genotype A |
| HBPr141 | T CAA GGC AAC TCT ATG TTG | 141 | HBsAg, genotype A |
| HBPr142 | ATC CCA TCA TCT TGG G | 142 | HBsAg, genotype B |
| HBPr143 | ATC CCA TCA TCT TGG GCG G | 143 | HBsAg, genotype B |
| HBPr144 | TC CCA TCA TCT TGG GCG G | 144 | HBsAg, genotype B |
| HBPr145 | C CCA TCA TCT TGG GCT GG | 145 | HBsAg, genotype B |
| HBPr146 | TTC GCA AAA TAC CTA TGG | 146 | HBsAg, genotype B |
| HBPr147 | T TTC GCA AAA TAC CTA TG | 147 | HBsAg, genotype B |
| HBPr148 | CT TTC GCA AAA TAC CTA TG | 148 | HBsAg, genotype B |
| HBPr149 | TC GCA AAA TAC CTA TGG G | 149 | HBsAg, genotype B |
| HBPr150 | T CTA CTT CCA GGA ACA T | 150 | HBsAg, genotype C |
| HBPr151 | T CTA CTT CCA GGA ACA TC | 151 | HBsAg, genotype C |
| HBPr152 | CT CTA CTT CCA GGA ACA T | 152 | HBsAg, genotype C |
| HBPr153 | CT CTA CTT CCA GGA ACA G | 153 | HBsAg, genotype C |
| HBPr154 | C TGC ACG ATT CCT GCT | 154 | HBsAg, genotype C |
| HBPr155 | TGC ACG ATT CCT GCT CA | 155 | HBsAg, genotype C |
| HBPr156 | C TGC ACG ATT CCT GCT C | 156 | HBsAg, genotype C |
| HBPr157 | TGC ACG ATT CCT GCT CAA | 157 | HBsAg, genotype C |
| HBPr158 | TTC GCA AGA TTC CTA TG | 158 | HBsAg, genotype C |
| HBPr159 | CT TTC GCA AGA TTC CTA T | 159 | HBsAg, genotype C |
| HBPr160 | CT TTC GCA AGA TTC CTA | 160 | HBsAg, genotype C |
| HBPr161 | CT TTC GCA AGA TTC CTA TG | 161 | HBsAg, genotype C |
| HBPr162 | C TCT ATG TAT CCC TCC T | 162 | HBsAg, genotype D |
| HBPr163 | TCT ATG TAT CCC TCC TG | 163 | HBsAg, genotype D |
| HBPr164 | C TCT ATG TAT CCC TCC TGG | 164 | HBsAg, genotype D |
| HBPr165 | CC TCT ATG TAT CCC TCC T | 165 | HBsAg, genotype D |
| HBPr166 | C TGT ACC AAA CCT TCG G | 166 | HBsAg, genotype D |
| HBPr167 | C TGT ACC AAA CCT TCG | 167 | HBsAg, genotype D |
| HBPr168 | GC TGT ACC AAA CCT TCG G | 168 | HBsAg, genotype D |

TABLE 1-continued

HBV probe and primer design

| Name | Sequence | SEQ ID NO | Region |
|---|---|---|---|
| HBPr169 | TGT ACC AAA CCT TCG GAG | 169 | HBsAg, genotype D |
| HBPr170 | GGA CCC TGC CGA ACC T | 170 | HBsAg, genotype E |
| HBPr171 | GGA CCC TGC CGA ACC G | 171 | HBsAg, genotype E |
| HBPr172 | G GGA CCC TGC CGA AC | 172 | HBsAg, genotype E |
| HBPr173 | GGA CCC TGC CGA AC | 173 | HBsAg, genotype E |
| HBPr174 | GT TGC TGT TCA AAA CCT T | 174 | HBsAg, genotype E |
| HBPr175 | GT TGC TGT TCA AAA CCT G | 175 | HBsAg, genotype E |
| HBPr176 | TGT TGC TGT TCA AAA CCT G | 176 | HBsAg, genotype E |
| HBPr177 | A TGT TGC TGT TCA AAA CCT G | 177 | HBsAg, genotype E |
| HBPr178 | GA TCC ACG ACC ACC A | 178 | HBsAg, genotype F |
| HBPr179 | GGA TCC ACG ACC ACC A | 179 | HBsAg, genotype F |
| HBPr180 | GGA TCC ACG ACC ACC | 180 | HBsAg, genotype F |
| HBPr181 | GA TCC ACG ACC ACC AGG | 181 | HBsAg, genotype F |
| HBPr182 | TGT TCC AAA CCC TCG G | 182 | HBsAg, genotype F |
| HBPr183 | C TGT TCC AAA CCC TCG | 183 | HBsAg, genotype F |
| HBPr184 | C TGT TCC AAA CCC TCG G | 184 | HBsAg, genotype F |
| HBPr185 | GT TCC AAA CCC TCG GAT | 185 | HBsAg, genotype F |
| HBPr186 | G CCA AAT CTG TGC AGC | 186 | HBsAg, genotype F |
| HBPr187 | CCA AAT CTG TGC AGC AT | 187 | HBsAg, genotype F |
| HBPr188 | G CCA AAT CTG TGC AGC AG | 188 | HBsAg, genotype F |
| HBPr189 | GG CCA AAT CTG TGC AGC | 189 | HBsAg, genotype F |
| HBPr190 | A TCA ACA ACA ACC AGT A | 190 | HBsAg, genotype A |
| HBPr191 | GA TCA ACA ACA ACC AGT | 191 | HBsAg, genotype A |
| HBPr192 | GA TCA ACA ACA ACC AGT A | 192 | HBsAg, genotype A |
| HBPr193 | GGA TCA ACA ACA ACC AGT | 193 | HBsAg, genotype A |
| HBPr194 | T CAA GGC AAC TCT ATG TGG | 194 | HBsAg, genotype A |
| HBPr195 | AGG TTA AAG GTC TTT GT | 195 | promoter genotype A wild type |
| HBPr196 | T AGG TTA AAG GTC TTT GG | 196 | promoter genotype A wild type |
| HBPr197 | TT AGG TTA AAG GTC TTT | 197 | promoter genotype A wild type |
| HBPr198 | GG TTA AAG GTC TTT GTA GG | 198 | promoter genotype A wild type |
| HBPr199 | AGG TTA ATG ATC TTT GT | 199 | promoter genotype A mutant |
| HBPr200 | T AGG TTA ATG ATC TTT GG | 200 | promoter genotype A mutant |
| HBPr201 | CT TTC GCA AGA TTC CTA TGG | 201 | HBsAg genotype C codon 160 |
| HBPr202 | GCT TTC GCA AGA TTC CTA TG | 202 | HBsAg genotype C codon 160 |
| HBPr203 | GCT TTC GCA AGA TTC CTA TGG | 203 | HBsAg genotype C codon 160 |
| HBPr204 | CT TTC GCA AGA TTC CTA TGG G | 204 | HBsAg genotype C codon 160 |
| HBPr205 | GC TGT ACC AAA CCT TCG GAG | 205 | HBsAg genotype D codon 140 |
| HBPr206 | TGC TGT ACC AAA CCT TCG G | 206 | HBsAg genotype D codon 140 |
| HBPr207 | TGC TGT ACC AAA CCT TCG GAG | 207 | HBsAg genotype D codon 140 |
| HBPr208 | GC TGT ACC AAA CCT TCG GAT | 208 | HBsAg genotype D codon 140 |
| HBPr209 | TGG TTC GCC GGG CTT T | 209 | HBsAg genotype E codon 184 |
| HBPr210 | G TGG TTC GCC GGG CTT G | 210 | HBsAg genotype E codon 184 |
| HBPr211 | GG TTC GCC GGG CTT TC | 211 | HBsAg genotype E codon 184 |
| HBPr212 | TGG TTC GCC GGG CTT TC | 212 | HBsAg genotype E codon 184 |
| HBPr213 | AG TGG TTC GCC GGG CTG G | 213 | HBsAg genotype E codon 184 |
| HBPr214 | A GGA TCC ACG ACC ACC AGG | 214 | HBsAg genotype F |
| HBPr215 | A GGA TCC ACG ACC ACC AGT | 215 | HBsAg genotype F |
| HBPr216 | CA GGA TCC ACG ACC ACC AGG | 216 | HBsAg genotype F |
| HBPr217 | C TGT TCC AAA CCC TCG GAG | 217 | HBsAg genotype F |
| HBPr218 | C TGT TCC AAA CCC TCG GAT | 218 | HBsAg genotype F |
| HBPr219 | GC TGT TCC AAA CCC TCG GAG | 219 | HBsAg genotype F |
| HBPr220 | CTGAACCTTTACCCCGTTGC | 220 | enhancer primer |
| HBPr221 | CTCGCCAACTTACAAGGCCTTTC | 221 | enhancer primer |
| HBPr222 | AGAATGGCTTGCCTGAGTGC | 222 | Core primer anti-sense |
| HBPr223 | GCT TTC GCA AGA TTC CTA TGG G | 223 | HBsAg genotype C codon 160 |
| HBPr224 | G GCT TTC GCA AGA TTC CTA TGG | 224 | HBsAg genotype C codon 160 |
| HBPr225 | G GCT TTC GCA AGA TTC CTA TGG G | 225 | HBsAg genotype C codon 160 |
| HBPr226 | G GCT TTC GCA AGA TTC CTA TGG GA | 226 | HBsAg genotype C codon 160 |
| HBPr227 | C AGC TAT ATG GAT GAT GTG | 227 | YMDDV motif |
| HBPr228 | AGC TAT ATG GAT GAT GTG GG | 228 | YMDDV motif |
| HBPr229 | GC TAT ATG GAT GAT GTG GT | 229 | YMDDV motif |
| HBPr230 | AGC TAT ATG GAT GAT GTG GT | 230 | YMDDV motif |
| HBPr231 | C AGC TAT ATG GAT GAT ATA | 231 | YMDDI MOTIF |
| HBPr232 | AGC TAT ATG GAT GAT ATA GG | 232 | YMDDI MOTIF |
| HBPr233 | GC TAT ATG GAT GAT ATA GT | 233 | YMDDI MOTIF |
| HBPr234 | AGC TAT ATG GAT GAT ATA GT | 234 | YMDDI MOTIF |
| HBPr235 | CCA TCA TCT TGG GCT TG | 235 | HBSAg GENOTYPE B CODON 155 |
| HBPr236 | CA TCA TCT TGG GCT TT | 236 | HBSAg GENOTYPE B CODON 155 |
| HBPr237 | CCA TCA TCT TGG GCT TT | 237 | HBSAg GENOTYPE B CODON 155 |
| HBPr238 | CCA TCA TCT TGG GCT TTC | 238 | HBSAg GENOTYPE B CODON 155 |
| HBPr239 | CCC ACT GTC TGG CTT TC | 239 | HBSAg GENOTYPE B CODON 190 |
| HBPr240 | CC ACT GTC TGG CTT TC | 240 | HBSAg GENOTYPE B CODON 190 |
| HBPr241 | CC ACT GTC TGG CTT T | 241 | HBSAg GENOTYPE B CODON 190 |
| HBPr242 | CCC ACT GTC TGG CTT G | 242 | HBSAg GENOTYPE B CODON 190 |
| HBPr243 | TAT ATG GAT GAT GTG GTA | 243 | YMDDV MOTIF |

TABLE 1-continued

HBV probe and primer design

| Name | Sequence | SEQ ID NO | Region |
|---|---|---|---|
| HBPr244 | TAT GTG GAT GAT GTG GTA | 244 | YVDDV MOTIF |
| HBPr245 | TAT ATA GAT GAT GTG GTA | 245 | YIDDV MOTIF |
| HBPr246 | TAT ATT GAT GAT GTG GTA | 246 | YIDDV MOTIF |
| HBPr247 | TAT GTA GAT GAT GTG GTA | 247 | YVDDV MOTIF |
| HBPr248 | TAT GTT GAT GAT GTG GTA | 248 | YVDDV MOTIF |
| HBPr249 | TAT ATG GAT GAT ATA GTA | 249 | YMDDI MOTIF |
| HBPr250 | TAT ATG GAT GAT ATC GTA | 250 | YMDDI MOTIF |
| HBPr251 | TAT GTG GAT GAT ATA GTA | 251 | YVDDI MOTIF |
| HBPr252 | TAT GTG GAT GAT ATC GTA | 252 | YVDDI MOTIF |
| HBPr253 | TAT ATA GAT GAT ATA GTA | 253 | YIDDI MOTIF |
| HBPr254 | TAT ATA GAT GAT ATC GTA | 254 | YIDDI MOTIF |
| HBPr255 | TAT ATT GAT GAT ATA GTA | 255 | YIDDI MOTIF |
| HBPr256 | TAT ATT GAT GAT ATC GTA | 256 | YIDDI MOTIF |
| HBPr257 | TAT GTA GAT GAT ATA GTA | 257 | YVDDI MOTIF |
| HBPr258 | TAT GTA GAT GAT ATC GTA | 258 | YVDDI MOTIF |
| HBPr259 | TAT GTT GAT GAT ATA GTA | 259 | YVDDI MOTIF |
| HBPr260 | TAT GTT GAT GAT ATC GTA | 260 | YVDDI MOTIF |
| HBPr261 | TAT ATG GAT GAT CTG GTA | 261 | YMDDL MOTIF |
| HBPr262 | TAT GTG GAT GAT CTG GTA | 262 | YVDDL MOTIF |
| HBPr263 | TAT ATA GAT GAT CTG GTA | 263 | YIDDL MOTIF |
| HBPr264 | TAT ATT GAT GAT CTG GTA | 264 | YIDDL MOTIF |
| HBPr265 | TAT GTA GAT GAT CTG GTA | 265 | YVDDL MOTIF |
| HBPr266 | TAT GTT GAT GAT CTG GTA | 266 | YVDDL MOTIF |
| HBPr267 | T ATG GGA GTG GGC CTC AG | 267 | MGVGL |
| HBPr268 | T ATG GGA TTG GGC CTC AG | 268 | MGLGL |
| HBPr269 | C AGT CCG TTT CTC TTG GC | 269 | SPFLL |

EXAMPLES

Example 1

HBV DNA Preparation and PCR Amplification

Serum samples were collected from HBsAg-positive individuals and stored at minus 20° C. until use in 0.5 ml aliquots. To prepare the viral genome, 18 μl serum was mixed with 2 μl 1N NaOH and incubated at 37° C. for 60 minutes. The denaturation was stopped and neutralized by adding 20 μl of 0.1N HCl. After a 15 minutes centrifugation step, the supernatant was collected and the pellet discarded. PCR was carried out on this lysate as follows: 32 μl H$_2$O was mixed with 5 μl of 10×PCR buffer, 1 μl 10 mM dXTPs, 1 μl of each biotinylated primer (10 pmol/μl), 10 μl of serum lysate, and 2 U Taq enzyme. The amplification scheme contained 40 cycles of 95° C. 1 min, annealing at 45° C. for 1 min, and extension at 72° C. for 1 min. Amplification products were visualized on 3% agarose gel.

The outer primer set for preS1 has the following sequence:

outer sense: HBPr 1: 5'-bio-GGGTCACCATATTCTTGGG-3' outer antisense HBPr 4: 5'-bio-GTTCC(T/G)GAACTG-GAGCCACCAG-3'

The outer primer set for preCore has the following sequence:

outer sense: HBPr 69: 5'-bio-ACATAAGAGGACTCTTG-GAC-3' outer antisense HBPr 8: 5'-bio-GAAGGAAAGAAGTCA-GAAGGC-3'

The outer primer set for HBsAg has the following sequence:

outer sense: HBPr 341: 5'-bio-TGCTGCTATGCCT-CATCTTC-3' outer antisense: HBPr 135: 5'-bio-CA(G/A)AGACAAAA-GAAAATTGG-3'.

Samples that were negative in the first round PCR were retested in a nested reaction composed of the following: μl H$_2$O, 5 μl 10×Taq buffer, 1 μl 10 mM dXTPs, 1 μl of each nested primer (10 pmol/μl), 1 μl of the first round PCR product, and 2 U Taq polymerase. The amplification scheme was identical as for the first round PCR. The sequence of the nested primers were as follows, for the preS1 region:

nested sense HBPr 2: 5'-bio-GAACAAGAGCTACAG-CATGGG-3' nested antisense HBPr 3: 5'-bio-CCACTGCATGGCCT-GAGGATG-3';

and for the preCore region:

nested sense HBPr 70: 5'-bio-TACTTCAAAGACTGTGT-GTTTA-3' nested antisense HBPr 7: 5'-bio-CTCCACAG(T/A)AGCTCCAAATTC-3'

In a second reaction the HBsAg region can be amplified in a similar protocol by using the following primers: HBPr 75: 5'-bio-CAAGGTATGTTGCCCGTTTGTCC-3' in combination with either HBPr 76: 5'-bio-CCAAACAGTGGGG-GAAAGCCC-3'; or with HBPr 94: 5'-bio-GGTA(A/T)AAAGGGACTCA(C/A)GATG-3'.

Example 2

Preparation of the Line Probe Assays

Probes were designed to cover the universal, genotypic and mutant motifs. In principle only probes that discriminate between one single nucleotide variation were retained. However, for certain polymorphisms at the extreme ends of the probe, cross-reactivity was tolerated. Specificity was reached experimentally for each probe individually after considering the % (G+C), the probe length, the final concentration, and hybridization temperature. Optimized probes were provided enzymatically with a poly-T-tail using the TdT (Pharmacia) in a standard reaction condition. Briefly, 400 μmol probe was incubated at 37° C. in a 30 μl reaction mix containing 5.3 mM dTTP, 25 mM Tris.HCL pH 7.5, 0.1 M sodium cacodylate, 1 mM CoCl$_2$, 0.1 M DTT and 170 U terminal deoxynucleotidyl transferase (Pharmacia). After one hour incubation, the reaction was stopped and the tailed probes were precipitated and washed with ice-old ethanol. Probes were dissolved in 6× SSC at their respectively specific concentrations and applied as horizontal lines on membrane strips in concentrations between 0.2 and 2.5 pM/ml. Biotinylated DNA was applied alongside as positive control (LiPA line 1). The oligonucleotides were fixed To the membrane by baking at 80° C. for 12 hours. The membrane was than sliced into 4 mm strips. The design of this strip is indicated in FIG. 2.

Example 3

LiPA Test Performance

Equal volumes (10 μl each) of the biotinylated PCR fragment and of the denaturation solution (DS; 400 mM NaOH/10 mM EDTA) were mixed in test troughs and incubated at room temperature for 5 minutes. Then, 2 ml of the 37° C. prewarmed hybridization solution (HS, 3× SSC/ 0.1% SDS) was added, followed by the addition of one strip per test trough. Hybridisation occurred for 1 hour at 50±0.5° C. in a closed shaking water bath. The strips were washed twice with 2 ml of stringent wash solution (3× SSC/0.1% SDS) at room temperature for 20 seconds, and once at 50° C. for 30 minutes. Following this stringent wash, strips were rinsed two times with 2 ml of the Innogenetics standard Rinse Solution (RS). Strips were incubated on a rotating platform with the alkaline phosphatase-labelled streptavidin conjugate, diluted in standard Conjugate Solution for 30 minutes at room temperature (20 to 25° C.). Strips were than washed twice with 2 ml of RS and once with standard Substrate Buffer (SB), and the colour reaction was started by adding BCIP and NBT to the SB. After maximum 30 minutes at room temperature, the colour reaction was stopped by replacing the colour compounds by distilled water immediately after drying, the strips were interpreted. Reactivities were considered positive whenever the reactivity was stronger than the reaction on the negative control. Strips can be stored on a dry dark place. The complete procedure described above can also The replaced by the standardized Inno-LiPA automation device (auto-LiPA).

Example 4

Selection of Reference Material

PCR fragments were prepared, derived from members of the different genotypes, the different preCore wild type and mutant sequences, drug resistant motifs and vaccine escape mutants. The PCR fragments were amplified with primes lacking the biotine group at their 5'-end and cloned into the pretreated EcoRV site of the pGEMT vector (Promega). Recombinant clones were selected after α-complementation and restriction fragment length analysis, and sequenced with plasmid primers. Other biotinylated fragments were directly sequenced with a dye-terminator protocol (Applied Biosystems) using the amplification primers. Alternatively, nested PCR was carried out with analogs of the primers, in which the biotine group was replaced with the T7- and SP6-primer sequence, respectively. These amplicons were than sequenced with an SP6- and T7-dye-primer procedure. By doing so, a reference panel of recombinant clones was prepared, which is necessary for optimizing LiPA probes.

Example 5

Genotyping HBV-infected Serum Samples

Only after creating a sequence alignment as shown in FIG. 1, it became clear which regions could be useful for HBV genotyping. The preS1 region seems to be suitable because of the high degree of variability. Probes were therefore designed to cover most of these variable regions as shown in Table 1. Only a limited selection of probes was retained because of their specific reaction with the reference panel. The most important ones are indicated as boxed regions in FIG. 1. These selected probes were then applied in a LiPA format indicated in FIG. 2, as line number 2 to 14. Some of the probes could be applied together in one line, because of their universal character, while others need to be applied separately. With the selection of probes thus obtained, serum samples collected in different parts of the world (Europe, South-America, Africa, Middle-East) were tested. The upper part of FIG. 3 shows the reactivity of a selection of samples on these probes. Genotyping of these samples is straightforward, with samples 2 to 8 belonging to genotype A, samples 9 and 10 belonging to genotype B, samples 11 and 12 belonging to genotype C, samples 13 to 19 belonging to genotype D, samples 20 to 23 belonging to genotype E, and sample 24 belonging to genotype F.

Genotyping can also be performed in the HBsAg region. Again, probes were designed to cover most of the variable regions shown in FIG. 1. Only a limited selection of probes were retained. These probes are boxed in FIG. 1 and are listed in FIG. 4. A LiPA strip was prepared carrying these probes and samples belonging of the different genotypes were characterized, as shown in FIG. 5.

Example 6

Scanning the PreCore Region for Mutations

HBeAg expression can be regulated at the transcriptional and translational level. It is postulated that a transcriptional regulation exists due to the presence of a dinucleotide variation in the promoter region of the preCore mRNA. Probes covering the wild type (e.g. probe HBPr 88) and the mutant (e.g. HBPr 89) motif were selected and their positions are indicated in the alignment shown in FIG. 1, and applied on the LiPA strip as line 15 and 16 (FIG. 2).

At the translational level, much more mutations might arise, all possibly resulting in abrogation of the HBeAg expression: any mutations at codon 1 (ATG) destroying translation initiation, codon 2 (CAA to TAA), codon 7 (TGC to TGA), codon 12 (TGT to TGA), codon 13 in genotype B, C, D, E, F (TCA to TGA or TAA), codon 14 (TGT to TGA), codon 18 (CAA to TAA), codon 21 (AAG to TAG), codon 23 (TGC to TGA), codon 26 (TGG to TAG or TGA), codon 28 (TGG to TAG or TGA). However, due to secondary contrain of the encapsidation signal, most of the mutations occur at codon 28 (TGG to TAG). Along with the mutation at codon 28, a second mutation at codon 29 (GGC to GAC) is often observed. In the case of genotype A and again as a consequence of the secondary constrain, stop codon mutations at codon 28 are only likely to occur after selection of a codon 15 mutation (CCC to CCT). Hence, correct interpretation of preCore mutations is genotype dependent. In addition to the above mentioned stop codons, a huge amount of different deletion- or insertion-mutations in the preCore open reading frame might give essentially the same result.

In order to develop a sensitive assay to detect the relevant mutations and the hypothetical mutations, a probe scanning procedure was developed. Partially overlapping probes were designed and applied in a LiPA format (FIG. 2, line 17 to 27). In this assay format, wild type sequences over the complete preCore region, together with the codon 15 variation for genotype A versus non-A genotypes, and the most common mutations at codon 28 (TAG), at codon 29 (GAC) and the combination of codon 28 and 29 (TAGGAC) are positively recognized. Absence of reactivity at one of the other probes is always indicative for the presence of a variation. The exact nature of this variation can then be revealed by sequence analysis or with further designed LiPA probes.

FIG. 3 shows the reactivity of the selected genotyped samples on the probes for the preCore region. Samples were previously tested for the presence of HBeAg or for anti-HBe. The interpretation of the reactivity on the LiPA probes for each sample is indicated below each strip. This approach allowed for the simultaneous screening of a sample for preCore mutations and the characterization of the viral genotype.

FIG. 6 also shows a panel of samples with mutations in the preCore region, as well as wild type samples. The probes used in this assay are listed in FIG. 4. This assay includes a codon 29 mutant (M4 motif), which was not present in the experiment in FIG. 3.

Example 7

Detection of Mutants in the HBsAg Region

Vaccine escape mutants have been described. The most commonly found mutant is the variation at codon 145 of HBsAg (G145R or GGA to AGA). LiPA probes are designed to detect wild type and mutant probes. Genotypic variations are present in the vicinity of codon 145. Therefore, genotype A is covered by probe 77, genotype B by probe 78, genotype C by probe 79, and genotype D/E by probe 80. Hence, in principle, it is possible to genotype and detect the wild type strains of the virus in one single experiment. Mutant target sequences are covered by probe 81 and 82 for genotype A and D, respectively. Probe 83 can be used as a positive control in these experiments. Further detection of mutants in the a determinant region is possible by means of a probe scanning approach. Herefore, probes are designed to cover the wild type sequence of the different genotypes over the HBsAg epitope region and applied in a LiPA format. Again here, absence of staining at one of these probes is indicative for the presence of a mutant strain. The exact nature of this variant is then determined by sequencing analysis.

Example 8

Detection of HBV Strains Resistant to Lamivudine

Through analogy with HIV and the resistance against the anti-viral compound 3TC (lamivudine or (−)-β-1-2',3'-dideoxy-3'-thiacytidine), it was predicted that upon treatment of HBV-infected patients with 3TC, viral strains would be selected showing resistance at the YMDD motif in the HB pol gene. The YMDD motif is physically located in the HBsAg region, but is encoded in another reading frame. Hence, this part of the HBV pol region is amplified with the primer combination HBPr 74-HBr 94, but not with the combination HBPr 74-HBr 76. Probes covering the wild type YMDD motif and YVDD mutant motif are indicated in FIG. 1, respectively probes 95 to 100 and 101 to 103, as well as probes 115, 116, 127 and 132, the latter probes yielding the best results in the LiPA assay. Such an assay was used to determine the presence of mutations in the YMDD motif in serum of a HBV-infected patient during treatment with lamivudine. FIG. 7 shows that in the first phase of the treatment (May 1995) no mutations were detected. During the treatment, the viral load decreased, reaching a level of approximately $10^4$ during November and December 1995, whereafter a breakthrough was observed, resulting in a level as high as during the first months of the treatment by June 1996. Interestingly, a LiPA assay performed in February 1996 indicated that the majority of virus present, possessed a mutation in the YMDD motif, which had changed to YVDD. In June 1996, no more wild type motif, but only mutant YVDD could be detected. With this assay, resistant HBV strains can thus easily be detected. Furthermore, the combined detection of the YMDD motif and preCore mutants might be clinically important in prediction and prognosis of further treatment.

REFERENCES

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297-301.

Barany F. Genetic disease detection and DNA amplification using cloned thermostable ligase. Proc Natl Acad Sci USA 1991; 88: 189-193.

Bej A, Mahbubani M, Miller R, Di Cesare J, Haff L, Atlas R. Mutiplex PCR amplification and immobilized capture probes for detection of bacterial pathogens and indicators in water. Mol Cell Probes 1990; 4:353-365.

Boom R., Sol C. J. A., Salimans M. M. M., et al. Rapid and simple method for purification of nucleic acids. J Clin Microbiol 1990; 28: 495-503.

Carman W, Zanetti A, Karayiannis P, Waters J, Manzillo G, Tanzi E, Zuckerman A, and Thomas H. Vaccine induced escape mutants. Lancet 1990; 336:325-329.

Carman W. Koruia J, Wallace L, MacPhee R., Mimms L, and Decker R. Fulminant reactivation of hepatitis B due to envelope protein mutant that escaped detection by monoclonal HBsAG ELISA. Lancet 1995; 345: 1400-1407.

Compton J. Nucleic acid sequence-based amplification. Nature 1991; 350: 91-92.

Crawford D. Hepatitis B virus 'escape' mutants: Arare event which causes vaccination failure. British Med. J. 1990; 301: 1058-1059.

Duck P. Probe amplifier system based on chimeric cycling oiigonucleotides. Biotechniques 1990; 9: 142-147.

Gao Q, Gu Z, Parniak M, Cameron I, Cammack N, Boucher C, and Wainberg M. The same mutation that encodes low-level human immunodeficiency virus type-1 resistance to 2',3'-dideoxyinosine and 2',3'-dideoxycytidine confers high level resistance to the (−) enantiomer of 2',3'-dideoxy-3'-thiacytidine. Antimicrob. Agents Chemother. 1993; 37: 1390-1392.

Guatelli J, Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874-1878.

Hadziyannis S. Hepaptis B e antigen negative chronic hepatitis B: from clinical recognition to pathogenesis and treatment. Viral Hepatitis 1995; 1: 7-36.

Honkoop P, de Man R, Zondervan P, Niesters H, and Schalm S. Histological improvement in patients with chronic hepatitis B virus infection treated with lavimudine is associated with a decrease in HBV-DNA by PCR. Hepatol. 1995; 22: abstract 887.

Kwoh D, Davis G, Whitfield K, Chappelle H, Dimichele L, Gingeras T. Transcription-based amplification system and detection of amplified human immunodeficiency virus type 1 with a bead-based sandwich hybridization format. Proc Natl Acad Sci USA 1989; 86: 1173-1177.

Kwok S, Kellogg D, McKinney N, Spasic D, Gode L, LevenSon C, Sinisky J. Effects of primer-template mismatches on the polymerase chain reaction: Human immunodeficiency views type 1 model studies. Nucl. Acids Res. 1990; 18: 999.

Landgren U, Kaiser R, Sanders J, Hood L. A ligase-mediated gene detection technique. Science 1988; 241:1077-1080.

Li J-S, Tong S-P, Wen Y-M, Vivitski L, Zhang Q, and Trépo C. Hepatitis B virus genotype A rarely circulates as an Hbe-minus mutant: possible contribution of a single nucleotide in the preCore region. J. Virol. 1993; 67: 5402-5410.

Ling, R., Mutimer, D., Ahmed, M., Boxall, E. H., Elias, E., Dusheiko, G. M. and Harrison, T. J. Selection of mutations in the Hepatitis B Virus polymerase during therapy of transplant recipients with lamivudne. Hepatology 1996; 24: 711-713.

Lok A, Akarca U, and Greene S. Mutations in the precore region of hepatitis B virus serve to enhance of the secondary structure of the pre-genome encapsidation signal. Proc. Natl. Acad. Sci. USA 1994; 91: 4077-4081.

Lomeli H, Tyagi S, Printchard C, Lisardi P, Kramer F. Quantitative assays based on the use of replicatable hybridization probes. Clin Chem 1989; 35: 1826-1831.

Magnius L, and Norder H. Subtypes, genotypes and molecular epidemiology of the hepatitis B virus as reflected by sequence variability of the S-gene. Intervirology 1995; 38: 24-34.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 54(21):7706-10.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134-43.

Naoumov N, Perilio R, Chokshi S, Dienstag J, Vicary C, Brown N, and Williams R. Reduction in hepatitis B virus quasispecies during lamivudine treatment is associated with enhanced virus replication and hepatocytolisis. Hepatol. 1995; 22: abstract 885.

Nielsen P, Egholm M, Berg R, Buchardt O (1991) Sequence-selective recognition of DNA by strand displacement with a thymine-substituted polyamide. Science 254(5037):1497-500.

Nielsen P, Egholm M, Berg R, Buchardt O (1993) Sequence specific inhibition of DNA restriction enzyme cleavage by PNA. Nucleic-Acids-Res. 21(2):197-200.

Okamoto H. Yotsumoto S, Akahane Y, Yamanaka T, Miyazaki Y, Sugai Y, Tsuda F, Tanaka T, Miyakawa Y, and Mayumi M. Hepatitis B virus with precore region defects prevail in persistently infected hosts along with seroconversion to the antibody against e antigen. J. Virol. 1990; 64: 1298-1303.

Saiki R, Walsh P, Levenson C, Erlich H. Genetic analysis of amplified DNA with immobilized sequence-specific oligonucleotide probes Proc Natl Acad Sci USA 1989; 86:6230-6234.

Sato S, Suzuki K, Akahane Y, Akamatsu K, Akiyama K, Yunomura K, Tsuda F, Tanaka T, Okamoto H, Miyakawa Y, Mayumi M. Hepatitis B virus strains with mutations in the core promoter in patients with fulminant hepatitis. Ann. Intern. Medicine 1995; 122: 241-248.

Shaw, T., Mok, S. S., Locarnini, S. A. Inhibition of hepatitis B virus DNA polymerase by enantiomers of penciclovir triphosphate and metabolic basis for selective inhibition ox HBV replication by penciclovir. Hepatology 1996; 24: 996-1002.

Stuyver L, Rossau R, Wyseur A, et al. Typing of hepatitis C virus isolates and characterization of new subtypes using a line probe assay. J. Gen. Virol. 1993; 74: 1093-1102.

Takahashi K, Aoyama K, Onhno N, Iwata K, Akahane Y, Baba K, Yoshizawa H, and Mishiro S. The precore/core promoter mutant (T1762A1764) of hepatitis B virus: clinical significance and an easy method for detection. J. Gen. Virol. 1995; 76: 3159-3164.

Tipples, G. A., Ma, M. M., Fischer, K. P., Bain, V. G., Kneteman, N. M. and Tyrell, D. L. J. Mutation in HBV RNA-dependent DNA polymerase confers resistance to lamivudine in vivo. Hepatology 1996; 24: 714-717.

Waters J, Kennedy M, Voet P, Hauser P, Petre J, Carman W, and Thomas H. Loss of the common 'a' determinant of hepatitis B surface antigen by vaccine-induced escape mutants. J. Clin. Invest. 1992; 90: 2543-2547.

Wu D, Wallace B. The ligation amplification reaction (LAR)—amplification of specific DNA sequences using sequential rounds of template-dependent ligation. Genomics 1989; 4:560-569.

Yuan T, Faruqi A, Shih J, and Shih C. The mechanism of natural occurrence of two closely linked HBV precore predominant mutations. Virol. 1995; 211: 144-156.

Zhang X, Zoulim F, Habersetzer F, Xiong S, and Trépo C. Analysis of hepatitis B virus genotypes and preCore region variability during interferon treatment of Hbe antigen negative chronic hepatitis B. J. Med. Virol. 1996; xxx-xxx.

The invention claimed is:

1. An isolated HBV mutant comprising a nucleotide sequence containing a drug-resistant mutation in the HBV RT pol gene, wherein the mutation results in a amino acid change in the YMDD motif of the HBV polymerase.

2. The HBV mutant according to claim 1, wherein the amino acid change is positioned at codon 552 of the HBV polymerase.

3. The HBV mutant according to claim 2, wherein said amino acid change is M to V at position 552.

4. The HBV mutant according to claim 1, wherein said amino acid change is M to V in the YMDD motif.

* * * * *